United States Patent
Kuwada et al.

(10) Patent No.: US 9,193,695 B2
(45) Date of Patent: Nov. 24, 2015

(54) 1, 2, 4-TRIAZOLONE DERIVATIVE AND USE THEREOF AS AN ANTAGONIST ON THE ARGININE-VASOPRESSIN 1B RECEPTOR

(75) Inventors: Takeshi Kuwada, Toshima-ku (JP);
Mitsukane Yoshinaga, Toshima-ku (JP);
Tomoko Ishizaka, Toshima-ku (JP);
Daisuke Wakasugi, Toshima-ku (JP);
Shin-ichi Shirokawa, Toshima-ku (JP);
Nobutaka Hattori, Toshima-ku (JP);
Youichi Shimazaki, Toshima-ku (JP);
Naoki Miyakoshi, Toshima-ku (JP)

(73) Assignee: TAISHO PHARMACEUTICAL CO., LTD., Tokyo (JP)

( * ) Notice: Subject to any disclaimer, the term of this patent is extended or adjusted under 35 U.S.C. 154(b) by 92 days.

(21) Appl. No.: 13/824,174

(22) PCT Filed: Sep. 30, 2011

(86) PCT No.: PCT/JP2011/072556
§ 371 (c)(1),
(2), (4) Date: Mar. 15, 2013

(87) PCT Pub. No.: WO2012/043791
PCT Pub. Date: Apr. 5, 2012

(65) Prior Publication Data
US 2013/0197217 A1    Aug. 1, 2013

(30) Foreign Application Priority Data

Oct. 1, 2010   (JP) .................................. 2010-224233
Mar. 11, 2011  (JP) .................................. 2011-054500

(51) Int. Cl.
| | |
|---|---|
| C07D 265/30 | (2006.01) |
| C07D 249/12 | (2006.01) |
| C07D 401/04 | (2006.01) |
| C07D 401/10 | (2006.01) |
| C07D 403/10 | (2006.01) |
| C07D 405/10 | (2006.01) |
| C07D 405/12 | (2006.01) |
| C07D 413/10 | (2006.01) |
| C07D 413/14 | (2006.01) |
| C07D 451/06 | (2006.01) |
| C07D 491/08 | (2006.01) |
| C07D 491/107 | (2006.01) |
| C07D 498/08 | (2006.01) |

(52) U.S. Cl.
CPC ............ *C07D 249/12* (2013.01); *C07D 401/04* (2013.01); *C07D 401/10* (2013.01); *C07D 403/10* (2013.01); *C07D 405/10* (2013.01); *C07D 405/12* (2013.01); *C07D 413/10* (2013.01); *C07D 413/14* (2013.01); *C07D 451/06* (2013.01); *C07D 491/08* (2013.01); *C07D 491/107* (2013.01); *C07D 498/08* (2013.01)

(58) Field of Classification Search
CPC .. C07D 211/60; C07D 401/04; C07D 211/58; C07D 211/62; C07D 211/16
USPC .......................................... 544/106; 540/544
See application file for complete search history.

(56) References Cited

U.S. PATENT DOCUMENTS

| 7,745,630 B2 | 6/2010 | Bryans et al. |
| 2006/0276449 A1 | 12/2006 | Kumagai et al. |

(Continued)

FOREIGN PATENT DOCUMENTS

| JP | 2000-063363 A | 2/2000 |
| JP | 2010-173978 A | 8/2010 |

(Continued)

OTHER PUBLICATIONS

Sugimoto, Toru, et al., "Molecular Cloning and Functional Expression of a cDNA Encoding the Human $V_{1b}$ Vasopressin Receptor," Journal of Biological Chemistry, Oct. 28, 1994, pp. 27088-27092, vol. 269, No. 43.

(Continued)

*Primary Examiner* — Nyeemah A Grazier
*Assistant Examiner* — Sagar Patel
(74) *Attorney, Agent, or Firm* — Sughrue Mion, PLLC

(57) ABSTRACT

The present invention provides a 1,2,4-triazolone derivative represented by Formula (1A) having an antagonistic activity on the arginine-vasopressin 1b receptor or a pharmaceutically acceptable salt thereof and provides a pharmaceutical composition comprising the compound or the salt as an active ingredient, in particular, a therapeutic or preventive agent exhibiting favorable pharmacokinetics in a disease such as mood disorder, anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, or alopecia.

[Formula 1]

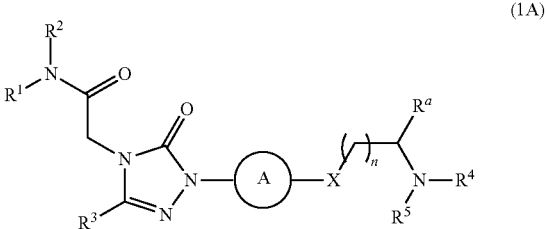

13 Claims, No Drawings

(56) References Cited

U.S. PATENT DOCUMENTS

| | | |
|---|---|---|
| 2007/0037822 A1 | 2/2007 | Letourneau et al. |
| 2007/0225333 A1 | 9/2007 | Bryans et al. |
| 2009/0312381 A1 | 12/2009 | Meier et al. |
| 2013/0190330 A1 | 7/2013 | Furstner et al. |
| 2014/0275006 A1* | 9/2014 | Yoshinaga et al. .......... 514/210.2 |

FOREIGN PATENT DOCUMENTS

| | | |
|---|---|---|
| WO | 01/55130 A2 | 8/2001 |
| WO | WO 2004058731 A1 * | 7/2004 |
| WO | 2005/021534 A1 | 3/2005 |
| WO | 2005/030755 A1 | 4/2005 |
| WO | 2005/063754 A1 | 7/2005 |
| WO | 2005/105779 A1 | 11/2005 |
| WO | 2006/095014 A1 | 9/2006 |
| WO | 2006/102308 A2 | 9/2006 |
| WO | 2006/133242 A2 | 12/2006 |
| WO | 2007/109098 A2 | 9/2007 |
| WO | 2007/134862 A1 | 11/2007 |
| WO | 2008/025736 A1 | 3/2008 |
| WO | 2008/033757 A2 | 3/2008 |
| WO | 2008/033764 A2 | 3/2008 |
| WO | 2009/017236 A1 | 2/2009 |
| WO | 2009/130231 A1 | 10/2009 |
| WO | 2009/130232 A1 | 10/2009 |
| WO | 2011096461 | 8/2011 |
| WO | 2011/104322 A1 | 9/2011 |

OTHER PUBLICATIONS

Lolait, Stephen, J., et al., "Extrapituitary expression of the rat V1b vasopressin receptor gene," Proc. Natl. Acad. Sci., USA, Jul. 1995, pp. 6783-6787, vol. 92.

Vaccari, Christopher, et al., "Comparative Distribution of Vasopressin V1b and Oxytocin Receptor Messenger Ribonucleic Acids in Brain," Endocrinology, 1998, pp. 5015-5033, vol. 139, No. 12.

Hernando, Fernando, et al., "Immunohistochemical Localization of the Vasopressin V1b Receptor in the Rat Brain and Pituitary Gland: Anatomical Support for Its Involvement in the Central Effects of Vasopressin," Endocrinology, 2001, pp. 1659-1668, vol. 142, No. 4.

Wersinger, S.R., et al., "Vasopressin V1b receptor knockout reduces aggressive behavior in male mice," Molecular Psychiatry, 2002, pp. 975-984, vol. 7.

Liebsch, Gudrun, et al., "Septal vasopressin modulates anxiety-related behaviour in rats," Neuroscience Letters, 1996, pp. 101-104, vol. 217.

Serradeil-Le Gal, Claudine, et al., "Characterization of (2S,4R)-1-[5-Chloro-1-[(2,4-dimethoxyphenyl)sulfonyl]-3-(2-methoxyphenyl)-2-oxo-2,3-dihydro-1H-indol-3-yl]-4-hydroxy-N,N-dimethyl-2-pyrrolidine carboxamide (SSR149415), a Selective and Orally Active Vasopressin V1b Receptor Antagonist," Journal of Pharmacology and Experimental Therapeutics, 2002, pp. 1122-1130, vol. 300, No. 3.

Griebel, Guy, et al., "Anxiolytic-and antidepressant-like effects of the non-peptide vasopressin V1b receptor antagonist, SSR149415, suggest an innovative approach for the treatment of stress-related disorders," PNAS, Apr. 30, 2002, pp. 6370-6375, vol. 99, No. 9.

Scott, Jack D., et al., "Tetrahydroquinoline sulfonamides as vasopressin 1b receptor antagonists," Bioorganic & Medicinal Chemistry Letters, 2009, pp. 6018-6022, vol. 19.

Smethurst, Chris A., et al., "The characterization of a novel V1b antagonist lead series," Bioorganic & Medicinal Chemistry Letters, 2011, pp. 92-96, vol. 21.

Baker et al., "Identification and optimisation of novel sulfonamide, selective vasopressin $V_{1B}$ receptor antagonists", Bioorganic & Medicinal Chemistry Letters, 21:3603-3607 (2011).

Zhou et al, "Involvement of Arginine Vasopressin and V1b receptor in alcohol drinking in Sardinian alcohol-preferring rats", Alcoholism: Clinical and Experimental Research, 35(10):1876-1883 (2011).

Zhou et al., "Persistent increase in hypothalamic arginine vasopressin gene expression during protracted withdrawal from chronic escalating-dose cocaine in rodents", Neuropsychopharmacology, 36:2062-2075 (2011).

* cited by examiner

1, 2, 4-TRIAZOLONE DERIVATIVE AND USE THEREOF AS AN ANTAGONIST ON THE ARGININE-VASOPRESSIN 1B RECEPTOR

CROSS REFERENCE TO RELATED APPLICATIONS

This application is a National Stage of International Application No. PCT/JP2011/072556, filed on Sep. 30, 2011, which claims priority from Japanese Patent Application Nos. 2010-224233, filed Oct. 1, 2010 and JP 2011-054500, filed Mar. 11, 2011, the contents of all of which are incorporated herein by reference in their entirety.

TECHNICAL FIELD

The present invention relates to a compound having a 1,2,4-triazolone skeleton showing an antagonistic activity on the arginine-vasopressin (AVP) V1b receptor and a pharmaceutical composition comprising the compound as an active ingredient, in particular, to a therapeutic or preventive agent for diseases such as mood disorder, anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, and alopecia.

BACKGROUND ART

The arginine-vasopressin (AVP) is a peptide composed of nine amino acids, is biosynthesized mainly in the hypothalamus, and is highly involved in regulation of plasma osmolality, blood pressure, and body fluid volume as a posterior pituitary hormone.

Three subtypes of AVP receptors, V1a, V1b, and V2 receptors, have been cloned until now. They are all known to be seven-transmembrane receptors. The V2 receptor is coupled to Gs to increase the cAMP level. The V1a receptor is coupled to Gq/11 to facilitate PI response and increase the intracellular Ca level. The V1a receptor is expressed in, for example, the brain, liver, adrenal gland, and vascular smooth muscle and is involved in vasoconstriction. The V1b receptor is also coupled to Gq/11, like the V1a receptor, to facilitate PI response (see Non-Patent Literatures 1 and 2). The V1b receptor is observed most commonly in the pituitary gland (expressed in 90% or more ACTH secreting cells of the anterior lobe) and is supposed to participate in the ACTH secretion from the anterior pituitary by AVP. The V1b receptor is present in various areas of the brain at high levels: the limbic cortex system including the hippocampus, amygdala, and entorhinal cortex, the cerebral cortex, the olfactory bulb, and the raphe nucleus, which are the origin of the serotonin nervous system, in addition to the pituitary gland (see Non-Patent Literatures 3 and 4).

In recent years, involvement of the V1b receptor in mood disorder or anxiety disorder has been suggested, and usefulness of V1b receptor antagonists has been being studied. The V1b receptor KO mice exhibit reduced aggressive behavior (see Non-Patent Literature 5). In addition, injection of a V1b receptor antagonist in the septal area prolonged the time spent in the open arm (anxiolytic-like effect) in an elevated plus-maze test (see Non-Patent Literature 6). In recent years, a V1b receptor specific antagonist, a 1,3-dihydro-2H-indol-2-one compound that can be administered peripherally, has been discovered (see Patent Literatures 1 to 3). In addition, the 1,3-dihydro-2H-indol-2-one compound was reported to show antidepressant- and anxiolytic-like effects in a variety of animal models (see Non-Patent Literatures 7 and 8). The compound disclosed in Patent Literature 1 shows a high affinity ($1 \times 10^{-9}$ mol/L to $4 \times 10^{-9}$ mol/L) for and selectively acts on the V1b receptor, and this compound antagonizes AVP, AVP+CRF, and restraint stress-induced ACTH increases.

Recently, V1b receptor antagonists having structures different from that of the 1,3-dihydro-2H-indol-2-one compound have been reported, such as quinazolin-4-on derivatives (see Patent Literatures 4 and 10), β-lactam derivatives (see Patent Literatures 5 and 7), azinon/diazinon derivatives (see Patent Literature 6), benzimidazolone derivatives (Patent Literature 8), isoquinoline derivatives (see Patent Literatures 9 and 10), pyridopyrimidin-4-one derivatives (see Patent Literature 11), pyrrolo[1,2-a]pyrazine derivatives (see Patent Literature 12), pyrazolo[1,2-a]pyrazine derivatives (see Patent Literature 13), tetrahydroquinoline sulfonamide derivatives (see Non-Patent Literature 9), and thiazole derivatives (see Non-Patent Literature 10). However, compounds with a 1,2,4-triazolone skeleton disclosed in the present invention have not been reported.

CITATION LIST

Patent Literature

Patent Literature 1: WO2001/055130
Patent Literature 2: WO2005/021534
Patent Literature 3: WO2005/030755
Patent Literature 4: WO2006/095014
Patent Literature 5: WO2006/102308
Patent Literature 6: WO2006/133242
Patent Literature 7: WO2007/109098
Patent Literature 8: WO2008/025736
Patent Literature 9: WO2008/033757
Patent Literature 10: WO2008/033764
Patent Literature 11: WO2009/017236
Patent Literature 12: WO2009/130231
Patent Literature 13: WO2009/130232

Non-Patent Literature

Non-Patent Literature 1: Sugimoto T, Kawashima G, J. Biol. Chem., 269, 27088-27092, 1994
Non-Patent Literature 2: Lolait S, Brownstein M, PNAS, 92, 6783-6787, 1995
Non-Patent Literature 3: Vaccari C, Ostrowski N, Endocrinology, 139, 5015-5033, 1998
Non-Patent Literature 4: Hernando F, Burbach J, Endocrinology, 142, 1659-1668, 2001
Non-Patent Literature 5: Wersinger S R, Toung W S, Mol. Psychiatry, 7, 975-984, 2002
Non-Patent Literature 6: Liebsch G, Engelmann M, Neurosci. Lett., 217, 101-104, 1996
Non-Patent Literature 7: Gal C S, Le Fur G, 300, JPET, 1122-1130, 2002
Non-Patent Literature 8: Griebel G, Soubrie P, PNAS, 99, 6370-6375, 2002
Non-Patent Literature 9: Jack D. Scott, et al., Bioorganic & Medicinal Chemistry Letters, 19, 21, 6018-6022, 2009
Non-Patent Literature 10: Chris A S, et. al., Bioorganic & Medicinal Chemistry Letters, 21, 92-96, 2011

SUMMARY OF INVENTION

Technical Problem

It is an object of the present invention to find a novel compound having a V1b receptor antagonistic activity and to provide a therapeutic or preventive agent for diseases such as mood disorder, anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, and alopecia. More specifically, the object is to find a novel compound having an excellent V1b receptor antagonistic activity and showing satisfactory drug migration to a target organ and high safety.

Solution to Problem

The present inventors, as a result of diligent studies, have found a novel compound with a 1,2,4-triazolone skeleton having a V1b receptor antagonistic activity (hereinafter, referred to as "1,2,4-triazolone derivative"), and have accomplished the present invention.

The present invention includes the following embodiments:

(I) A 1,2,4-triazolone derivative represented by Formula (1A):

[Formula 1]

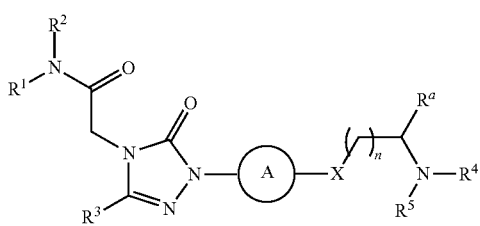

(1A)

[in Formula (1A), $R^1$ represents a $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated heterocycle;

$R^2$ represents a hydrogen atom or $C_{1-5}$ alkyl;

$R^3$ represents aryl or heteroaryl (the aryl or heteroaryl is optionally substituted by one or two groups selected from the group consisting of $C_{1-5}$ alkoxy, $C_{1-5}$ alkyl, halogen atoms, trifluoromethyl, trifluoromethoxy, cyano, hydroxy, difluoromethoxy, and $C_{1-5}$ alkylsulfonyl);

$R^4$ and $R^5$ may be the same or different and each represent a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated or unsaturated heterocycle containing one or more nitrogen, oxygen, or sulfur atoms in the ring (the 4- to 8-membered saturated or unsaturated heterocycle is optionally substituted by one or two groups selected from the group consisting of hydroxy, $C_{1-5}$ alkyl, $C_{1-5}$ alkoxy, halogen atoms, cyano, $C_{2-5}$ alkanoyl, and trifluoromethyl), or $R^4$ and $R^5$ optionally, together with the adjoining nitrogen atom, form a 4- to 8-membered saturated or unsaturated heterocycle optionally containing one or more nitrogen, oxygen, or sulfur atoms, in addition to the adjoining nitrogen atom, in the ring (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxy), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl, trifluoromethyl, and amino (the amino is optionally substituted by one or two groups selected from the group consisting of $C_{1-5}$ alkyl and $C_{2-5}$ alkanoyl), and the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl or 7-oxa-2-azaspiro[3.5]non-2-yl;

A represents phenylene or 6-membered heteroarylene (the phenylene and 6-membered heteroarylene are optionally substituted by one or two groups selected from halogen atoms and $C_{1-5}$ alkoxy);

X represents a single bond, —O—, or —$NR^6$—;

$R^6$ represents a hydrogen atom, $C_{1-5}$ alkyl, or $C_{2-5}$ alkanoyl;

$R^a$ represents a hydrogen atom or $C_{1-5}$ alkyl; and n is an integer of 0 to 3], or a pharmaceutically acceptable salt of the 1,2,4-triazolone derivative;

(II) A 1,2,4-triazolone derivative represented by Formula (1A):

[Formula 2]

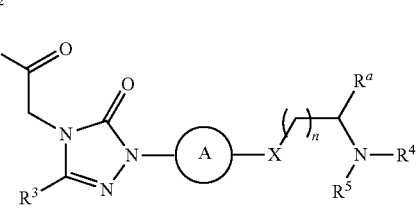

(1A)

[in Formula (1A), $R^1$ represents a $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated heterocycle;

$R^2$ represents a hydrogen atom or $C_{1-5}$ alkyl;

$R^3$ represents aryl or heteroaryl (the aryl or heteroaryl is optionally substituted by one or two groups selected from the group consisting of $C_{1-5}$ alkoxy, $C_{1-5}$ alkyl, halogen atoms, trifluoromethyl, trifluoromethoxy, cyano, hydroxy, difluoromethoxy, and $C_{1-5}$ alkylsulfonyl);

$R^4$ and $R^5$ may be the same or different and each represent a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated or unsaturated heterocycle containing one or more nitrogen, oxygen, or sulfur atoms in the ring (the 4- to 8-membered saturated or unsaturated heterocycle is optionally substituted by one or two groups selected from the group consisting of hydroxy, $C_{1-5}$ alkyl, $C_{1-5}$ alkoxy, halogen atoms, cyano, $C_{2-5}$ alkanoyl, and trifluoromethyl), or $R^4$ and $R^5$ optionally, together with the adjoining nitrogen atom, form a 4- to 8-membered saturated or unsaturated heterocycle optionally containing one or more nitrogen, oxygen, or sulfur atoms, in addition to the adjoining nitrogen atom, in the ring (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxy), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl, and trifluoromethyl, and the 4-to 8-membered saturated or unsaturated heterocycle optionally has a $C_{1-5}$ alkylene group crosslinking two different carbon atoms in the ring) or form 2-oxa-6-azaspiro[3.3]hept-6-yl;

A represents phenylene or 6-membered heteroarylene (the phenylene and 6-membered heteroarylene are optionally substituted by one or two groups selected from halogen atoms and $C_{1-5}$ alkoxy);

X represents a single bond, —O—, or —NR$^6$—;

$R^6$ represents a hydrogen atom, $C_{1-5}$ alkyl, or $C_{2-5}$ alkanoyl;

$R^a$ represents a hydrogen atom or $C_{1-5}$ alkyl; and n is an integer of 1 to 3], or a pharmaceutically acceptable salt of the 1,2,4-triazolone derivative;

(III) A 1,2,4-triazolone derivative represented by Formula (1a):

[Formula 3]

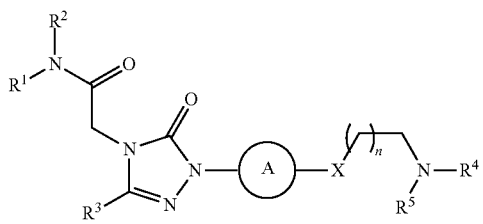

(1a)

[in Formula (1a), $R^1$ represents a $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated heterocycle;

$R^2$ represents a hydrogen atom or $C_{1-5}$ alkyl;

$R^3$ represents aryl or heteroaryl (the aryl or heteroaryl is optionally substituted by one or two groups selected from the group consisting of $C_{1-5}$ alkoxy, $C_{1-5}$ alkyl, halogen atoms, trifluoromethyl, trifluoromethoxy, cyano, hydroxy, and difluoromethoxy);

$R^4$ and $R^5$ may be the same or different and each represent a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated or unsaturated heterocycle containing one or more nitrogen, oxygen, or sulfur atoms in the ring (the 4- to 8-membered saturated or unsaturated heterocycle is optionally substituted by one or two groups selected from the group consisting of hydroxy, $C_{1-5}$ alkyl, $C_{1-5}$ alkoxy, halogen atoms, cyano, $C_{2-5}$ alkanoyl, and trifluoromethyl), or $R^4$ and $R^5$ optionally, together with the adjoining nitrogen atom, form a 4- to 8-membered saturated or unsaturated heterocycle optionally containing one or more nitrogen, oxygen, or sulfur atoms, in addition to the adjoining nitrogen atom, in the ring (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxy), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl, and trifluoromethyl, and the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl;

A represents phenylene or 6-membered heteroarylene;

X represents a single bond, —O—, or —NR$^6$—;

$R^6$ represents a hydrogen atom, $C_{1-5}$ alkyl, or $C_{2-5}$ alkanoyl; and n is an integer of 1 to 3], or a pharmaceutically acceptable salt of the 1,2,4-triazolone derivative;

(IV) The 1,2,4-triazolone derivative or pharmaceutically acceptable salt thereof according to any one of embodiments (I) to (III), wherein $R^1$ is a $C_{1-5}$ alkyl;

$R^2$ is a hydrogen atom; and $R^3$ is phenyl or pyridyl (the phenyl or pyridyl is optionally substituted by one or two groups selected from the group consisting of $C_{1-5}$ alkyl, $C_{1-5}$ alkoxy, halogen atoms, cyano, hydroxy, trifluoromethyl, difluoromethoxy, and trifluoromethoxy);

(V) The 1,2,4-triazolone derivative or pharmaceutically acceptable salt thereof according to any one of embodiments (I) to (IV), wherein A is phenylene, pyridinediyl, or pyrimidinediyl (the phenylene, pyridinediyl, and pyrimidinediyl are optionally substituted by one or two groups selected from halogen atoms and $C_{1-5}$ alkoxy);

(VI) The 1,2,4-triazolone derivative or pharmaceutically acceptable salt thereof according to any one of embodiments (I) to (IV), wherein A is phenylene or pyridinediyl (the phenylene and pyridinediyl are optionally substituted by one or two groups selected from halogen atoms and $C_{1-5}$ alkoxy);

(VII) The 1,2,4-triazolone derivative or pharmaceutically acceptable salt thereof according to embodiments (VI), wherein A represents any one of Formulae (2) to (4):

[Formula 4]

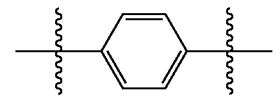 (2)

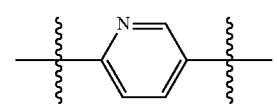 (3)

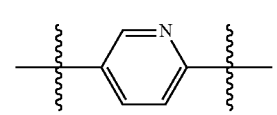 (4)

(VIII) The 1,2,4-triazolone derivative or pharmaceutically acceptable salt thereof according to any one of embodiments (I) to (VII), wherein X is a single bond;

n is an integer of 1; and $R^4$ and $R^5$ optionally, together with the adjoining nitrogen atom, form a 4- to 8-membered saturated or unsaturated heterocycle optionally containing one or more nitrogen, oxygen, or sulfur atoms, in addition to the adjoining nitrogen atom, in the ring (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxy), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl, and trifluoromethyl, and the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl;

(IX) The 1,2,4-triazolone derivative or pharmaceutically acceptable salt thereof according to any one of embodiments (I) to (VIII), wherein
$R^4$ and $R^5$, together with the adjoining nitrogen atom, form a 5- or 6-membered saturated heterocycle optionally containing one or more nitrogen, oxygen, or sulfur atoms, in addition to the adjoining nitrogen atom, in the ring (the 5- or 6-membered saturated heterocycle is optionally substituted by one or two groups selected from the group consisting of hydroxy and $C_{1-5}$ alkyl, and the 5- or 6-membered saturated heterocycle optionally has a $C_{1-5}$ alkylene group crosslinking two different carbon atoms in the ring) or form 2-oxa-6-azaspiro[3.3]hept-6-yl;

(X) The 1,2,4-triazolone derivative or pharmaceutically acceptable salt thereof according to any one of embodiments (I) to (VIII), wherein
$R^4$ and $R^5$, together with the adjoining nitrogen atom, form a 6-membered saturated heterocycle optionally containing one or more oxygen atoms, in addition to the adjoining nitrogen atom, in the ring (the 6-membered saturated heterocycle is optionally substituted by one or two hydroxy, and the 6-membered saturated heterocycle optionally has a $C_{1-5}$ alkylene group crosslinking two different carbon atoms in the ring) or form 2-oxa-6-azaspiro[3.3]hept-6-yl;

(XI) One substance selected from, or a mixture of two or more substances selected from the group consisting of the following compounds and pharmaceutically acceptable salts thereof according to embodiment (I):

2-[3-(3-chlorophenyl)-1-{4-[2-(morpholin-4-yl)ethyl]phenyl}-5-oxo-1,5-dihydro-4H-1,2,4-triazol-4-yl]-N-(propan-2-yl)acetamide, 2-[3-(3-chlorophenyl)-1-{4-[2-(3-hydroxypyrrolidin-1-yl)ethyl]phenyl}-5-oxo-1,5-dihydro-4H-1,2,4-triazol-4-yl]-N-(propan-2-yl)acetamide, 2-[3-(3-chlorophenyl)-1-(4-{2-[3-(hydroxymethyl)pyrrolidin-1-yl]ethyl}phenyl)-5-oxo-1,5-dihydro-4H-1,2,4-triazol-4-yl]-N-(propan-2-yl)acetamide, 2-[3-(3-chlorophenyl)-1-{4-[2-(3-hydroxy-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chlorophenyl)-1-{4-[2-(8-oxa-3-azabicyclo[3.2.1]oct-3-yl)ethyl]phenyl}-5-oxo-1,5-dihydro-4H-1,2,4-triazol-4-yl]-N-(propan-2-yl)acetamide, 2-[3-(3-chlorophenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chlorophenyl)-5-oxo-1-{4-[2-(piperidin-1-yl)ethyl]phenyl}-1,5-dihydro-4H-1,2,4-triazol-4-yl]-N-(propan-2-yl)acetamide, 2-[3-(3-chlorophenyl)-1-{4-[2-(1,4-oxazepan-4-yl)ethyl]phenyl}-5-oxo-1,5-dihydro-4H-1,2,4-triazol-4-yl]-N-(propan-2-yl)acetamide, 2-[3-(3-chlorophenyl)-1-{5-[2-(morpholin-4-yl)ethyl]pyridin-2-yl}-5-oxo-1,5-dihydro-4H-1,2,4-triazol-4-yl]-N-(propan-2-yl)acetamide, 2-[3-(3-chlorophenyl)-1-{5-[2-(3-hydroxy-8-azabicyclo[3.2.1]oct-8-yl)ethyl]pyridin-2-yl}-5-oxo-1,5-dihydro-4H-1,2,4-triazol-4-yl]-N-(propan-2-yl)acetamide, 2-[3-(3-chlorophenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]-N-(propan-2-yl)acetamide, 2-[3-(3-chlorophenyl)-1-{6-[2-(morpholin-4-yl)ethyl]pyridin-3-yl}-5-oxo-1,5-dihydro-4H-1,2,4-triazol-4-yl]-N-(propan-2-yl)acetamide, N-tert-butyl-2-[3-(3-chlorophenyl)-1-{4-[2-(morpholin-4-yl)ethyl]phenyl}-5-oxo-1,5-dihydro-4H-1,2,4-triazol-4-yl]acetamide, 2-[3-(3-chlorophenyl)-1-{4-[2-(morpholin-4-yl)ethyl]phenyl}-5-oxo-1,5-dihydro-4H-1,2,4-triazol-4-yl]-N-(1,1,1-trifluoropropan-2-yl)acetamide, 2-[3-(3-chlorophenyl)-1-{4-[2-(morpholin-4-yl)ethyl]phenyl}-5-oxo-1,5-dihydro-4H-1,2,4-triazol-4-yl]-N-(1-hydroxy-2-methylpropan-2-yl)acetamide, 2-[3-(3-chlorophenyl)-1-{4-[2-(morpholin-4-yl)ethyl]phenyl}-5-oxo-1,5-dihydro-4H-1,2,4-triazol-4-yl]-N-cyclobutylacetamide, 2-[3-(3-chlorophenyl)-1-{4-[2-(morpholin-4-yl)ethyl]phenyl}-5-oxo-1,5-dihydro-4H-1,2,4-triazol-4-yl]-N-(oxetan-3-yl)acetamide, 2-[3-(3-chlorophenyl)-1-{4-[2-(morpholin-4-yl)ethyl]phenyl}-5-oxo-1,5-dihydro-4H-1,2,4-triazol-4-yl]-N-(cyclopropylmethyl)acetamide, 2-[3-(3-methoxyphenyl)-1-{4-[2-(morpholin-4-yl)ethyl]phenyl}-5-oxo-1,5-dihydro-4H-1,2,4-triazol-4-yl]-N-(propan-2-yl)acetamide, 2-[3-(4-fluoro-3-methoxyphenyl)-5-oxo-1-{4-[2-(piperidin-1-yl)ethyl]phenyl}-1,5-dihydro-4H-1,2,4-triazol-4-yl]-N-(propan-2-yl)acetamide, 2-[3-(4-fluoro-3-methoxyphenyl)-1-{4-[2-(morpholin-4-yl)ethyl]phenyl}-5-oxo-1,5-dihydro-4H-1,2,4-triazol-4-yl]-N-(propan-2-yl)acetamide, 2-[3-(4-fluoro-3-methoxyphenyl)-1-{4-[2-(3-hydroxy-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(4-fluoro-3-methoxyphenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(4-fluoro-3-methoxyphenyl)-1-{5-[2-(morpholin-4-yl)ethyl]pyridin-2-yl}-5-oxo-1,5-dihydro-4H-1,2,4-triazol-4-yl]-N-(propan-2-yl)acetamide, 2-[3-(4-fluoro-3-methoxyphenyl)-1-{5-[2-(3-hydroxy-8-azabicyclo[3.2.1]oct-8-yl)ethyl]pyridin-2-yl}-5-oxo-1,5-dihydro-4H-1,2,4-triazol-4-yl]-N-(propan-2-yl)acetamide, 2-[3-(4-fluoro-3-methoxyphenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]-N-(propan-2-yl)acetamide, 2-[3-(3-chloro-4-fluorophenyl)-5-oxo-1-{4-[2-(piperidin-1-yl)ethyl]phenyl}-1,5-dihydro-4H-1,2,4-triazol-4-yl]-N-(propan-2-yl)acetamide, 2-[3-(3-chloro-4-fluorophenyl)-1-{4-[2-(morpholin-4-yl)ethyl]phenyl}-5-oxo-1,5-dihydro-4H-1,2,4-triazol-4-yl]-N-(propan-2-yl)acetamide, 2-[3-(3-chloro-4-fluorophenyl)-1-{4-[2-(2-oxa-6-azaspiro[3.3]hept-6-yl)ethyl]phenyl}-5-oxo-1,5-dihydro-4H-1,2,4-triazol-4-yl]-N-(propan-2-yl)acetamide, 2-[3-(3-chloro-4-fluorophenyl)-1-{4-[2-(1,4-oxazepan-4-yl)ethyl]phenyl}-5-oxo-1,5-dihydro-4H-1,2,4-triazol-4-yl]-N-(propan-2-yl)acetamide, 2-[3-(3-chloro-4-fluorophenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chloro-4-fluorophenyl)-1-{4-[2-(3-hydroxy-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chloro-4-fluorophenyl)-5-oxo-1-{5-[2-(piperidin-1-yl)ethyl]pyridin-2-yl}-1,5-dihydro-4H-1,2,4-triazol-4-yl]-N-(propan-2-yl)acetamide,
2-[3-(3-chloro-4-fluorophenyl)-1-{5-[2-(morpholin-4-yl)ethyl]pyridin-2-yl}-5-oxo-1,5-dihydro-4H-1,2,4-triazol-4-yl]-N-(propan-2-yl)acetamide,
2-[3-(3-chloro-4-fluorophenyl)-1-{5-[2-(2-oxa-6-azaspiro[3.3]hept-6-yl)ethyl]pyridin-2-yl}-5-oxo-1,5-dihydro-4H-1,2,4-triazol-4-yl]-N-(propan-2-yl)acetamide,
2-[3-(3-chloro-4-fluorophenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]-N-(propan-2-yl)acetamide,
2-[3-(3-cyanophenyl)-1-{4-[2-(morpholin-4-yl)ethyl]phenyl}-5-oxo-1,5-dihydro-4H-1,2,4-triazol-4-yl]-N-(propan-2-yl)acetamide,
2-[3-(3-fluorophenyl)-1-{4-[2-(morpholin-4-yl)ethyl]phenyl}-5-oxo-1,5-dihydro-4H-1,2,4-triazol-4-yl]-N-(propan-2-yl)acetamide,
2-(1-{4-[2-(morpholin-4-yl)ethyl]phenyl}-5-oxo-3-phenyl-1,5-dihydro-4H-1,2,4-triazol-4-yl)-N-(propan-2-yl)acetamide,
2-[3-(3-chlorophenyl)-1-{3-fluoro-4-[2-(morpholin-4-yl)ethyl]phenyl}-5-oxo-1,5-dihydro-4H-1,2,4-triazol-4-yl]-N-(propan-2-yl)acetamide,
2-[3-(3-chlorophenyl)-1-{3-fluoro-4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide,
2-[3-(3-chlorophenyl)-1-{3-methoxy-4-[2-(morpholin-4-yl)ethyl]phenyl}-5-oxo-1,5-dihydro-4H-1,2,4-triazol-4-yl]-N-(propan-2-yl)acetamide,
2-[3-(3-chlorophenyl)-1-{3-methoxy-4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide,
2-[3-(3-chlorophenyl)-1-{4-[2-(morpholin-4-yl)propyl]phenyl}-5-oxo-1,5-dihydro-4H-1,2,4-triazol-4-yl]-N-(propan-2-yl)acetamide,
2-[3-(3-chlorophenyl)-1-{4-[2-(3-oxa-8-azabicyclo[3.2.1]oct-8-yl)propyl]phenyl}-5-oxo-1,5-dihydro-4H-1,2,4-triazol-4-yl]-N-(propan-2-yl)acetamide,
2-[3-(3-chlorophenyl)-1-{5-[2-(morpholin-4-yl)propyl]pyridin-2-yl}-5-oxo-1,5-dihydro-4H-1,2,4-triazol-4-yl]-N-(propan-2-yl)acetamide,
2-[3-(3-chlorophenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide,
N-tert-butyl-2-[3-(3-chlorophenyl)-1-{5-[2-(morpholin-4-yl)ethyl]pyridin-2-yl}-5-oxo-1,5-dihydro-4H-1,2,4-triazol-4-yl]acetamide,
N-tert-butyl-2-[3-(3-chlorophenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]acetamide,
2-[3-(3-methoxyphenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide,
N-tert-butyl-2-[3-(3-methoxyphenyl)-1-{5-[2-(morpholin-4-yl)ethyl]pyridin-2-yl}-5-oxo-1,5-dihydro-4H-1,2,4-triazol-4-yl]acetamide,
N-tert-butyl-2-[3-(3-methoxyphenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]acetamide,
2-[3-(2-bromo-5-chlorophenyl)-1-{4-[2-(morpholin-4-yl)ethyl]phenyl}-5-oxo-1,5-dihydro-4H-1,2,4-triazol-4-yl]-N-(propan-2-yl)acetamide,
2-(3-[3-(methylsulfonyl)phenyl]-1-{4-[2-(morpholin-4-yl)ethyl]phenyl}-5-oxo-1,5-dihydro-4H-1,2,4-triazol-4-yl)-N-(propan-2-yl)acetamide,
2-[3-(3-chlorophenyl)-1-{4-[2-(morpholin-4-yl)ethyl]phenyl}-5-oxo-1,5-dihydro-4H-1,2,4-triazol-4-yl]-N-(propan-2-yl)acetamide,
(+)-2-[3-(3-chlorophenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide,
(−)-2-[3-(3-chlorophenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide,
2-[3-(4-fluoro-3-methoxyphenyl)-1-{4-[2-(3-oxa-8-azabicyclo[3.2.1]oct-8-yl)propyl]phenyl}-5-oxo-1,5-dihydro-4H-1,2,4-triazol-4-yl]-N-(propan-2-yl)acetamide,
2-[3-(4-fluoro-3-methoxyphenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide,
N-tert-butyl-2-[3-(3-methoxyphenyl)-1-{4-[2-(3-oxa-8-azabicyclo[3.2.1]oct-8-yl)propyl]phenyl}-5-oxo-1,5-dihydro-4H-1,2,4-triazol-4-yl]acetamide,
N-tert-butyl-2-[3-(3-methoxyphenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]acetamide,
2-[3-(6-methoxypyridin-2-yl)-1-{4-[2-(morpholin-4-yl)ethyl]phenyl}-5-oxo-1,5-dihydro-4H-1,2,4-triazol-4-yl]-N-(propan-2-yl)acetamide, and
2-[3-(6-methoxypyridin-2-yl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide;

(XII) A pharmaceutical composition comprising the 1,2,4-triazolone derivative or pharmaceutically acceptable salt thereof according to any one of embodiments (I) to (XI) as an active ingredient; and (XIII) A therapeutic or preventive agent comprising the 1,2,4-triazolone derivative or pharmaceutically acceptable salt thereof according to any one of embodiments (I) to (XI) as an active ingredient for mood disorder, anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, or alopecia.

Advantageous Effects of Invention

The novel 1,2,4-triazolone derivative of the invention shows an affinity for the V1b receptor and has an antagonistic activity on a stimulus to the receptor by a physiological ligand.

DESCRIPTION OF EMBODIMENTS

The terms used in the specification have the following meanings.

The term "halogen atom" refers to a fluorine atom, a chlorine atom, a bromine atom, or an iodine atom.

The term "$C_{1-5}$ alkyl" refers to a linear or branched alkyl group having 1 to 5 carbon atoms, and examples thereof include methyl, ethyl, n-propyl, isopropyl, n-butyl, isobutyl, sec-butyl, tert-butyl, n-pentyl, isopentyl, neopentyl, and tert-pentyl.

The term "$C_{3-7}$ cycloalkyl" refers to a group such as cyclopropyl, cyclobutyl, cyclopentyl, cyclohexyl, or cycloheptyl.

The term "$C_{1-5}$ alkoxy" refers to a linear or branched alkoxy group having 1 to 5 carbon atoms, and examples thereof include methoxy, ethoxy, n-propoxy, isopropoxy, n-butoxy, isobutoxy, sec-butoxy, tert-butoxy, n-pentyloxy, isopentyloxy, neopentyloxy, and tert-pentyloxy.

The term "$C_{1-5}$ alkylsulfonyl" refers to a sulfonyl group substituted by "$C_{1-5}$ alkyl" defined above, and examples thereof include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, neopentylsulfonyl, and tert-pentylsulfonyl.

The term "$C_{2-5}$ alkanoyl" refers to a linear or branched alkanoyl group having 2 to 5 carbon atoms, and examples thereof include acetyl, propionyl, butyryl, isobutyryl, valeryl, isovaleryl, and pivaloyl.

The term "mono-$C_{1-5}$ alkylaminocarbonyl" refers to a carbonyl group substituted by amino having one "$C_{1-5}$ alkyl" group defined above as a substituent, and examples thereof include methylaminocarbonyl, ethylaminocarbonyl, n-propylaminocarbonyl, isopropylaminocarbonyl, n-butylaminocarbonyl, isobutylaminocarbonyl, s-butylaminocarbonyl, t-butylaminocarbonyl, n-pentylaminocarbonyl, isopentylaminocarbonyl, and neopentylaminocarbonyl.

The term "di-$C_{1-5}$ alkylaminocarbonyl" refers to a carbonyl group substituted by amino having two identical or different "$C_{1-5}$ alkyl" groups defined above as substituents, and examples thereof include dimethylaminocarbonyl, diethylaminocarbonyl, di(n-propyl)aminocarbonyl, di(isopropyl)aminocarbonyl, ethylmethylaminocarbonyl, methyl(n-propyl)aminocarbonyl, and methyl(isopropyl)aminocarbonyl.

The term "aryl" refers to a monocyclic or bicyclic aromatic carbocycle, and examples thereof include phenyl, 1-naphthyl, and 2-naphthyl.

The term "heteroaryl" refers to a mono- or bi-cyclic aromatic group having 2 to 9 carbon atoms and having at least one hetero atom selected from oxygen, nitrogen, and sulfur atoms, and examples thereof include thienyl, furyl, pyrazolyl, imidazolyl, thiazolyl, isoxazolyl, oxazolyl, isoxazolyl, pyridyl, pyrimidinyl, quinolyl, indolyl, and benzofuranyl.

The term "4- to 8-membered saturated heterocycle" refers to a 4- to 8-membered saturated ring containing at least one hetero atom selected from nitrogen, oxygen, and sulfur atoms in the ring, and examples thereof include oxetan-3-yl, azetidin-1-yl, 1-pyrrolidinyl, piperidino, 2-piperidyl, 3-piperidyl, 1-piperazinyl, morpholin-4-yl, morpholin-3-yl, thiomorpholin-4-yl, thiomorpholin-3-yl, azepan-1-yl, 1,4-oxazepan-4-yl, and azocan-1-yl.

The term "4- to 8-membered saturated or unsaturated heterocycle containing one or more nitrogen, oxygen, or sulfur atoms in the ring" refers to, for example, oxetan-3-yl, azetidin-1-yl, 1-pyrrolidinyl, piperidino, 2-piperidyl, 3-piperidyl, 1-piperazinyl, morpholin-4-yl, morpholin-3-yl, thiomorpholin-4-yl, thiomorpholin-3-yl, azepan-1-yl, 1,4-oxazepan-4-yl, azocan-1-yl, 5,6-dihydropyridin-1(2H)-yl, 1,4-diazepan-1-yl, or 1,2,3,6-tetrahydropyridin-1-yl.

The term "a 4- to 8-membered saturated or unsaturated heterocycle formed together with the adjoining nitrogen atom and optionally containing one or more nitrogen, oxygen, or sulfur atoms, in addition to the adjoining nitrogen atom, in the ring" refers to a group such as azetidin-1-yl, 1-pyrrolidinyl, piperidino, 1-piperazinyl, morpholin-4-yl, thiomorpholin-4-yl, azepan-1-yl, 1,4-oxazepan-4-yl, azocan-1-yl, 5,6-dihydropyridin-1(2H)-yl, 1,4-diazepan-1-yl, or 1,2,3,6-tetrahydropyridin-1-yl.

The term "$C_{1-5}$ alkylene" refers to a divalent group having one hydrogen atom removed from "$C_{1-5}$ alkyl" defined above, and examples thereof include methylene, ethylene, methylmethylene, trimethylene, propylene, tetramethylene, and pentamethylene.

The term "4- to 8-membered saturated or unsaturated heterocycle having a $C_{1-5}$ alkylene group crosslinking two different carbon atoms in the ring" refers to a ring which is "4- to 8-membered saturated or unsaturated heterocycle formed together with the adjoining nitrogen atom and optionally containing one or more nitrogen, oxygen, or sulfur atoms, in addition to the adjoining nitrogen atom, in the ring" defined above, and has a $C_{1-5}$ alkylene crosslinking two different carbon atoms in the ring; and examples thereof include 8-azabicyclo[3.2.1]oct-8-yl (tropinyl), 8-oxa-3-azabicyclo[3.2.1]oct-3-yl, and 3-oxa-8-azabicyclo[3.2.1]oct-8-yl. Examples of the 8-azabicyclo[3.2.1]oct-8-yl having a hydroxy substituent include 3-hydroxy-8-azabicyclo[3.2.1]oct-8-yl.

The term "a 5- or 6-membered saturated heterocycle formed together with the adjoining nitrogen atom and optionally containing one or more nitrogen, oxygen, or sulfur atoms, in addition to the adjoining nitrogen atom, in the ring (the 5- or 6-membered saturated heterocycle optionally has a $C_{1-5}$ alkylene group crosslinking two different carbon atoms in the ring)" refers to a group such as 1-pyrrolidinyl, piperidino, 1-piperazinyl, morpholin-4-yl, thiomorpholin-4-yl, 8-azabicyclo[3.2.1]oct-8-yl (tropinyl), 8-oxa-3-azabicyclo[3.2.1]oct-3-yl, or 3-oxa-8-azabicyclo[3.2.1]oct-8-yl.

The term "a 6-membered saturated heterocycle formed together with the adjoining nitrogen atom and optionally containing one or more oxygen atoms, in addition to the adjoining nitrogen atom, in the ring (the 6-membered saturated heterocycle optionally has a $C_{1-5}$ alkylene group crosslinking two different carbon atoms in the ring)" refers to a group such as piperidino, morpholin-4-yl, 8-azabicyclo[3.2.1]oct-8-yl (tropinyl), 8-oxa-3-azabicyclo[3.2.1]oct-3-yl, or 3-oxa-8-azabicyclo[3.2.1]oct-8-yl.

The term "phenylene" refers to a group such as 1,2-phenylene, 1,3-phenylene, or 1,4-phenylene.

The term "6-membered heteroarylene" refers to a group such as 2,3-pyridinediyl, 2,4-pyridinediyl, 2,5-pyridinediyl, 2,6-pyridinediyl, 3,5-pyridinediyl, or 2,5-pyrimidinediyl.

In the present invention, $R^1$ is preferably $C_{1-5}$ alkyl and more preferably isopropyl or tert-butyl.

In the present invention, $R^2$ is preferably a hydrogen atom.

In the present invention, $R^3$ is preferably phenyl or pyridyl (the phenyl or pyridyl is optionally substituted by one or two groups selected from the group consisting of $C_{1-5}$ alkyl, $C_{1-5}$ alkoxy, halogen atoms, cyano, hydroxy, trifluoromethyl, difluoromethoxy, trifluoromethoxy, and $C_{1-5}$ alkylsulfonyl).

More preferably, $R^3$ is phenyl (the phenyl is optionally substituted by one or two groups selected from $C_{1-5}$ alkyl, $C_{1-5}$ alkoxy, halogen atoms, cyano, hydroxy, trifluoromethyl, difluoromethoxy, trifluoromethoxy, and $C_{1-5}$ alkylsulfonyl) or pyridyl (the pyridyl is optionally substituted by one or two groups selected from $C_{1-5}$ alkyl, $C_{1-5}$ alkoxy, halogen atoms, cyano, hydroxy, trifluoromethyl, difluoromethoxy, and trifluoromethoxy).

More preferably, $R^3$ is phenyl (the phenyl is optionally substituted by one or two groups selected from $C_{1-5}$ alkoxy, chlorine atoms, fluorine atoms, cyano, and $C_{1-5}$ alkylsulfonyl) or pyridyl (the pyridyl is optionally substituted by $C_{1-5}$ alkoxy).

More preferably, $R^3$ is a group represented by Formula (5), (6), (7), (8), (9), (10), (11), (12), or (13). Most preferably, $R^3$ is a group represented by Formula (5), (6), (7), (8), or (9).

[Formula 5]

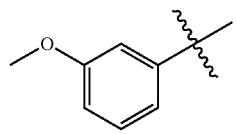

(5)

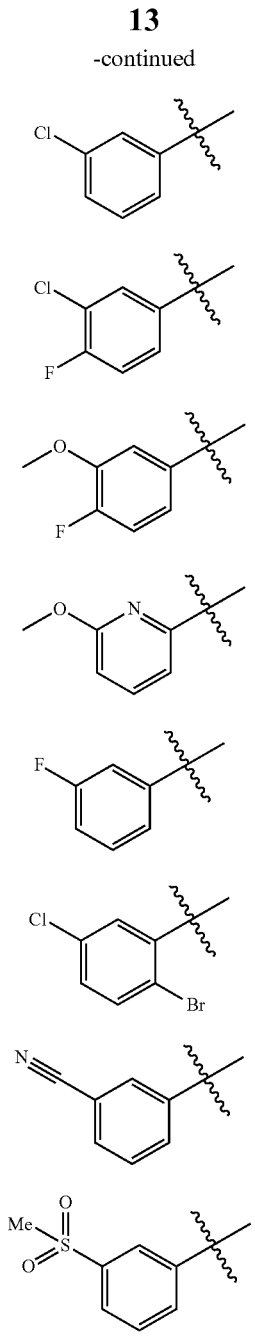

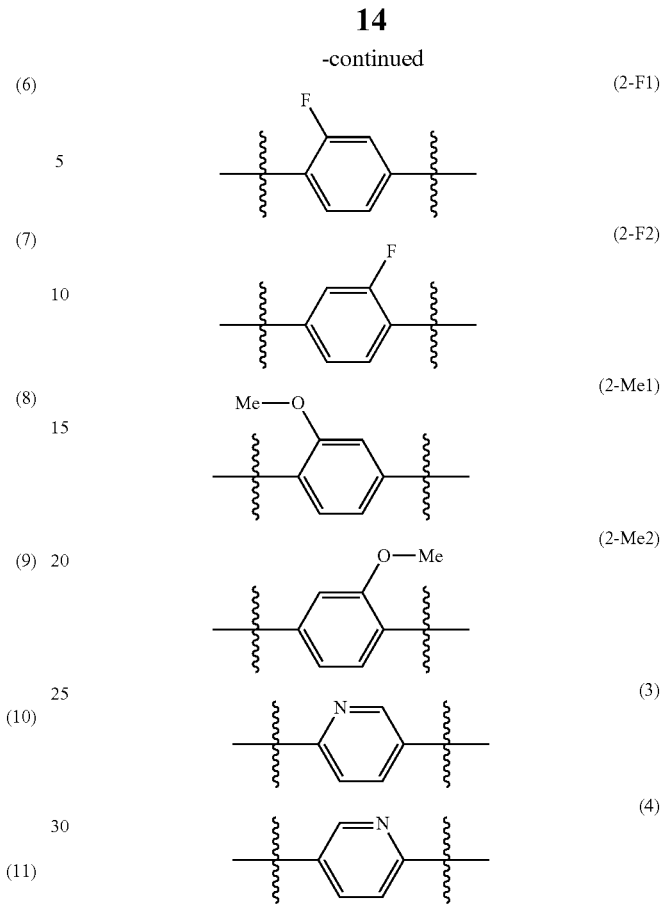

In the present invention, A is preferably phenylene, pyridinediyl, or pyrimidinediyl (the phenylene, pyridinediyl, and pyrimidinediyl are optionally substituted by one or two groups selected from halogen atoms and $C_{1-5}$ alkoxy).

More preferably, A is a group represented by Formula (2), (2-F1), (2-F2), (2-Me1), (2-Me2), (3), or (4). Most preferably, A is a group represented by Formula (2) or (3).

[Formula 6]

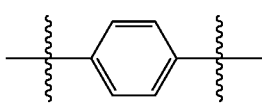
(2)

In the present invention, X is preferably a single bond.

In the present invention, $R^a$ is preferably a hydrogen atom or a methyl group.

In the present invention, n is preferably 1.

In the present invention, $R^4$ and $R^5$ preferably, together with the adjoining nitrogen atom, form a 4- to 8-membered saturated or unsaturated heterocycle optionally containing one or more nitrogen, oxygen, or sulfur atoms, in addition to the adjoining nitrogen atom, in the ring (the 4- to 8-membered saturated or unsaturated heterocycle is optionally substituted by one or two groups selected from the group consisting of hydroxy, $C_{1-5}$ alkyl (the $C_{1-5}$ alkyl is optionally substituted by one or two hydroxy), $C_{1-5}$ alkoxy, halogen atoms, cyano, $C_{2-5}$ alkanoyl, and trifluoromethyl, or the 4- to 8-membered saturated or unsaturated heterocycle optionally has a $C_{1-5}$ alkylene group crosslinking two different carbon atoms in the ring) or form 2-oxa-6-azaspiro[3.3]hept-6-yl. More preferably, $R^4$ and $R^5$, together with the adjoining nitrogen atom, form a 5- or 6-membered saturated heterocycle optionally containing one or more nitrogen, oxygen, or sulfur atoms, in addition to the adjoining nitrogen atom, in the ring (the 5- or 6-membered saturated heterocycle is optionally substituted by one or two groups selected from the group consisting of hydroxy and $C_{1-5}$ alkyl, or the 5- or 6-membered saturated heterocycle optionally has a $C_{1-5}$ alkylene group crosslinking two different carbon atoms in the ring) or form 2-oxa-6-azaspiro[3.3]hept-6-yl. More preferably, $R^4$ and $R^5$, together with the adjoining nitrogen atom, form a 6-membered saturated heterocycle optionally containing one or more oxygen atoms, in addition to the adjoining nitrogen atom, in the ring (the 6-membered saturated heterocycle is optionally substituted by one or two hydroxy, or the 6-membered saturated heterocycle optionally has a $C_{1-5}$ alkylene group crosslinking two different carbon atoms in the ring) or form 2-oxa-6-azaspiro[3.3]hept-6-yl. Most preferred examples of the ring formed by $R^4$ and $R^5$ together with the adjoining nitrogen atom include 1-pyrrolidinyl, piperidino (here, 1-pyrrolidinyl and piperidino are optionally substituted by one or two hydroxy), morpholin-4-yl (here, the morpholinyl group is optionally substituted by one or two $C_{1-5}$ alkyl groups, and the morpholin-4-yl can be, for example, 3-methylmorpholin-4-yl), 1,4-oxazepan-4-yl, thiomorpholin-4-yl, 8-azabicyclo[3.2.1]oct-8-yl (tropinyl), 3-hydroxy-8-azabicyclo[3.2.1]oct-8-yl, 8-oxa-3-azabicyclo[3.2.1]oct-3-yl, 3-oxa-8-azabicyclo[3.2.1]oct-8-yl, 2-oxa-6-azaspiro[3.3]hept-6-yl, and 7-oxa-2-azaspiro[3.5]non-2-yl.

1,2,4-Triazolone derivatives represented by Formulae (1A) and (1a) or pharmaceutically acceptable salts thereof show high safety. The safety was confirmed by various safety tests such as a cytochrome P450 (CYP) activity inhibition test, a CYP metabolism-dependent inhibition test, a covalent bonding test, a trapping test, a hERG test, a cytotoxicity test, a phototoxicity test, a single-dose safety test, and a repeated-dose safety test.

Examples of the "pharmaceutically acceptable salt" include salts with inorganic acids, such as sulfuric acid, hydrochloric acid, hydrobromic acid, phosphoric acid, and nitric acid; salts with organic acids such as formic acid, trifluoroacetic acid, acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, and naphthalene-2-sulfonic acid; salts with one or more metal ions such as lithium, sodium, potassium, calcium, magnesium, zinc, and aluminum ions; and salts with amines such as ammonia, arginine, lysine, piperazine, choline, diethylamine, 4-phenylcyclohexylamine, 2-aminoethanol, and benzathine.

The compound of the present invention can be also present in the form of a solvate. From the aspect of applicability as medicine, the compound may be present in the form of a hydrate.

The compound of the present invention includes its enantiomers, diastereomers, equilibrium compounds, mixtures thereof at any proportion, and racemic mixtures.

The compound of the present invention can be formulated into a pharmaceutical preparation together with one or more pharmaceutically acceptable carriers, excipients, or diluents. Examples of the carrier, excipient, and diluent include water, lactose, dextrose, fructose, sucrose, sorbitol, mannitol, polyethylene glycol, propylene glycol, starch, gum, gelatin, alginate, calcium silicate, calcium phosphate, cellulose, water syrup, methylcellulose, polyvinylpyrrolidone, alkyl parahydroxybenzosorbate, talc, magnesium stearate, stearic acid, glycerine, and various oils such as sesame oil, olive oil, and soybean oil.

The above-mentioned carrier, excipient, or diluent is optionally mixed with commonly used additives, such as an bulking agent, a binder, a disintegrant, a pH adjuster, or a solubilizer, and can be prepared in the form of oral or parenteral agents, such as tablets, pills, capsules, granules, powder, liquid, emulsion, suspension, ointment, injection, or patches, by common preparation technology. The compound of the present invention can be orally or parenterally administered to adult patients in a dosage of 0.001 to 500 mg once or several times per day. The dosage can be appropriately adjusted depending on, for example, the type of the disease to be treated and the age, weight, and symptoms of the patient.

In the compound of the present invention, one or more of the hydrogen, fluorine, carbon, nitrogen, oxygen, and sulfur atoms may be replaced with radioisotopes or stable isotopes thereof. These labeled compounds are useful, for example, for metabolic or pharmacokinetic study or as ligands of receptors in biological analysis.

The compound of the present invention can be produced, for example, in accordance with the method shown below.

The compound represented by Formula (1) can be produced by the synthetic process shown in Scheme 1:

Scheme 1

[Formula 7]

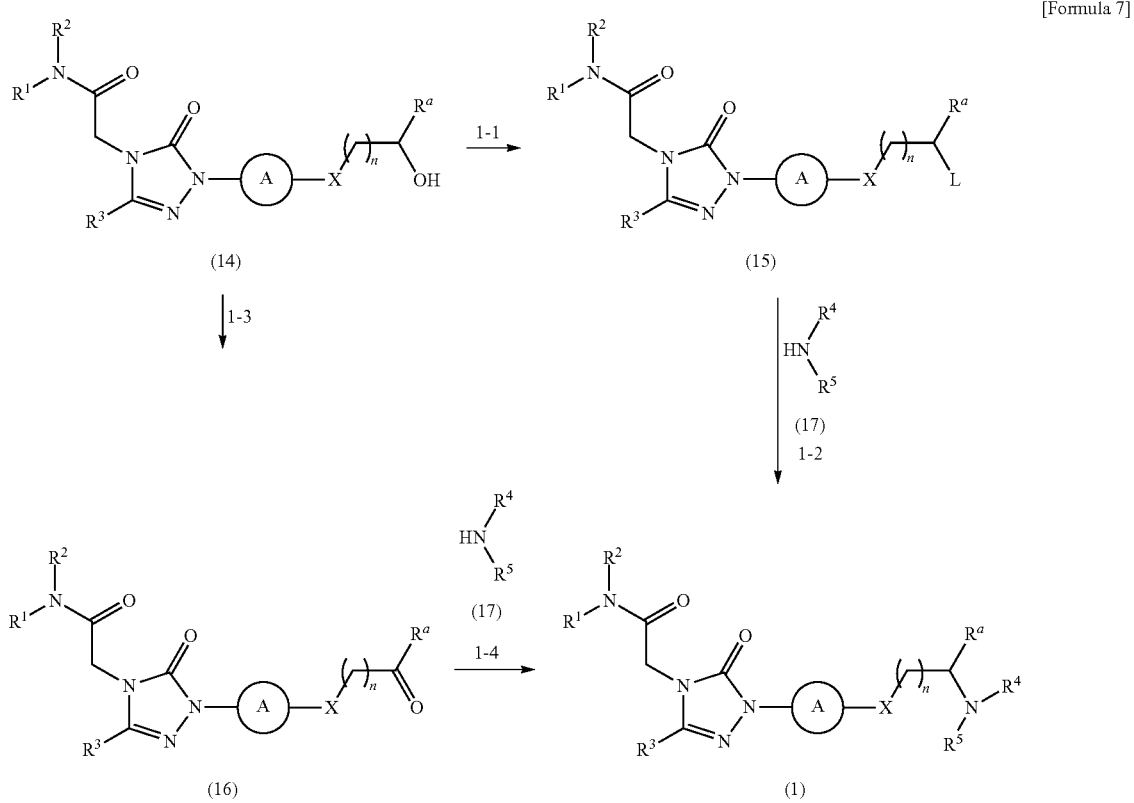

(wherein, $R^1$, $R^2$, $R^3$, $R^4$, $R^5$, $R^a$, A, X, and n are the same as above; and L represents a leaving group such as a p-toluenesulfonyloxy group, a methanesulfonyloxy group, or a halogen atom).

The compound represented by Formula (1) can be prepared by conversion of the hydroxy group of a compound represented by Formula (14) into a common leaving group (Step 1-1) and reaction of the leaving group with a corresponding amine (17) (Step 1-2). The reaction in Step 1-1 (conversion to a leaving group) is performed by, for example, chlorination, bromination, iodination, methanesulfonylation, or p-toluenesulfonylation.

Examples of the chlorination include a method of using carbon tetrachloride and triphenylphosphine, a method of using thionyl chloride or phosphorus oxychloride, and a method of introducing a leaving group using p-toluenesulfonyl chloride or the like and substituting the leaving group by lithium chloride or any other reagent. These reactions can be performed using a solvent such as tetrahydrofuran, dioxane, dichloromethane, chloroform, N,N-dimethylformamide, or a mixture thereof at −50 to 100° C.

Examples of the bromination include a method of using carbon tetrabromide and triphenylphosphine. This reaction can be performed in a solvent such as tetrahydrofuran, dioxane, dichloromethane, chloroform, N,N-dimethylformamide, or a mixture thereof at −50 to 50° C.

Examples of the iodination include a method of using iodine, triphenylphosphine, and imidazole. This reaction can be performed using a solvent such as tetrahydrofuran, dioxane, dichloromethane, chloroform, N,N-dimethylformamide, or a mixture thereof at a temperature of −50 to 100° C.

The methanesulfonylation and the p-toluenesulfonylation can be performed using, for example, methanesulfonyl chloride and p-toluenesulfonyl chloride, respectively. These reactions may be performed in the presence of an appropriate base. Examples of the base include organic amines such as triethylamine and diisopropylethylamine; and inorganic bases such as potassium carbonate. The reactions can be performed in a reaction solvent such as N,N-dimethylformamide, tetrahydrofuran, dioxane, dichloromethane, chloroform, 1,2-dichloroethane, or a mixture thereof at a temperature of −50 to 50° C.

The reaction in Step 1-2 proceeds in the absence of solvent, or in a solvent such as tetrahydrofuran, acetonitrile, N,N-dimethylformamide, dimethyl sufoxide, ethanol, isopropyl alcohol, or a mixture thereof at a temperature of room temperature to near the boiling point of the solvent. The reaction more smoothly proceeds in the presence of sodium iodide or potassium iodide, in addition to an inorganic base, such as potassium carbonate or cesium carbonate, or an organic base such as triethylamine or diisopropylethylamine.

The compound represented by Formula (1) can be prepared through common oxidation to convert the hydroxy group of a compound represented by Formula (14) into a carbonyl group (Step 1-3) and reductive amination with a corresponding amine (17) (Step 1-4).

The oxidation reaction in Step 1-3 can be performed using chromic acid such as pyridinium chlorochromate or pyridinium dichromate in a reaction solvent such as dichloromethane or chloroform at a reaction temperature of 0° C. to near the boiling point of the reaction solvent.

In addition, the oxidation reaction can be performed using, for example, a Dess-Martin reagent (1,1,1-triacetoxy-1,1-dihydro-1,2-benziodoxol-3(1H)-one) in a reaction solvent such as dichloromethane or chloroform at a reaction temperature of 0 to 40° C.

In another example, the oxidation reaction can be performed using, for example, IBX (1-hydroxy-1,2-benziodoxol-3(1H)-one 1-oxide) in a reaction solvent, such as dimethyl sufoxide, by further diluting with a solvent not participating in the reaction, such as tetrahydrofuran, dichloromethane, or chloroform, at a reaction temperature of 0 to 40° C.

In addition to the above-described methods, the oxidation reaction may be performed by any method that can oxidize alcohol into carbonyl, such as a reaction of dimethyl sufoxide with an activating reagent (e.g., oxalyl chloride, N-chlorosuccinimide, or dicyclohexyl carbodiimide) or oxidation using tetra-n-propylammonium perruthenate (VII) and N-methylmorpholine oxide. The comprehensive general view of the oxidation reaction can be found in Richard C. Larock, Comprehensive Organic Transformation, WILEY-VCH, 1999, 604.

The reductive amination in Step 1-4 is achieved through a reaction between carbonyl (16) and a corresponding amine (17) to generate an imine derivative and reduction with a reducing agent such as sodium triacetoxyborohydride. The reaction proceeds in an inert solvent such as methanol, ethanol, tetrahydrofuran, dichloromethane, chloroform, or a mixture thereof at a temperature of −70° C. to room temperature. The reaction can be also performed using, for example, a hydrogen gas with a catalyst such as palladium on carbon or another boron reagent such as borohydride, sodium borohydride, or sodium cyanoborohydride.

Among the compounds represented by Formula (14), the compound represented by Formula (25) can be produced by the synthetic process shown in Scheme 2:

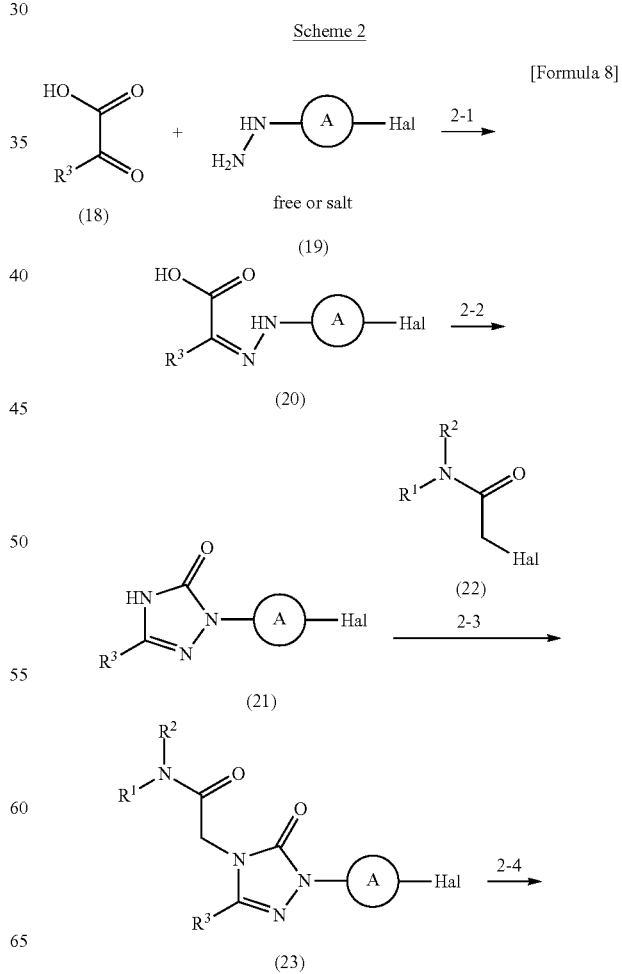

Scheme 2

[Formula 8]

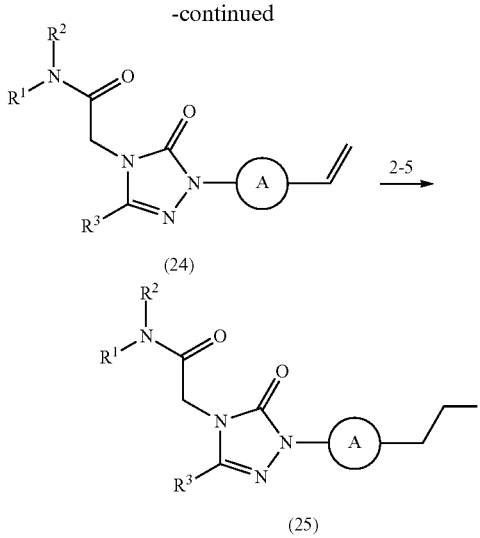

(wherein, $R^1$, $R^2$, $R^3$, and A are the same as above; and Hal represents a halogen atom).

The compound represented by Formula (20) can be prepared by a reaction of ketocarboxylic acid (18) with a hydrazine derivative (19) under an acidic condition (Step 2-1). The reaction in Step 2-1 proceeds in a solvent such as water, ethanol, isopropyl alcohol, acetonitrile, tetrahydrofuran, N,N-dimethylformamide, or dimethyl sufoxide or mixture thereof, in the presence of an inorganic acid such as hydrochloric acid or sulfuric acid or an organic acid such as p-toluenesulfonic acid, methanesulfonic acid, or camphorsulfonic acid.

The compound represented by Formula (21) can be prepared by a Curtius rearrangement reaction of the compound represented by Formula (20) (Step 2-2). The Curtius rearrangement reaction in this step proceeds by the use of diphenylphosphonyl azide (DPPA) in a solvent such as toluene, tetrahydrofuran, acetonitrile, or a mixture thereof, in the presence of a base such as triethylamine or diisopropylethylamine. The comprehensive general view of the Curtius rearrangement reaction is found in Chem. Rev., 1988, 88, 297-368 and Tetrahedron, 1974, 30, 2151-2157.

The compound represented by Formula (23) can be prepared by reacting the compound represented by Formula (21) with a separately prepared alkyl halide (22) in a solvent such as tetrahydrofuran, N,N-dimethylformamide, dimethyl sulfoxide, acetonitrile, or a mixture thereof, in the presence of an inorganic base such as potassium carbonate, cesium carbonate, or sodium hydride, or an organic base such as diisopropylethylamine, at a temperature of room temperature to near the boiling point of the solvent (Step 2-3).

The compound represented by Formula (24) can be prepared by introducing ethylene into the compound represented by Formula (23) by a Migita-Kosugi-Stille cross coupling reaction or a Suzuki-Miyaura cross coupling reaction (Step 2-4). The comprehensive general view of the Migita-Kosugi-Stille cross coupling reaction is found in Angew. Chem. Int., Ed. 2004, 43, 4704-4734. The comprehensive general view of the Suzuki-Miyaura cross coupling reaction is found in Chem. Rev., 1995, 95, 2457-2483.

The compound represented by Formula (25) can be prepared through common hydroboration of the compound represented Formula (24) and a subsequent oxidation reaction (Step 2-5). The reaction in Step 2-5 proceeds by hydroboration of the alkene moiety of the compound represented by Formula (24) with, for example, a borane-tetrahydrofuran complex, 9-borabicyclo[3.3.1]nonane, disiamylborane, or thexylborane in a solvent such as tetrahydrofuran, toluene, acetonitrile, or a mixture thereof at a temperature of near −10° C. to near room temperature; and subsequent use of, for example, hydrogen peroxide in the presence of a base such as sodium perborate (monohydrate or tetrahydrate) or sodium hydroxide.

The comprehensive general view of the hydroboration is found in J. Am. Chem. Soc., 1956, 78, 5694-5695 and J. Org. Chem., 1986, 51, 439-445.

Among the compounds represented by Formula (1), the compound represented by Formula (32) can be produced by the synthetic process shown in Scheme 3:

Scheme 3

[Formula 9]

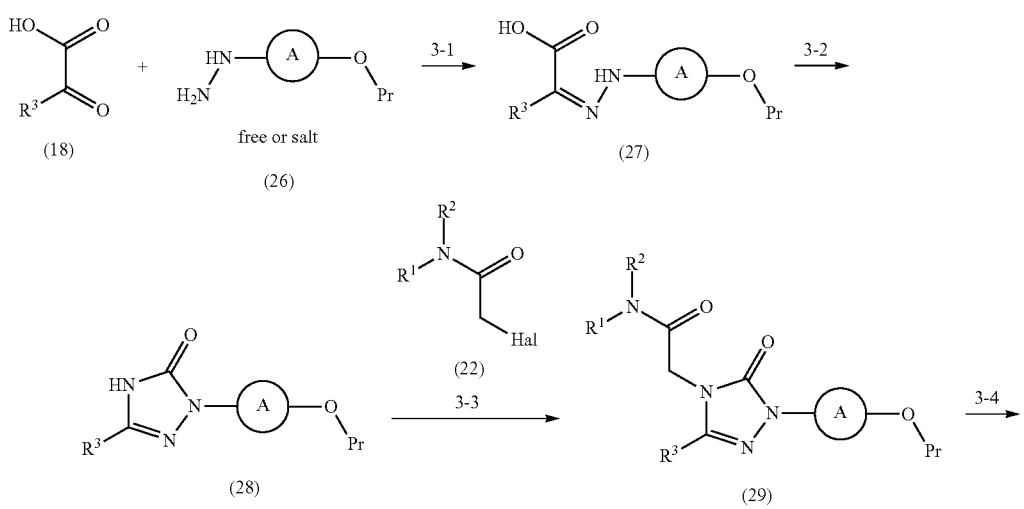

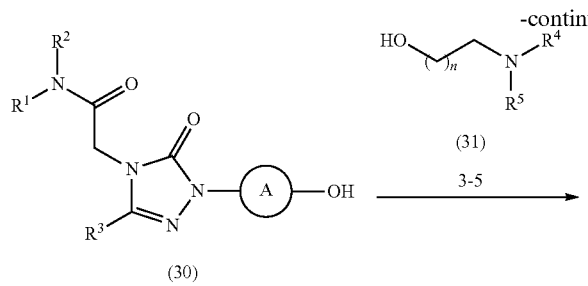
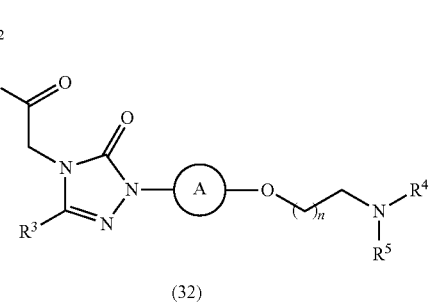

(wherein, $R^1$, $R^2$, $R^3$, $R^4$, $R^5$, A, Hal, and n are the same as above; $L^1$ and $L^2$ each represent the same leaving group as that defined above; and Pr represents a common protecting group described in Protective Groups in Organic Chemistry written by J. F. W. McOmie or Protective Groups in Organic Synthesis written by T. W. Greene and P. G. M. Wuts and is used for protection and deprotection).

The compound represented by Formula (29) can be prepared through imine formation with an oxygen-function hydrazine derivative (26) as in Scheme 2 (Step 3-1), a Curtius rearrangement reaction (Step 3-2), and alkylation (Step 3-3). The compound represented by Formula (30) can be prepared by deprotecting the protecting group of the compound represented by Formula (29) under appropriate conditions.

The compound represented by Formula (32) can be prepared by reacting the compound represented by Formula (30) with a compound represented by Formula (31) under Mitsunobu reaction conditions (Step 3-5). The comprehensive general view of the Mitsunobu reaction is found in Synthesis, 1981, 1-28; Chem. Asian J., 2007, 2, 1340-1355; and Chem. Pharm. Bull., 2003, 51(4), 474-476.

The compound represented by Formula (34) can be prepared by reacting the compound represented by Formula (30) with a compound represented by Formula (33) under basic conditions (Step 3-6). The reaction in Step 3-6 proceeds in a solvent such as N,N-dimethylformamide, dimethyl sulfoxide, tetrahydrofuran, acetonitrile, ethanol, isopropyl alcohol, or a mixture thereof, in the presence of an inorganic base such as potassium carbonate or cesium carbonate, or an organic base such as triethylamine or diisopropylethylamine, at a temperature of near 0° C. to near the boiling point of the solvent.

The compound represented by Formula (32) can be prepared by a reaction between the compound represented by Formula (34) and an amine compound represented by Formula (17) (Step 3-7). The reaction in Step 3-7 proceeds under the same conditions as those in Step 1-2.

The compound represented by Formula (1) can also be produced by the synthetic process shown in Scheme 4:

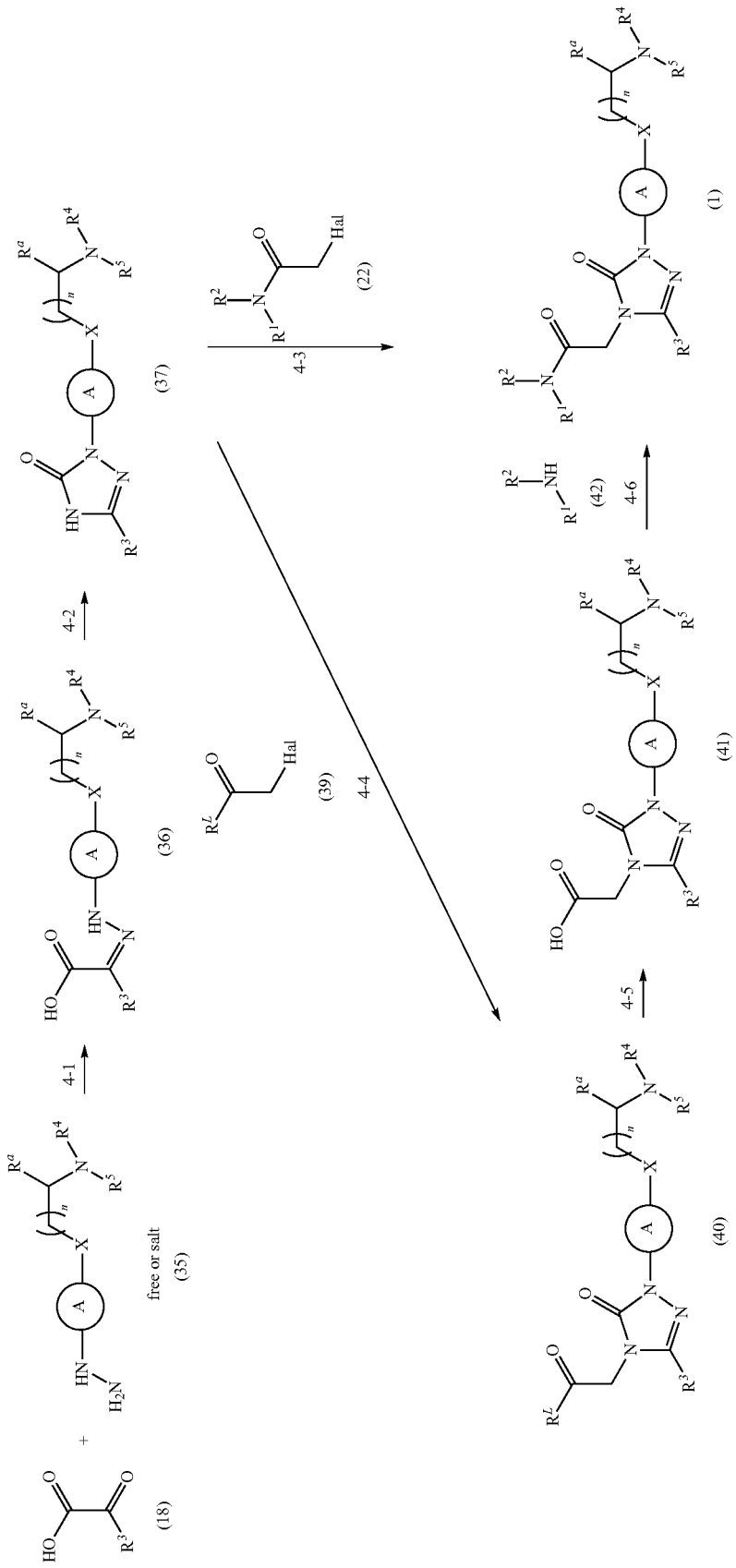

(wherein, $R^1$, $R^2$, $R^3$, $R^4$, $R^5$, A, n, X, $R^a$ and Hal are the same as above; and $R^L$ represents a common protecting group for carboxylic acid, such as $C_{1-5}$ alkoxy or benzyloxy).

The compound represented by Formula (1) can be prepared through imine formation using a hydrazine derivative (35) (Step 4-1), a Curtius rearrangement reaction (Step 4-2), and alkylation (Step 4-3) as in Scheme 2. The compound represented by Formula (1) can also be prepared through alkylation of a compound represented by Formula (37) (Step 4-4), deprotection (Step 4-5), and then amidation (Step 4-6). The reaction in Step 4-4 proceeds under the same conditions as those in Step 2-3. The deprotection in Step 4-5 can be performed under conditions described in Protective Groups in Organic Chemistry written by J. F. W. McOmie or Protective Groups in Organic Synthesis written by T. W. Greene and P. G. M. Wuts. Examples of the amidation reaction usable in Step 4-6 include a method using a dehydration-condensation agent. Examples of the dehydration-condensation agent include 1-ethyl-3-(3-dimethylaminopropyl)carbodiimide hydrochloride, dicyclohexyl carbodiimide, diphenylphosphonyl azide, and carbonyldiimidazole. In addition, an activating reagent such as 1-hydroxybenzotriazole or hydroxysuccinimide can be optionally used. Examples of the reaction solvent include dichloromethane, chloroform, 1,2-dichloroethane, N,N-dimethylformamide, tetrahydrofuran, dioxane, toluene, ethyl acetate, and mixtures thereof. The reaction in this step can be performed using a base, examples of which include organic amines, such as triethylamine and diisopropylethylamine; organic acid salts, such as sodium 2-ethylhexoate and potassium 2-ethylhexoate; and inorganic bases, such as potassium carbonate. The reaction can be performed at a temperature of –50° C. to near the boiling point of the reaction solvent.

The compound represented by Formula (18) can be produced by the synthetic process shown in Scheme 5:

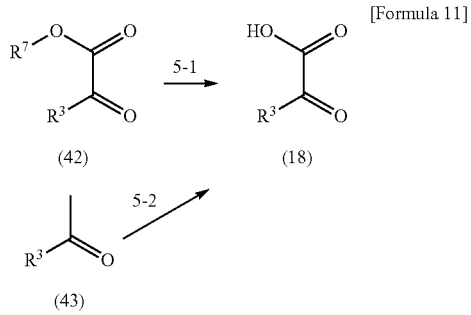

(wherein, $R^3$ is the same as above; and $R^7$ represents $C_{1-5}$ alkyl).

The compound represented by Formula (18) can be prepared through hydrolysis of a compound represented by Formula (42) (Step 5-1). The reaction in Step 5-1 proceeds in a solvent such as water, methanol, ethanol, or a mixture thereof, in the presence of a base such as sodium hydroxide, potassium hydroxide, lithium hydroxide, or barium hydroxide, at a temperature of near 0° C. to near the boiling point of the solvent.

The compound represented by Formula (18) can also be prepared through oxidation of a compound represented by Formula (43) (Step 5-2). The reaction in Step 5-2 proceeds in a solvent such as pyridine, in the presence of selenium dioxide, at a temperature of room temperature to near the boiling point of the solvent.

Among the compounds represented by Formula (22), commercially available are 2-chloro-N-methylacetamide, 2-chloro-N-ethylacetamide, 2-chloro-N-propylacetamide, N-isopropyl-2-chloroacetamide, N-butyl-2-chloroacetamide, N-(sec-butyl)-2-chloroacetamide, 2-chloro-N-isobutylacetamide, N-(tert-butyl)-2-chloroacetamide, N1-cyclopropyl-2-chloroacetamide, 2-chloro-N-(cyclopropylmethyl)acetamide, and 2-chloro-N-cyclobutylacetamide.

The hydrazine derivatives represented by Formulae (19) and (26) can be produced using a corresponding raw-material amine by the method described in, for example, JCS, Transactions, 1922, 121, 715-721; J. Am. Chem. Soc., 1953, 75, 1873-1876; or US Patent Publication No. 20050215577.

The compound represented by Formula (31) can be produced by the synthetic process shown in Scheme 6:

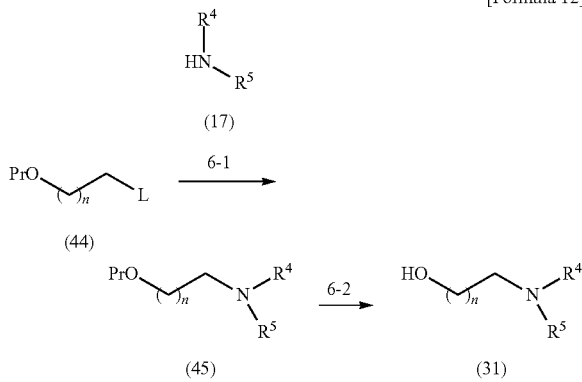

(wherein, $R^4$, $R^5$, n, Pr, and L are the same as above).

The compound represented by Formula (45) can be prepared by reacting an amine (17) with a compound represented by Formula (44) under basic conditions (Step 6-1). The reaction conditions in Step 6-1 are the same as those in Step 1-2. The compound represented by Formula (31) can be prepared by deprotection of the protecting group (Pr) of the compound represented by Formula (45) by a common procedure (Step 6-2).

Among the compounds represented by Formula (31), commercially available are, for example, 3-dimethylamino-1-propanol, 3-diethylamino-1-propanol, 3-(isopropylamino)-propan-1-ol, 3-(dibutylamino)-1-propanol, 3-piperidin-1-yl-propan-1-ol, 1-(3-hydroxypropyl)-pyrrolidine, 4-(3-hydroxypropyl)morpholine, and 1-(3-hydroxypropyl)-piperazine.

The hydrazine derivative represented by Formula (35) can be prepared by the synthetic process shown in Scheme 7:

Scheme 7

[Formula 13]

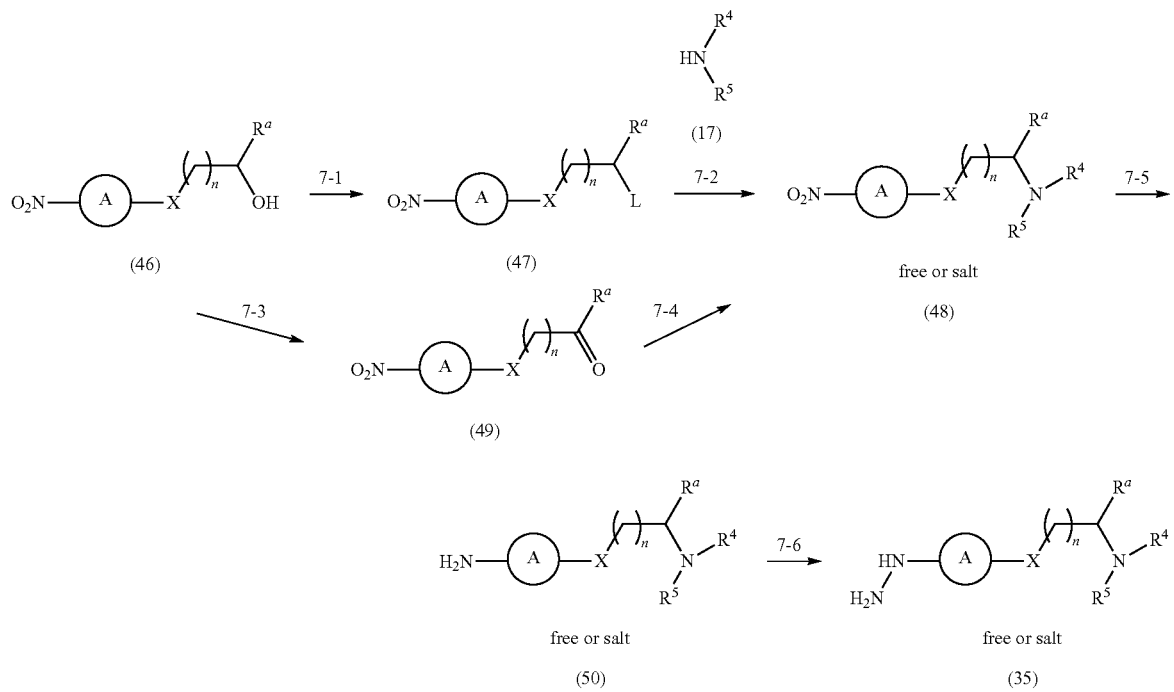

(wherein, $R^4$, $R^5$, $R^a$, X, n, and L are the same as above).

The compound represented by Formula (48) can be prepared by conversion of the hydroxy group of a compound represented by Formula (46) into a common leaving group (Step 7-1) and then reaction of the leaving group with a corresponding amine (17) (Step 7-2). The reactions in Steps 7-1 and 7-2 proceed under the same reaction conditions as those in Steps 1-1 and 1-2, respectively. The compound represented by Formula (48) can also be prepared through a common oxidation reaction to convert the hydroxy group of a compound represented by Formula (46) into carbonyl (Step 7-3) and common reductive amination with a corresponding amine (17) (Step 7-4). The reactions in Steps 7-3 and 7-4 proceed under the same reaction conditions as those in Steps 1-3 and 1-4, respectively. The compound represented by Formula (50) can be prepared by reduction of the nitro group of the compound represented by Formula (48) (Step 7-5). The comprehensive general view of the reduction in Step 7-5 is found in Comprehensive Organic Transformation, Second Edition, written by Richard C. Larock. The hydrazine derivative compound represented by Formula (35) can be prepared through diazotization of the amino group of the compound represented by Formula (50) and subsequent reduction (Step 7-6). The reaction shown by Step 7-6 is the same process as that described in JCS, Transactions, 121, 715-21 (1922); J. Am. Chem. Soc., 1953, 75, 1873-6; or US Patent Application No. 20050215577.

The compound represented by Formula (1) can also be synthesized by the synthetic process shown in Scheme 8:

Scheme 8

[Formula 14]

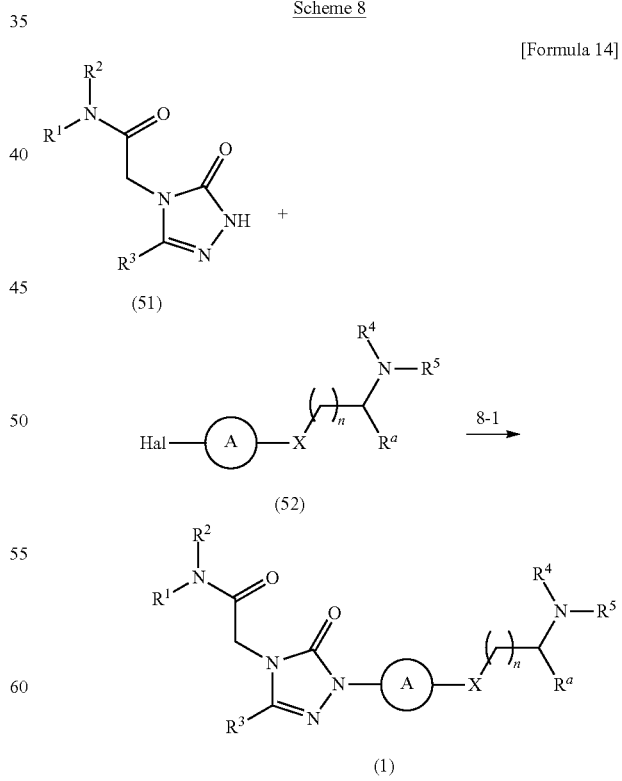

(wherein, $R^1$, $R^2$, $R^3$, $R^4$, $R^5$, $R^a$, X, n, Hal, and A are the same as above.).

The compound represented by Formula (1) can be prepared by a coupling reaction between a compound represented by Formula (51) and a compound represented by Formula (52) (Step 8-1). The reaction in Step 8-1 is performed by common Ullmann reaction or Buchwald-Hartwig amination. The comprehensive general view of the Ullmann reaction is found in Ley, S. V., Thomas, A. W., Angew. Chem. Int. Ed., 2003, 42, 5400-5449. The comprehensive general view of the Buchwald-Hartwig amination is found in A. S. Guram, R. A. Rennels, S. L. Buchwald, Angew. Chem., Int. Ed. Engl., 1995, 34, 1348; J. Louie, J. F. Hartwig, Tetrahedron Lett., 1995, 36, 3609; J. F. Hartwig, Angew. Chem. Int. Ed. Engl., 1998, 37, 2046-2067; Muci, A. R., Buchwald, S. L., Top. Curr. Chem., 2002, 219, 131; or J. P. Wolfe, H. Tomori, J. P. Sadighi, J. Yin, S. L. Buchwald, J. Org. Chem., 2000, 365, 1158-1174.

The compound represented by Formula (51) can be prepared by the synthetic process shown in Scheme 9:

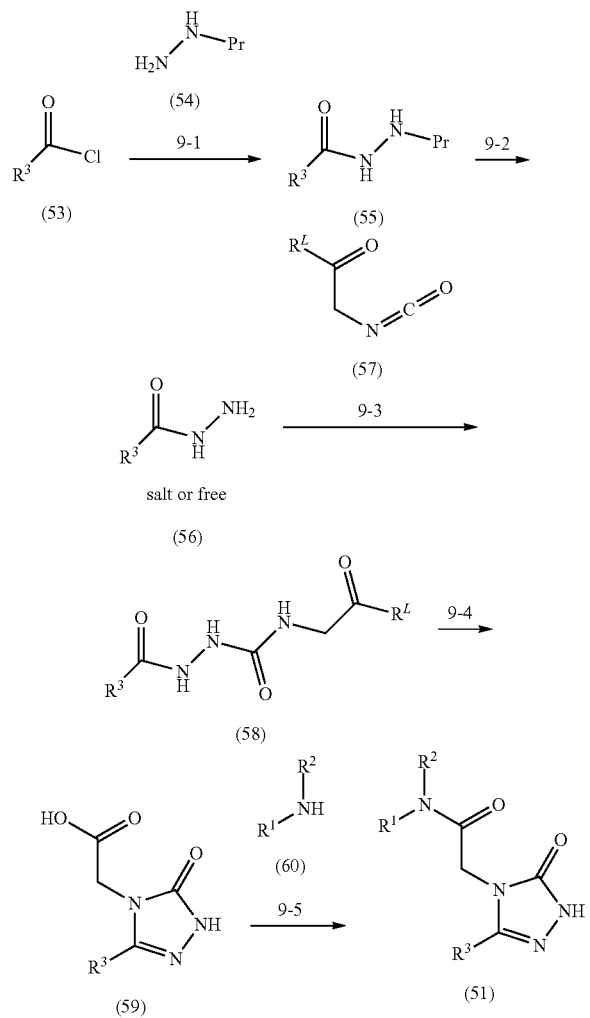

(wherein, $R^1$, $R^2$, $R^3$, $R^L$ and Pr are the same as above).

The compound represented by Formula (55) can be prepared through a reaction between an acid chloride represented by Formula (53) and a hydrazine protected by protecting group (54) (Step 9-1). The reaction in Step 9-1 proceeds in a solvent such as chloroform, toluene, tetrahydrofuran, acetonitrile, or a mixture thereof, in the presence of a base such as triethylamine or diisopropylethylamine, at a temperature of near 0° C. to near room temperature. The compound represented by Formula (56) can be prepared by a conventional deprotection of the protecting group of the compound represented by Formula (55) (Step 9-2). The reaction conditions for Step 9-2 are those for a common deprotection reaction described in Protective Groups in Organic Chemistry written by J. F. W. McOmie or Protective Groups in Organic Synthesis written by T. W. Greene and P. G. M. Wuts. The compound represented by Formula (56) may be prepared in the form of a salt of an acid, while it can be prepared in a free form by treating with a base. The compound represented by Formula (58) can be prepared by a reaction of an isocyanate derivative (57) with the compound represented by Formula (56) (Step 9-3). The reaction in Step 9-3 proceeds in a solvent such as chloroform, toluene, tetrahydrofuran, acetonitrile, or a mixture thereof at a temperature of near room temperature to near the boiling point of the solvent. The compound represented by Formula (59) can be prepared through a reaction of the compound represented by Formula (58) under basic conditions (Step 9-4). The reaction in Step 9-4 proceeds in a solvent such as water, tetrahydrofuran, 1,4-dioxane, N,N-dimethylformamide, or a mixture thereof, in the presence of an inorganic base such as sodium hydroxide, potassium hydroxide, lithium hydroxide, or barium hydroxide, at a temperature of near room temperature to near the boiling point of the solvent. The compound represented by Formula (51) can be prepared through amidation of the compound represented by Formula (59) with an amine (60) (Step 9-5). Examples of the amidation reaction usable in Step 9-5 include a method using a dehydration-condensation agent. Examples of the dehydration-condensation agent include 1-ethyl-3-(3-dimethylaminopropyl)carbodiimide hydrochloride, dicyclohexyl carbodiimide, diphenylphosphonyl azide, and carbonyldiimidazole. An activating reagent, such as 1-hydroxybenzotriazole or hydroxysuccinimide, can also be optionally used. Examples of the reaction solvent include dichloromethane, chloroform, 1,2-dichloroethane, N,N-dimethylformamide, tetrahydrofuran, dioxane, toluene, ethyl acetate, and mixtures thereof. The reaction in this step can be performed using a base, examples of which include organic amines, such as triethylamine and diisopropylethylamine; organic acid salts, such as sodium 2-ethylhexoate and potassium 2-ethylhexoate; and inorganic bases, such as potassium carbonate. The reaction can be performed at a temperature of −50° C. to near the boiling point of the reaction solvent.

Among the compounds represented by Formula (57), commercially available are methyl isocyanatoacetate, ethyl isocyanatoacetate, isopropyl isocyanatoacetate, and n-butyl isocyanatoacetate.

Among the compounds represented by Formula (52), the compounds represented by Formulae (65) and (70) can be prepared by the synthetic process shown in Scheme 10:

Scheme 10

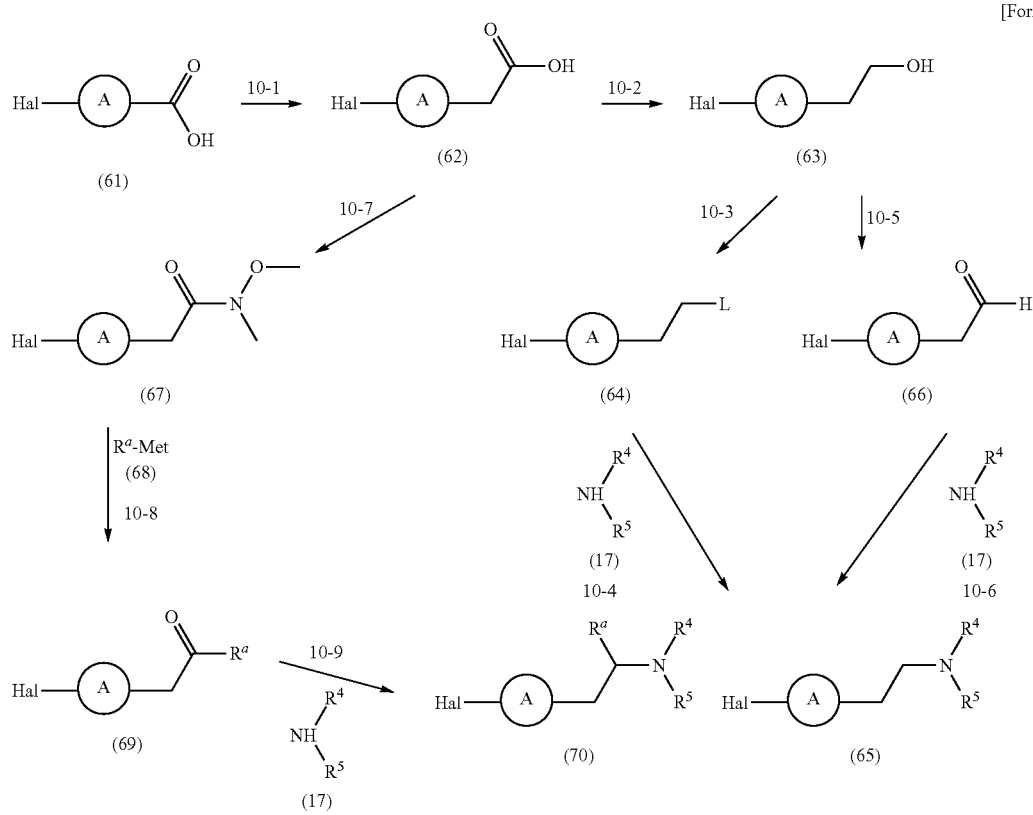

[Formula 16]

(wherein, $R^4$, $R^5$, Hal, and L are the same as above; $R^a$ represents $C_{1-5}$ alkyl; and Met represents MgBr, MgCl, or a metal such as Li).

The compound represented by Formula (62) can be prepared through Arndt-Eistert reaction of a compound represented by Formula (61) (Step 10-1). The overview of the Arndt-Eistert reaction can be found in Chem. Ber., 1927, 60, 1364. The compound represented by Formula (63) can be prepared by reduction of the compound represented by Formula (62) (Step 10-2). The reduction in Step 10-2 proceeds in a solvent such as tetrahydrofuran, 1,4-dioxane, diethyl ether, diisopropyl ether, or a mixture thereof, in the presence of a reducing agent such as a borane-THF complex or lithium aluminum hydride, at a temperature of −78° C. to near room temperature. The compound represented by Formula (65) can be prepared by conversion of the hydroxy group of the compound represented by Formula (63) into a leaving group (Step 10-3) and then reaction of the resulting compound with an amine (17) (Step 10-4). The compound represented by Formula (65) can also be prepared through oxidation of the hydroxy group of the compound represented by Formula (63) into aldehyde (Step 10-5) and subsequent reductive amination with an amine (17). Step 10-3, Step 10-4, Step 10-5, and Step 10-6 proceed under the same reaction conditions as those for Step 1-1, Step 1-2, Step 1-3, and Step 1-4, respectively. The compound represented by Formula (70) can be prepared through conversion of the compound represented by Formula (62) into a Weinreb amide (Step 10-7), conversion of the amide into a ketone (69) by a reaction with a corresponding organic metal reagent (e.g., a Grignard reagent or an organic lithium reagent) (Step 10-8), and then reductive amination with an amine (17) (Step 10-9). The reaction in Step 10-7 proceeds in the presence of N,O-dimethylhydroxylamine, under similar amidation conditions to those in Step 9-5. The reaction in Step 10-8 is a reaction of the compound (a metal reagent such as a Grignard reagent or an organic lithium reagent) represented by Formula (68) in a solvent such as tetrahydrofuran, 1,4-dioxane, diethyl ether, diisopropyl ether, or a mixture thereof at a temperature of −78° C. to near room temperature.

Among the compounds represented by Formula (14), the compound represented by Formula (74) can be prepared by the synthetic process shown in Scheme 11:

Scheme 11

[Formula 17]

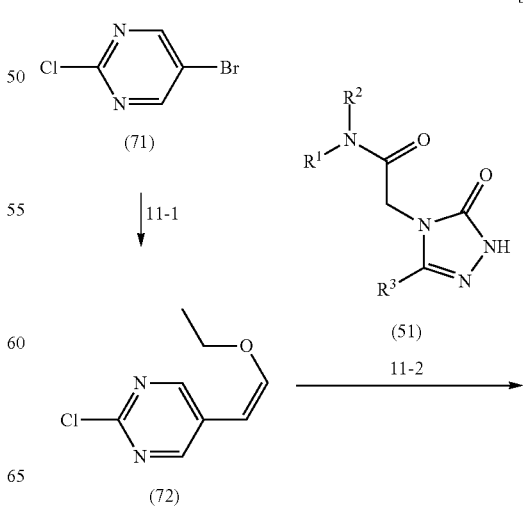

-continued

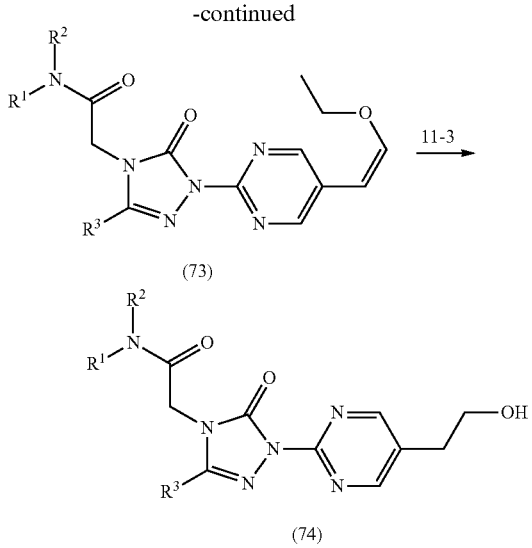

The compound represented by Formula (72) can be prepared by introducing ethoxyethylene into the compound represented by (71) by a Migita-Kosugi-Stille cross coupling reaction or a Suzuki-Miyaura cross coupling reaction (Step 11-1). The reaction in Step 11-1 is performed under the same conditions as those in the reaction in Step 2-4. The compound represented by Formula (73) can be prepared by a coupling reaction of the compound represented by Formula (73) and a compound represented by Formula (51) (Step 11-2). The reaction in Step 11-2 proceeds in a solvent such as tetrahydrofuran, 1,4-dioxane, N,N-dimethylformamide, or a mixture thereof, in the presence of an inorganic base such as sodium hydroxide, potassium hydroxide, lithium hydroxide, barium hydroxide, or cesium carbonate, at a temperature of near room temperature to near the boiling point of the solvent. The compound represented by Formula (74) can be produced by inducing the compound represented by Formula (73) into corresponding aldehyde in a solvent such as water, ethanol, isopropyl alcohol, acetonitrile, tetrahydrofuran, N,N-dimethylformamide, dimethyl sulfoxide, or a mixture thereof, in the presence of an inorganic acid such as hydrochloric acid or sulfuric acid, or an organic acid such as p-toluenesulfonic acid, methanesulfonic acid, or camphorsulfonic acid, and reacting a reducing agent with the aldehyde (see Comprehensive Organic Transformations Second Edition, 1999, John Wiley & Sons, Inc.). The reducing agent in the step can reduce an aldehyde compound into an alcohol compound, and examples thereof include lithium borohydride, sodium borohydride, calcium borohydride, zinc borohydride, lithium aluminum hydride, sodium aluminum hydride, and diisobutyl aluminum hydride.

EXAMPLES

The present invention will now be described in more detail by Reference Examples, Examples, and Test Examples, which are not intended to limit the present invention and may be modified within the scope of the present invention.

In Reference Examples and Examples, the "phase separator" in post-treatment is an ISOLUTE® Phase Separator of Biotage Inc. In purification by column chromatography, "SNAP Cartridge KP-NH" of Biotage Inc., "SNAP Cartridge HP-Sil" of Biotage Inc., or "Chromatorex® NH" of Fuji Silysia Chemical Ltd. was used. In purification by preparative thin-layer chromatography (PTLC), Silica Gel 60$F_{254}$, 20×20 cm, of Merck was used. In purification by "reverse-phase column chromatography", Waters SunFire prep C18 OBD, 5.0 µm, φ 30×50 mm was used.

The data described in Reference Examples and Examples below were obtained by measurement with the following instruments:

NMR spectrometer: JNM-ECA 600 (600 MHz, JEOL Ltd.), JNM-ECA 500 (500 MHz, JEOL Ltd.), UNITY INOVA 300 (300 MHz, Varian, Inc.), or GEMINI 2000/200 (200 MHz, Varian, Inc.), MS spectrometer: LCMS-2010EV (Shimadzu Corporation) or Platform LC (Micromass, Ltd.).

In Reference Examples and Examples, high-performance liquid chromatography-mass spectrum (LCMS) was measured under the following conditions:

Condition 1
Instrument: Platform LC (Micromass, Ltd.) and Agilent 1100 (Agilent Technologies, Inc.),
Column: SunFire C18, 2.5 µm, φ 4.6×50 mm (Waters Corporation),
Solvent: Solution A: water containing 0.1% trifluoroacetic acid, and Solution B: acetonitrile containing 0.1% trifluoroacetic acid,
Gradient: 0 min (Solution A/Solution B=90/10), 0.5 min (Solution A/Solution B=90/10), 5.5 min (Solution A/Solution B=20/80), 6.0 min (Solution A/Solution B=1/99), and 6.3 min (Solution A/Solution B=1/99),
Flow rate: 1 mL/min, Detection: 254 nm, and
Ionization: electron spray ionization (ESI);
Condition 2-1
Instrument: Agilent 2900 and Agilent 6150,
Column: Waters Acquity CSH C18, 1.7 µm, φ 2.1×50 mm,
Solvent: Solution A: water containing 0.1% formic acid, and Solution B: acetonitrile containing 0.1% formic acid,
Gradient: 0 min (Solution A/Solution B=80/20), 1.2 to 1.4 min (Solution A/Solution B=1/99), and
Flow rate: 0.8 mL/min, Detection: 254 nm;
Condition 2-2
Instrument, column, and solvent are the same as those in Condition 2-1,
Gradient and flow rate: 0.8 mL/min for 0 min (Solution A/Solution B=95/5), 1.20 min (Solution A/Solution B=50/50), and 1.0 mL/min for 1.38 min (Solution A/Solution B=3/97), and
Detection: 254 nm.

In Reference Examples and Examples, optical isomers were measured under the following conditions:
Instrument: HPLC system (Gilson, Inc.),
Solvent: n-hexane/EtOH=70/30 (v/v),
Column: CHIRALPAK AD-H, 3.0 µm, φ 4.6×250 mm, and
Flow rate: 1 mL/min.

In Reference Examples and Examples, optical rotations were measured with the following instrument:
Instrument: JASCO P-2300 Polarimeter.

In Reference Examples and Examples, compounds were named using ACD/Name (ACD/Labs 12.01, Advanced Chemistry Development Inc.).

Terms and reagent names in Examples are denoted by the following abbreviations:

Brine (saturated brine), MeOH (methanol), $MgSO_4$ (anhydrous magnesium sulfate), $K_2CO_3$ (potassium carbonate), $Na_2CO_3$ (sodium carbonate), $Na_2SO_4$ (anhydrous sodium sulfate), $NaHCO_3$ (sodium bicarbonate), NaOH (sodium hydroxide), KOH (potassium hydroxide), HCl (hydrochloric acid), IPE (diisopropyl ether), THF (tetrahydrofuran), DMF (N,N-dimethylformamide), $Et_2O$ (diethyl ether), EtOH (ethanol), NH₄OH (25 to 28% aqueous ammonia), EtOAc (ethyl acetate), CHCl₃ (chloroform), DMSO (dimethyl sulfoxide), MeCN (acetonitrile), n-Hexane (n-hexane), Et₃N (triethylamine), iPr₂NEt (diisopropylethylamine), Pd(PPh₃)₄ [tetrakistriphenylphosphine palladium(0)], HATU [O-(7-azabenzotriazol-1-yl)-N,N,N,N-tetramethyluronium hexafluorophosphate], DPPA (diphenylphosphoryl azide), BH₃.THF (borane-tetrahydrofuran complex), NaBO₃.4H₂O (sodium perborate tetrahydrate), 9-BBN (9-borabicyclo [3.3.1]nonane), IBX (1-hydroxy-1,2-benziodoxol-3(1H)-one 1-oxide), BBr₃ (boron tribromide), MsCl (methanesulfonyl chloride), TMSCH₂N₂ (TMS diazomethane), n-BuLi (n-butyllithium), EDC.HCl [1-ethyl-3-(3-dimethylaminopropyl)carbodiimide hydrochloride], HOBt.H₂O (1-hydroxybenzotriazole monohydrate), Cs₂CO₃ (cesium carbonate), PdCl₂(PPh₃)₂ [bis(triphenylphosphine)palladium(II) dichloride], and NaBH₄ (sodium borohydride).

Synthesis of Reference Example P-A1

(3-Chlorophenyl)(oxo)acetic acid

[Formula 18]

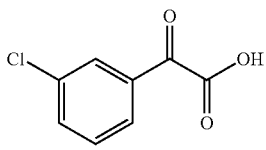

An aqueous 2 mol/L NaOH solution (24 mL) was added to a solution of ethyl (3-chlorophenyl)(oxo)acetate (2.00 g) in THF/MeOH (1:1) (48 mL) in an ice bath, followed by stirring at room temperature overnight. The solvent was distilled off under reduced pressure, and an aqueous 3 mol/L HCl solution was added thereto in an ice bath. The precipitated solid was collected by filtration to yield the title compound (2.00 g, colorless solid).

MS (ESI neg.) m/z: 183 ([M–H]⁻).

The following compound was synthesized as in Reference Example P-A1.

Reference Example P-A2

(3-Chloro-4-fluorophenyl)(oxo)acetic acid

Synthesis from ethyl (3-chloro-4-fluorophenyl)(oxo)acetate

[Formula 19]

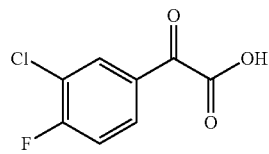

Synthesis of Reference Example P-A3

(3-Methoxyphenyl)(oxo)acetic acid

[Formula 20]

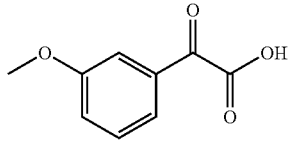

A pyridine solution (27 mL) containing 1-(3-methoxyphenyl)ethanone (8.00 g) and selenium dioxide (8.87 g) was stirred at an outside temperature of 100° C. for 4 hours. After cooling, the reaction solution was filtered through Celite (registered trademark). The filtrate was diluted with EtOAc, followed by washing with an aqueous 1 mol/L HCl solution and brine and drying with Na₂SO₄. The solvent was distilled off under reduced pressure to yield the title compound (10.6 g, gray solid).

MS (ESI neg.) m/z: 179 ([M–H]⁻).

The following compounds were synthesized as in Reference Example P-A3.

Reference Example P-A4

(4-Fluoro-3-methoxyphenyl)(oxo)acetic acid

Synthesis from 1-(4-fluoro-3-methoxyphenyl)ethanone

[Formula 21]

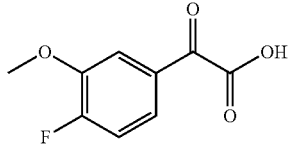

MS (ESI neg.) m/z: 197 ([M–H]⁻).

Reference Example P-A5

(3-Cyanophenyl)(oxo)acetic acid

Synthesis from 3-acetylbenzonitrile

[Formula 22]

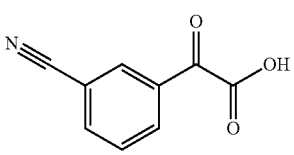

Reference Example P-A6

(3-Fluorophenyl)(oxo)acetic acid

Synthesis from 1-(3-fluorophenyl)ethanone

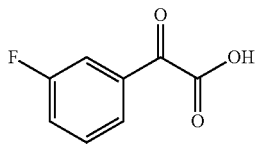

[Formula 23]

Reference Example P-A7

(2-Bromo-5-chlorophenyl)(oxo)acetic acid

Synthesis from 1-(2-bromo-5-chlorophenyl)ethanone

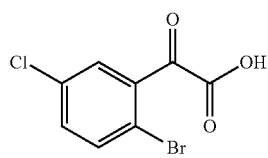

[Formula 24]

MS (ESI neg.) m/z: 261 ([M−H]−).

Synthesis of Reference Example P-B1

2-Chloro-5-hydrazinylpyridine hydrochloride

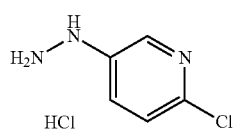

[Formula 25]

An aqueous sodium nitrite solution (3.49 g of sodium nitrite in 12.5 mL of water) was dropwise added to a solution of 6-chloropyridine-3-amine (5.00 g) in hydrochloric acid (77.8 mL) over 10 minutes (such that the temperature does not exceed −20° C.) under dry ice-acetone cooling (−20 to −40° C.), followed by stirring under the same conditions for 1 hour. A solution of tin chloride (14.8 g) in hydrochloric acid (25 mL) was dropwise added thereto over 15 minutes, followed by stirring at approximately 0° C. for 2 hours. The precipitated solid was collected by filtration (washed with water and n-hexane) and was vacuum dried at 40° C. to yield the title compound (9.45 g, brown solid).

MS (ESI pos.) m/z: 144 ([M+H]+).

Synthesis of Reference Example P-C1

2-[2-(4-Bromophenyl)hydrazinylidene]3-chlorophenyl)ethanoic acid

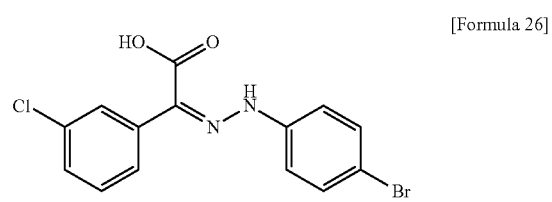 [SMILES: O=C(O)/C(=N\Nc1ccc(Br)cc1)c1cccc(Cl)c1]

[Formula 26]

Concentrated hydrochloric acid (0.4 mL) and a suspension of the compound (3.00 g) prepared in Reference Example P-A1 in water (10 mL) were sequentially added to a suspension of (4-bromophenyl)hydrazine hydrochloride (3.58 g) in water (15 mL) at room temperature, followed by stirring for 3 days. The solid in the system was collected by filtration to yield the title compound (5.14 g, yellow solid).

MS (ESI neg.) m/z: 351, 353 ([M−H]−).

The following compounds were synthesized as in Reference Example P-C1.

Reference Example P-C2

2-[2-(4-Bromophenyl)hydrazinylidene](3-cyanophenyl)ethanoic acid (Synthesis from Reference Example P-A5 and (4-bromophenyl)hydrazine hydrochloride)

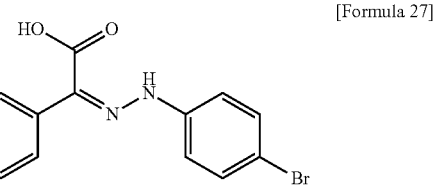

[Formula 27]

MS (ESI neg.) m/z: 342, 344 ([M−H]−).

Reference Example P-C3

2-(3-Chlorophenyl) [2-(4-methoxyphenyl)hydrazinylidene]ethanoic acid (Synthesis from Reference Example P-A1 and (4-methoxyphenyl)hydrazine hydrochloride)

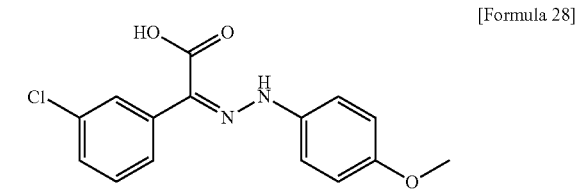 [SMILES: COc1ccc(N/N=C(\C(=O)O)c2cccc(Cl)c2)cc1]

[Formula 28]

MS (ESI neg.) m/z: 303 ([M−H]−).

Reference Example P-C4

2-[2-(5-Bromopyridin-2-yl)hydrazinylidene]3-chlorophenyl)ethanoic acid (Synthesis from Reference Example P-A1 and 5-bromo-2-hydrazinylpyridine)

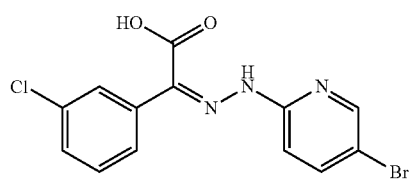

[Formula 29]

MS (ESI pos.) m/z: 354, 356 ([M+H]$^+$).

Reference Example P-C5

2-(3-Chlorophenyl) [2-(6-chloropyridin-3-yl)hydrazinylidene]ethanoic acid (Synthesis from Reference Example P-A1 and Reference Example P-B1)

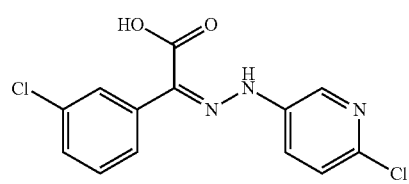

[Formula 30]

MS (ESI pos.) m/z: 310 ([M+H]$^+$).

Reference Example P-C6

2-[2-(4-Bromophenyl)hydrazinylidene](3-methoxyphenyl)ethanoic acid (Synthesis from Reference Example P-A3 and (4-bromophenyl)hydrazine hydrochloride)

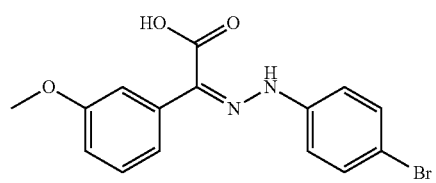

[Formula 31]

Reference Example P-C7

2-[2-(4-Bromophenyl)hydrazinylidene](4-fluoro-3-methoxyphenyl)ethanoic acid (Synthesis from Reference Example P-A4 and (4-bromophenyl)hydrazine hydrochloride)

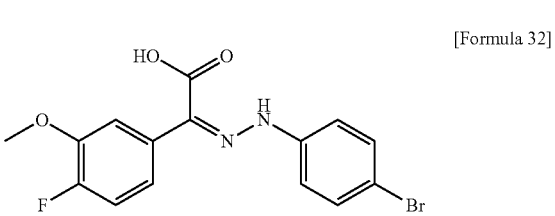 [SMILES: COc1cc(/C(=N/Nc2ccc(Br)cc2)C(=O)O)ccc1F]

[Formula 32]

MS (ESI neg.) m/z: 365, 367 ([M−H]$^-$).

Reference Example P-C8

2-[2-(5-Bromopyridin-2-yl)hydrazinylidene](4-fluoro-3-methoxyphenyl)ethanoic acid (Synthesis from Reference Example P-A4 and 5-bromo-2-hydrazinylpyridine)

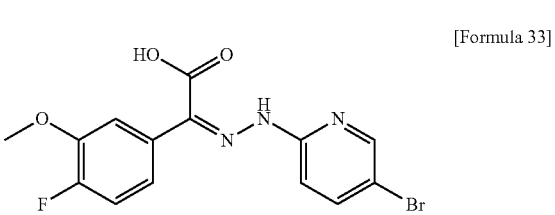 [SMILES: COc1cc(/C(=N/Nc2ccc(Br)cn2)C(=O)O)ccc1F]

[Formula 33]

MS (ESI pos.) m/z: 368, 370 ([M+H]$^+$).

Reference Example P-C9

2-[2-(4-Bromophenyl)hydrazinylidene](3-chloro-4-fluorophenyl)ethanoic acid (Synthesis from Reference Example P-A2 and (4-bromophenyl)hydrazine hydrochloride)

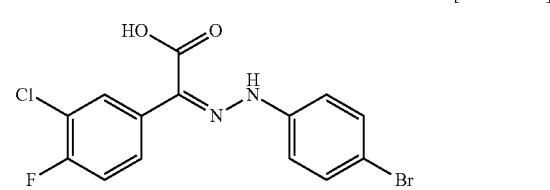

[Formula 34]

Reference Example P-C10

2-[2-(5-Bromopyridin-2-yl)hydrazinylidene](3-chloro-4-fluorophenyl)ethanoic acid (Synthesis from Reference Example P-A2 and 5-bromo-2-hydrazinylpyridine)

[Formula 35]

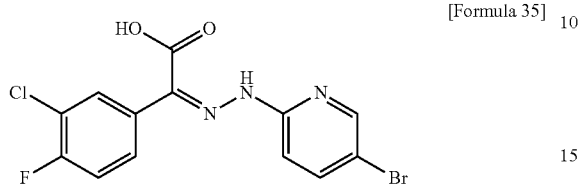

Reference Example P-C11

2-[2-(5-Bromopyridin-2-yl)hydrazinylidene](3-methoxyphenyl)ethanoic acid (Synthesis from Reference Example P-A3 and 5-bromo-2-hydrazinylpyridine)

[Formula 36]

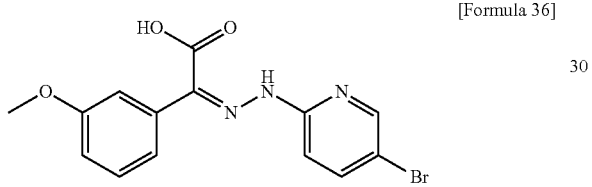

MS (ESI pos.) m/z: 350, 352 ([M+H]$^+$).

Synthesis of Reference Example P-D1

2-(4-Bromophenyl)-5-(3-chlorophenyl)-2,4-dihydro-3H-1,2,4-triazol-3-one

[Formula 37]

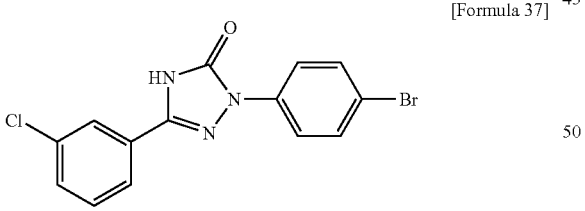

Et$_3$N (2.1 mL) was added to a suspension of the compound (5.14 g) prepared in Reference Example P-C1 in toluene (100 mL) under a nitrogen atmosphere, followed by stirring at room temperature to give a solution. DPPA (3.1 mL) was added thereto, and the mixture was gradually heated with stirring, followed by reflux for 8 hours. After cooling, an aqueous 10% KOH solution (120 mL) was added to the reaction solution, followed by stirring at room temperature for a while. The organic layer was removed, and concentrated hydrochloric acid was added to the aqueous layer in an ice bath. The precipitated solid was collected by filtration to yield the title compound (4.92 g, colorless solid).

MS (ESI neg.) m/z: 348, 350 ([M−H]$^−$).

The following compounds were synthesized as in Reference Example P-D1.

Reference Example P-D2

3-[1-(4-Bromophenyl)-5-oxo-4,5-dihydro-1H-1,2,4-triazol-3-yl]benzonitrile (Synthesis from Reference Example P-C2)

[Formula 38]

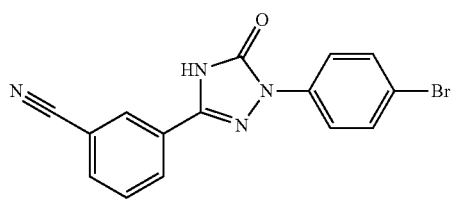

MS (ESI neg.) m/z: 339, 341 ([M−H]$^−$).

Reference Example P-D3

5-(3-Chlorophenyl)-2-(4-methoxyphenyl)-2,4-dihydro-3H-1,2,4-triazol-3-one (Synthesis from Reference Example P-C3)

[Formula 39]

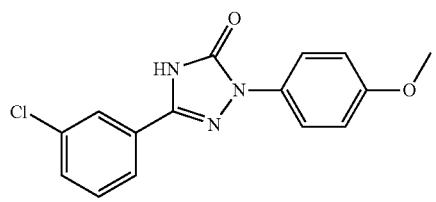

MS (ESI pos.) m/z: 324 ([M+Na]$^+$).

Reference Example P-D4

2-(5-Bromopyridin-2-yl)-5-(3-chlorophenyl)-2,4-dihydro-3H-1,2,4-triazol-3-one (Synthesis from Reference Example P-C4)

[Formula 40]

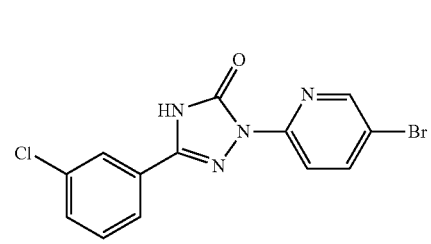

MS (ESI pos.) m/z: 351, 353 ([M+H]$^+$).

Reference Example P-D5

5-(3-Chlorophenyl)-2-(6-chloropyridin-3-yl)-2,4-dihydro-3H-1,2,4-triazol-3-one (Synthesis from Reference Example P-C5)

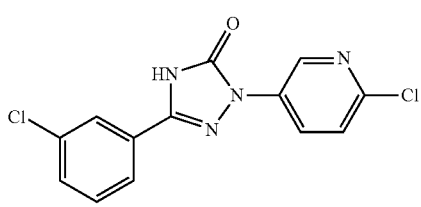

[Formula 41]

MS (ESI pos.) m/z: 307 ([M+H]$^+$).

Reference Example P-D6

2-(4-Bromophenyl)-5-(3-methoxyphenyl)-2,4-dihydro-3H-1,2,4-triazol-3-one (Synthesis from Reference Example P-C6)

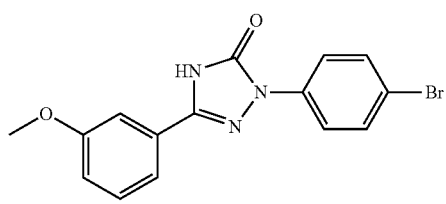

[Formula 42]

MS (ESI pos.) m/z: 346, 348 ([M+H]$^+$).

Reference Example P-D7

2-(4-Bromophenyl)-5-(4-fluoro-3-methoxyphenyl)-2,4-dihydro-3H-1,2,4-triazol-3-one (Synthesis from Reference Example P-C7)

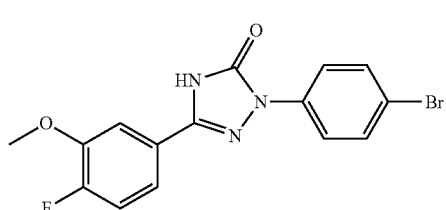

[Formula 43]

MS (ESI neg.) m/z: 362, 364 ([M−H]$^−$).

Reference Example P-D8

2-(5-Bromopyridin-2-yl)-5-(4-fluoro-3-methoxyphenyl)-2,4-dihydro-3H-1,2,4-triazol-3-one (Synthesis from Reference Example P-C8)

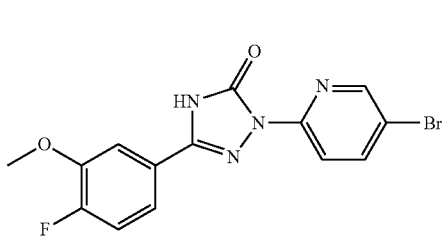

[Formula 44]

MS (ESI pos.) m/z: 365, 367 ([M+H]$^+$).

Reference Example P-D9

2-(4-Bromophenyl)-5-(3-chloro-4-fluorophenyl)-2,4-dihydro-3H-1,2,4-triazol-3-one (Synthesis from Reference Example P-C9)

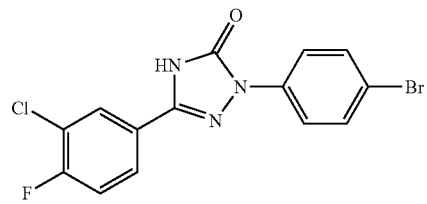

[Formula 45]

MS (ESI neg.) m/z: 366, 368 ([M−H]$^−$).

Reference Example P-D10

2-(5-Bromopyridin-2-yl)-5-(3-chloro-4-fluorophenyl)-2,4-dihydro-3H-1,2,4-triazol-3-one (Synthesis from Reference Example P-C10)

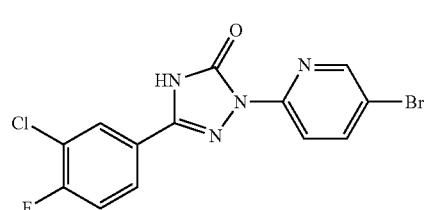

[Formula 46]

MS (ESI pos.) m/z: 369, 371 ([M+H]$^+$).

Reference Example P-D11

2-(5-Bromopyridin-2-yl)-5-(3-methoxyphenyl)-2,4-dihydro-3H-1,2,4-triazol-3-one (Synthesis from Reference Example P-C11)

[Formula 47]

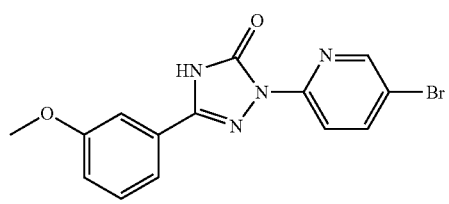

MS (ESI pos.) m/z: 347 ([M+H]$^+$).

Synthesis of Reference Example P-E1

2-[1-(4-Bromophenyl)-3-(3-chlorophenyl)-5-oxo-1,5-dihydro-4H-1,2,4-triazol-4-yl]-N-(propan-2-yl)acetamide

[Formula 48]

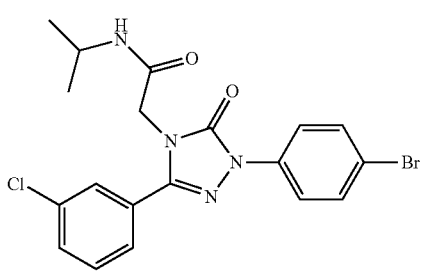

$K_2CO_3$ (3.87 g) and 2-bromo-N-(propan-2-yl)acetamide (3.78 g) were added to a suspension of the compound (4.92 g) prepared in Reference Example P-D1 in DMF (90 mL), followed by stirring at an outside temperature of 90° C. for 1.5 hours. After cooling, water (200 mL) was added thereto. The precipitated solid was collected by filtration to yield title compound (5.40 g, colorless solid).

MS (ESI pos.) m/z: 449, 451 ([M+H]$^+$).

The following compounds were synthesized as in Reference Example P-E1.

Reference Example P-E2

2-[1-(4-Bromophenyl)-3-(3-cyanophenyl)-5-oxo-1,5-dihydro-4H-1,2,4-triazol-4-yl]-N-(propan-2-yl)acetamide (Synthesis from Reference Example P-D2 and 2-bromo-N-(propan-2-yl)acetamide)

[Formula 49]

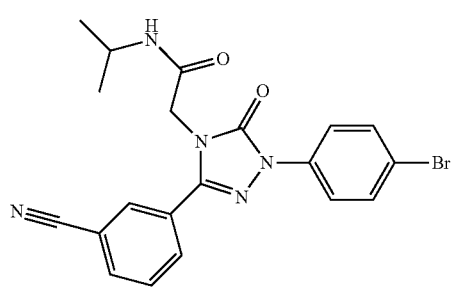

MS (ESI pos.) m/z: 462, 464 ([M+Na]$^+$).

Reference Example P-E3

2-[3-(3-Chlorophenyl)-1-(4-methoxyphenyl)-5-oxo-1,5-dihydro-4H-1,2,4-triazol-4-yl]-N-(propan-2-yl)acetamide (Synthesis from Reference Example P-D3 and 2-bromo-N-(propan-2-yl)acetamide)

[Formula 50]

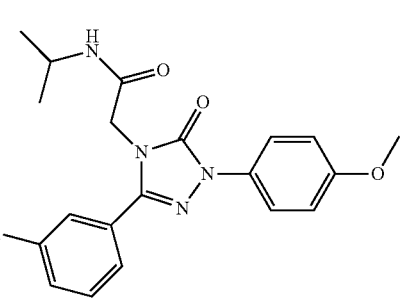

MS (ESI pos.) m/z: 401 ([M+H]$^+$).

Reference Example P-E4

2-[1-(5-Bromopyridin-2-yl)-3-(3-chlorophenyl)-5-oxo-1,5-dihydro-4H-1,2,4-triazol-4-yl]-N-(propan-2-yl)acetamide (Synthesis from Reference Example P-D4 and 2-bromo-N-(propan-2-yl)acetamide)

[Formula 51]

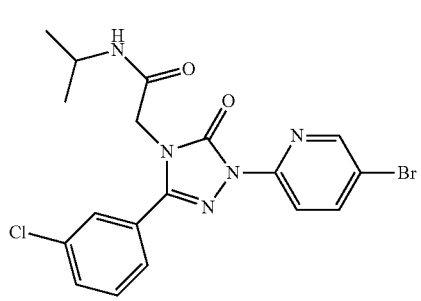

MS (ESI pos.) m/z: 450, 452 ([M+H]$^+$).

Reference Example P-E5

2-[3-(3-Chlorophenyl)-1-(6-chloropyridin-3-yl)-5-oxo-1,5-dihydro-4H-1,2,4-triazol-4-yl]-N-(propan-2-yl)acetamide (Synthesis from Reference Example P-D5 and 2-bromo-N-(propan-2-yl)acetamide)

[Formula 52]

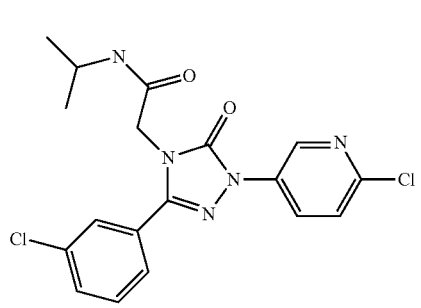

MS (ESI pos.) m/z: 406 ([M+H]$^+$).

Reference Example P-E6

2-[1-(4-Bromophenyl)-3-(3-methoxyphenyl)-5-oxo-1,5-dihydro-4H-1,2,4-triazol-4-yl]-N-(propan-2-yl)acetamide (Synthesis from Reference Example P-D6 and 2-bromo-N-(propan-2-yl)acetamide)

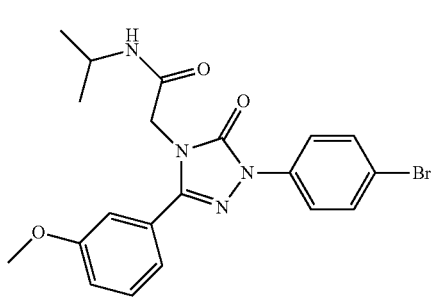

[Formula 53]

MS (ESI pos.) m/z: 445, 447 ([M+H]$^+$).

Reference Example P-E7

2-[1-(4-Bromophenyl)-3-(4-fluoro-3-methoxyphenyl)-5-oxo-1,5-dihydro-4H-1,2,4-triazol-4-yl]-N-(propan-2-yl)acetamide (Synthesis from Reference Example P-D7 and 2-bromo-N-(propan-2-yl)acetamide)

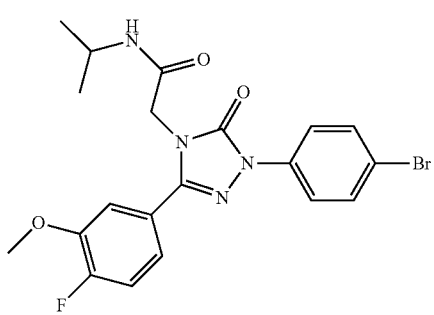

[Formula 54]

MS (ESI pos.) m/z: 463, 465 ([M+H]$^+$).

Reference Example P-E8

2-[1-(5-Bromopyridin-2-yl)-3-(4-fluoro-3-methoxyphenyl)-5-oxo-1,5-dihydro-4H-1,2,4-triazol-4-yl]-N-(propan-2-yl)acetamide (Synthesis from Reference Example P-D8 and 2-bromo-N-(propan-2-yl)acetamide)

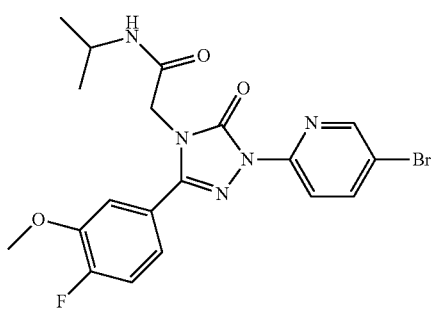

[Formula 55]

MS (ESI pos.) m/z: 464, 466 ([M+H]$^+$).

Reference Example P-E9

2-[1-(4-Bromophenyl)-3-(3-chloro-4-fluorophenyl)-5-oxo-1,5-dihydro-4H-1,2,4-triazol-4-yl]-N-(propan-2-yl)acetamide (Synthesis from Reference Example P-D9 and 2-bromo-N-(propan-2-yl)acetamide)

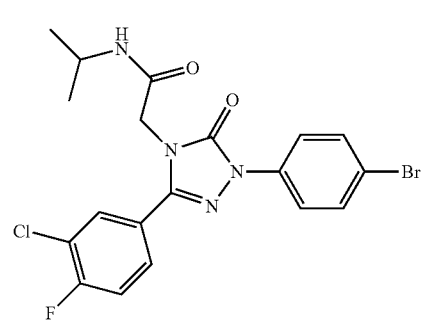

[Formula 56]

MS (ESI pos.) m/z: 467, 469 ([M+H]$^+$).

Reference Example P-E10

2-[1-(5-Bromopyridin-2-yl)-3-(3-chloro-4-fluorophenyl)-5-oxo-1,5-dihydro-4H-1,2,4-triazol-4-yl]-N-(propan-2-yl)acetamide (Synthesis from Reference Example P-D10 and 2-bromo-N-(propan-2-yl)acetamide)

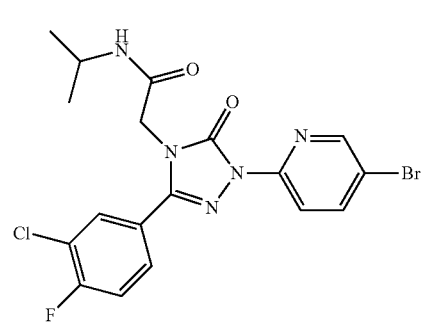

[Formula 57]

MS (ESI pos.) m/z: 468, 470 ([M+H]$^+$).

Reference Example P-E11

2-[1-(5-Bromopyridin-2-yl)-3-(3-chlorophenyl)-5-oxo-1,5-dihydro-4H-1,2,4-triazol-4-yl]-N-tert-butylacetamide (Synthesis from Reference Example P-D4 and 2-bromo-N-tert-butylacetamide)

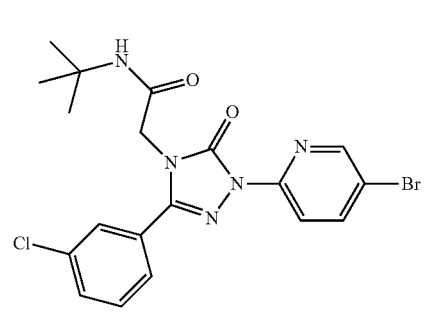

[Formula 58]

MS (ESI pos.) m/z: 464, 466 ([M+H]$^+$).

Reference Example P-E12

2-[1-(5-Bromopyridin-2-yl)-3-(3-methoxyphenyl)-5-oxo-1,5-dihydro-4H-1,2,4-triazol-4-yl]-N-tert-butylacetamide (Synthesis from Reference Example P-D11 and 2-bromo-N-tert-butylacetamide)

[Formula 59]

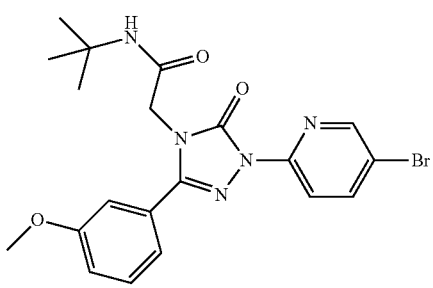

MS (ESI pos.) m/z: 460, 462 ([M+H]$^+$).

Synthesis of Reference Example P-F1

2-[3-(3-Chlorophenyl)-1-(4-ethenylphenyl)-5-oxo-1,5-dihydro-4H-1,2,4-triazol-4-yl]-N-(propan-2-yl)acetamide

[Formula 60]

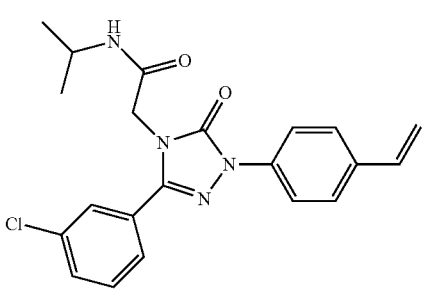

A mixture of the compound (500 mg) prepared in Reference Example P-E1, tributyl(vinyl) tin (0.25 mL), Pd(PPh$_3$)$_4$ (128 mg), and toluene (10 mL) was stirred under a nitrogen atmosphere at an outside temperature of 100° C. for 5 hours. After cooling, the solvent was distilled off under reduced pressure, and the residue was purified by column chromatography (SNAP Cartridge KP-NH: 28 g, mobile phase: n-hexane/CHCl$_3$=75/25 to 0/100 (v/v)). The resulting crude product was washed with a solvent mixture of EtOAc and n-hexane (EtOAc/n-hexane=1/6 (v/v)) with stirring to yield the title compound (222 mg; colorless solid).

MS (ESI pos.) m/z: 397 ([M+H]$^+$).

The following compounds were synthesized as in Reference Example P-F1.

Reference Example P-F2

2-[3-(3-Cyanophenyl)-1-(4-ethenylphenyl)-5-oxo-1,5-dihydro-4H-1,2,4-triazol-4-yl]-N-(propan-2-yl)acetamide (Synthesis from Reference Example P-E2)

[Formula 61]

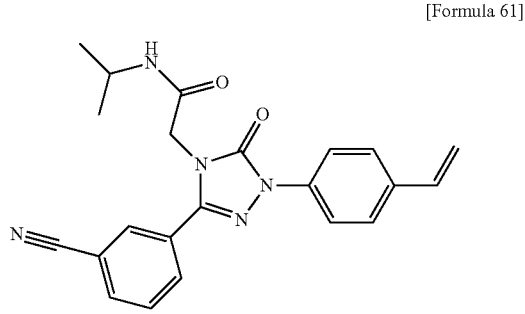 [SMILES: C=Cc1ccc(-n2nc(-c3cccc(C#N)c3)n(CC(=O)NC(C)C)c2=O)cc1]

MS (ESI pos.) m/z: 388 ([M+H]$^+$).

Reference Example P-F3

2-[3-(3-Chlorophenyl)-1-(5-ethenylpyridin-2-yl)-5-oxo-1,5-dihydro-4H-1,2,4-triazol-4-yl]-N-(propan-2-yl)acetamide (Synthesis from Reference Example P-E4)

[Formula 62]

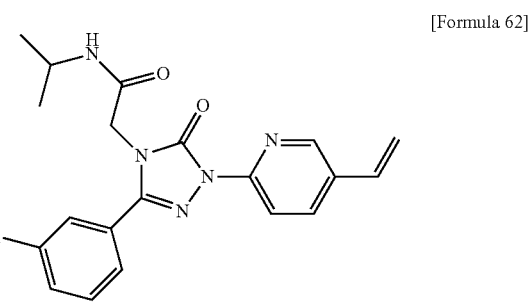

MS (ESI pos.) m/z: 398 ([M+H]$^+$).

Reference Example P-F4

2-[3-(3-Chlorophenyl)-1-(6-ethenylpyridin-3-yl)-5-oxo-1,5-dihydro-4H-1,2,4-triazol-4-yl]-N-(propan-2-yl)acetamide (Synthesis from Reference Example P-E5)

[Formula 63]

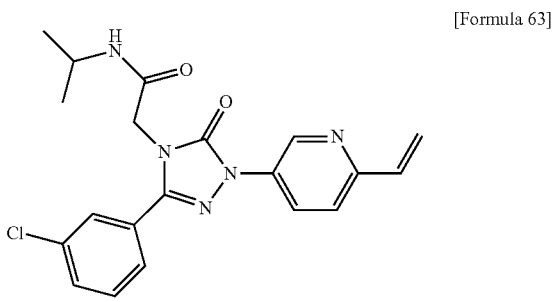 [SMILES: C=Cc1ccc(-n2nc(-c3cccc(Cl)c3)n(CC(=O)NC(C)C)c2=O)cn1]

MS (ESI pos.) m/z: 398 ([M+H]$^+$).

Reference Example P-F5

2-[1-(4-Ethenylphenyl)-3-(3-methoxyphenyl)-5-oxo-1,5-dihydro-4H-1,2,4-triazol-4-yl]-N-(propan-2-yl)acetamide (Synthesis from Reference Example P-E6)

[Formula 64]

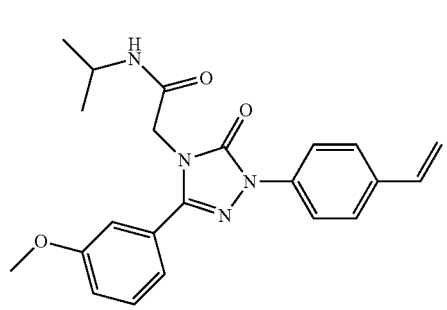

MS (ESI pos.) m/z: 393 ([M+H]$^+$).

Reference Example P-F6

2-[1-(4-Ethenylphenyl)-3-(4-fluoro-3-methoxyphenyl)-5-oxo-1,5-dihydro-4H-1,2,4-triazol-4-yl]-N-(propan-2-yl)acetamide (Synthesis from Reference Example P-E7)

[Formula 65]

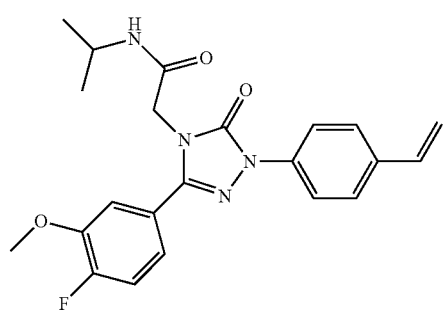

MS (ESI pos.) m/z: 411 ([M+H]$^+$).

Reference Example P-F7

2-[1-(5-Ethenylpyridin-2-yl)-3-(4-fluoro-3-methoxyphenyl)-5-oxo-1,5-dihydro-4H-1,2,4-triazol-4-yl]-N-(propan-2-yl)acetamide (Synthesis from Reference Example P-E8)

[Formula 66]

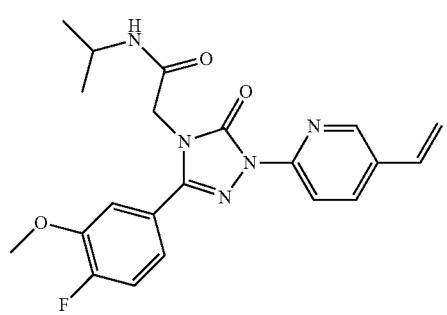

MS (ESI pos.) m/z: 412 ([M+H]$^+$).

Reference Example P-F8

2-[3-(3-Chloro-4-fluorophenyl)-1-(4-ethenylphenyl)-5-oxo-1,5-dihydro-4H-1,2,4-triazol-4-yl]-N-(propan-2-yl)acetamide (Synthesis from Reference Example P-E9)

[Formula 67]

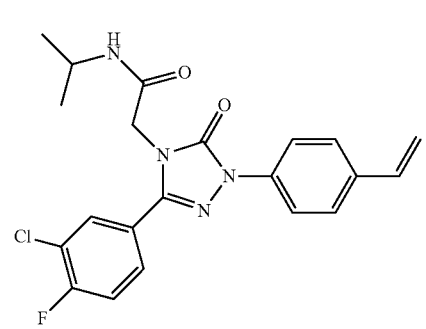

MS (ESI pos.) m/z: 415 ([M+H]$^+$).

Reference Example P-F9

2-[3-(3-Chloro-4-fluorophenyl)-1-(5-ethenylpyridin-2-yl)-5-oxo-1,5-dihydro-4H-1,2,4-triazol-4-yl]-N-(propan-2-yl)acetamide (Synthesis from Reference Example P-E10)

[Formula 68]

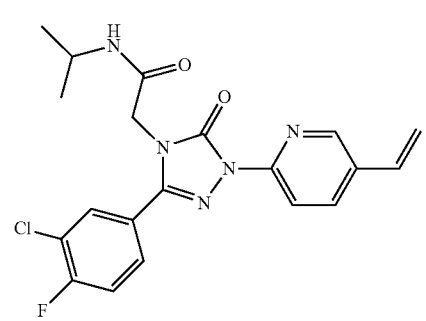

MS (ESI pos.) m/z: 416 ([M+H]$^+$).

Reference Example P-F10

N-Tert-Butyl-2-[3-(3-chlorophenyl)-1-(5-ethenylpyridin-2-yl)-5-oxo-1,5-dihydro-4H-1,2,4-triazol-4-yl]acetamide (Synthesis from Reference Example P-E11)

[Formula 69]

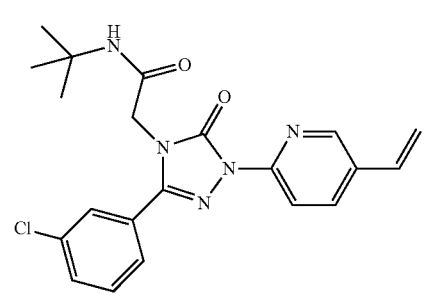

MS (ESI pos.) m/z: 412 ([M+H]$^+$).

Reference Example P-F11

N-Tert-Butyl-2-[1-(5-ethenylpyridin-2-yl)-3-(3-methoxyphenyl)-5-oxo-1,5-dihydro-4H-1,2,4-triazol-4-yl]acetamide (Synthesis from Reference Example P-E12)

[Formula 70]

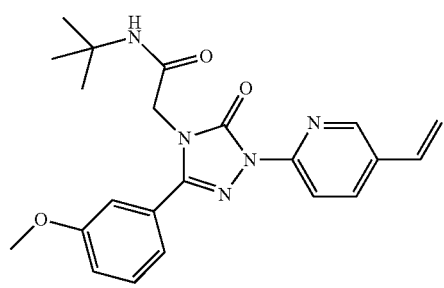

MS (ESI pos.) m/z: 408 ([M+H]⁺).

Synthesis of Reference Example P-G1

2-{3-(3-Chlorophenyl)-1-[4-(2-hydroxyethyl)phenyl]-5-oxo-1,5-dihydro-4H-1,2,4-triazol-4-yl}-N-(propan-2-yl)acetamide

[Formula 71]

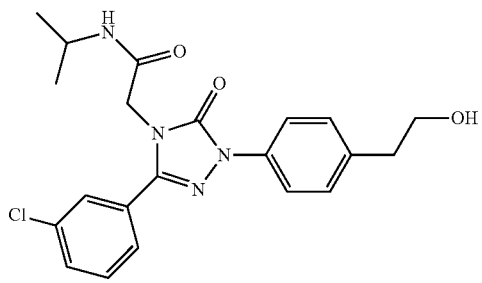

A 1.09 mol/L solution of BH₃.THF in THF (0.77 mL) was dropwise added to a solution of the compound (222 mg) prepared in Reference Example P-F1 in THF (6.0 mL) under a nitrogen atmosphere in an ice bath, followed by stirring for 1 hour. Subsequently, water (9 mL) and NaBO₃.4H₂O (387 mg) were added thereto, followed by stirring at room temperature overnight. The solvent was distilled off under reduced pressure, and water was added to the residue, followed by extraction with CHCl₃. The organic layer was filtered through a phase separator, and the solvent was distilled off under reduced pressure. The residue was washed with a solvent mixture of EtOAc and n-hexane (EtOAc/n-hexane=1/4 (v/v)) with stirring to yield the title compound (170 mg, colorless solid).

MS (ESI pos.) m/z: 415 ([M+H]⁺).

The following compounds were synthesized as in Reference Example P-G1.

Reference Example P-G2

2-{3-(3-Cyanophenyl)-1-[4-(2-hydroxyethyl)phenyl]-5-oxo-1,5-dihydro-4H-1,2,4-triazol-4-yl}-N-(propan-2-yl)acetamide (Synthesis from Reference Example P-F2)

[Formula 72]

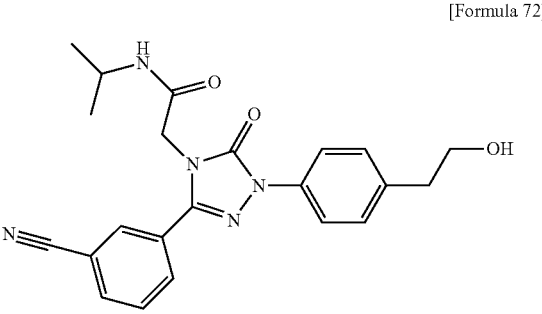 [SMILES: CC(C)NC(=O)Cn1c(-c2cccc(C#N)c2)nn(-c2ccc(CCO)cc2)c1=O]

MS (ESI pos.) m/z: 428 ([M+Na]⁺).

Reference Example P-G3

2-{3-(3-Chlorophenyl)-1-[5-(2-hydroxyethyl)pyridin-2-yl]-5-oxo-1,5-dihydro-4H-1,2,4-triazol-4-yl}-N-(propan-2-yl)acetamide (Synthesis from Reference Example P-F3)

[Formula 73]

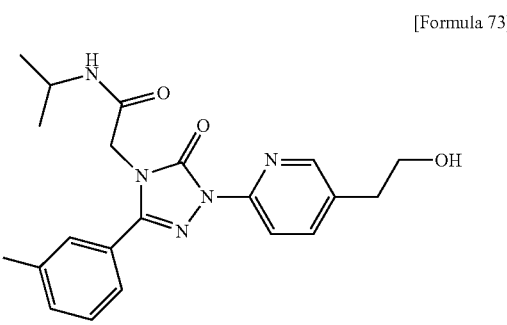

MS (ESI pos.) m/z: 416 ([M+H]⁺).

Reference Example P-G4

2-{1-[4-(2-Hydroxyethyl)phenyl]-3-(3-methoxyphenyl)-5-oxo-1,5-dihydro-4H-1,2,4-triazol-4-yl}-N-(propan-2-yl)acetamide (Synthesis from Reference Example P-F5)

[Formula 74]

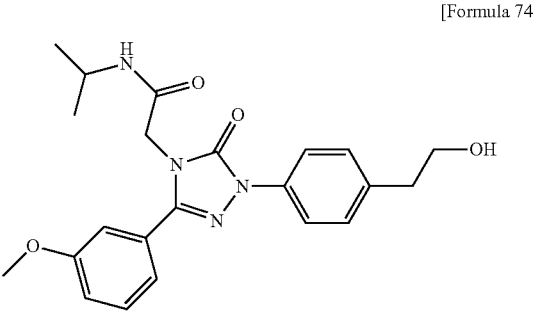 [SMILES: COc1cccc(-c2nn(-c3ccc(CCO)cc3)c(=O)n2CC(=O)NC(C)C)c1]

MS (ESI pos.) m/z: 411 ([M+H]⁺).

Reference Example P-G5

2-{3-(4-Fluoro-3-methoxyphenyl)-1-[4-(2-hydroxyethyl)phenyl]-5-oxo-1,5-dihydro-4H-1,2,4-triazol-4-yl}-N-(propan-2-yl)acetamide (Synthesis from Reference Example P-F6)

[Formula 75]

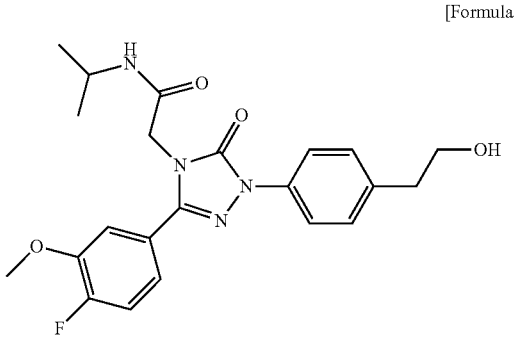

MS (ESI pos.) m/z: 429 ([M+H]$^+$).

Reference Example P-G6

2-{3-(4-Fluoro-3-methoxyphenyl)-1-[5-(2-hydroxyethyl)pyridin-2-yl]-5-oxo-1,5-dihydro-4H-1,2,4-triazol-4-yl}-N-(propan-2-yl)acetamide (Synthesis from Reference Example P-F7)

[Formula 76]

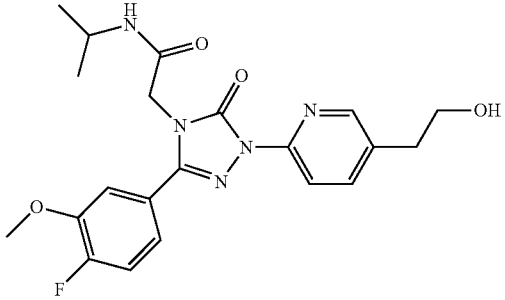

MS (ESI pos.) m/z: 430 ([M+H]$^+$).

Reference Example P-G7

2-{3-(3-Chloro-4-fluorophenyl)-1-[4-(2-hydroxyethyl)phenyl]-5-oxo-1,5-dihydro-4H-1,2,4-triazol-4-yl}-N-(propan-2-yl)acetamide (Synthesis from Reference Example P-F8)

[Formula 77]

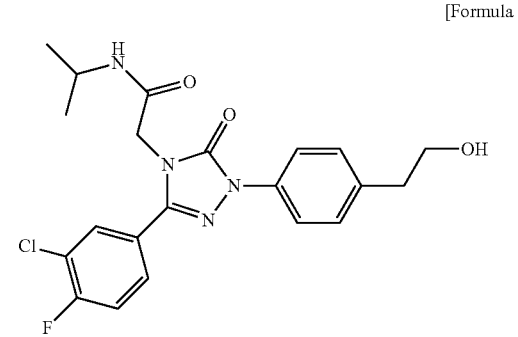

MS (ESI pos.) m/z: 433 ([M+H]$^+$).

Synthesis of Reference Example P-H1

2-{3-(3-Chlorophenyl)-1-[6-(2-hydroxyethyl)pyridin-3-yl]-5-oxo-1,5-dihydro-4H-1,2,4-triazol-4-yl}-N-(propan-2-yl)acetamide

[Formula 78]

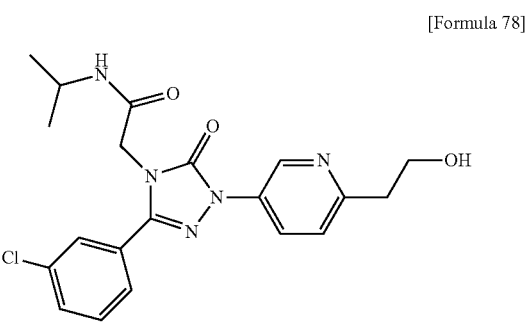 [SMILES: CC(C)NC(=O)Cn1c(-c2cccc(Cl)c2)nn(-c2ccc(CCO)nc2)c1=O]

A solution of 0.5 mol/L 9-BBN in THF (0.25 mL) was added to a solution of the compound (50 mg) prepared in Reference Example P-F4 in THF (1.5 mL) under a nitrogen atmosphere in an ice bath, followed by stirring at room temperature overnight. A solution of 0.5 mol/L 9-BBN in THF (0.5 mL) was added thereto in an ice bath, followed by stirring at room temperature for 6 hours. Furthermore, a solution of 0.5 mol/L 9-BBN in THF (0.5 mL) was added thereto in an ice bath, followed by stirring at room temperature overnight. An aqueous 2 M NaOH solution (1.0 mL) and a hydrogen peroxide solution (1.0 mL) were added thereto in an ice bath, followed by stirring at room temperature overnight. Subsequently, 80 mg of Na$_2$SO$_3$ was added thereto, and the mixture was stirred for 30 minutes. The solvent was distilled off under reduced pressure, and water was added to the residue, followed by extraction with CHCl$_3$. The organic layer was filtered through a phase separator, and the solvent was distilled off under reduced pressure. The residue was purified by column chromatography (SNAP Cartridge HP-Sil: 10 g, mobile phase: CHCl$_3$/MeOH=99/1 to 90/10 (v/v)) to yield the title compound (15.2 mg, light yellow powder).

MS (ESI pos.) m/z: 416 ([M+H]$^+$).

The following compounds were synthesized as in Reference Example P-H1.

Reference Example P-H2

2-{3-(3-Chloro-4-fluorophenyl)-1-[5-(2-hydroxyethyl)pyridin-2-yl]-5-oxo-1,5-dihydro-4H-1,2,4-triazol-4-yl}-N-(propan-2-yl)acetamide (Synthesis from Reference Example P-F9)

[Formula 79]

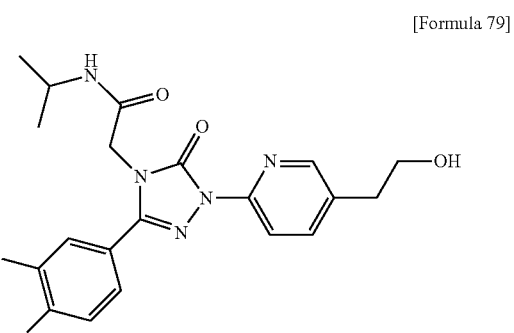

Reference Example P-H3

N-Tert-Butyl-2-{3-(3-chlorophenyl)-1-[5-(2-hydroxyethyl)pyridin-2-yl]-5-oxo-1,5-dihydro-4H-1,2,4-triazol-4-yl}acetamide (Synthesis from Reference Example P-F10)

[Formula 80]

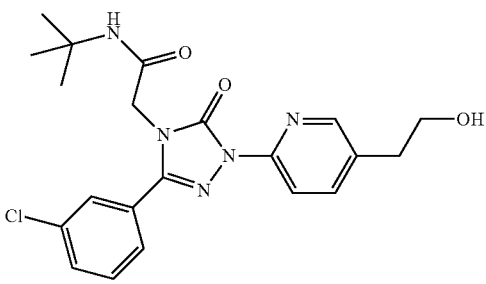

MS (ESI pos.) m/z: 430 ([M+H]$^+$).

Reference Example P-H4

N-Tert-Butyl-2-{1-[5-(2-hydroxyethyl)pyridin-2-yl]-3-(3-methoxyphenyl)-5-oxo-1,5-dihydro-4H-1,2,4-triazol-4-yl}acetamide (Synthesis from Reference Example P-F11)

[Formula 81]

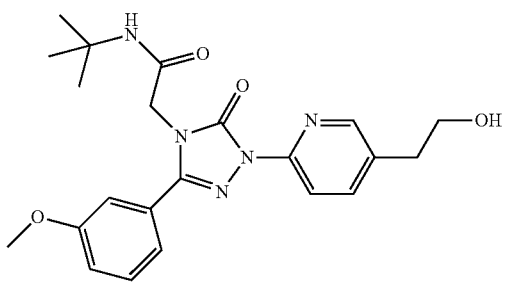

MS (ESI pos.) m/z: 426 ([M+H]$^+$).

Synthesis of Reference Example P-I1

2-(4-{3-(3-Chlorophenyl)-5-oxo-4-[2-oxo-2-(propan-2-ylamino)ethyl]-4,5-dihydro-1H-1,2,4-triazol-1-yl}phenyl)ethyl methanesulfonate

[Formula 82]

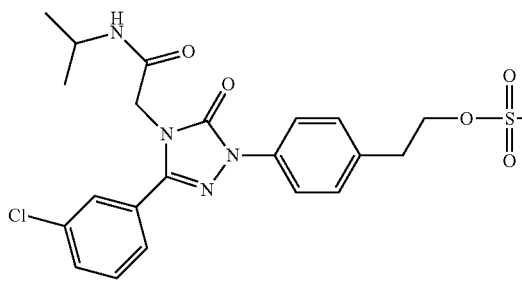

Et$_3$N (0.09 mL) and MsCl (0.04 mL) were added to a suspension of the compound (170 mg) prepared in Reference Example P-G1 in CHCl$_3$ (5.0 mL) in an ice bath, followed by stirring at room temperature overnight. Water was added to the reaction solution in an ice bath, followed by extraction with CHCl$_3$. The organic layer was filtered through a phase separator, and the solvent was distilled off under reduced pressure. The residue was purified by column chromatography (SNAP Cartridge HP-Sil: 10 g, mobile phase: CHCl$_3$/MeOH=99/1 to 94/6 (v/v)) to yield the title compound (100 mg, colorless solid).

MS (ESI pos.) m/z: 493 ([M+H]$^+$).

The following compounds were synthesized as in Reference Example P-I1.

Reference Example P-I2

2-(4-{3-(3-Cyanophenyl)-5-oxo-4-[2-oxo-2-(propan-2-ylamino)ethyl]-4,5-dihydro-1H-1,2,4-triazol-1-yl}phenyl)ethyl methanesulfonate (Synthesis from Reference Example P-G2)

[Formula 83]

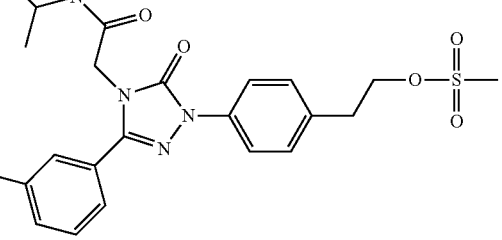

MS (ESI pos.) m/z: 506 ([M+Na]$^+$).

Reference Example P-I3

2-(6-{3-(3-Chlorophenyl)-5-oxo-4-[2-oxo-2-(propan-2-ylamino)ethyl]-4,5-dihydro-1H-1,2,4-triazol-1-yl}pyridin-3-yl)ethyl methanesulfonate (Synthesis from Reference Example P-G3)

[Formula 84]

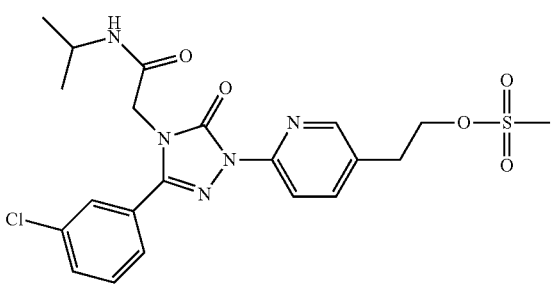

MS (ESI pos.) m/z: 494 ([M+H]$^+$).

Reference Example P-I4

2-(5-{3-(3-Chlorophenyl)-5-oxo-4-[2-oxo-2-(propan-2-ylamino)ethyl]-4,5-dihydro-1H-1,2,4-triazol-1-yl}pyridin-2-yl)ethyl methanesulfonate (Synthesis from Reference Example P-H1)

[Formula 85]

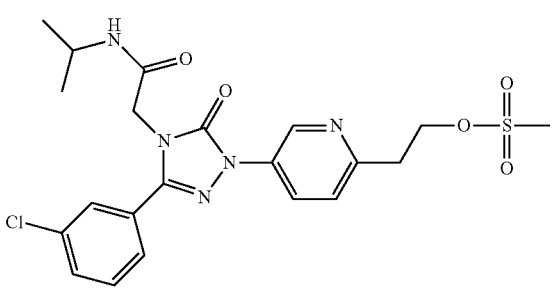

MS (ESI pos.) m/z: 494 ([M+H]$^+$).

Reference Example P-I5

2-(4-{3-(3-Methoxyphenyl)-5-oxo-4-[2-oxo-2-(propan-2-ylamino)ethyl]-4,5-dihydro-1H-1,2,4-triazol-1-yl}phenyl)ethyl methanesulfonate (Synthesis from Reference Example P-G4)

[Formula 86]

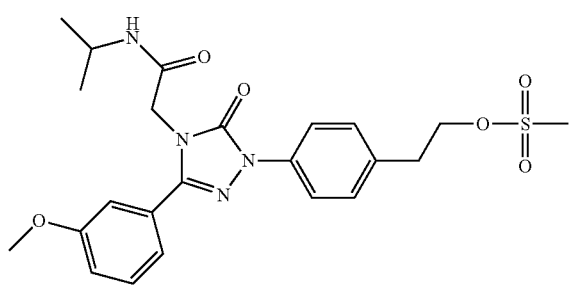

MS (ESI pos.) m/z: 489 ([M+H]$^+$).

Reference Example P-I6

2-(4-{3-(4-Fluoro-3-methoxyphenyl)-5-oxo-4-[2-oxo-2-(propan-2-ylamino)ethyl]-4,5-dihydro-1H-1,2,4-triazol-1-yl}phenyl)ethyl methanesulfonate (Synthesis from Reference Example P-G5)

[Formula 87]

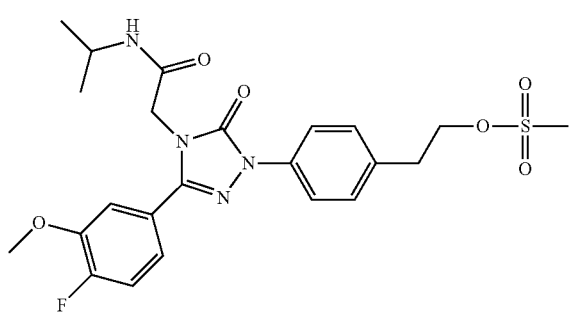

MS (ESI pos.) m/z: 507 ([M+H]$^+$).

Reference Example P-I7

2-(6-{3-(4-Fluoro-3-methoxyphenyl)-5-oxo-4-[2-oxo-2-(propan-2-ylamino)ethyl]-4,5-dihydro-1H-1,2,4-triazol-1-yl}pyridin-3-yl)ethyl methanesulfonate (Synthesis from Reference Example P-G6)

[Formula 88]

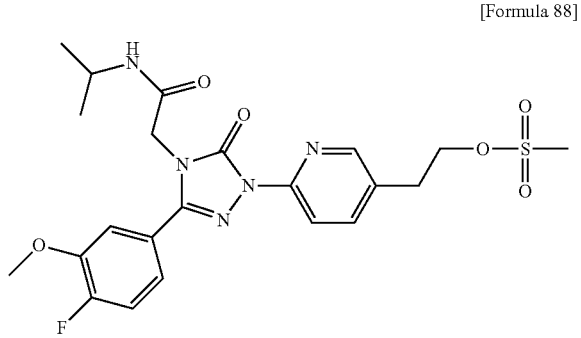

MS (ESI pos.) m/z: 508 ([M+H]$^+$).

Reference Example P-I8

2-(4-{3-(3-Chloro-4-fluorophenyl)-5-oxo-4-[2-oxo-2-(propan-2-ylamino)ethyl]-4,5-dihydro-1H-1,2,4-triazol-1-yl}phenyl)ethyl methanesulfonate (Synthesis from Reference Example P-G7)

[Formula 89]

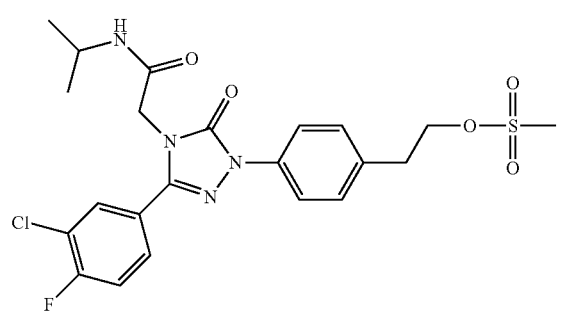

MS (ESI pos.) m/z: 511 ([M+H]$^+$).

Reference Example P-I9

2-(6-{3-(3-Chloro-4-fluorophenyl)-5-oxo-4-[2-oxo-2-(propan-2-ylamino)ethyl]-4,5-dihydro-1H-1,2,4-triazol-1-yl}pyridin-3-yl)ethyl methanesulfonate (Synthesis from Reference Example P-H2)

[Formula 90]

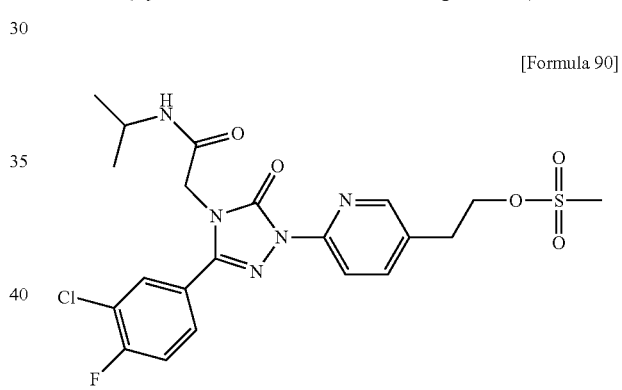

MS (ESI pos.) m/z: 512 ([M+H]$^+$).

Reference Example P-I10

2-(6-{4-[2-(Tert-Butylamino)-2-oxoethyl]-3-(3-chlorophenyl)-5-oxo-4,5-dihydro-1H-1,2,4-triazol-1-yl}pyridin-3-yl)ethyl methanesulfonate (Synthesis from Reference Example P-H3)

[Formula 91]

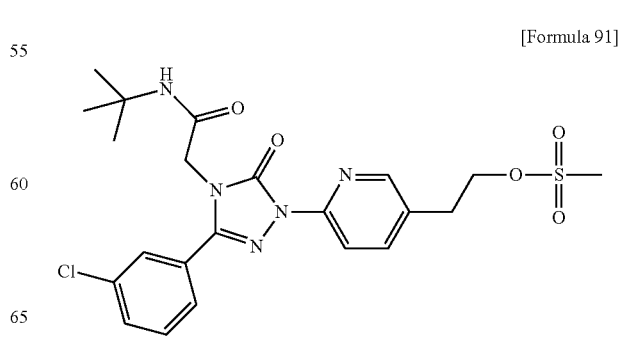

MS (ESI pos.) m/z: 508 ([M+H]$^+$).

Reference Example P-I11

2-(6-{4-[2-(Tert-Butylamino)-2-oxoethyl]-3-(3-methoxyphenyl)-5-oxo-4,5-dihydro-1H-1,2,4-triazol-1-yl}pyridin-3-yl)ethyl methanesulfonate (Synthesis from Reference Example P-H4)

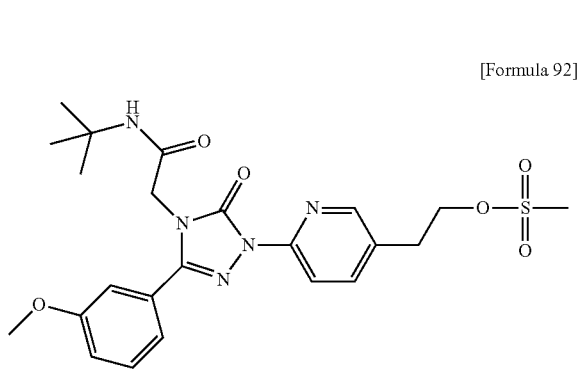

[Formula 92]

MS (ESI pos.) m/z: 504 ([M+H]+).

Synthesis of Reference Example P-J1

2-{3-(3-Chlorophenyl)-5-oxo-1-[4-(2-oxoethyl)phenyl]-1,5-dihydro-4H-1,2,4-triazol-4-yl}-N-(propan-2-yl)acetamide

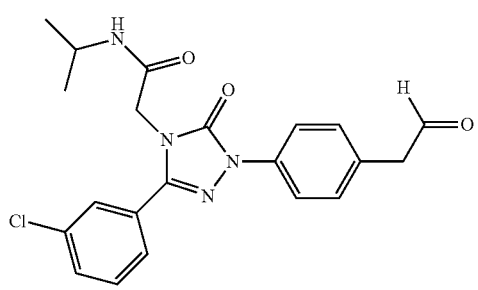

[Formula 93]

The compound (300 mg) prepared in Reference Example P-G1 was added to a solution of IBX (243 mg) in DMSO (5 mL), followed by stirring at room temperature for 4 hours. The mixture was diluted with EtOAc, and a saturated NaHCO$_3$ solution was added thereto, followed by extraction with EtOAc. The organic layer was washed with water and saturated brine and was then dried over Na$_2$SO$_4$. The desiccant was removed by filtration. The solvent was distilled off under reduced pressure to yield the title compound (360 mg, colorless solid).

MS (ESI pos.) m/z: 413 ([M+H]+).

Synthesis of Reference Example P-K1

2-[3-(3-Chlorophenyl)-1-(4-hydroxyphenyl)-5-oxo-1,5-dihydro-4H-1,2,4-triazol-4-yl]-N-(propan-2-yl)acetamide

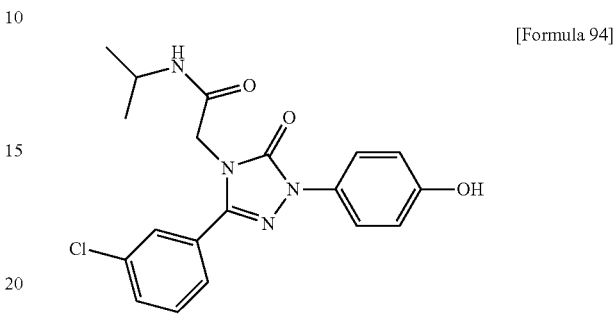

[Formula 94]

Under a nitrogen atmosphere, a solution of 1 mol/L BBr$_3$ in n-hexane (1.8 mL) was gradually added to a suspension of the compound (286 mg) prepared in Reference Example P-E3 in CHCl$_3$ (3 mL) in an ice bath, followed by stirring at room temperature overnight. A saturated aqueous NaHCO$_3$ solution was gradually added thereto in a salt-ice bath. IPE (containing 10% EtOAc) was added to the mixture, followed by stirring at room temperature for 1 hour. The precipitated solid was collected by filtration to yield the title compound (254 mg, colorless solid).

MS (ESI pos.) m/z: 409 ([M+Na]+).

Synthesis of Reference Example P-L1

2-(4-Nitrophenyl)ethyl methanesulfonate

[Formula 95]

O$_2$N—⟨phenyl⟩—CH$_2$CH$_2$—OMs

Under a nitrogen atmosphere, MsCl (13.9 mL) was dropwise added to a suspension of 2-(4-nitrophenyl)ethanol (25.0 g) and Et$_3$N (31.3 mL) in CHCl$_3$ (including amylene, 625 mL) over 10 minutes under ice cooling, followed by stirring at room temperature for 2 hours. A saturated aqueous NaHCO$_3$ solution was added to the reaction solution, and the aqueous layer was extracted with CHCl$_3$. The combined organic layer was dried over MgSO$_4$, and then the desiccant was removed by filtration. The filtrate was concentrated under reduced pressure to yield the title compound (41.8 g, light yellow solid).

$^1$H-NMR (600 MHz, CDCl$_3$)δ(ppm); 2.95 (3H, s), 3.18 (2H, t, J=6.4 Hz), 4.47 (2H, t, J=6.6 Hz), 7.39-7.45 (2H, m), 8.17-8.23 (2H, m).

Synthesis of Reference Example P-L2

4-[2-(4-Nitrophenyl)ethyl]morpholine

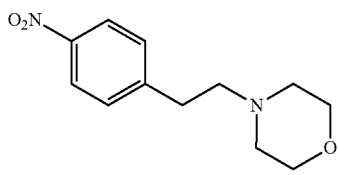

[Formula 96]

A suspension of the compound (41.8 g) prepared in Reference Example P-L1, morpholine (24.8 g), potassium iodide (23.6 g), and N,N-diisopropylethylamine (36.8 g) in MeCN (712 mL) was heated with stirring under a nitrogen atmosphere at 80° C. for 3.5 hours and then at 100° C. for 6 hours. After cooling, EtOAc and water were added to the reaction solution, and then were separated between EtOAc and water. The aqueous layer was extracted with EtOAc. The combined organic layer was washed with brine and dried over MgSO$_4$, and the desiccant was removed by filtration. The filtrate was concentrated under reduced pressure to give a crude product, which was purified by silica gel column chromatography (Chromatorex NH, mobile phase: EtOAc/n-hexane=1/9 to 1/1 (v/v)) to yield the title compound (30.9 g, orange oily compound).

MS (ESI pos.) m/z: 237 ([M+H]$^+$).

Synthesis of Reference Example P-L3

4-[2-(Morpholin-4-yl)ethyl]aniline

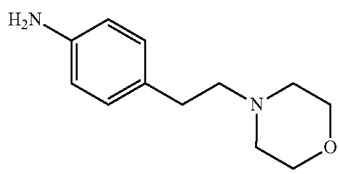

[Formula 97]

A solution of the compound (30.0 g) prepared in Reference Example P-L2 and tin chloride (96.3 g) in hydrochloric acid (100 mL) was heated under reflux for 1 hour. After cooling, the reaction solution was stirred at room temperature for 1 hour. CHCl$_3$ was added thereto, and the mixture was neutralized with a saturated aqueous NaHCO$_3$ solution. The solution was filtered through Celite (registered trademark). The filtrate was separated into two layers, and the aqueous layer was extracted with CHCl$_3$. The insoluble matter separated by Celite (registered trademark) filtration was stirred in a mixture of the aqueous layers obtained by the separation and an organic layer at room temperature for 4 hours. The insoluble matter was removed by filtration, and the filtrate was separated into two layers. The aqueous layer was extracted with CHCl$_3$, and the combined organic layer was dried over MgSO$_4$. The desiccant was removed by filtration, and the filtrate was concentrated under reduced pressure. The residue was dissolved in IPE (100 mL) by heating with stirring. The solution was cooled to room temperature with stirring, followed by stirring under ice cooling for 1 hour. The precipitated solid was collected by filtration (washed with IPE) to yield the title compound (24.6 g, orange solid).

MS (ESI pos.) m/z: 207 ([M+H]$^+$).

Synthesis of Reference Example P-L4

4-[2-(4-Hydrazinylphenyl)ethyl]morpholine

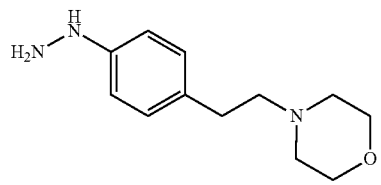

[Formula 98]

An aqueous sodium nitrite (7.53 g) solution (dissolved in 105 mL of water) was dropwise added to a solution of the compound (15.0 g) prepared in Reference Example P-L3 in hydrochloric acid (150 mL) over 30 minutes under dry ice-acetone cooling (−20 to 40° C.), followed by stirring under the same conditions for 1 hour and then at room temperature for about 17 hours. A solution of tin chloride (55.1 g) in hydrochloric acid (105 mL) was dropwise added thereto over 15 minutes under dry ice-acetone cooling (−20 to 40° C.), followed by stirring at approximately 0° C. for 2 hours. Chloroform was added to the reaction solution, and the mixture was neutralized with a saturated aqueous NaHCO$_3$ solution, followed by separation into two layers. The aqueous layer was extracted with chloroform. The combined organic layer was dried over MgSO$_4$, and the desiccant was removed by filtration. The filtrate was concentrated under reduced pressure. The residue was purified by silica gel column chromatography (Silica gel 60, mobile phase: CHCl$_3$/MeOH/NH$_4$OH=99/1/0.1 to 95/5/0.5 (v/v/v)) to yield the title compound (3.88 g, orange oily compound).

MS (ESI pos.) m/z: 222 ([M+H]$^+$).

Synthesis of Reference Example P-M1

2-(3-Fluorophenyl)(2-{4-[2-(morpholin-4-yl)ethyl]phenyl}hydrazinylidene)ethanoic acid

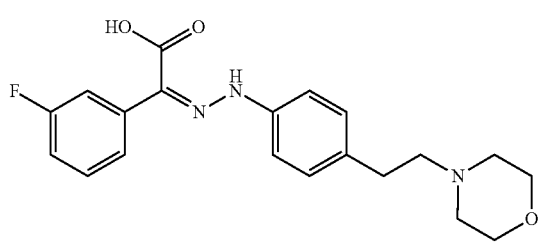

[Formula 99]

A solution of 2 mol/L HCl in IPA (0.669 mL) was added to a suspension of the compound (150 mg) prepared in Reference Example P-A6 and the compound (197 mg) prepared in Reference Example P-L4 in EtOH (3.0 mL), followed by stirring at room temperature for 16 hours. The reaction solution was concentrated under reduced pressure to yield the title compound (453 mg, brown solid)

MS (ESI pos.) m/z: 372 ([M+H]$^+$).

The following compounds were synthesized as in Reference Example P-M1.

Reference Example P-M2

2-(3-Chlorophenyl)(2-{4-[2-(morpholin-4-yl)ethyl]phenyl}hydrazinylidene)ethanoic acid (Synthesis from Reference Example P-A1 and Reference Example P-L4)

[Formula 100]

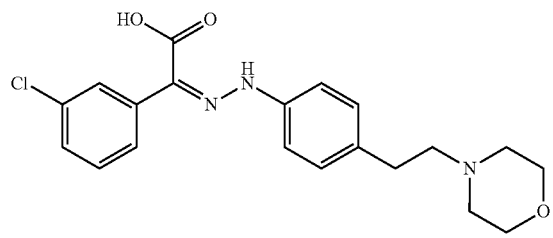

MS (ESI pos.) m/z: 388 ([M+H]+).

Reference Example P-M3

2-(2-Bromo-5-chlorophenyl)(2-{4-[2-(morpholin-4-yl)ethyl]phenyl}hydrazinylidene)ethanoic acid (Synthesis from Reference Example P-A7 and Reference Example P-L4)

[Formula 101]

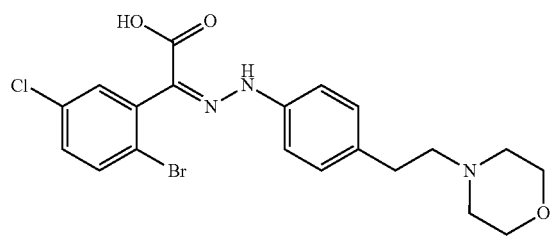

MS (ESI pos.) m/z: 467 ([M+H]+).

Synthesis of Reference Example P-N1

5-(3-Fluorophenyl)-2-{4-[2-(morpholin-4-yl)ethyl]phenyl}-2,4-dihydro-3H-1,2,4-triazol-3-one

[Formula 102]

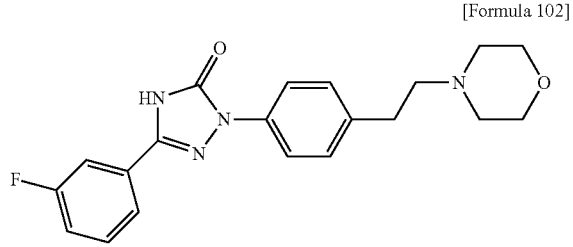 [SMILES: O=c1[nH]c(-c2cccc(F)c2)nn1-c1ccc(CCN2CCOCC2)cc1]

A solution of the compound (453 mg) prepared in Reference Example P-M1, Et₃N (0.261 mL), and DPPA (0.211 mL) in toluene (8.9 mL) was heated at 100° C. with stirring for 3 hours. After cooling, the solution was separated between CHCl₃ and a saturated aqueous NaHCO₃ solution. The aqueous layer was extracted with CHCl₃. The combined organic layer was dried over MgSO₄. The desiccant was removed by filtration, and the filtrate was concentrated under reduced pressure. The residue was purified by silica gel column chromatography (SNAP Cartridge HP-Sil: 50 g, mobile phase: CHCl₃/MeOH/NH₄OH=99/1/0.1 to 95/5/0.5 (v/v/v)) to yield the title compound (209 mg, orange solid).

MS (ESI pos.) m/z: 369 ([M+H]+).

The following compounds were synthesized as in Reference Example P-N1.

Reference Example P-N2

5-(3-Chlorophenyl)-2-{4-[2-(morpholin-4-yl)ethyl]phenyl}-2,4-dihydro-3H-1,2,4-triazol-3-one (Synthesis from Reference Example P-M2)

[Formula 103]

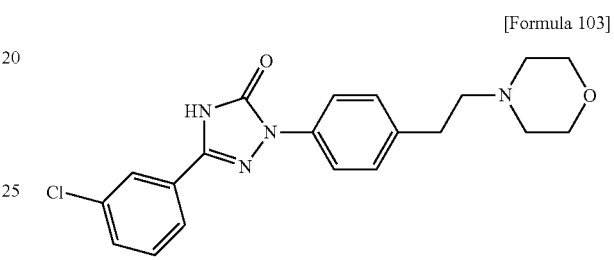

MS (ESI pos.) m/z: 385 ([M+H]+).

P-N3: 5-(2-Bromo-5-chlorophenyl)-2-{4-[2-(morpholin-4-yl)ethyl]phenyl}-2,4-dihydro-3H-1,2,4-triazol-3-one (Synthesis from Reference Example P-M3)

[Formula 104]

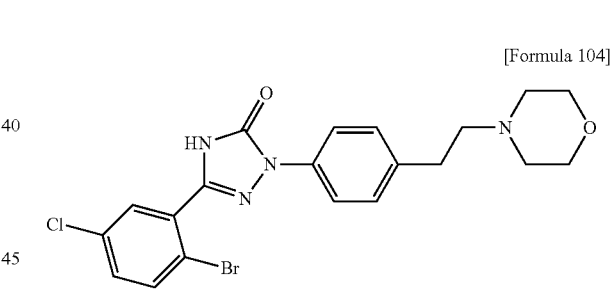

MS (ESI pos.) m/z: 463, 465 ([M+H]+).

Synthesis of Reference Example P-O1

Tert-Butyl[3-(3-chlorophenyl)-1-{4-[2-(morpholin-4-yl)ethyl]phenyl}-5-oxo-1,5-dihydro-4H-1,2,4-triazol-4-yl]acetate

[Formula 105]

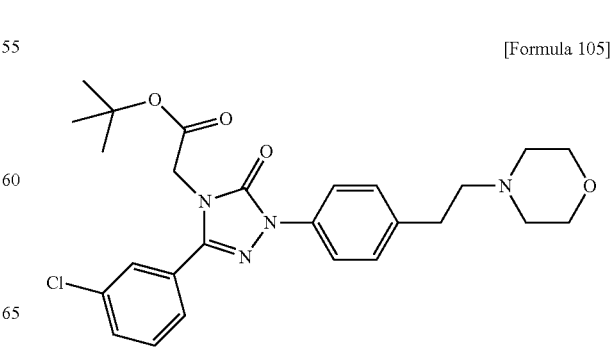

K₂CO₃ (405 mg) and tert-butyl bromoacetate (0.258 mL) were added to a suspension of the compound (564 mg) prepared in Reference Example P-N2 in DMF (10 mL), followed by stirring at room temperature for 3 hours. The reaction solution was separated between water (30 mL) and ethyl acetate (30 mL). The organic layer was washed with saturated brine (30 mL) and was dried over Na₂SO₄. The desiccant was removed by filtration, and the filtrate was concentrated under reduced pressure. The residue was purified by silica gel column chromatography (SNAP Cartridge HP-Sil: 50 g, mobile phase: CHCl₃/MeOH=100/0 to 96/4 (v/v)) to yield the title compound (550 mg, light brown oil).

MS (ESI pos.) m/z: 499 ([M+H]⁺).

Synthesis of Reference Example P-P1

[3-(3-Chlorophenyl)-1-{4-[2-(morpholin-4-yl)ethyl]phenyl}-5-oxo-1,5-dihydro-4H-1,2,4-triazol-4-yl]acetic acid

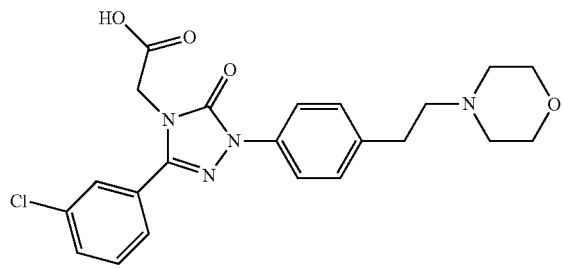

[Formula 106]

Trifluoroacetic acid (5 mL) was added to a solution of the compound (440 mg) prepared in Reference Example P-O1 in chloroform (15 mL), followed by stirring at room temperature for 1 day. After ice cooling, the pH of the reaction solution was adjusted to about 7 with an aqueous NaOH solution. The solution was separated between chloroform (20 mL) and saturated brine (20 mL). The aqueous layer was extracted with chloroform (20 mL) four times. The combined organic layer was dried over Na₂SO₄. The desiccant was removed by filtration, and the mother liquid was concentrated. Chloroform was added to the residue, and the solid was collected by filtration and dried to yield the title compound (321 mg, colorless solid).

MS (ESI pos.) m/z: 443 ([M+H]⁺).

Synthesis of Reference Example P-Q1a 3-(Methylsulfonyl)benzoyl chloride

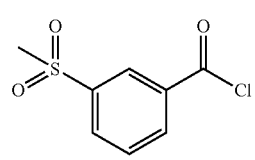

[Formula 107]

DMF (0.4 mL) and oxalyl chloride (1.90 g) were added to a solution of 3-(methylsulfonyl)benzoic acid (2.00 g) in CHCl₃ (including amylene, 40 mL) in a nitrogen gas flow under ice cooling, followed by stirring at room temperature for 2 hours. The reaction solution was concentrated under reduced pressure to yield a crude product as a yellow solid, which was used in the subsequent reaction.

Synthesis of Reference Example P-Q1b

Tert-Butyl 2-[3-(methylsulfonyl)benzoyl]hydrazinecarboxylate

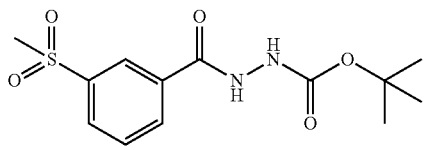

[Formula 108]

A solution of the compound (9.99 mmol) prepared in Reference Example P-Q1a in CHCl₃ (10 mL) was dropwise added to a solution of tert-butyl carbazate (1.58 g) and triethylamine (2.09 mL) in CHCl₃ (including amylene, 40 mL) over 5 minutes in a nitrogen gas flow under ice cooling, followed by stirring at room temperature overnight. A saturated aqueous sodium bicarbonate solution (100 mL) and ethyl acetate (100 mL) were added to the reaction solution, followed by stirring at room temperature. The solid was collected by filtration to yield a colorless solid (2.00 g). The filtrate was separated into two layers, and the aqueous layer was extracted with ethyl acetate. The combined organic layer was concentrated to yield the title compound (2.53 g, colorless solid).

MS (ESI pos.) m/z: 337 ([M+Na]⁺).

Synthesis of Reference Example P-Q1c 3-(Methylsulfonyl)benzohydrazide

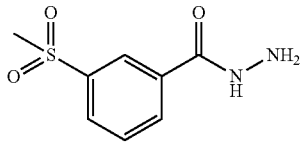

[Formula 109]

A solution of 4 mol/L hydrochloric acid in 1,4-dioxane (20 mL) was added to a solution of the compound (1.95 g+2.50 g) prepared in Reference Example P-Q1b in 1,4-dioxane (50 mL) in a nitrogen gas flow, followed by heating at 60° C. with stirring for 4 hours. The reaction solution was cooled and was then concentrated under reduced pressure to give a crude product. Ethyl acetate (100 mL) and a saturated aqueous NaHCO₃ solution (100 mL) were added to the crude product, and ammonium sulfate was added thereto until precipitation occurs, followed by separation into two layers. The aqueous layer was extracted with ethyl acetate (100 mL×6). The combined organic layer was dried over MgSO₄, and the desiccant was removed by filtration. The filtrate was concentrated under reduced pressure to yield the title compound (1.56 g, light yellow solid).

MS (ESI pos.) m/z: 237 ([M+Na]⁺).

Synthesis of Reference Example P-Q1d

Ethyl N-({2-[3-(methylsulfonyl)benzoyl]hydrazinyl}carbonyl)glycinate

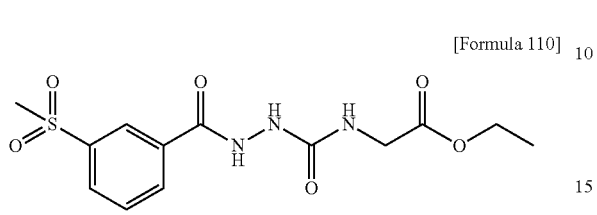

[Formula 110]

A solution of ethyl isocyanatoacetate (0.83 mL) in THF (5 mL) was dropwise added to a solution of the compound (1.52 g) prepared in Reference Example Q1c in THF (20 mL) over 2 minutes with heating at 50° C. in a nitrogen gas flow, followed by stirring under the same conditions for 1 hour and then at room temperature for 1 hour. The reaction solution was purified by silica gel column chromatography (SNAP Cartridge KP-NH: 55 g, mobile phase: CHCl$_3$/MeOH/NH$_4$OH=98/2/0.2 to 90/10/1 (v/v/v)) to yield the title compound (2.20 g, yellow amorphous compound).

MS (ESI pos.) m/z: 366 ([M+Na]$^+$).

Synthesis of Reference Example P-Q1e

{3-[3-(Methylsulfonyl)phenyl]-5-oxo-1,5-dihydro-4H-1,2,4-triazol-4-yl}acetic acid

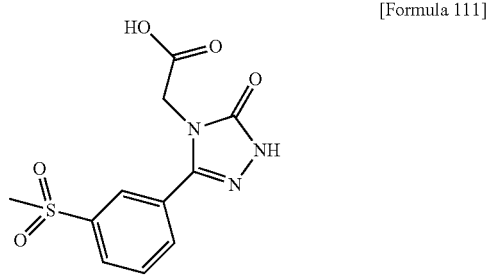 [SMILES: CS(=O)(=O)c1cccc(-c2n[nH]c(=O)n2CC(=O)O)c1]

[Formula 111]

The compound (1.52 g) prepared in Reference Example P-Q1d was heated in an aqueous 3 mol/L sodium hydroxide solution (16.3 mL) with stirring at 120° C. for 2 hours and then at 100° C. for 18.5 hours. The pH of the reaction solution was adjusted to be lower than 1 with a concentrated hydrochloric acid, followed by extraction with ethyl acetate. The combined organic layer was dried over MgSO$_4$, and the desiccant was removed by filtration. The filtrate was concentrated under reduced pressure to yield the title compound (1.56 g, light yellow solid).

MS (ESI pos.) m/z: 320 ([M+Na]$^+$).

Synthesis of Reference Example P-Q1

2-{3-[3-(Methylsulfonyl)phenyl]-5-oxo-1,5-dihydro-4H-1,2,4-triazol-4-yl}-N-(propan-2-yl)acetamide

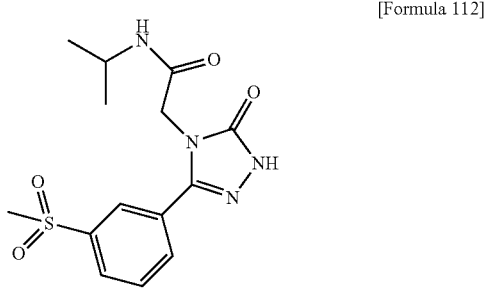 [SMILES: CC(C)NC(=O)Cn1c(-c2cccc(S(C)(=O)=O)c2)n[nH]c1=O]

[Formula 112]

EDC.HCl (1.18 g) was added to a solution of the compound (1.52 g) prepared in Reference Example P-Q1e and HOBt.H$_2$O (1.17 g) in DMF (20 mL) in a nitrogen gas flow, followed by stirring at room temperature for 10 minutes. Isopropylamine (0.66 mL) was added thereto, followed by stirring for 1 hour. The reaction solution was separated between a saturated aqueous NaHCO$_3$ solution (100 mL) and CHCl$_3$ (50 mL). The aqueous layer was extracted with CHCl$_3$ (30 mL). The combined organic layer was dried over MgSO$_4$, and the desiccant was removed by filtration. The filtrate was concentrated under reduced pressure. The residue was purified by silica gel column chromatography (SNAP Cartridge HP-Sil: 50 g, mobile phase: CHCl$_3$/MeOH/NH$_4$OH=99/1/0.1 to 92/8/0.8 (v/v/v)) to yield the title compound (580 mg, colorless solid).

MS (ESI pos.) m/z: 361 ([M+Na]$^+$).

Synthesis of Reference Example P-Q2a

Tert-Butyl 2-(3-chlorobenzoyl)hydrazinecarboxylate

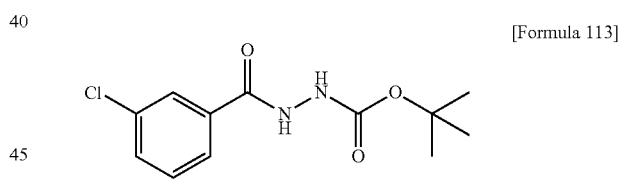

[Formula 113]

The title compound (4.41 g, colorless powder) was synthesized from 3-chlorobenzoyl chloride (2 mL) and tert-butyl carbazate (2.49 g), as in Reference Example P-Q1b.

MS (ESI neg.) m/z: 269 ([M–H]$^-$).

Synthesis of Reference Example P-Q2b

3-Chlorobenzohydrazide hydrochloride

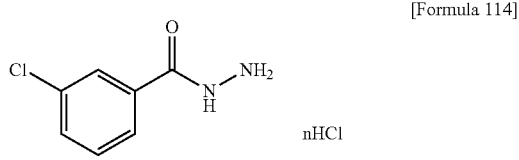 [SMILES: NNC(=O)c1cccc(Cl)c1]

[Formula 114]

The title compound (3.26 g, colorless powder) was synthesized from the compound (4.41 g) prepared in Reference Example P-Q2a, as in Reference Example P-Q1c.

MS (ESI pos.) m/z: 171 ([M+H]$^+$).

Synthesis of Reference Example P-Q2b-f

3-Chlorobenzohydrazide

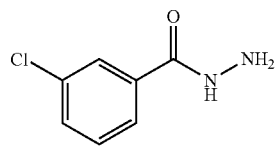

[Formula 115]

A saturated aqueous NaHCO$_3$ solution (40 mL) was added to a suspension of the compound (2.73 g) prepared in Reference Example P-Q2b in water (20 mL) under ice cooling. EtOAc (50 mL) was added thereto, followed by stirring at room temperature for a while. EtOAc was added to the mixture with heating until the suspension was dissolved. The solution was separated to two layers, and the aqueous layer was extracted with EtOAc (50 mL×6). The combined organic layer was dried over Na$_2$SO$_4$, and the desiccant was removed by filtration. The filtrate was concentrated under reduced pressure to yield the title compound (2.18 g, colorless powder).
MS (ESI pos.) m/z: 171 ([M+H]$^+$).

Synthesis of Reference Example P-Q2c

Ethyl N-{[2-(3-chlorobenzoyl)hydrazinyl]carbonyl}glycinate

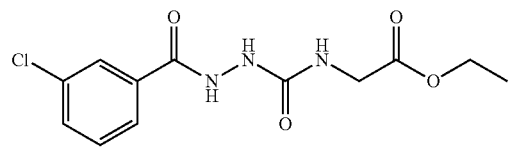

[Formula 116]

The title compound (430 mg, colorless powder) was synthesized from the compound (500 mg) prepared in Reference Example P-Q2b-f, as in Reference Example P-Q1d.
MS (ESI pos.) m/z: 322 ([M+Na]$^+$).

Synthesis of Reference Example P-Q2d

[3-(3-Chlorophenyl)-5-oxo-1,5-dihydro-4H-1,2,4-triazol-4-yl]acetic acid

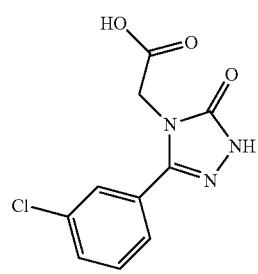

[Formula 117]

The title compound (2.85 g, colorless powder) was synthesized from the compound (3.89 g) prepared in Reference Example P-Q2c, as in Reference Example P-Q1e.
MS (ESI pos.) m/z: 254 ([M+H]$^+$).

Synthesis of Reference Example P-Q2

2-[3-(3-Chlorophenyl)-5-oxo-1,5-dihydro-4H-1,2,4-triazol-4-yl]-N-(propan-2-yl)acetamide

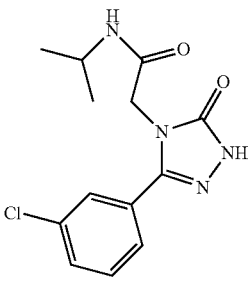

[Formula 118]

The title compound (2.23 g, colorless powder) was synthesized from the compound (2.84 g) prepared in Reference Example P-Q2d, as in Reference Example P-Q1.
MS (ESI pos.) m/z: 295 ([M+H]$^+$).

Synthesis of Reference Example P-Q3a

4-Fluoro-3-methoxybenzoyl chloride

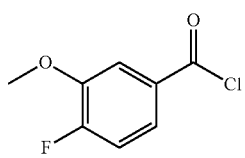

[Formula 119]

The title compound was prepared from 4-fluoro-3-methoxybenzoic acid (5.00 g), as in Reference Example P-Q1a. The crude product was used in the subsequent reaction.

Synthesis of Reference Example P-Q3b

Tert-Butyl 2-(4-fluoro-3-methoxybenzoyl)hydrazinecarboxylate

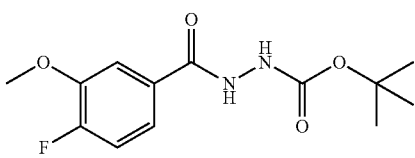

[Formula 120]

The title compound (8.19 g, colorless solid) was prepared from Reference Example P-Q3a, as in Reference Example P-Q1b.
MS (ESI pos.) m/z: 307 ([M+Na]$^+$).

Synthesis of Reference Example P-Q3c

4-Fluoro-3-methoxybenzohydrazide

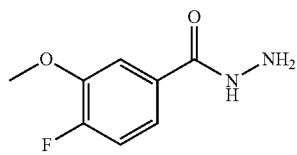
[Formula 121]

The title compound (5.12 g, colorless solid) was prepared from Reference Example P-Q3b (8.19 g), as in Reference Example P-Q1c.
MS (ESI pos.) m/z: 185 ([M+H]$^+$).

Synthesis of Reference Example P-Q3d

Ethyl N-{[2-(4-fluoro-3-methoxybenzoyl)hydrazinyl]carbonyl}glycinate

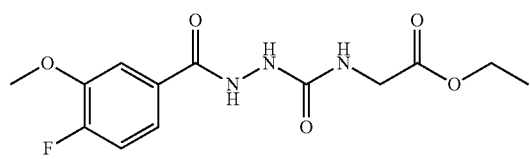
[Formula 122]

The title compound (8.55 g, colorless solid) was prepared from Reference Example P-Q3c (5.12 g), as in Reference Example P-Q1d.
MS (ESI pos.) m/z: 314 ([M+H]$^+$).

Synthesis of Reference Example P-Q3e

[3-(4-Fluoro-3-methoxyphenyl)-5-oxo-1,5-dihydro-4H-1,2,4-triazol-4-yl]acetic acid

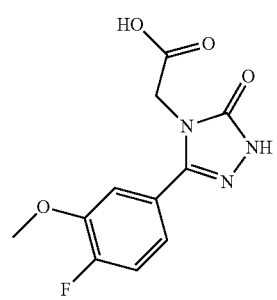
[Formula 123]

The title compound (7.25 g, colorless solid) was prepared from Reference Example P-Q3d (8.55 g), as in Reference Example P-Q1e.
MS (ESI pos.) m/z: 290 ([M+Na]$^+$).

Synthesis of Reference Example P-Q3

2-[3-(4-Fluoro-3-methoxyphenyl)-5-oxo-1,5-dihydro-4H-1,2,4-triazol-4-yl]-N-(propan-2-yl)acetamide

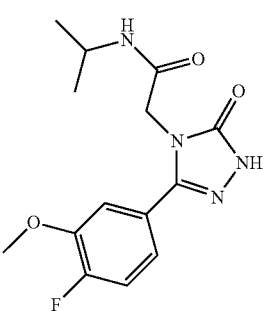
[Formula 124]

The title compound (5.82 g, colorless solid) was prepared from Reference Example P-Q3e (7.25 g), as in Reference Example P-Q1.
MS (ESI pos.) m/z: 309 ([M+H]$^+$).

Synthesis of Reference Example P-Q4d

Ethyl N-{[2-(3-methoxybenzoyl)hydrazinyl]carbonyl}glycinate

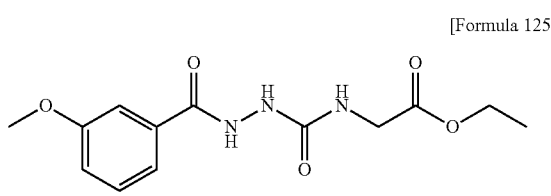
[Formula 125]

The title compound (17.5 g, colorless solid) was prepared from 3-methoxybenzohydrazide (10.0 g), as in Reference Example P-Q1d.
MS (ESI pos.) m/z: 296 ([M+H]$^+$).

Synthesis of Reference Example P-Q4e

[3-(3-Methoxyphenyl)-5-oxo-1,5-dihydro-4'-1,2,4-triazol-4-yl]acetic acid

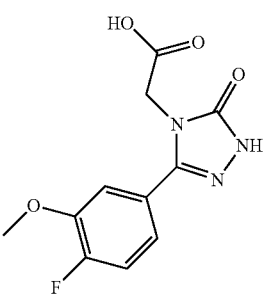
[Formula 126]

The title compound (14.4 g, colorless solid) was prepared from Reference Example P-Q4d (17.4 g), as in Reference Example P-Q1e.
MS (ESI pos.) m/z: 250 ([M+H]$^+$).

Synthesis of Reference Example P-Q4

N-Tert-Butyl-2-[3-(3-methoxyphenyl)-5-oxo-1,5-dihydro-4H-1,2,4-triazol-4-yl]acetamide

[Formula 127]

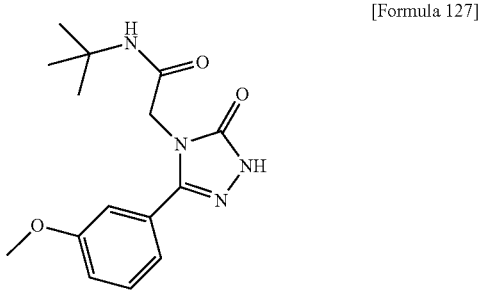 [SMILES: COc1cccc(-c2n[nH]c(=O)n2CC(=O)NC(C)(C)C)c1]

A mixture of Reference Example P-Q4e (1.00 g), tert-butylamine (4.2 mL), HATU (2.29 g), DIEA (1.4 mL), and DMF (10 mL) was stirred at room temperature overnight. Water (20 mL) and an aqueous 3 M HCl solution (20 mL) were added thereto in an ice bath, followed by extraction with ethyl acetate. The organic layer was washed with water and brine, and the solvent was distilled off under reduced pressure. The residue was purified by silica gel column chromatography (SNAP Cartridge HP-Sil: 50 g, mobile phase: $CHCl_3$/MeOH=98/2 to 90/10 (v/v)) to yield the title compound (743 mg, colorless solid).

MS (ESI pos.) m/z: 305 ([M+H]$^+$).

Synthesis of Reference Example P-Q5a

6-Methoxypyridine-2-carbonyl chloride

[Formula 128]

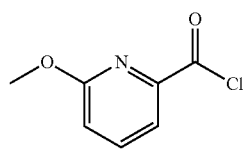

The title compound was prepared from 6-methoxypyridine-2-carboxylic acid (2.50 g), as in Reference Example P-Q1a. The crude product was used in the subsequent reaction.

Synthesis of Reference Example P-Q5b

Tert-Butyl 2-[(6-methoxypyridin-2-yl)carbonyl]hydrazinecarboxylate

[Formula 129]

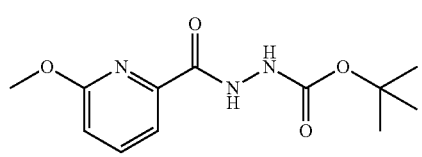

The title compound (4.62 g, colorless solid) was prepared from Reference Example P-Q5a, as in Reference Example P-Q1b.

MS (ESI pos.) m/z: 290 ([M+Na]$^+$).

Synthesis of Reference Example P-Q5c

6-Methoxypyridine-2-carbohydrazide

[Formula 130]

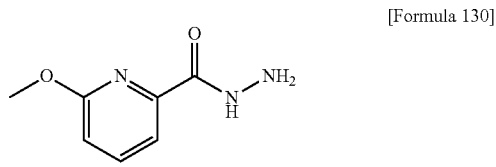

The title compound (2.81 g, light yellow solid) was prepared from Reference Example P-Q5b (4.62 g), as in Reference Example P-Q1c.

MS (ESI pos.) m/z: 168 ([M+H]$^+$).

Synthesis of Reference Example P-Q5d

Ethyl N-({2-[(6-methoxypyridin-2-yl)carbonyl]hydrazinyl}carbonyl)glycinate

[Formula 131]

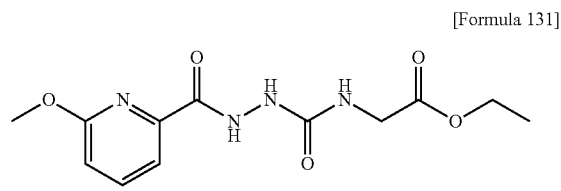 [SMILES: CCOC(=O)CNC(=O)NNC(=O)c1cccc(OC)n1]

The title compound (4.72 g, colorless solid) was prepared from Reference Example P-Q5c (2.81 g), as in Reference Example P-Q1d.

MS (ESI pos.) m/z: 297 ([M+H]$^+$).

Synthesis of Reference Example P-Q5e

[3-(6-Methoxypyridin-2-yl)-5-oxo-1,5-dihydro-4H-1,2,4-triazol-4-yl]acetic acid

[Formula 132]

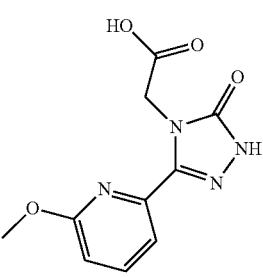

The title compound (4.83 g, colorless solid) was prepared from Reference Example P-Q5d (4.72 g) as in Reference Example P-Q1e.

MS (ESI pos.) m/z: 251 ([M+H]$^+$).

Synthesis of Reference Example P-Q5

2-[3-(6-Methoxypyridin-2-yl)-5-oxo-1,5-dihydro-4H-1,2,4-triazol-4-yl]-N-(propan-2-yl)acetamide

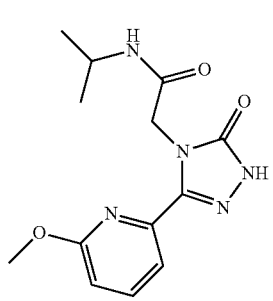
[Formula 133]

The title compound (1.80 g, colorless solid) was prepared from Reference Example P-Q5e (2.00 g), as in Reference Example P-Q1.

MS (ESI pos.) m/z: 292 ([M+H]$^+$).

Synthesis of Reference Example P-R1a (4-Bromo-2-fluorophenyl)acetic acid

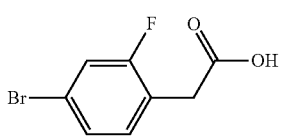
[Formula 134]

Oxalyl chloride (3.2 mL) and DMF (one drop) were added to a suspension of 4-bromo-2-fluorobenzoic acid (4.0 g) in CHCl$_3$ (40 mL) in an ice bath, followed by stirring at room temperature for 3 hours. After concentration, a mixture of THF and MeCN (1/1 (v/v), 40 mL) was added to the residue. TMSCH$_2$N$_2$ (2 mol/L Et$_2$O solution, 18.3 mL) was added thereto at 0° C., followed by stirring at room temperature for 2 hours. After concentration, a mixture of 1,4-dioxane and water (1/1 (v/v), 60 mL) and then silver acetate (916 mg) were added thereto, followed by stirring at 100° C. for 2 hours. After concentration, a saturated aqueous NaHCO$_3$ solution was added thereto, followed by stirring at room temperature for 1 hour. EtOAc was added thereto, and the solid was removed by filtration through Celite (registered trademark) to separate the organic layer. Under ice cooling, 3 mol/L HCl was added to the aqueous layer to make the system acidic. The aqueous layer was extracted from CHCl$_3$ (50 mL×9). The combined organic layer was filtered through a phase separator, and the filtrate was concentrated under reduced pressure to yield the title compound (2.46 g, colorless powder).

MS (ESI neg.) m/z: 231, 233 ([M–H]$^-$).

The following compounds were synthesized as in Reference Example P-R1a.

Reference Example P-R2a (4-Bromo-2-methoxyphenyl)acetic acid (Synthesis from 4-bromo-2-methoxybenzoic acid)

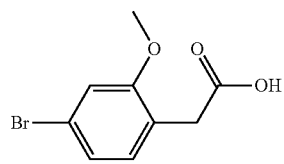
[Formula 135]

MS (ESI neg.) m/z: 243, 245 ([M–H]$^-$).

Synthesis of Reference Example P-R3a (4-Bromo-3-fluorophenyl)acetic acid (Synthesis from 4-bromo-3-fluorobenzoic acid)

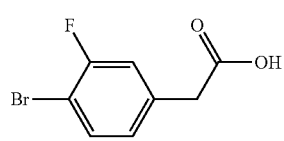
[Formula 136]

MS (ESI neg.) m/z: 231, 233 ([M–H]$^-$).

Synthesis of Reference Example P-R4a (4-Bromo-3-methoxyphenyl)acetic acid (Synthesis from 4-bromo-3-methoxybenzoic acid)

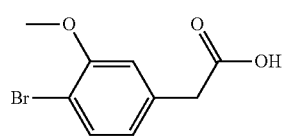
[Formula 137]

MS (ESI neg.) m/z: 243, 245 ([M–H]$^-$).

Synthesis of Reference Example P-R1b 2-(4-Bromo-2-fluorophenyl)ethanol

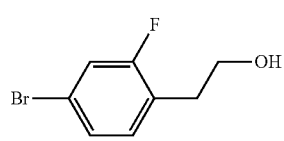
[Formula 138]

Under ice cooling, 1.09 mol/L BH$_3$.THF (14.5 mL) was added to a solution of the compound (2.460 g) prepared in Reference Example P-R1a in THF (40 mL). The mixture was stirred with gradually raising the temperature to room temperature for 5 hours. Under ice cooling, MeOH was added to the reaction system until foaming stopped. The solvent was distilled off under reduced pressure. Water (40 mL) and CHCl₃ (20 mL) were added to the residue, followed by stirring at room temperature. After extraction with CHCl₃, filtration through a phase separator was performed. The solvent was distilled off under reduced pressure. The residue was purified by silica gel column chromatography (SNAP Cartridge HP-Sil: 50 g, n-hexane/EtOAc=90/10 to 50/50 (v/v)) to yield the title compound (1.93 g, colorless oil).

MS (E1 pos.) m/z: 218, 220 (M⁺).

The following compounds were synthesized as in Reference Example P-R1b.

Synthesis of Reference Example P-R2b 2-(4-Bromo-2-methoxyphenyl)ethanol (Synthesis from Reference Example P-2a)

[Formula 139]

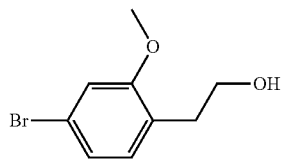

MS (ESI pos.) m/z: 231, 233 ([M+H]⁺).

Synthesis of Reference Example P-R3b 2-(4-Bromo-3-fluorophenyl)ethanol (Synthesis from Reference Example P-R3a)

[Formula 140]

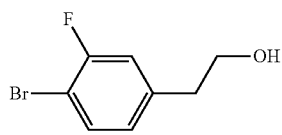

MS (E1 pos.) m/z: 218, 220 (M⁺).

Synthesis of Reference Example P-R4b 2-(4-Bromo-3-methoxyphenyl)ethanol (Synthesis from Reference Example P-R4a)

[Formula 141]

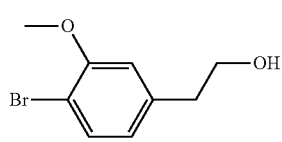

MS (ESI neg.) m/z: 227, 229 ([M−H]⁻).

Synthesis of Reference Example P-R1c 2-(4-Bromo-2-fluorophenyl)ethyl methanesulfonate

[Formula 142]

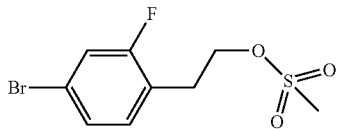

Under ice cooling, Et₃N (0.48 mL) and mesyl chloride (0.21 mL) were sequentially added to a solution of the compound (500 mg) prepared in Reference Example P-R1b in CHCl₃ (8 mL), followed by stirring at room temperature for 1 hour. Water (10 mL) was added thereto, followed by extraction with CHCl₃. The organic layer was filtered through a phase separator. The filtrate was concentrated under reduced pressure to yield the title compound (675 mg, light yellow oily compound).

MS (E1, pos.) m/z: 296, 298 (M⁺).

The following compounds were synthesized as in Reference Example P-R1c.

Synthesis of Reference Example P-R2c 2-(4-Bromo-2-methoxyphenyl)ethyl methanesulfonate (Synthesis from Reference Example P-R2b)

[Formula 143]

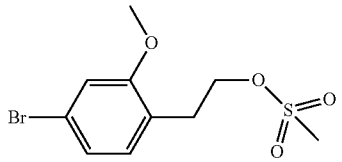

MS (E1 pos.) m/z: 308, 310 (M⁺).

Synthesis of Reference Example P-R3c 2-(4-Bromo-3-fluorophenyl)ethyl methanesulfonate (Synthesis from Reference Example P-R3b)

[Formula 144]

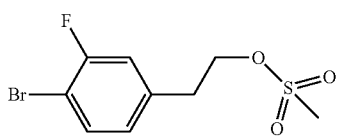

MS (E1 pos.) m/z: 296, 298 (M⁺).

Synthesis of Reference Example P-R4c 2-(4-Bromo-3-methoxyphenyl)ethyl methanesulfonate (Synthesis from Reference Example P-R4b)

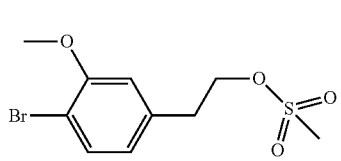

[Formula 145]

MS (E1 pos.) m/z: 308, 310 (M+).

Synthesis of Reference Example P-R1-1

4-[2-(4-Bromo-2-fluorophenyl)ethyl]morpholine

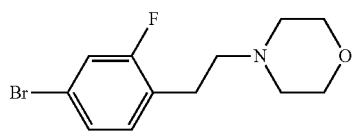

[Formula 146]

The compound (337 mg) prepared in Reference Example P-R1c was dissolved in MeCN (6 mL), and iPr$_2$NEt (0.40 mL) and morpholine (0.20 mL) were added thereto, followed by stirring at 100° C. overnight. After concentration, the residue was purified by silica gel column chromatography (SNAP Cartridge HP-Sil: 10 g, mobile phase: CHCl$_3$/MeOH=99/1 to 95/5 (v/v)) to yield the title compound (315 mg, light brown oil).

MS (ESI pos.) m/z: 288, 290 ([M+H]+).

The following compounds were synthesized as in Reference Example P-R1-1.

Synthesis of Reference Example P-R1-2

8-[2-(4-Bromo-2-fluorophenyl)ethyl]-3-oxa-8-azabicyclo[3.2.1]octane (Synthesis from the compound prepared in Reference Example P-R1c and 3-oxa-8-azabicyclo[3.2.1]octane)

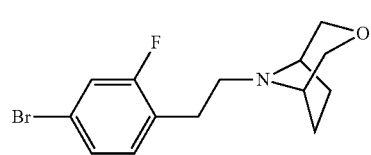

[Formula 147]

MS (ESI pos.) m/z: 314, 316 ([M+H]+).

Synthesis of Reference Example P-R2-1

4-[2-(4-Bromo-2-methoxyphenyl)ethyl]morpholine (Synthesis from the compound prepared in Reference Example P-R2c and morpholine)

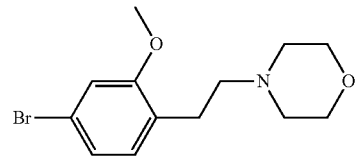

[Formula 148]

MS (ESI pos.) m/z: 300, 302 ([M+H]+).

Synthesis of Reference Example P-R2-2

8-[2-(4-Bromo-2-methoxyphenyl)ethyl]-3-oxa-8-azabicyclo[3.2.1]octane (Synthesis from the compound prepared in Reference Example P-R2c and 3-oxa-8-azabicyclo[3.2.1]octane)

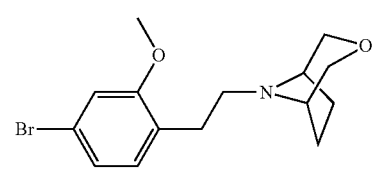

[Formula 149]

MS (ESI pos.) m/z: 326, 328 ([M+H]+).

Synthesis of Reference Example P-R3-1

4-[2-(4-Bromo-3-fluorophenyl)ethyl]morpholine (Synthesis from the compound prepared in Reference Example P-R3c and morpholine)

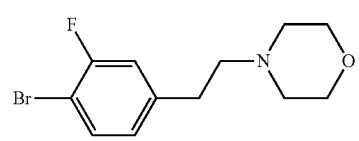

[Formula 150]

MS (ESI pos.) m/z: 288, 290 ([M+H]+).

Reference Example P-R4-1

4-[2-(4-Bromo-3-methoxyphenyl)ethyl]morpholine (Synthesis from the compound prepared in Reference Example P-R4c and morpholine)

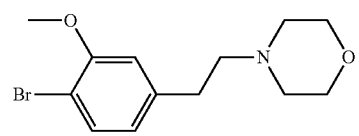

[Formula 151]

MS (ESI pos.) m/z: 300, 302 ([M+H]+).

Synthesis of Reference Example P-R5-1

4-[1-(4-Bromophenyl)propan-2-yl]morpholine

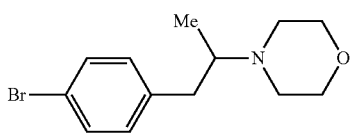

[Formula 152]

1-(4-Bromophenyl)propan-2-one (2.03 g) was dissolved in CHCl₃ (40 mL), and morpholine (1.24 mL) was added thereto, followed by stirring at room temperature overnight and then at 60° C. for 4 hours. NaBH(OAc)₃ (4.03 g) and acetic acid (1.1 mL) were sequentially added thereto, followed by stirring overnight. The reaction was terminated by addition of water, and the reaction solution was separated between CHCl₃ and a saturated aqueous NaHCO₃ solution. The residue was purified by silica gel column chromatography (mobile phase: CHCl₃/EtOAc=80/20 to 60/40 (v/v)) to yield the title compound (1.67 g, colorless oil).

MS (ESI pos.) m/z: 284, 286 ([M+H]⁺).

Synthesis of Reference Example P-R5-2

8-[1-(4-Bromophenyl)propan-2-yl]-3-oxa-8-azabicyclo[3.2.1]octane

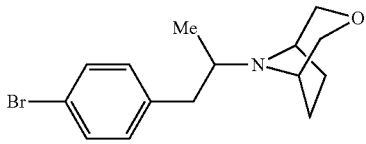

[Formula 153]

The title compound (54 mg, colorless oil) was prepared from 1-(4-bromophenyl)propan-2-one (130 mg) and 3-oxa-8-azabicyclo[3.2.1]octane (100 mg), as in Reference Example P-R5-1.

MS (ESI pos.) m/z: 310, 312 ([M+H]⁺).

Synthesis of Reference Example P-R6a 2-(6-Chloropyridin-3-yl)-N-methoxy-N-methylacetamide

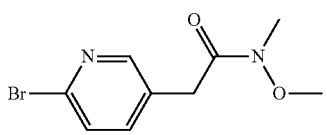

[Formula 154]

A solution of (6-chloropyridin-3-yl)acetic acid (5.0 g), N,O-dimethylhydroxyamine hydrochloride (2.98 g), EDC.HCl (5.87 g), and N-methylmorpholine (9.6 mL) in DMF (70 mL) was stirred at room temperature for 4 days. Under ice cooling, water (150 mL) was added thereto, followed by extraction with EtOAc. The organic layer was sequentially washed with water and brine and was dried over Na₂SO₄. The desiccant was removed by filtration and the filtrate was concentrated under reduced pressure. The residue was purified by silica gel column chromatography (SNAP Cartridge HP-Sil: 50 g, mobile phase: n-hexane/EtOAc=75/25 to 0/100 (v/v)) to yield the title compound (3.56 g, light yellow oil).

MS (ESI pos.) m/z: 215 ([M+H]⁺).

Synthesis of Reference Example P-R6b 1-(6-Chloropyridin-3-yl)propan-2-one

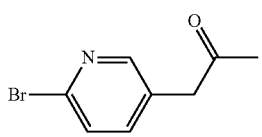

[Formula 155]

Under ice cooling, a solution of 3 mol/L methyl magnesium bromide in Et₂O (1.6 mL) was dropwise added to a solution of the compound (1.0 g) prepared in Reference Example P-R6a in THF (15 mL) in a nitrogen gas flow, followed stirring at room temperature for 1 hour. Under ice cooling, a 3 mol/L hydrochloric acid (2 mL) and an aqueous 2 mol/L sodium hydroxide solution (30 mL) was added thereto. After extraction with EtOAc, the organic layer was washed with brine. After drying with Na₂SO₄, the desiccant was removed by filtration. The filtrate was concentrated under reduced pressure. The residue was purified by silica gel column chromatography (SNAP Cartridge HP-Sil: 50 g, mobile phase: n-hexane/EtOAc=80/20 to 0/100 (v/v)) to yield the title compound (235 mg, light yellow oil).

MS (ESI pos.) m/z: 170 ([M+H]⁺).

Synthesis of Reference Example P-R6-1

4-[1-(6-Chloropyridin-3-yl)propan-2-yl]morpholine

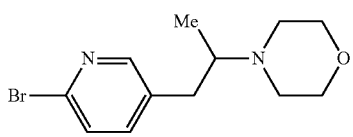

[Formula 156]

A borane-2-picoline complex (252 mg) was added to a solution of the compound (235 mg) prepared in Reference Example P-R6b and morpholine (0.21 mL) in a mixture of methanol and acetic acid (5 ml, 10/1 (v/v)), followed by stirring at an outside temperature of 60° C. for 5 hours and then at an outside temperature of 70° C. overnight. After extraction with CHCl₃, the organic layer was filtered through a phase separator. The solvent was distilled off under reduced pressure. The residue was purified by silica gel column chromatography (SNAP Cartridge HP-Sil: 25 g, mobile phase: EtOAc/MeOH=100/0 to 90/10 (v/v)) to yield the title compound (166 mg, light yellow oil).

MS (ESI pos.) m/z: 241 ([M+H]⁺).

The following compounds were synthesized as in Reference Example P-R6-1.

Reference Example P-R6-2

8-[1-(6-Chloropyridin-3-yl)propan-2-yl]-3-oxa-8-azabicyclo[3.2.1]octane (Synthesis from the compound prepared in Reference Example P-R6b and 3-oxa-8-azabicyclo[3.2.1]octane)

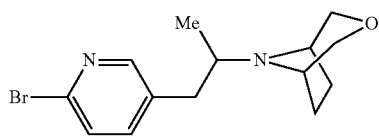

[Formula 157]

MS (ESI pos.) m/z: 267 ([M+H]+).

Synthesis of Reference Example P-R7-1

8-[2-(4-Bromophenyl)ethyl]-3-oxa-8-azabicyclo[3.2.1]octane

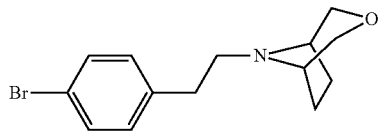

[Formula 158]

Under ice cooling, Et₃N (1.3 mL) and methanesulfonyl chloride (0.64 mL) were sequentially added to a solution of 2-(4-bromophenyl)ethanol (1.5 g) in CHCl₃ (10 mL), followed by stirring at room temperature for 2 hours. Under ice cooling, water was added thereto, followed by extraction with CHCl₃. The organic layer was filtered through a phase separator, and the filtrate was concentrated under reduced pressure.

A mixture of the residue (light brown oil), 3-oxa-8-azabicyclo[3.2.1]octane (904 mg), 2,2,6,6-tetramethylpiperidine (2.0 mL), and MeCN (10 mL) was stirred at an outside temperature of 95° C. for 4 days. After cooling, water was added thereto, followed by extraction with CHCl₃. The organic layer was filtered through a phase separator, and the solvent was distilled off under reduced pressure. The residue was purified by silica gel column chromatography (SNAP Cartridge HP-Sil: 50 g, mobile phase: EtOAc/MeOH=99/1 to 90/10 (v/v)) to yield the title compound (1.47 g, light brown solid).
MS (ESI pos.) m/z: 296, 298 ([M+H]+).

Synthesis of Reference Example P-S1

{4-[2-(Morpholin-4-yl)propyl]phenyl}boronic acid

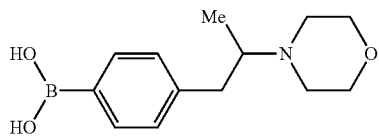

[Formula 159]

The compound (1.61 g) prepared in Reference Example P-R5-1 was dissolved in THF (32.3 mL). A solution of 2.66 mol/L n-BuLi in n-hexane (2.6 mL) was added to the resulting solution at −78° C., followed by stirring for 30 minutes. Subsequently, triisopropyl borate (1.6 mL) was added thereto, followed by stirring with gradually raising the temperature to room temperature for 3 hours. A 2 mol/L hydrochloric acid solution (16 mL) was added thereto, followed by stirring overnight. Subsequently, the reaction solution was adjusted to basic with a saturated aqueous NaHCO₃ solution. After concentration, extraction with CHCl₃ was performed. The organic layer was purified by silica gel column chromatography (mobile phase: CHCl₃/MeOH=100/0 to 90/10 (v/v)) to yield the title compound (1.09 g, cream-colored powder).
MS (ESI pos.) m/z: 250 ([M+H]+).

Synthesis of Reference Example P-T1

2-{3-(4-Fluoro-3-methoxyphenyl)-1-[5-(2-hydroxyethyl)pyrimidin-2-yl]-5-oxo-1,5-dihydro-4H-1,2,4-triazol-4-yl}-N-(propan-2-yl)acetamide

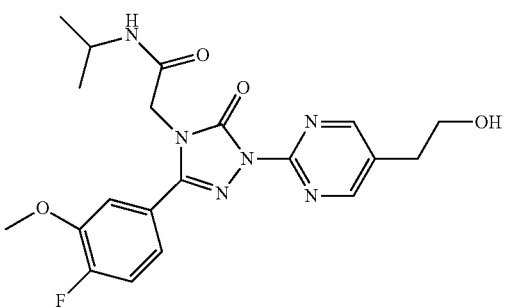

[Formula 160]

A mixture of 5-bromo-2-chloropyrimidine (800 mg), CIS-tributyl[2-ethoxyethenyl] tin (1.80 g), PdCl₂(PPh₃)₂ (30 mg), and toluene (10 mL) was stirred under a nitrogen atmosphere at an outside temperature of 100° C. for 4 hours. After cooling, the solvent was distilled off under reduced pressure. The residue was purified by column chromatography (SNAP Cartridge KP-NH: 28 g, mobile phase: n-hexane/EtOAc=100/0 to 85/15 (v/v)) to yield 2-chloro-5-[(Z)-2-ethoxyethenyl]pyrimidine (250 mg, colorless solid).

Cs₂CO₃ (975 mg) was added to a solution of the resulting 2-chloro-5-[(Z)-2-ethoxyethenyl]pyrimidine (184 mg) and the compound (308 mg) prepared in Reference Example P-Q3 in DMSO (4.0 mL), followed by stirring at room temperature for 12 hours and then at an outside temperature of 85° C. for 8 hours. After cooling, CHCl₃ and water were added to the reaction solution, and then were separated between CHCl₃ and water. The aqueous layer was extracted with CHCl₃. The combined organic layer was washed with water and brine and was concentrated under reduced pressure. The residue was purified by silica gel column chromatography (SNAP Cartridge HP-Sil: 25 g, mobile phase: CHCl₃/MeOH=100/0 to 90/10 (v/v)) to yield 2-[1-{5-[(Z)-2-ethoxyethenyl]pyrimidin-2-yl}-3-(4-fluoro-3-methoxyphenyl)-5-oxo-1,5-dihydro-4H-1,2,4-triazol-4-yl]-N-(propan-2-yl)acetamide (50 mg).

A solution of 4 mol/L hydrochloric acid in 1,4-dioxane (10 drops) was added to a solution of the resulting 2-[1-{5-[(Z)-2-ethoxyethenyl]pyrimidin-2-yl}-3-(4-fluoro-3-methoxyphenyl)-5-oxo-1,5-dihydro-4H-1,2,4-triazol-4-yl]-N-(propan-2-yl)acetamide (50 mg) in a mixture of MeCN and H₂O (10/1 (v/v)), followed by stirring at room temperature for 12 hours. After concentration, CHCl₃ and a saturated aqueous sodium bicarbonate solution were added to the residue, and then were separated between CHCl₃ and a saturated aqueous sodium bicarbonate solution. The aqueous layer was extracted with CHCl₃. The combined organic layer was sequentially washed with water and brine and was dried over Na₂SO₄. The desiccant was removed by filtration. The filtrate was concentrated under reduced pressure to yield an aldehyde. NaBH₄ was added to a solution of the aldehyde in MeOH (5 mL), followed by stirring at room temperature for 30 minutes. A saturated aqueous sodium bicarbonate solution and CHCl₃ were added to the reaction solution, and then were separated between a saturated aqueous sodium bicarbonate solution and CHCl₃. The aqueous layer was extracted with CHCl₃. The combined organic layer was sequentially washed with water and brine and was dried over Na₂SO₄. The desiccant was removed by filtration, and the filtrate was concentrated under reduced pressure. The residue was purified by silica gel column chromatography (SNAP Cartridge HP-Sil: 10 g, mobile phase: CHCl₃/MeOH=100/0 to 90/10 (v/v)) to yield the title compound (70 mg, light yellow solid).

¹H-NMR (600 MHz, CDCl₃)δ(ppm); 1.18 (6H, m), 2.90 (2H, s), 3.88-3.93 (2H, m), 3.98 (3H, d, J=0.8 Hz), 4.03-4.15 (1H, m), 4.33 (2H, s), 6.51-6.63 (1H, m), 7.14-7.23 (1H, m), 7.36-7.47 (1H, m), 7.51-7.63 (1H, m), 8.74 (2H, s).

Synthesis of Reference Example P-U1

Tert-Butyl[2-(4-{3-(3-chlorophenyl)-5-oxo-4-[2-oxo-2-(propan-2-ylamino)ethyl]-4,5-dihydro-1H-1,2,4-triazol-1-yl}phenyl)ethyl]carbamate

[Formula 161]

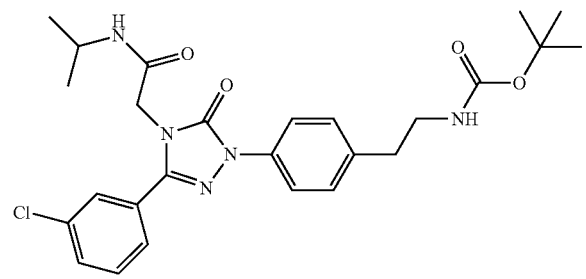

A suspension of the compound (73 mg) prepared in Reference Example P-Q2, N-BOC-2-(4-bromophenyl)-ethylamine (78 mg), copper iodide (47 mg), tripotassium phosphate (105 mg), and trans-(1R,2R)-N,N'-bismethyl-1,2-cyclohexanediamine (0.039 mL) in 1,4-dioxane (2 mL) was stirred in a nitrogen gas flow at an outside temperature of 100° C. for 2 days. After cooling, 20% aqueous ammonia was added thereto, followed by extraction with CHCl₃. The organic layer was filtered through a phase separator, and the filtrate was concentrated under reduced pressure. The residue was purified by silica gel column chromatography (SNAP Cartridge HP-Sil: 10 g, mobile phase: CHCl₃/MeOH=100/0 to 90/10 (v/v)) to yield the title compound (84 mg, colorless solid).

MS (ESI pos.) m/z: 536 ([M+Na]⁺).

Synthesis of Example Aa-1

2-[3-(3-Chlorophenyl)-1-{4-[2-(morpholin-4-yl)ethyl]phenyl}-5-oxo-1,5-dihydro-4H-1,2,4-triazol-4-yl]-N-(propan-2-yl)acetamide

[Formula 162]

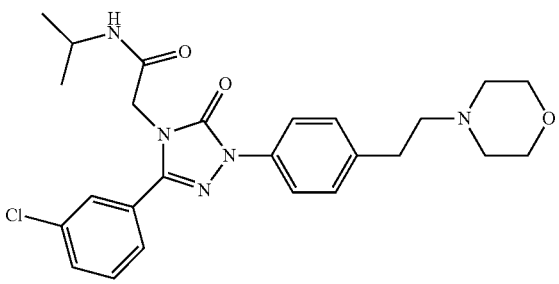

A mixture of the compound (100 mg) prepared in Reference Example P-I1, morpholine (0.03 mL), N,N-diisopropylethylamine (0.35 mL), and MeCN (3.00 mL) was stirred at an outside temperature of 80° C. overnight. After cooling, the solvent was distilled off under reduced pressure. The residue was purified by column chromatography (SNAP Cartridge HP-Sil: 10 g, mobile phase: CHCl₃/MeOH=98/2 to 85/15 (v/v); and SNAP Cartridge KP-NH: 28 g, mobile phase: n-hexane/CHCl₃=80/20 to 0/100 (v/v)) and preparative thin-layer chromatography (PTLC) (1.0 mm silica gel 60F₂₅₄ plate, mobile phase: EtOAc/MeOH=95/5 (v/v)). The resulting crude product was washed with a solvent mixture of EtOAc and n-hexane (EtOAc/n-hexane=1/4 (v/v)) with stirring to yield the title compound (70 mg, colorless solid).

MS (ESI pos.) m/z: 484 ([M+H]⁺).

¹H-NMR (600 MHz, CDCl₃)δ(ppm); 1.20 (6H, d, J=6.4 Hz), 2.48-2.67 (6H, m), 2.80-2.88 (2H, m), 3.76 (4H, br. s.), 4.06-4.13 (1H, m), 4.36 (2H, s), 6.37-6.45 (1H, m), 7.31 (2H, d, J=8.3 Hz), 7.46-7.50 (1H, m), 7.51-7.55 (1H, m), 7.74-7.77 (1H, m), 7.85-7.88 (1H, m), 7.94 (2H, d, J=8.7 Hz).

Synthesis of Example Aa-2

2-[3-(3-Chlorophenyl)-1-{4-[2-(2-oxa-6-azaspiro[3.3]hept-6-yl)ethyl]phenyl}-5-oxo-1,5-dihydro-4H-1,2,4-triazol-4-yl]-N-(propan-2-yl)acetamide

[Formula 163]

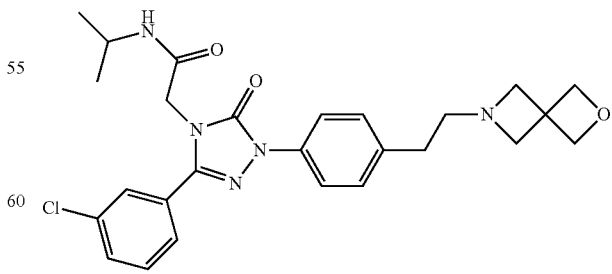

A suspension of the compound (150 mg) prepared in Reference Example P-J1, 2-oxa-6-azaspiro[3.3]heptane oxalate (2:1) (157 mg), and acetic acid (0.1 mL) in CHCl₃ (3 mL) was stirred at room temperature for a while, and then sodium triacetoxyborohydride (231 mg) was added thereto, followed by stirring for 3 days. A saturated NaHCO₃ solution was added to the reaction solution, followed by extraction with CHCl₃. The organic layer was filtered through a phase separator, and the solvent was distilled off under reduced pressure. The residue was purified by preparative thin-layer chromatography (PTLC) (1.0 mm silica gel 60F$_{254}$ plate, mobile phase: CHCl₃/MeOH=90/10 (v/v)) and column chromatography (SNAP Cartridge KP-NH: 11 g, mobile phase: EtOAc/MeOH=100/0 to 95/5 (v/v)). The resulting crude product was washed with a solvent mixture of EtOAc and n-hexane (EtOAc/n-hexane=1/6 (v/v)) with stirring to yield the title compound (13 mg, colorless solid).

MS (ESI pos.) m/z: 496 ([M+H]⁺).

¹H-NMR (600 MHz, CDCl₃)δ(ppm); 1.19 (6H, d, J=6.9 Hz), 2.59-2.72 (4H, m), 3.36 (4H, br. s.), 4.06-4.13 (1H, m), 4.35 (2H, s), 4.74 (4H, s), 6.36-6.43 (1H, m), 7.23-7.29 (2H, m), 7.49 (1H, d, J=7.8 Hz), 7.51-7.54 (1H, m), 7.75 (1H, d, J=9.2 Hz), 7.85-7.88 (1H, m), 7.93 (2H, d, J=8.3 Hz).

Synthesis of Example Aa-3

2-[3-(3-Chlorophenyl)-5-oxo-1-{4-[2-(piperidin-1-yl)ethoxy]phenyl}-1,5-dihydro-4H-1,2,4-triazol-4-yl]-N-(propan-2-yl)acetamide

[Formula 164]

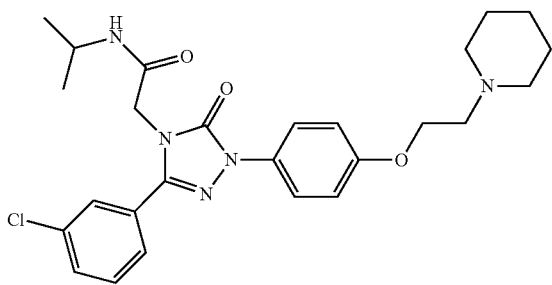

A mixture of the compound (70.0 mg) prepared in Reference Example P-K1, 1-piperidineethanol (0.03 mL), a solution of 1.9 mol/L diisopropyl azodicarboxylate in toluene (0.29 mL), triphenylphosphine (142 mg), and THF (2.0 mL) was stirred under a nitrogen atmosphere at an outside temperature of 40° C. for 3 hours and then at room temperature overnight. Furthermore, 1-piperidine ethanol (0.06 mL), a solution of 1.9 mol/L diisopropyl azodicarboxylate in toluene (0.29 mL), and triphenylphosphine (142 mg) were added thereto, followed by stirring at an outside temperature of 85° C. for 8 hours. After cooling, the solvent was distilled off under reduced pressure. The residue was purified by column chromatography (SNAP Cartridge KP-Sil: 25 g, mobile phase: CHCl₃/MeOH=98/2 to 95/5 (v/v)). The resulting crude product was washed with a solvent mixture of EtOAc and IPE (EtOAc/IPE=1/1 (v/v)) with stirring to yield the title compound (53 mg, colorless solid).

MS (ESI pos.) m/z: 498 ([M+H]⁺).

¹H-NMR (600 MHz, CDCl₃)δ(ppm); 1.20 (6H, d, J=6.4 Hz), 1.43-1.50 (2H, m), 1.60-1.68 (4H, m), 2.46-2.61 (4H, m), 2.77-2.86 (2H, m), 4.06-4.19 (3H, m), 4.35 (2H, s), 6.44-6.49 (1H, m), 6.97-7.01 (2H, m), 7.46-7.54 (2H, m), 7.74-7.77 (1H, m), 7.85-7.91 (3H, m).

The following compounds were synthesized as in Example Aa-1:

Example Aa-4: 2-[3-(3-Chlorophenyl)-1-{4-[2-(4-hydroxypiperidin-1-yl)ethyl]phenyl}-5-oxo-1,5-dihydro-4H-1,2,4-triazol-4-yl]-N-(propan-2-yl)acetamide (Synthesis from Reference Example P-I1 and piperidin-4-ol), Example Aa-5: 2-[3-(3-Chlorophenyl)-1-{4-[2-(3-hydroxypiperidin-1-yl)ethyl]phenyl}-5-oxo-1,5-dihydro-4H-1,2,4-triazol-4-yl]-N-(propan-2-yl)acetamide (Synthesis from Reference Example P-I1 and piperidin-3-ol), Example Aa-6: 2-[3-(3-Chlorophenyl)-1-{4-[2-(3-hydroxypyrrolidin-1-yl)ethyl]phenyl}-5-oxo-1,5-dihydro-4H-1,2,4-triazol-4-yl]-N-(propan-2-yl)acetamide (Synthesis from Reference Example P-I1 and pyrrolidin-3-ol), Example Aa-7: 2-[3-(3-Chlorophenyl)-1-(4-{2-[3-(hydroxymethyl)pyrrolidin-1-yl]ethyl}phenyl)-5-oxo-1,5-dihydro-4H-1,2,4-triazol-4-yl]-N-(propan-2-yl)acetamide (Synthesis from Reference Example P-I1 and pyrrolidin-3-ylmethanol), Example Aa-8: 2-[3-(3-Chlorophenyl)-1-{4-[2-(3-hydroxy-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-I1 and 8-azabicyclo[3.2.1]octan-3-ol), Example Aa-9: 2-[3-(3-Chlorophenyl)-1-{4-[2-(8-oxa-3-azabicyclo[3.2.1]oct-3-yl)ethyl]phenyl}-5-oxo-1,5-dihydro-4H-1,2,4-triazol-4-yl]-N-(propan-2-yl)acetamide (Synthesis from Reference Example P-I1 and 8-oxa-3-azabicyclo[3.2.1]octane), Example Aa-10: 2-[3-(3-Chlorophenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-I1 and 3-oxa-8-azabicyclo[3.2.1]octane), Example Aa-11: 2-[3-(3-Chlorophenyl)-5-oxo-1-{4-[2-(piperidin-1-yl)ethyl]phenyl}-1,5-dihydro-4H-1,2,4-triazol-4-yl]-N-(propan-2-yl)acetamide (Synthesis from Reference Example P-I1 and piperidine), Example Aa-12: 2-[3-(3-Chlorophenyl)-1-(4-{2-[(2-hydroxyethyl)amino]ethyl}phenyl)-5-oxo-1,5-dihydro-4H-1,2,4-triazol-4-yl]-N-(propan-2-yl)acetamide (Synthesis from Reference Example P-I1 and 2-aminoethanol), Example Aa-13: 2-[3-(3-Chlorophenyl)-1-{4-[2-(1,4-oxazepan-4-yl)ethyl]phenyl}-5-oxo-1,5-dihydro-4H-1,2,4-triazol-4-yl]-N-(propan-2-yl)acetamide (Synthesis from Reference Example P-I1 and 1,4-oxazepam), Example Ab-1: 2-[3-(3-Chlorophenyl)-5-oxo-1-{5-[2-(piperidin-1-yl)ethyl]pyridin-2-yl}-1,5-dihydro-4H-1,2,4-triazol-4-yl]-N-(propan-2-yl)acetamide (Synthesis from Reference Example P-I3 and piperidine), Example Ab-2: 2-[3-(3-Chlorophenyl)-1-{5-[2-(morpholin-4-yl)ethyl]pyridin-2-yl}-5-oxo-1,5-dihydro-4H-1,2,4-triazol-4-yl]-N-(propan-2-yl)acetamide (Synthesis from Reference Example P-I3 and morpholine), Example Ab-3: 2-[3-(3-Chlorophenyl)-1-{5-[2-(1,4-oxazepan-4-yl)ethyl]pyridin-2-yl}-5-oxo-1,5-dihydro-4H-1,2,4-triazol-4-yl]-N-(propan-2-yl)acetamide (Synthesis from Reference Example P-I3 and 1,4-oxazepam), Example Ab-4: 2-[3-(3-Chlorophenyl)-1-{5-[2-(3-hydroxy-8-azabicyclo[3.2.1]oct-8-yl)ethyl]pyridin-2-yl}-5-oxo-1,5-dihydro-4H-1,2,4-triazol-4-yl]-N-(propan-2-yl)acetamide (Synthesis from Reference Example P-I3 and 8-azabicyclo[3.2.1]octan-3-ol), Example Ab-5: 2-[3-(3-Chlorophenyl)-1-{5-[2-(3-oxa-8-azabicyclo[3.2.1]oct-8-yl)ethyl]pyridin-2-yl}-5-oxo-1,5- dihydro-4H-1,2,4-triazol-4-yl]-N-(propan-2-yl)acetamide (Synthesis from Reference Example P-I3 and 3-oxa-8-azabicyclo[3.2.1]octane), Example Ac-1: 2-[3-(3-Chlorophenyl)-5-oxo-1-{6-[2-(piperidin-1-yl)ethyl]pyridin-3-yl}-1,5-dihydro-4H-1,2,4-triazol-4-yl]-N-(propan-2-yl)acetamide (Synthesis from Reference Example P-I4 and piperidine), Example Ac-2: 2-[3-(3-Chlorophenyl)-1-{6-[2-(morpholin-4-yl)ethyl]pyridin-3-yl}-5-oxo-1,5-dihydro-4H-1,2,4-triazol-4-yl]-N-(propan-2-yl)acetamide (Synthesis from Reference Example P-I4 and morpholine), Example Ba-1: 2-[3-(3-Methoxyphenyl)-5-oxo-1-{4-[2-(piperidin-1-yl)ethyl]phenyl}-1,5-dihydro-4H-1,2,4-triazol-4-yl]-N-(propan-2-yl)acetamide (Synthesis from Reference Example P-I5 and piperidine), Example Ba-2: 2-[3-(3-Methoxyphenyl)-1-{4-[2-(morpholin-4-yl)ethyl]phenyl}-5-oxo-1,5-dihydro-4H-1,2,4-triazol-4-yl]-N-(propan-2-yl)acetamide (Synthesis from Reference Example P-I5 and morpholine), Example Ca-1: 2-[3-(4-Fluoro-3-methoxyphenyl)-5-oxo-1-{4-[2-(piperidin-1-yl)ethyl]phenyl}-1,5-dihydro-4H-1,2,4-triazol-4-yl]-N-(propan-2-yl)acetamide (Synthesis from Reference Example P-I6 and piperidine), Example Ca-2: 2-[3-(4-Fluoro-3-methoxyphenyl)-1-{4-[2-(morpholin-4-yl)ethyl]phenyl}-5-oxo-1,5-dihydro-4H-1,2,4-triazol-4-yl]-N-(propan-2-yl)acetamide (Synthesis from Reference Example P-I6 and morpholine), Example Ca-3: 2-[3-(4-Fluoro-3-methoxyphenyl)-1-{4-[2-(3-hydroxy-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-I6 and 8-azabicyclo[3.2.1]octan-3-ol), Example Ca-4: 2-[3-(4-Fluoro-3-methoxyphenyl)-1-{4-[2-(8-oxa-3-azabicyclo[3.2.1]oct-3-yl)ethyl]phenyl}-5-oxo-1,5-dihydro-4H-1,2,4-triazol-4-yl]-N-(propan-2-yl)acetamide (Synthesis from Reference Example P-I6 and 8-oxa-3-azabicyclo[3.2.1]octane), Example Ca-5: 2-[3-(4-Fluoro-3-methoxyphenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-I6 and 3-oxa-8-azabicyclo[3.2.1]octane), Example Cb-1: 2-[3-(4-Fluoro-3-methoxyphenyl)-5-oxo-1-{5-[2-(piperidin-1-yl)ethyl]pyridin-2-yl}-1,5-dihydro-4H-1,2,4-triazol-4-yl]-N-(propan-2-yl)acetamide (Synthesis from Reference Example P-I7 and piperidine), Example Cb-2: 2-[3-(4-Fluoro-3-methoxyphenyl)-1-{5-[2-(morpholin-4-yl)ethyl]pyridin-2-yl}-5-oxo-1,5-dihydro-4H-1,2,4-triazol-4-yl]-N-(propan-2-yl)acetamide (Synthesis from Reference Example P-I7 and morpholine), Example Cb-3: 2-[3-(4-Fluoro-3-methoxyphenyl)-1-{5-[2-(1,4-oxazepan-4-yl)ethyl]pyridin-2-yl}-5-oxo-1,5-dihydro-4H-1,2,4-triazol-4-yl]-N-(propan-2-yl)acetamide (Synthesis from Reference Example P-I7 and 1,4-oxazepam), Example Cb-4: 2-[3-(4-Fluoro-3-methoxyphenyl)-1-{5-[2-(3-hydroxy-8-azabicyclo[3.2.1]oct-8-yl)ethyl]pyridin-2-yl}-5-oxo-1,5-dihydro-4H-1,2,4-triazol-4-yl]-N-(propan-2-yl)acetamide (Synthesis from Reference Example P-I7 and 8-azabicyclo[3.2.1]octan-3-ol), Example Cb-5: 2-[3-(4-Fluoro-3-methoxyphenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]-N-(propan-2-yl)acetamide (Synthesis from Reference Example P-I7 and 3-oxa-8-azabicyclo[3.2.1]octane), Example Da-1: 2-[3-(3-Chloro-4-fluorophenyl)-5-oxo-1-{4-[2-(piperidin-1-yl)ethyl]phenyl}-1,5-dihydro-4H-1,2,4-triazol-4-yl]-N-(propan-2-yl)acetamide (Synthesis from Reference Example P-I8 and piperidine), Example Da-2: 2-[3-(3-Chloro-4-fluorophenyl)-1-{4-[2-(morpholin-4-yl)ethyl]phenyl}-5-oxo-1,5-dihydro-4H-1,2,4-triazol-4-yl]-N-(propan-2-yl)acetamide (Synthesis from Reference Example P-I8 and morpholine), Example Da-3: 2-[3-(3-Chloro-4-fluorophenyl)-1-{4-[2-(2-oxa-6-azaspiro[3.3]hept-6-yl)ethyl]phenyl}-5-oxo-1,5-dihydro-4H-1,2,4-triazol-4-yl]-N-(propan-2-yl)acetamide (Synthesis from Reference Example P-I8 and 2-oxa-6-azaspiro[3.3]heptane), Example Da-4: 2-[3-(3-Chloro-4-fluorophenyl)-1-{4-[2-(1,4-oxazepan-4-yl)ethyl]phenyl}-5-oxo-1,5-dihydro-4H-1,2,4-triazol-4-yl]-N-(propan-2-yl)acetamide (Synthesis from Reference Example P-I8 and 1,4-oxazepam), Example Da-5: 2-[3-(3-Chloro-4-fluorophenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-I8 and 3-oxa-8-azabicyclo[3.2.1]octane), Example Da-6: 2-[3-(3-Chloro-4-fluorophenyl)-1-{4-[2-(3-hydroxy-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-I8 and 8-azabicyclo[3.2.1]octan-3-ol), Example Db-1: 2-[3-(3-Chloro-4-fluorophenyl)-5-oxo-1-{5-[2-(piperidin-1-yl)ethyl]pyridin-2-yl}-1,5-dihydro-4H-1,2,4-triazol-4-yl]-N-(propan-2-yl)acetamide (Synthesis from Reference Example P-I9 and piperidine), Example Db-2: 2-[3-(3-Chloro-4-fluorophenyl)-1-{5-[2-(morpholin-4-yl)ethyl]pyridin-2-yl}-5-oxo-1,5-dihydro-4H-1,2,4-triazol-4-yl]-N-(propan-2-yl)acetamide (Synthesis from Reference Example P-I9 and morpholine), Example Db-3: 2-[3-(3-Chloro-4-fluorophenyl)-1-{5-[2-(2-oxa-6-azaspiro[3.3]hept-6-yl)ethyl]pyridin-2-yl}-5-oxo-1,5-dihydro-4H-1,2,4-triazol-4-yl]-N-(propan-2-yl)acetamide (Synthesis from Reference Example P-I9 and 2-oxa-6-azaspiro[3.3]heptane), Example Db-4: 2-[3-(3-Chloro-4-fluorophenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]-N-(propan-2-yl)acetamide (Synthesis from Reference Example P-I9 and 3-oxa-8-azabicyclo[3.2.1]octane), Example Db-5: 2-[3-(3-Chloro-4-fluorophenyl)-1-{5-[2-(3-hydroxy-8-azabicyclo[3.2.1]oct-8-yl)ethyl]pyridin-2-yl}-5-oxo-1,5-dihydro-4H-1,2,4-triazol-4-yl]-N-(propan-2-yl)acetamide (Synthesis from Reference Example P-I9 and 8-azabicyclo[3.2.1]octan-3-ol), Example Ea-1: 2-[3-(3-Cyanophenyl)-5-oxo-1-{4-[2-(piperidin-1-yl)ethyl]phenyl}-1,5-dihydro-4H-1,2,4-triazol-4-yl]-N-(propan-2-yl)acetamide (Synthesis from Reference Example P-I2 and piperidine), Example Ea-2: 2-[3-(3-Cyanophenyl)-1-{4-[2-(morpholin-4-yl)ethyl]phenyl}-5-oxo-1,5-dihydro-4H-1,2,4-triazol-4-yl]-N-(propan-2-yl)acetamide (Synthesis from Reference Example P-I2 and morpholine), Example Ea-3: 2-[3-(3-Cyanophenyl)-1-{4-[2-(2-oxa-6-azaspiro[3.3]hept-6-yl)ethyl]phenyl}-5-oxo-1,5-dihydro-4H-1,2,4-triazol-4-yl]-N-(propan-2-yl)acetamide (Synthesis from Reference Example P-I2 and 2-oxa-6-azaspiro[3.3]heptane)

Example Ad-17: N-Tert-Butyl-2-[3-(3-chlorophenyl)-1-{5-[2-(morpholin-4-yl)ethyl]pyridin-2-yl}-5-oxo-1,5-dihydro-4H-1,2,4-triazol-4-yl]acetamide (Synthesis from Reference Example P-I10 and morpholine), Example Ad-18: N-Tert-Butyl-2-[3-(3-chlorophenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]acetamide (Synthesis from Reference Example P-I10 and 3-oxa-8-azabicyclo[3.2.1]octane), Example Ba-3: 2-[3-(3-Methoxyphenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-I5 and 3-oxa-8-azabicyclo[3.2.1]octane), Example Bd-1: N-Tert-Butyl-2-[3-(3-methoxyphenyl)-1-{5-[2-(morpholin-4-yl)ethyl]pyridin-2-yl}-5-oxo-1,5-dihydro-4H-1,2,4-triazol-4-yl]acetamide (Synthesis from Reference Example P-I11 and morpholine), and Example Bd-2: N-Tert-Butyl-2-[3-(3-methoxyphenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]acetamide (Synthesis from Reference Example P-I11 and 3-oxa-8-azabicyclo[3.2.1]octane).

The results of $^1$H-NMR and MS of Examples Aa-4 to Aa-13, Ab-1 to Ab-5, Ac-1 to Ac-2, Ba-1 to Ba-2, Ca-1 to Ca-5, Cb-1 to Cb-5, Da-1 to Da-6, Db-1 to Db-5, Ea-1 to Ea-3, Ad-17, Ad-18, Ba-3, Bd-1, and Bd-2 are shown in Tables 1-1 to 1-8.

TABLE 1-1

| Example | Structure | $^1$H NMR | MS (ESI pos.) m/z |
|---|---|---|---|
| Aa-4 | 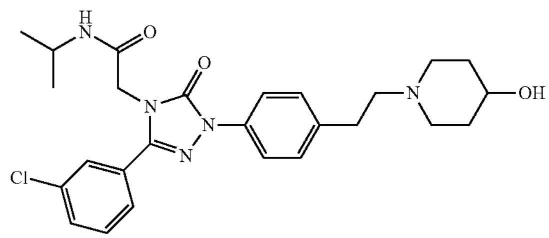 [SMILES: CC(C)NC(=O)Cn1c(-c2cccc(Cl)c2)nn(-c2ccc(CCN3CCC(O)CC3)cc2)c1=O] | $^1$H-NMR (600 MHz, CDCl$_3$) δ (ppm); 1.19 (6H, d, J = 6.4 Hz), 1.35-1.44 (1H, m), 1.60-1.70 (2H, m), 1.89-2.00 (2H, m), 2.18-2.31 (2H, m), 2.57-2.68 (2H, m), 2.78-2.94 (4H, m), 3.68-3.79 (1H, m), 4.06-4.13 (1H, m), 4.36 (2H, s), 6.38-6.46 (1H, m), 7.30 (2H, d, J = 8.3 Hz), 7.45-7.50 (1H, m), 7.50-7.54 (1H, m), 7.76 (1H, d, J = 7.8 Hz), 7.85-7.88 (1H, m), 7.03 (2H, d, J = 8.3 Hz). | 498([M + H]$^+$) |
| Aa-5 | 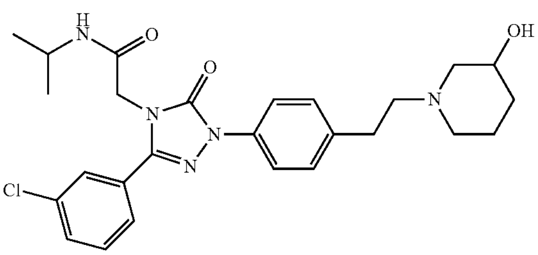 [SMILES: CC(C)NC(=O)Cn1c(-c2cccc(Cl)c2)nn(-c2ccc(CCN3CCCC(O)C3)cc2)c1=O] | $^1$H-NMR (600 MHz, CDCl$_3$) δ (ppm); 1.20 (6H, d, J = 6.9 Hz), 1.50-1.68 (4H, m), 1.80-1.92 (1H, m), 2.31-2.72 (6H, m), 2.80-2.89 (2H, m), 3.83-3.91 (1H, m), 4.06-4.13 (1H, m), 4.36 (2H, s), 6.38-6.46 (1H, m), 7.29 (2H, d, J = 8.3 Hz), 7.46-7.50 (1H, m), 7.51-7.54 (1H, m), 7.76 (1H, d, J = 7.8 Hz), 7.85-7.88 (1H, m), 7.94 (2H, d, J = 8.7 Hz). | 498([M + H]$^+$) |
| Aa-6 | 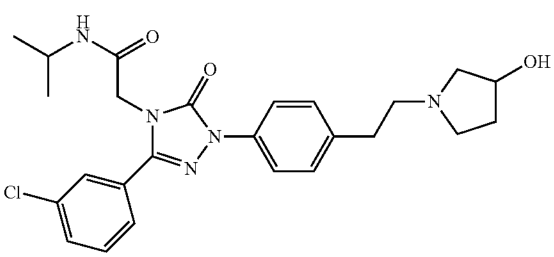 [SMILES: CC(C)NC(=O)Cn1c(-c2cccc(Cl)c2)nn(-c2ccc(CCN3CCC(O)C3)cc2)c1=O] | $^1$H-NMR (600 MHz, CDCl$_3$) δ (ppm); 1.19 (6H, d, J = 6.9 Hz), 1.75-1.82 (1H, m), 2.18-2.25 (1H, m), 2.34-2.41 (1H, m), 2.57-2.62 (1H, m), 2.73-2.82 (3H, m), 2.84-2.90 (2H, m), 2.97-3.02 (1H, m), 4.06-4.13 (1H, m), 4.34-4.40 (3H, m), 6.40-6.45 (1H, m), 7.31 (2H, d, J = 8.7 Hz), 7.46-7.50 (1H, m), 7.51-7.54 (1H, m), 7.76 (1H, d, J = 7.8 Hz), 7.86 (1H, t, J = 1.8 Hz), 7.93 (2H, d, J = 8.7 Hz). | 484([M + H]$^+$) |
| Aa-7 | 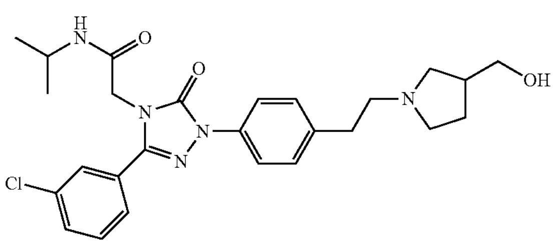 [SMILES: CC(C)NC(=O)Cn1c(-c2cccc(Cl)c2)nn(-c2ccc(CCN3CCC(CO)C3)cc2)c1=O] | $^1$H-NMR (600 MHz, CDCl$_3$) δ (ppm); 1.19 (6H, d, J = 6.9 Hz), 1.74-1.82 (1H, m), 2.02-2.12 (1H, m), 2.40-2.47 (1H, m), 2.66-3.07 (8H, m), 3.58 (1H, dd, J = 10.1, 5.5 Hz), 3.71 (1H, dd, J = 10.3, 4.4 Hz), 4.06-4.13 (1H, m), 4.35 (2H, s), 6.41-6.45 (1H, m), 7.30 (2H, d, J = 8.7 Hz), 7.46-7.54 (2H, m), 7.75 (1H, d, J = 7.8 Hz), 7.85-7.87 (1H, m), 7.95 (2H, d, J = 8.3 Hz). | 498([M + H]$^+$) |
| Aa-8 | 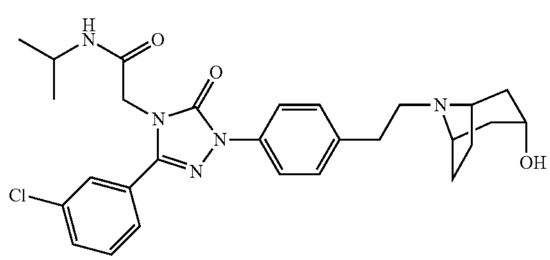 [SMILES: CC(C)NC(=O)Cn1c(-c2cccc(Cl)c2)nn(-c2ccc(CCN3C4CCC3CC(O)C4)cc2)c1=O] | $^1$H-NMR (600 MHz, CDCl$_3$) δ (ppm); 1.18 (6H, d, J = 6.9 Hz,) 1.24-1.33 (2H, m), 1.67-1.76 (2H, m), 1.93-2.03 (2H, m), 2.09-2.24 (3H, m), 2.60-2.76 (2H, m), 2.82-2.98 (2H, m), 3.26-3.41 (2H, m), 4.05-4.13 (1H, m), 4.35 (2H, s), 6.38-6.44 (1H, m), 7.28-7.34 (2H, m), 7.45-7.50 (1H, m), 7.50-7.54 (1H, m) 7.72-7.77 (1H, m), 7.85 (1H, t, J = 1.8 Hz), 7.90-7.95 (2H, m). | 524([M + H]$^+$) |

TABLE 1-1-continued

| Example | Structure | ¹H NMR | MS (ESI pos.) m/z |
|---|---|---|---|
| Aa-9 | 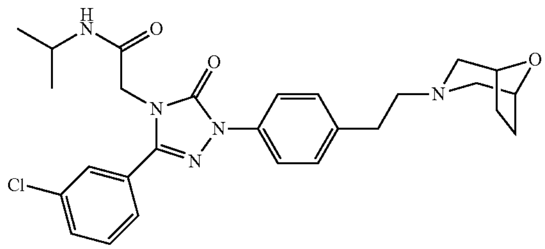 [SMILES: CC(C)NC(=O)Cn1c(-c2cccc(Cl)c2)nn(-c2ccc(CCN3CC4CCC(C3)O4)cc2)c1=O] | ¹H-NMR (600 MHz, CDCl₃) δ (ppm); 1.19 (6H, d, J = 6.9 Hz), 1.80-1.91 (4H, m), 2.34-2.38 (2H, m), 2.56 (2H, t, J = 7.6 Hz), 2.60-2.64 (2H, m), 2.76 (2H, t, J = 7.6 Hz), 4.05-4.12 (1H, m), 4.26-4.30 (2H, m), 4.35 (2H, s), 6.40-6.45 (1H, m), 7.30 (2H, d, J = 8.3 Hz), 7.45-7.53 (2H, m), 7.74-7.77 (1H, m), 7.85-7.87 (1H, m), 7.89-7.94 (2H, m). | 510([M + H]⁺) |

TABLE 1-2

| Example | Structure | ¹H NMR | MS (ESI pos.) m/z |
|---|---|---|---|
| Aa-10 | 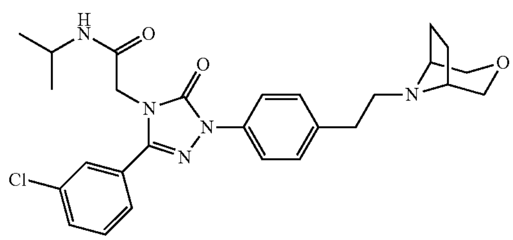 [SMILES: CC(C)NC(=O)Cn1c(-c2cccc(Cl)c2)nn(-c2ccc(CCN3C4CCC3COC4)cc2)c1=O] | ¹H-NMR (600 MHz, CDCl₃) δ (ppm); 1.18 (6H, d, J = 6.4 Hz), 1.85-1.94 (4H, m), 2.49-2.56 (2H, m), 2.77-2.84 (2H, m), 3.05-3.12 (2H, m), 3.49-3.58 (2H, m), 3.69-3.77 (2H, m), 4.04-4.13 (1H, m), 4.35 (2H, s), 6.45 (1H, d, J = 7.3 Hz), 7.28-7.33 (2H, m), 7.44-7.54 (2H, m), 7.75 (1H, d, J = 7.8 Hz), 7.85 (1H, s), 7.89-7.95 (2H, m). | 510([M + H]⁺) |
| Aa-11 | 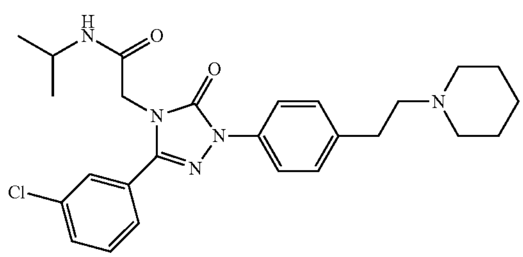 [SMILES: CC(C)NC(=O)Cn1c(-c2cccc(Cl)c2)nn(-c2ccc(CCN3CCCCC3)cc2)c1=O] | ¹H NMR (600 MHz, DMSO-d₆) δ (ppm); 1.00 (6H, d, J = 6.9 Hz), 1.34-1.42 (2H, m), 1.46-1.52 (4H, m), 2.39 (4H, d, J = 1.4 Hz), 2.44-2.53 (2H, m), 2.71-2.77 (2H, m), 3.74-3.82 (1H, m), 4.38 (2H, s), 7.34 (2H, d, J = 8.7 Hz), 7.56-7.61 (1H, m), 7.63-7.69 (2H, m), 7.73 (1H, s), 7.86 (2H, d, J = 8.3 Hz), 8.21 (1H, d, J = 7.8 Hz). | 482([M + H]⁺) |
| Aa-12 | 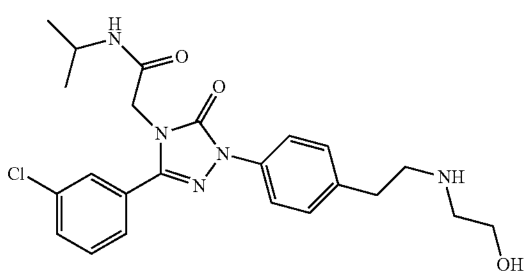 [SMILES: CC(C)NC(=O)Cn1c(-c2cccc(Cl)c2)nn(-c2ccc(CCNCCO)cc2)c1=O] | ¹H-NMR (600 MHz, CDCl₃) δ (ppm); 1.18 (6H, d, J = 6.4 Hz), 2.76-2.86 (4H, m), 2.89-2.95 (2H, m), 3.60-3.64 (2H, m), 4.05-4.13 (1H, m), 4.35 (2H, s), 6.43 (1H, d, J = 8.3 Hz), 7.30 (2H, d, J = 8.7 Hz), 7.45-7.54 (2H, m), 7.75 (1H, dt, J = 7.8, 1.4 Hz), 7.85 (1H, t, J = 1.8 Hz), 7.91-7.96 (2H, m) | 458([M + H]⁺) |
| Aa-13 | 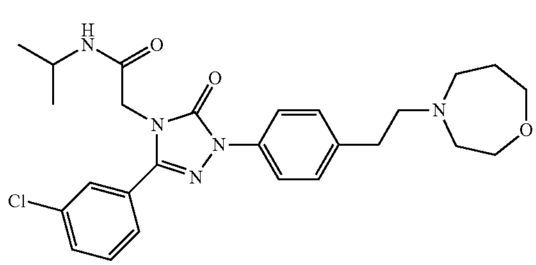 [SMILES: CC(C)NC(=O)Cn1c(-c2cccc(Cl)c2)nn(-c2ccc(CCN3CCCOCC3)cc2)c1=O] | ¹H-NMR (600 MHz, CDCl₃) δ (ppm); 1.20 (6H, d, J = 6.4 Hz), 1.90-1.96 (2H, m), 2.76-2.86 (6H, m), 3.74-3.78 (2H, m), 3.82 (2H, t, J = 6.0 Hz), 4.06-4.13 (1H, m), 4.36 (2H, s), 6.36-6.45 (1H, m), 7.30 (2H, d, J = 8.7 Hz), 7.46-7.51 (1H, m), 7.51-7.54 (1H, m), 7.74-7.78 (1H, m), 7.85-7.88 (1H, m), 7.93 (2H, d, J = 8.3 Hz) | 498([M + H]⁺) |

TABLE 1-2-continued

| | | | |
|---|---|---|---|
| Ab-1 | (structure) | ¹H-NMR (600 MHz, CDCl₃) δ (ppm); 1.17 (6H, d, J = 6.9 Hz), 1.44 (2H, br. s.), 1.57-1.61 (4H, m), 2.45 (4H, br. s.), 2.51-2.58 (2H, m), 2.78-2.86 (2H,m), 4.04-4.12 (1H, m), 4.34 (2H, s), 6.31 (1H, d, J = 7.3 Hz), 7.41-7.47 (1H, m), 7.47-7.52 (1H, m), 7.68 (1H, dd, J = 8.3, 2.3 Hz), 7.71-7.76 (1H, m), 7.88 (1H, t, J = 1.6 Hz), 8.02 (1H, d, J = 8.3 Hz), 8.43 (1H, d, J = 2.3 Hz) | 483([M + H]⁺) |
| Ab-2 | (structure) | ¹H-NMR (600 MHz, CDCl₃) δ (ppm); 1.18 (6H, d, J = 6.9 Hz), 2.52 (4H, br. s.), 2.61 (2H, t, J = 7.6 Hz), 2.84 (2H, t, J = 7.8 Hz), 3.73 (4H, t, J = 4.6 Hz), 4.05-4.15 (1H, m), 4.36 (2H, s), 6.28 (1H, d, J = 7.3 Hz), 7.44-7.48 (1H, m), 7.50-7.53 (1H, m), 7.70 (1H, dd, J = 8.3, 2.3 Hz), 7.75 (1H, d, J = 7.8 Hz), 7.88 (1H, t, J = 1.6 Hz), 8.05 (1H, d, J = 8.3 Hz), 8.45 (1H, d, J = 1.8 Hz) | 485([M + H]⁺) |

TABLE 1-3

| | | | |
|---|---|---|---|
| Ab-3 | (structure) | ¹H-NMR (600 MHz, CDCl₃) δ (ppm); 1.19 (6H, d, J = 6.4 Hz), 1.87-1.98 (2H, m), 2.72-2.89 (8H, m), 3.75 (2H, br. s.), 3.81 (2H, t, J = 6.0 Hz), 4.07-4.14 (1H, m), 4.36 (2H, s), 6.24-6.31 (1H, m), 7.45-7.49 (1H, m), 7.50-7.55 (1H, m), 7.69-7.73 (1H, m), 7.74-7.78 (1H, m), 7.88-7.91 (1H, m), 8.06 (1H, d, J = 8.3 Hz), 8.44-8.47 (1H, m) | 499([M + H]⁺) |
| Ab-4 | (structure) | ¹H NMR (600 MHz, DMSO-d₆) δ (ppm); 1.00 (6H, d, J = 6.4 Hz), 1.89-1.96 (2H, m), 2.11-2.25 (3H, m), 2.33-2.41 (2H, m), 3.02-3.13 (2H, m), 3.19-3.26 (2H, m), 3.74-3.82 (1H, m), 3.87-4.06 (3H, m), 4.39 (2H, s), 4.88-4.97 (1H, m), 7.55-7.63 (1H, m), 7.63-7.74 (3H, m), 7.91-8.02 (2H, m), 8.20-8.26 (1H, m), 8.45-8.51 (1H, m) | 525([M + H]⁺) |
| Ab-5 | (structure) | ¹H-NMR (600 MHz, CDCl₃) δ (ppm); 1.19 (6H, d, J = 6.4 Hz), 1.90 (4H, br. s.), 2.50-2.57 (2H, m), 2.78-2.84 (2H, m), 3.07 (2H, br. s.), 3.52 (2H, d, J = 9.6 Hz), 3.71 (2H, d, J = 10.5 Hz), 4.08-4.14 (1H, m), 4.36 (2H, s), 6.23-6.31 (1H, m), 7.45-7.49 (1H, m), 7.50-7.55 (1H, m), 7.71-7.79 (2H, m), 7.88-7.91 (1H, m), 8.06 (1H, d, J = 8.3 Hz), 8.46-8.49 (1H, m) | 511([M + H]⁺) |
| Ac-1 | (structure) | ¹H-NMR (600 MHz, CDCl₃) δ (ppm); 1.11-1.19 (6H, m), 1.39-1.83 (6H, m), 2.43-2.65 (4H, m), 2.73-2.90 (2H, m), 3.01-3.15 (2H, m), 3.98-4.14 (1H, m), 4.34 (2H, s), 6.27 (1H, d, J = 7.8 Hz), 7.29 (1H, d, J = 8.3 Hz), 7.44-7.51 (1H, m), 7.50-7.55 (1H, m), 7.73 (1H, dt, J = 7.8, 1.8 Hz), 7.82 (1H, t, J = 1.8 Hz), 8.23 (1H, dd, J = 8.3, 2.5 Hz), 9.18 (1H, d, J = 2.3 Hz) | 483([M + H]⁺) |

TABLE 1-3-continued

| | | | |
|---|---|---|---|
| Ac-2 | 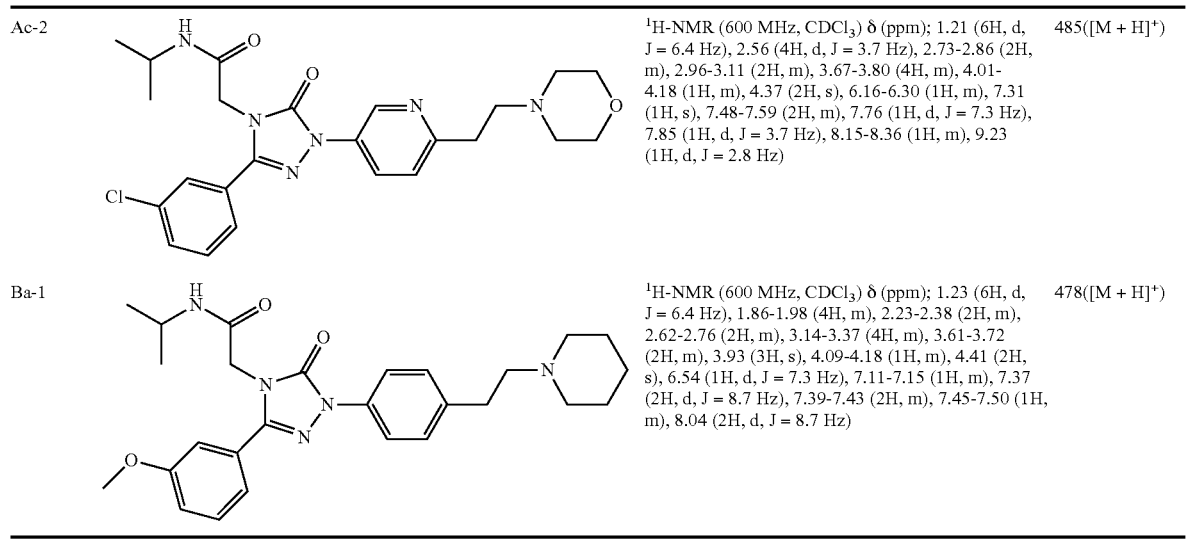 | ¹H-NMR (600 MHz, CDCl₃) δ (ppm); 1.21 (6H, d, J = 6.4 Hz), 2.56 (4H, d, J = 3.7 Hz), 2.73-2.86 (2H, m), 2.96-3.11 (2H, m), 3.67-3.80 (4H, m), 4.01-4.18 (1H, m), 4.37 (2H, s), 6.16-6.30 (1H, m), 7.31 (1H, s), 7.48-7.59 (2H, m), 7.76 (1H, d, J = 7.3 Hz), 7.85 (1H, d, J = 3.7 Hz), 8.15-8.36 (1H, m), 9.23 (1H, d, J = 2.8 Hz) | 485([M + H]⁺) |
| Ba-1 | | ¹H-NMR (600 MHz, CDCl₃) δ (ppm); 1.23 (6H, d, J = 6.4 Hz), 1.86-1.98 (4H, m), 2.23-2.38 (2H, m), 2.62-2.76 (2H, m), 3.14-3.37 (4H, m), 3.61-3.72 (2H, m), 3.93 (3H, s), 4.09-4.18 (1H, m), 4.41 (2H, s), 6.54 (1H, d, J = 7.3 Hz), 7.11-7.15 (1H, m), 7.37 (2H, d, J = 8.7 Hz), 7.39-7.43 (2H, m), 7.45-7.50 (1H, m), 8.04 (2H, d, J = 8.7 Hz) | 478([M + H]⁺) |

TABLE 1-4

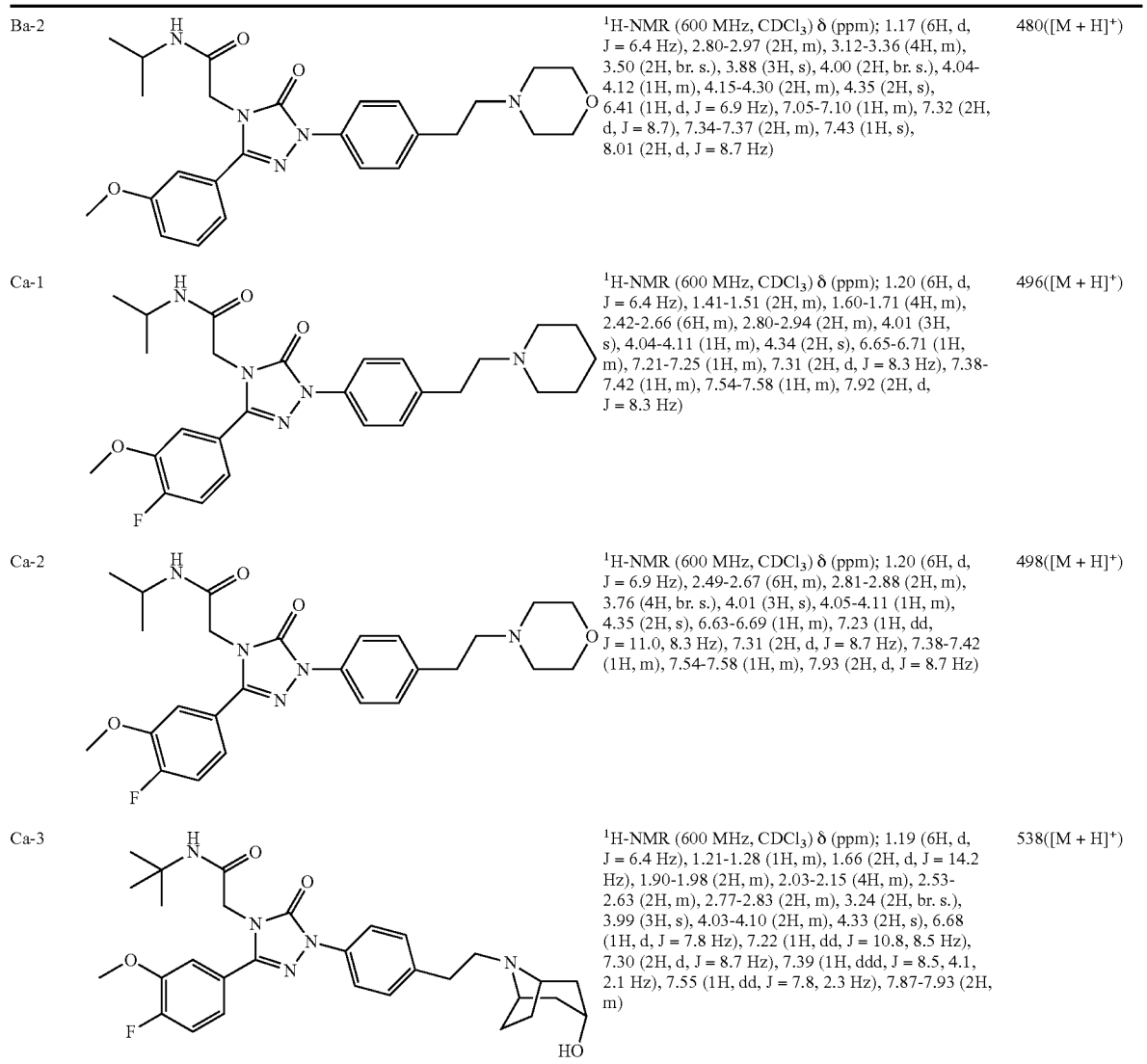

| | | | |
|---|---|---|---|
| Ba-2 | | ¹H-NMR (600 MHz, CDCl₃) δ (ppm); 1.17 (6H, d, J = 6.4 Hz), 2.80-2.97 (2H, m), 3.12-3.36 (4H, m), 3.50 (2H, br. s.), 3.88 (3H, s), 4.00 (2H, br. s.), 4.04-4.12 (1H, m), 4.15-4.30 (2H, m), 4.35 (2H, s), 6.41 (1H, d, J = 6.9 Hz), 7.05-7.10 (1H, m), 7.32 (2H, d, J = 8.7), 7.34-7.37 (2H, m), 7.43 (1H, s), 8.01 (2H, d, J = 8.7 Hz) | 480([M + H]⁺) |
| Ca-1 | | ¹H-NMR (600 MHz, CDCl₃) δ (ppm); 1.20 (6H, d, J = 6.4 Hz), 1.41-1.51 (2H, m), 1.60-1.71 (4H, m), 2.42-2.66 (6H, m), 2.80-2.94 (2H, m), 4.01 (3H, s), 4.04-4.11 (1H, m), 4.34 (2H, s), 6.65-6.71 (1H, m), 7.21-7.25 (1H, m), 7.31 (2H, d, J = 8.3 Hz), 7.38-7.42 (1H, m), 7.54-7.58 (1H, m), 7.92 (2H, d, J = 8.3 Hz) | 496([M + H]⁺) |
| Ca-2 | | ¹H-NMR (600 MHz, CDCl₃) δ (ppm); 1.20 (6H, d, J = 6.9 Hz), 2.49-2.67 (6H, m), 2.81-2.88 (2H, m), 3.76 (4H, br. s.), 4.01 (3H, s), 4.05-4.11 (1H, m), 4.35 (2H, s), 6.63-6.69 (1H, m), 7.23 (1H, dd, J = 11.0, 8.3 Hz), 7.31 (2H, d, J = 8.7 Hz), 7.38-7.42 (1H, m), 7.54-7.58 (1H, m), 7.93 (2H, d, J = 8.7 Hz) | 498([M + H]⁺) |
| Ca-3 | | ¹H-NMR (600 MHz, CDCl₃) δ (ppm); 1.19 (6H, d, J = 6.4 Hz), 1.21-1.28 (1H, m), 1.66 (2H, d, J = 14.2 Hz), 1.90-1.98 (2H, m), 2.03-2.15 (4H, m), 2.53-2.63 (2H, m), 2.77-2.83 (2H, m), 3.24 (2H, br. s.), 3.99 (3H, s), 4.03-4.10 (2H, m), 4.33 (2H, s), 6.68 (1H, d, J = 7.8 Hz), 7.22 (1H, dd, J = 10.8, 8.5 Hz), 7.30 (2H, d, J = 8.7 Hz), 7.39 (1H, ddd, J = 8.5, 4.1, 2.1 Hz), 7.55 (1H, dd, J = 7.8, 2.3 Hz), 7.87-7.93 (2H, m) | 538([M + H]⁺) |

TABLE 1-4-continued

| | | | |
|---|---|---|---|
| Ca-4 | 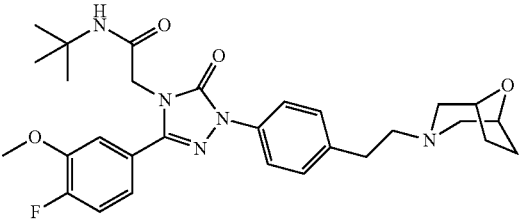 | ¹H-NMR (600 MHz, CDCl₃) δ (ppm); 1.16-1.21 (6H, m), 1.78-1.92 (4H, m), 2.33-2.39 (2H, m), 2.56 (2H, t, J = 7.6 Hz), 2.62 (2H, d, J = 11.0 Hz), 2.76 (2H, t, J = 7.3 Hz), 3.97-4.01 (3H, m), 4.07 (1H, dd, J = 14.2, 6.4 Hz), 4.28 (2H, d, J = 2.3 Hz), 4.34 (2H, s), 6.63-6.70 (1H, m), 7.22 (1H, dd, J = 11.0, 8.3 Hz), 7.30 (2H, d, J = 8.3 Hz), 7.39 (1H, ddd, J = 8.3, 4.1, 1.8 Hz), 7.53-7.57 (1H, m), 7.88-7.93 (2H, m) | 524([M + H]⁺) |
| Ca-5 | 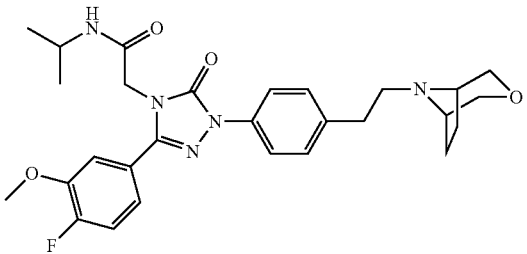 [SMILES: COc1cc(-c2nn(-c3ccc(CCN4C5CCC4COC5)cc3)c(=O)n2CC(=O)NC(C)C)ccc1F] | ¹H NMR (600 MHz, CDCl₃) δ (ppm); 1.20 (6H, d, J = 6.9 Hz), 1.86-1.96 (4H, m), 2.51-2.57 (2H, m), 2.79-2.85 (2H, m), 3.10 (2H, br. s.), 3.51-3.56 (2H, m), 3.74 (2H, d, J = 10.5 Hz), 4.01 (3H, s), 4.04-4.12 (1H, m), 4.35 (2H, s), 6.63-6.70 (1H, m), 7.23 (1H, dd, J = 10.8, 8.5 Hz), 7.32 (2H, d, J = 8.3 Hz), 7.38-7.42 (1H, m), 7.54-7.58 (1H, m), 7.92 (2H, d, J = 8.7 Hz) | 524([M + H]⁺) |

TABLE 1-5

| | | | |
|---|---|---|---|
| Cb-1 | 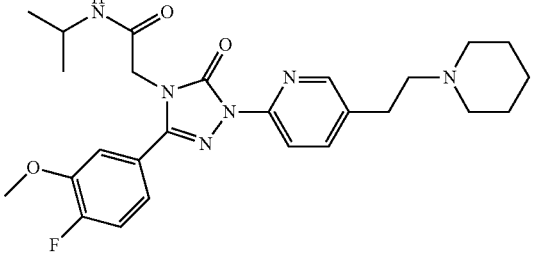 | ¹H-NMR (600 MHz, CDCl₃) δ (ppm); 1.19 (6H, d, J = 6.9 Hz), 1.43-1.50 (2H, m), 1.59-1.65 (4H, m), 2.42-2.51 (4H, m), 2.54-2.60 (2H, m), 2.82-2.87 (2H, m), 3.99 (3H, s), 4.05-4.12 (1H, m), 4.35 (2H, s), 6.48-6.55 (1H, m), 7.21 (1H, dd, J = 11.0, 8.3 Hz), 7.40-7.43 (1H, m), 7.56 (1H, dd, J = 8.0, 2.1 Hz), 7.71 (1H, dd, J = 8.3, 2.3 Hz), 8.03 (1H, d, J = 8.7 Hz), 8.45 (1H, d, J = 2.3 Hz) | 497([M + H]⁺) |
| Cb-2 | 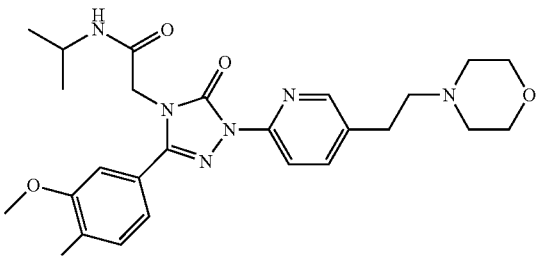 | ¹H-NMR (600 MHz, CDCl₃) δ (ppm); 1.20 (6H, d, J = 6.4 Hz), 2.53 (4H, br. s.), 2.60-2.65 (2H, m), 2.85 (2H, t, J = 7.6 Hz), 3.70-3.77 (4H, m), 3.99 (3H, s), 4.06-4.13 (1H, m), 4.35 (2H, s), 6.46-6.51 (1H, m), 7.21 (1H, dd, J = 10.8, 8.5 Hz), 7.39-7.44 (1H, m), 7.56 (1H, dd, J = 7.8, 2.3 Hz), 7.71 (1H, dd, J = 8.3, 2.3 Hz), 8.05 (1H, d, J = 8.7 Hz), 8.46 (1H, d, J = 1.8 Hz) | 499([M + H]⁺) |
| Cb-3 | 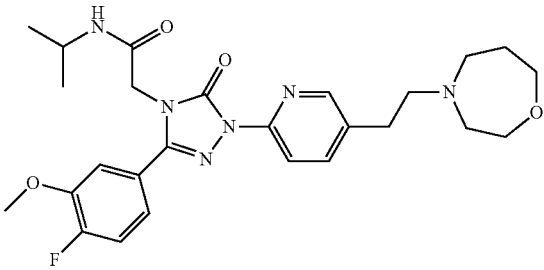 [SMILES: COc1cc(-c2nn(-c3ccc(CCN4CCCOCC4)cn3)c(=O)n2CC(=O)NC(C)C)ccc1F] | ¹H-NMR (600 MHz, CDCl₃) δ (ppm); 1.18-1.21 (8H, m), 1.88-1.96 (2H, m), 2.72-2.88 (8H, m), 3.72-3.77 (2H, m), 3.81 (2H, t, J = 6.0 Hz), 3.98-4.00 (3H, m), 4.05-4.13 (1H, m), 4.35 (2H, s), 6.47-6.54 (1H, m), 7.21 (1H, dd, J = 10.8, 8.5 Hz), 7.38-7.44 (1H, m), 7.56 (1H, dd, J = 7.8, 2.3 Hz), 7.71 (1H, dd, J = 8.3, 2.3 Hz), 8.05 (1H, d, J = 8.3 Hz), 8.45 (1H, d, J = 2.3 Hz) | 513([M + H]⁺) |

TABLE 1-5-continued

| | | | |
|---|---|---|---|
| Cb-4 | (structure) | ¹H-NMR (600 MHz, CDCl₃) δ (ppm); 1.19 (6H, d, J = 6.4 Hz), 1.21-1.25 (1H, m), 1.67 (2H, d, J = 14.2 Hz), 1.88-1.98 (2H, m), 2.02-2.15 (4H, m), 2.54-2.63 (2H, m), 2.77-2.84 (2H, m), 3.21 (2H, br. s.), 3.99 (3H, s), 4.03-4.13 (2H, m), 4.35 (2H, s), 6.46-6.55 (1H, m), 7.18-7.24 (1H, m), 7.39-7.44 (1H, m), 7.53-7.58 (1H, m), 7.69-7.75 (1H, m), 8.03 (1H, d, J = 8.3 Hz), 8.47 (1H, d, J = 2.3 Hz) | 539([M + H]⁺) |
| Cb-5 | (structure) | ¹H-NMR (600 MHz, CDCl₃ δ (ppm); 1.20 (6H, d, J = 6.4 Hz), 1.85-1.95 (4H, m), 2.51-2.57 (2H, m), 2.78-2.84 (2H, m), 3.07 (2H, br. s.), 3.52 (2H, d, J = 9.2 Hz), 3.70 (2H, d, J = 10.1 Hz), 3.99 (3H, s), 4.05-4.13 (1H, m), 4.35 (2H, s), 6.46-6.53 (1H, m), 7.19-7.24 (1H, m), 7.39-7.44 (1H, m), 7.53-7.58 (1H, m), 7.72-7.77 (1H, m), 8.05 (1H, d, J = 8.3 Hz), 8.48 (1H, d, J = 2.3 Hz) | 525([M + H]⁺) |
| Da-1 | (structure) | ¹H-NMR (600 MHz, CDCl₃) δ (ppm); 1.15-1.21 (6H, m), 1.82-2.05 (4H, m), 2.23-2.34 (2H, m), 2.59-2.68 (2H, m), 3.11-3.18 (2H, m), 3.25-3.31 (2H, m), 3.58-3.65 (2H, m), 4.03-4.11 (1H, m), 4.32 (2H, s), 6.35-6.41 (1H, m), 7.28-7.35 (3H, m), 7.79 (1H, ddd, J = 8.7, 4.1, 2.3 Hz), 7.93-8.00 (3H, m) | 500([M + H]⁺) |

TABLE 1-6

| | | | |
|---|---|---|---|
| Da-2 | (structure) | ¹H-NMR (600 MHz, CDCl₃) δ (ppm); 1.18 (6H, d, J = 6.9 Hz), 2.46-2.66 (6H, m), 2.76-2.88 (2H, m), 3.74 (4H, t, J = 4.6 Hz), 4.01-4.12 (1H, m), 4.31 (2H, s), 6.44 (1H, d, J = 7.3 Hz), 7.27-7.34 (3H, m), 7.77-7.83 (1H, m), 7.90 (2H, d, J = 8.3 Hz), 7.97 (1H, dd, J = 6.9, 2.3 Hz) | 502([M + H]⁺) |
| Da-3 | (structure) | ¹H-NMR (600 MHz, CDCl₃) δ (ppm); 1.19 (6H, d, J = 6.4 Hz), 2.66 (4H, br. s.), 3.29-3.42 (4H, m), 4.08 (1H, dq, J = 13.7, 6.7 Hz), 4.32 (2H, s), 4.73 (4H, s), 6.41 (1H, d, J = 6.4 Hz), 7.22-7.28 (2H, m), 7.31 (1H, t, J = 8.5 Hz), 7.80 (1H, ddd, J = 8.5, 4.4, 2.3 Hz), 7.91 (2H, d, J = 8.7 Hz), 7.97 (1H, dd, J = 6.9, 2.3 Hz) | 514([M + H]⁺) |

TABLE 1-6-continued

| | Structure | ¹H-NMR | MS |
|---|---|---|---|
| Da-4 | 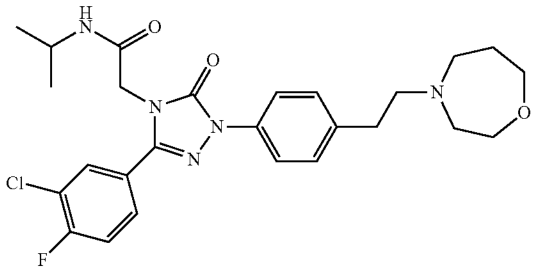 [SMILES: CC(C)NC(=O)Cn1c(-c2ccc(F)c(Cl)c2)nn(-c2ccc(CCN3CCCOCC3)cc2)c1=O] | ¹H-NMR (600 MHz, CDCl₃) δ (ppm); 1.18 (6H, dd, J = 6.6, 1.1 Hz), 1.46-1.54 (2H, m), 1.86-1.96 (2H, m), 2.67-2.73 (2H, m), 2.74-2.86 (4H, m), 3.65-3.70 (1H, m), 3.71-3.76 (1H, m), 3.77-3.85 (2H, m), 4.02-4.13 (1H, m), 4.29-4.35 (2H, m), 6.46 (1H, br. s.), 7.26-7.33 (2H, m), 7.43-7.48 (1H, m), 7.76-7.83 (1H, m), 7.86-7.94 (2H, m), 7.94-8.00 (1H, m) | 516([M + H]⁺) |
| Da-5 | 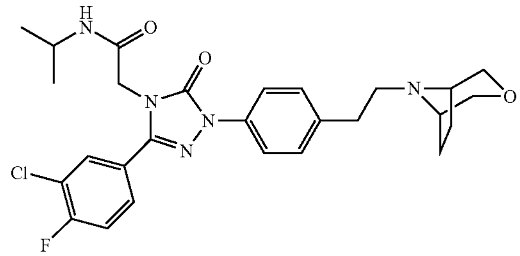 [SMILES: CC(C)NC(=O)Cn1c(-c2ccc(F)c(Cl)c2)nn(-c2ccc(CCN3C4CCC3COC4)cc2)c1=O] | ¹H-NMR (600 MHz, CDCl₃) δ (ppm); 1.18 (6H, d, J = 6.9 Hz), 1.83-2.04 (4H, m), 2.49-2.55 (2H, m), 2.77-2.83 (2H, m), 3.08 (2H, br. s.), 3.51 (2H, dd, J = 10.5, 1.8 Hz), 3.72 (2H, d, J = 10.1 Hz), 4.02-4.12 (1H, m), 4.31 (2H, s), 6.45 (1H, d, J = 6.9 Hz), 7.27-7.33 (3H, m), 7.78-7.82 (1H, m), 7.87-7.91 (2H, m), 7.97 (1H, dd, J = 6.9, 2.3 Hz) | 528([M + H]⁺) |
| Da-6 | 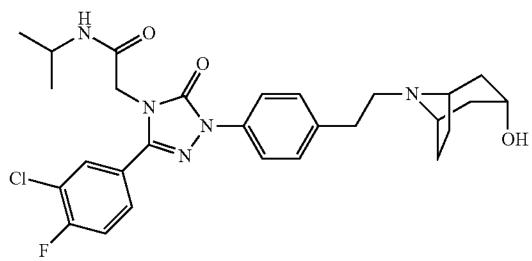 [SMILES: CC(C)NC(=O)Cn1c(-c2ccc(F)c(Cl)c2)nn(-c2ccc(CCN3C4CCC3CC(O)C4)cc2)c1=O] | ¹H-NMR (600 MHz, DMSO-d₆) δ (ppm); 0.97 (6H, d, J = 6.9 Hz), 1.83-1.92 (2H, m), 2.07-2.16 (2H, m), 2.18-2.26 (2H, m), 2.28-2.34 (2H, m), 3.04 (2H, dd, J = 8.7, 3.7 Hz), 3.09-3.19 (2H, m), 3.70-3.77 (1H, m), 3.81-3.90 (2H, m), 3.96 (1H, d, J = 5.5 Hz), 4.36 (2H, s), 4.90 (1H, d, J = 0.9 Hz), 7.40 (1H, d, J = 7.8 Hz), 7.56-7.66 (1H, m), 7.67-7.73 (1H, m), 7.86-7.96 (2H, m), 8.21 (1H, d, J = 7.8 Hz), 8.28 (1H, s), 9.40 (1H, br. s.) | 542([M + H]⁺) |
| Db-1 | 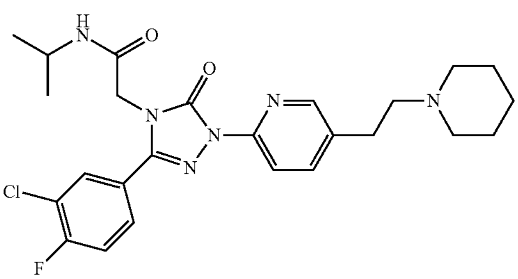 [SMILES: CC(C)NC(=O)Cn1c(-c2ccc(F)c(Cl)c2)nn(-c2ccc(CCN3CCCCC3)cn2)c1=O] | ¹H-NMR (600 MHz, CDCl₃) δ (ppm); 1.10-1.20 (6H, m), 1.45 (2H, br. s.), 1.70-1.80 (2H, m), 2.45 (4H, br. s.), 2.51-2.60 (2H, m), 2.78-2.88 (2H, m), 2.99-3.09 (2H, m), 3.99-4.14 (1H, m), 4.28-4.37 (2H, m), 6.27-6.38 (1H, m), 7.61-7.74 (2H, m), 7.76-7.84 (1H, m), 7.97-8.05 (2H, m), 8.43 (1H, s) | 501([M + H]⁺) |

TABLE 1-7

| | Structure | ¹H-NMR | MS |
|---|---|---|---|
| Db-2 | 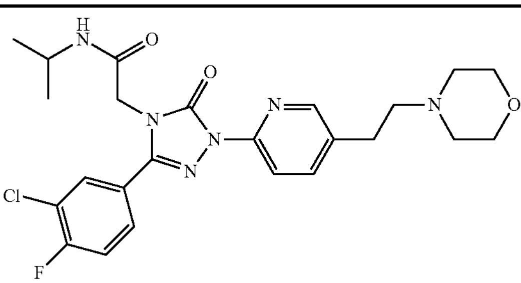 | ¹H-NMR (600 MHz, CDCl₃) δ (ppm); 1.15-1.20 (6H, m), 2.51 (4H, br. s.), 2.56-2.64 (2H, m), 2.83 (2H, t, J = 7.8 Hz), 3.72 (4H, t, J = 4.6 Hz), 4.02-4.13 (1H, m), 4.32 (2H, s), 6.30 (1H, d, J = 7.8 Hz), 7.26-7.32 (1H, m), 7.70 (1H, dd, J = 8.7, 2.3 Hz), 7.76-7.85 (1H, m), 7.98-8.07 (2H, m), 8.44 (1H, d, J = 2.3 Hz) | 503([M + H]⁺) |

TABLE 1-7-continued

| | | | |
|---|---|---|---|
| Db-3 | 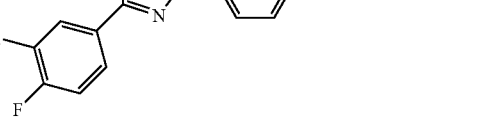 | ¹H-NMR (600 MHz, CDCl₃) δ (ppm); 1.19 (6H, d, J = 6.4 Hz), 3.11-3.23 (2H, m), 3.27-3.72 (4H, m), 3.78 (2H, d, J = 13.3 Hz), 3.98-4.14 (1H, m), 4.34 (2H, s), 4.68-4.92 (4H, m), 6.40 (1H, d, J = 1.4 Hz), 7.26-7.31 (1H, m), 7.73 (1H, d, J = 6.0 Hz), 7.79-7.86 (1H, m), 7.86-7.94 (1H, m), 8.02 (1H, d, J = 8.7 Hz), 8.49 (1H, s) | 515([M + H]⁺) |
| Db-4 | 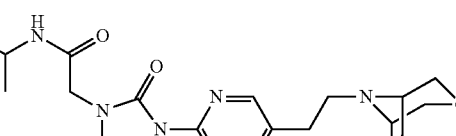 | ¹H-NMR (600 MHz, CDCl₃) δ (ppm); 1.19 (6H, d, J = 6.4 Hz), 3.11-3.23 (2H, m), 3.27-3.72 (4H, m), 3.78 (2H, d, J = 13.3 Hz), 3.98-4.14 (1H, m), 4.34 (2H, s), 4.68-4.92 (4H, m), 6.40 (1H, d, J = 1.4 Hz), 7.26-7.31 (1H, m), 7.73 (1H, d, J = 6.0 Hz), 7.79-7.86 (1H, m), 7.86-7.94 (1H, m), 8.02 (1H, d, J = 8.7 Hz), 8.49 (1H, s) | 529([M + H]⁺) |
| Db-5 | 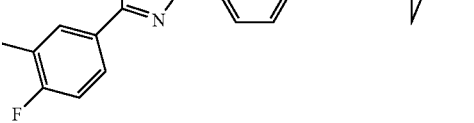 | ¹H-NMR (600 MHz, DMSO-d₆) δ (ppm); 0.97 (6H, d, J = 6.4 Hz), 1.88 (2H, s), 2.28 (6H, s), 3.05 (2H, br. s.), 3.18 (2H, br. s.), 3.65-3.79 (1H, m), 3.82-4.08 (2H, m), 4.36 (2H, s), 4.90 (1H, s), 7.62 (1H, d, J = 8.7 Hz), 7.71 (1H, s), 7.82-7.99 (3H, m), 8.14-8.30 (1H, m), 8.44 (1H, br. s.), 8.98-9.20 (1H, m) | 543([M + H]⁺) |
| Ea-1 | 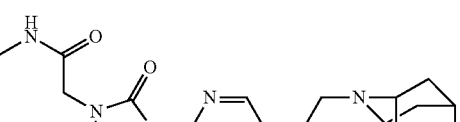 | ¹H-NMR (600 MHz, CDCl₃) δ (ppm): 1.19 (6H, d, J = 6.4 Hz), 1.42-1.66 (6H, m), 2.41-2.52 (4H, m), 2.54-2.60 (2H, m), 2.80-2.87 (2H, m), 4.04-4.12 (1H, m), 4.34 (2H, s), 6.41 (1H, d, J = 7.8 Hz), 7.30 (2H, d, J = 8.7 Hz), 7.67 (1H, t, J = 7.8 Hz), 7.79-7.84 (1H, m), 7.90 (2H, d, J = 8.7 Hz), 8.16-8.21 (2H, m) | 473([M + H]⁺) |
| Ea-2 | 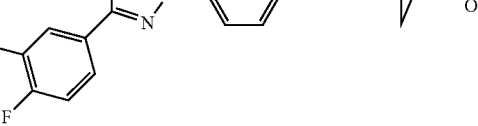 | ¹H-NMR (600 MHz, CDCl₃) δ (ppm); 1.19 (6H, d, J = 6.9 Hz), 2.53 (4H, br. s.), 2.59-2.64 (2H, m), 2.81-2.86 (2H, m), 3.74 (4H, t, J = 4.6 Hz), 4.08 (1H, dq, J = 13.8, 6.9 Hz), 4.34 (2H, s), 6.38 (1H, d, J = 7.3 Hz), 7.30 (2H, d, J = 8.7 Hz), 7.65-7.69 (1H, m), 7.80-7.83 (1H, m), 7.91 (2H, d, J = 8.7 Hz), 8.16-8.20 (2H, m) | 475([M + H]⁺) |

TABLE 1-8

| | | | |
|---|---|---|---|
| Ea-3 | | ¹H-NMR (600 MHz, CDCl₃) δ (ppm); 1.20 (6H, d, J = 6.4 Hz), 2.61-2.69 (4H, m), 3.35 (4H, s), 4.08 (1H, dq, J = 13.7, 6.7 Hz), 4.34 (2H, s), 4.73 (4H, s), 6.38 (1H, d, J = 6.9 Hz), 7.25-7.29 (2H, m), 7.68 (1H, t, J = 7.6 Hz), 7.82 (1H, d, J = 7.8 Hz), 7.91 (2H, d, J = 8.7 Hz), 8.17-8.20 (2H, m) | 487([M + H]⁺) |

TABLE 1-8-continued

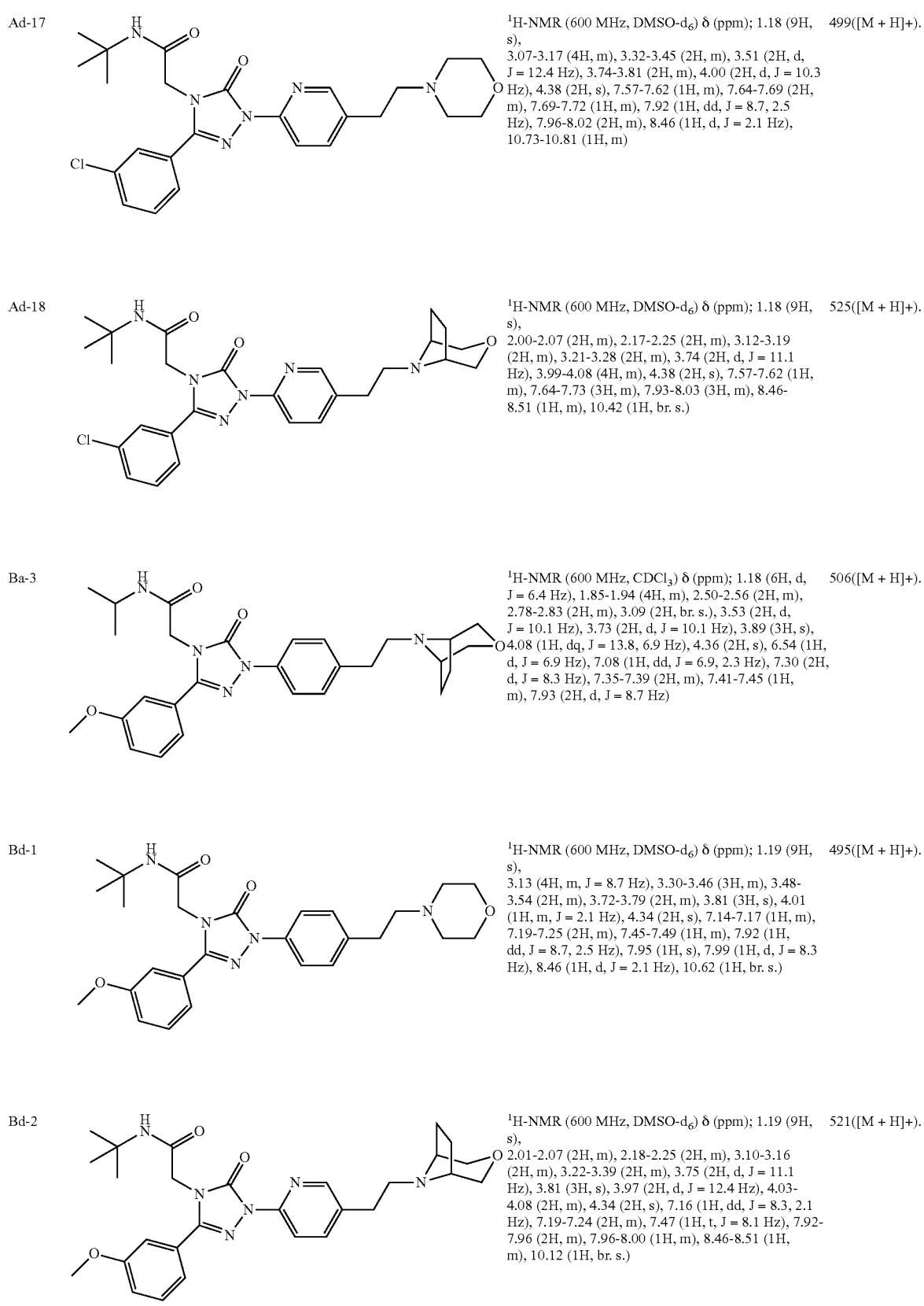

| | | |
|---|---|---|
| Ad-17 | | ¹H-NMR (600 MHz, DMSO-d₆) δ (ppm); 1.18 (9H, s), 3.07-3.17 (4H, m), 3.32-3.45 (2H, m), 3.51 (2H, d, J = 12.4 Hz), 3.74-3.81 (2H, m), 4.00 (2H, d, J = 10.3 Hz), 4.38 (2H, s), 7.57-7.62 (1H, m), 7.64-7.69 (2H, m), 7.69-7.72 (1H, m), 7.92 (1H, dd, J = 8.7, 2.5 Hz), 7.96-8.02 (2H, m), 8.46 (1H, d, J = 2.1 Hz), 10.73-10.81 (1H, m) | 499([M + H]+). |
| Ad-18 | | ¹H-NMR (600 MHz, DMSO-d₆) δ (ppm); 1.18 (9H, s), 2.00-2.07 (2H, m), 2.17-2.25 (2H, m), 3.12-3.19 (2H, m), 3.21-3.28 (2H, m), 3.74 (2H, d, J = 11.1 Hz), 3.99-4.08 (4H, m), 4.38 (2H, s), 7.57-7.62 (1H, m), 7.64-7.73 (3H, m), 7.93-8.03 (3H, m), 8.46-8.51 (1H, m), 10.42 (1H, br. s.) | 525([M + H]+). |
| Ba-3 | | ¹H-NMR (600 MHz, CDCl₃) δ (ppm); 1.18 (6H, d, J = 6.4 Hz), 1.85-1.94 (4H, m), 2.50-2.56 (2H, m), 2.78-2.83 (2H, m), 3.09 (2H, br. s.), 3.53 (2H, d, J = 10.1 Hz), 3.73 (2H, d, J = 10.1 Hz), 3.89 (3H, s), 4.08 (1H, dq, J = 13.8, 6.9 Hz), 4.36 (2H, s), 6.54 (1H, d, J = 6.9 Hz), 7.08 (1H, dd, J = 6.9, 2.3 Hz), 7.30 (2H, d, J = 8.3 Hz), 7.35-7.39 (2H, m), 7.41-7.45 (1H, m), 7.93 (2H, d, J = 8.7 Hz) | 506([M + H]+). |
| Bd-1 | | ¹H-NMR (600 MHz, DMSO-d₆) δ (ppm); 1.19 (9H, s), 3.13 (4H, m, J = 8.7 Hz), 3.30-3.46 (3H, m), 3.48-3.54 (2H, m), 3.72-3.79 (2H, m), 3.81 (3H, s), 4.01 (1H, m, J = 2.1 Hz), 4.34 (2H, s), 7.14-7.17 (1H, m), 7.19-7.25 (2H, m), 7.45-7.49 (1H, m), 7.92 (1H, dd, J = 8.7, 2.5 Hz), 7.95 (1H, s), 7.99 (1H, d, J = 8.3 Hz), 8.46 (1H, d, J = 2.1 Hz), 10.62 (1H, br. s.) | 495([M + H]+). |
| Bd-2 | | ¹H-NMR (600 MHz, DMSO-d₆) δ (ppm); 1.19 (9H, s), 2.01-2.07 (2H, m), 2.18-2.25 (2H, m), 3.10-3.16 (2H, m), 3.22-3.39 (2H, m), 3.75 (2H, d, J = 11.1 Hz), 3.81 (3H, s), 3.97 (2H, d, J = 12.4 Hz), 4.03-4.08 (2H, m), 4.34 (2H, s), 7.16 (1H, dd, J = 8.3, 2.1 Hz), 7.19-7.24 (2H, m), 7.47 (1H, t, J = 8.1 Hz), 7.92-7.96 (2H, m), 7.96-8.00 (1H, m), 8.46-8.51 (1H, m), 10.12 (1H, br. s.) | 521([M + H]+). |

Synthesis of Example Ad-1

N-Tert-Butyl-2-[3-(3-chlorophenyl)-1-{4-[2-(morpholin-4-yl)ethyl]phenyl}-5-oxo-1,5-dihydro-4H-1,2,4-triazol-4-yl]acetamide

[Formula 165]

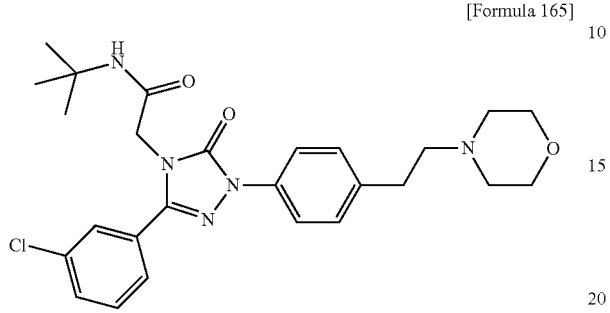

A mixture of the compound (36 mg) prepared in Reference Example P-P1, tert-butylamine (0.086 mL), HATU (0.046 g), DIEA (0.028 mL), and DMF (1.00 mL) was stirred at room temperature overnight. The mixture was separated between a saturated aqueous sodium bicarbonate solution (20 mL) and ethyl acetate (20 mL), and the aqueous layer was extracted with ethyl acetate (20 mL×3). The combined organic layer was filtered through a phase separator, and the filtrate was concentrated under reduced pressure. The residue was purified by silica gel column chromatography (SNAP Cartridge HP-Sil: 10 g, mobile phase: CHCl$_3$/MeOH=100/0 to 96/4 (v/v)). The resulting solid was washed with n-hexane and was collected by filtration to yield the title compound (9 mg, colorless solid).

MS (ESI pos.) m/z: 498 ([M+H]$^+$).

$^1$H-NMR (600 MHz, CDCl$_3$)δ(ppm); 1.37 (9H, s), 2.50-2.69 (6H, m), 2.81-2.88 (2H, m), 3.73-3.79 (4H, m), 4.30 (2H, s), 6.30-6.33 (1H, m), 7.27-7.31 (2H, m), 7.45-7.53 (2H, m), 7.73-7.76 (1H, m), 7.81-7.83 (1H, m), 7.91-7.95 (2H, m).

The following compounds were synthesized as in Example Ad-1

Example Ad-2

2-[3-(3-Chlorophenyl)-1-{4-[2-(morpholin-4-yl)ethyl]phenyl}-5-oxo-1,5-dihydro-4H-1,2,4-triazol-4-yl]-N-(1,1,1-trifluoropropan-2-yl)acetamide (Synthesis from Reference Example P-P1 and 1,1,1-trifluoropropane-2-amine)

[Formula 166]

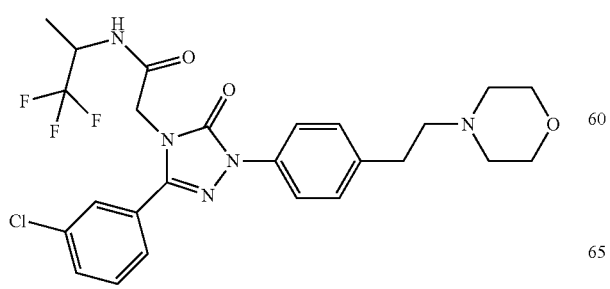

MS (ESI pos.) m/z: 538 ([M+H]$^+$).

$^1$H-NMR (600 MHz, CDCl$_3$)δ(ppm); 1.37 (3H, d, J=6.9 Hz), 2.49-2.57 (4H, m), 2.62 (2H, d, J=8.3 Hz), 2.82-2.86 (2H, m), 3.75 (4H, t, J=4.6 Hz), 4.43 (2H, s), 4.66-4.74 (1H, m), 7.04-7.09 (1H, m), 7.28-7.32 (2H, m), 7.46-7.51 (1H, m), 7.51-7.55 (1H, m), 7.66-7.69 (1H, m), 7.80-7.83 (1H, m), 7.89-7.93 (2H, m).

Example Ad-3

2-[3-(3-Chlorophenyl)-1-{4-[2-(morpholin-4-yl)ethyl]phenyl}-5-oxo-1,5-dihydro-4H-1,2,4-triazol-4-yl]-N-(1-hydroxy-2-methylpropan-2-yl)acetamide (Synthesis from Reference Example P-P1 and 2-amino-2-methylpropan-1-ol)

[Formula 167]

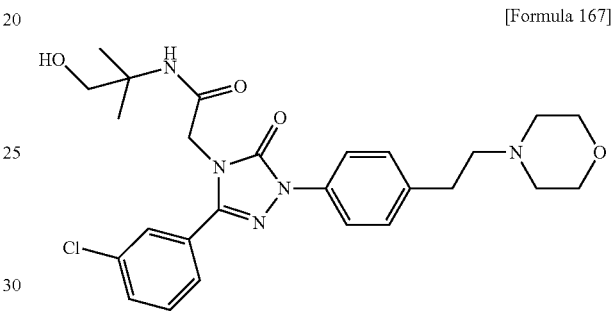

MS (ESI pos.) m/z: 514 ([M+H]$^+$).

$^1$H-NMR (600 MHz, CDCl$_3$)δ(ppm); 1.33 (6H, s), 2.49-2.56 (4H, m), 2.58-2.64 (2H, m), 2.81-2.86 (2H, m), 3.62 (2H, s), 3.75 (4H, t, J=4.6 Hz), 4.35 (2H, s), 6.57-6.60 (1H, m), 7.27-7.31 (2H, m), 7.46-7.50 (1H, m), 7.51-7.55 (1H, m), 7.68-7.72 (1H, m), 7.78-7.81 (1H, m), 7.89-7.93 (2H, m).

Example Ad-4

2-[3-(3-Chlorophenyl)-1-{4-[2-(morpholin-4-yl)ethyl]phenyl}-5-oxo-1,5-dihydro-4H-1,2,4-triazol-4-yl]-N-cyclobutylacetamide (Synthesis from Reference Example P-P1 and cyclobutanamine)

[Formula 168]

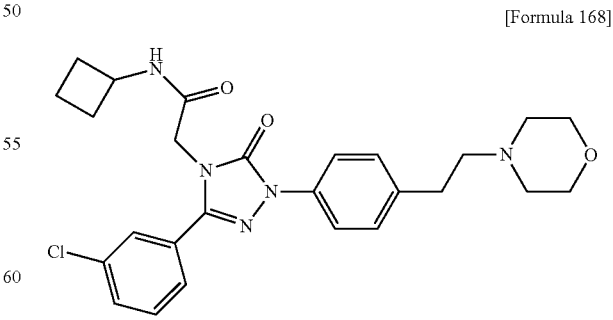

MS (ESI pos.) m/z: 496 ([M+H]$^+$).

$^1$H-NMR (600 MHz, CDCl$_3$)δ(ppm); 1.65-2.02 (4H, m), 2.31-2.40 (2H, m), 2.50-2.57 (4H, m), 2.59-2.64 (2H, m), 2.81-2.87 (2H, m), 3.75 (4H, t, J=4.6 Hz), 3.98-4.43 (3H, m), 6.87 (1H, d, J=7.3 Hz), 7.28-7.32 (2H, m), 7.45-7.54 (2H, m), 7.71-7.76 (1H, m), 7.84-7.86 (1H, m), 7.90-7.94 (2H, m).

Example Ad-5

2-[3-(3-Chlorophenyl)-1-{4-[2-(morpholin-4-yl)ethyl]phenyl}-5-oxo-1,5-dihydro-4H-1,2,4-triazol-4-yl]-N-(oxetan-3-yl)acetamide (Synthesis from Reference Example P-P1 and oxetane-3-amine)

[Formula 169]

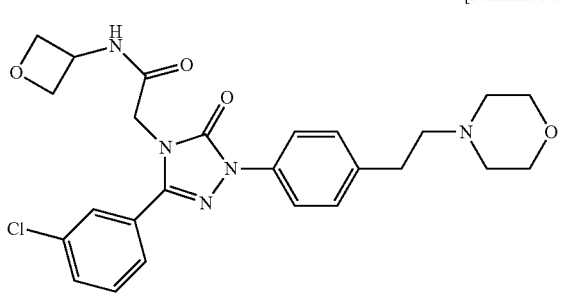

MS (ESI pos.) m/z: 498 ([M+H]$^+$).

$^1$H-NMR (600 MHz, CDCl$_3$)δ(ppm); 2.49-2.57 (4H, m), 2.60-2.64 (2H, m), 2.81-2.87 (2H, m), 3.75 (4H, t, J=4.4 Hz), 4.41 (2H, s), 4.56 (2H, t, J=6.6 Hz), 4.92 (2H, t, J=7.3 Hz), 5.03-5.09 (1H, m), 7.29-7.33 (2H, m), 7.47-7.50 (1H, m), 7.51-7.56 (2H, m), 7.69-7.72 (1H, m), 7.82-7.85 (1H, m), 7.89-7.93 (2H, m).

Example Ad-6

2-[3-(3-Chlorophenyl)-1-{4-[2-(morpholin-4-yl)ethyl]phenyl}-5-oxo-1,5-dihydro-4H-1,2,4-triazol-4-yl]-N-(cyclopropylmethyl)acetamide (Synthesis from Reference Example P-P1 and 1-cyclopropylmethanamine)

[Formula 170]

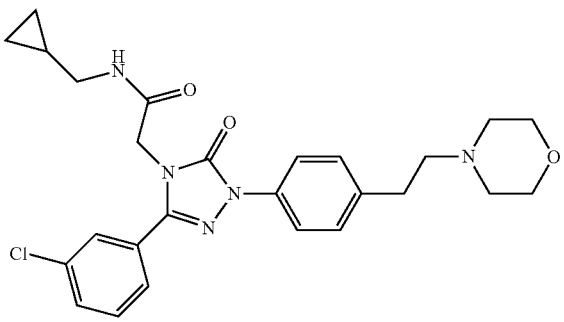

MS (ESI pos.) m/z: 496 ([M+H]$^+$).

$^1$H-NMR (600 MHz, CDCl$_3$)δ(ppm); 0.20-0.25 (2H, m), 0.50-0.55 (2H, m), 0.94-1.01 (1H, m), 2.49-2.57 (4H, m), 2.60-2.64 (2H, m), 2.81-2.87 (2H, m), 3.17 (2H, dd, J=7.1, 5.7 Hz), 3.75 (4H, t, J=4.4 Hz), 4.40 (2H, s), 6.67-6.75 (1H, m), 7.28-7.32 (2H, m), 7.45-7.55 (2H, m), 7.73-7.77 (1H, m), 7.84-7.88 (1H, m), 7.90-7.95 (2H, m).

Example Ad-20

2-[3-(3-Chlorophenyl)-1-{4-[2-(morpholin-4-yl)ethyl]phenyl}-5-oxo-1,5-dihydro-4H-1,2,4-triazol-4-yl]-N-(1-hydroxypropan-2-yl)acetamide (Synthesis from Reference Example P-P1 and DL-alaninol)

[Formula 171]

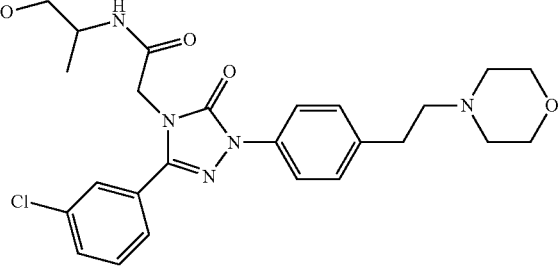

MS (ESI pos.) m/z: 500 ([M+H]$^+$).

$^1$H-NMR (600 MHz, DMSO-d$_6$)δ(ppm); 0.97 (3H, d, J=6.6 Hz), 2.40-2.46 (4H, m), 2.51-2.55 (2H, m), 2.74-2.80 (2H, m), 3.16-3.22 (1H, m), 3.26-3.31 (1H, m), 3.54-3.61 (4H, m), 3.67-3.76 (1H, m), 4.42 (2H, s), 4.71 (1H, t, J=5.6 Hz), 7.32-7.39 (2H, m), 7.55-7.61 (1H, m), 7.63-7.69 (2H, m), 7.71-7.75 (1H, m), 7.83-7.89 (2H, m), 8.17 (1H, d, J=8.3 Hz).

Synthesis of Example Ad-7

2-[3-(3-Chlorophenyl)-1-{3-fluoro-4-[2-(morpholin-4-yl)ethyl]phenyl}-5-oxo-1,5-dihydro-4H-1,2,4-triazol-4-yl]-N-(propan-2-yl)acetamide

[Formula 172]

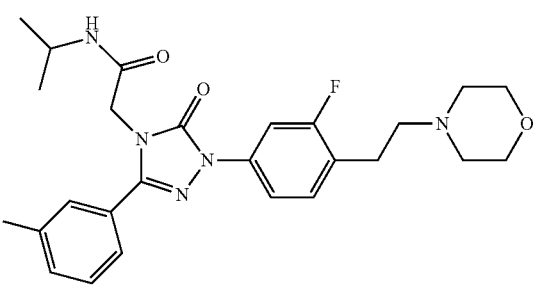

In a nitrogen gas flow, a suspension of the compound (80 mg) prepared in Reference Example P-Q2, Reference Example P-R1-1 (82 mg), copper iodide (52 mg), tripotassium phosphate (115 mg), and trans-(1R,2R)—N,N'-bismethyl-1,2-cyclohexanediamine (0.04 mL) in 1,4-dioxane (4 mL) was stirred at an outside temperature of 80° C. for 2 days. After cooling, 20% aqueous ammonia was added thereto, followed by extraction with toluene (containing 10% EtOAc). The organic layer was dried over Na$_2$SO$_4$. The desiccant was removed by filtration, and the filtrate was concentrated under reduced pressure. The residue was purified by silica gel column chromatography (SNAP Cartridge KP-NH: 28 g, mobile phase: n-hexane/CHCl₃=80/20 to 0/100 (v/v)). The resulting compound was washed with a solvent mixture (n-hexane/EtOAc=6/1 (v/v)), and the solid was collected by filtration to yield the title compound (3 mg, colorless powder).

¹H-NMR (600 MHz, CDCl₃)δ(ppm); 1.19 (6H, d, J=6.6 Hz), 2.53 (4H, br. s.), 2.58-2.63 (2H, m), 2.82-2.88 (2H, m), 3.74 (4H, t, J=4.3 Hz), 4.06-4.12 (1H, m), 4.34 (2H, s), 6.27 (1H, d, J=5.8 Hz), 7.21-7.32 (1H, m), 7.48 (1H, d, J=7.4 Hz), 7.51-7.54 (1H, m), 7.74 (1H, d, J=7.4 Hz), 7.76-7.80 (2H, m), 7.84 (1H, t, J=1.9 Hz).

MS (ESI pos.) m/z: 502 ([M+H]⁺).

The following compounds were synthesized as in Example Ad-7:

Example Ad-8: 2-[3-(3-Chlorophenyl)-1-{3-fluoro-4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-Q2 and Reference Example P-R1-2), Example Ad-9: 2-[3-(3-Chlorophenyl)-1-{3-methoxy-4-[2-(morpholin-4-yl)ethyl]phenyl}-5-oxo-1,5-dihydro-4H-1,2,4-triazol-4-yl]-N-(propan-2-yl)acetamide (Synthesis from Reference Example P-Q2 and Reference Example P-R2-1), Example Ad-10: 2-[3-(3-Chlorophenyl)-1-{3-methoxy-4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-Q2 and Reference Example P-R2-2), Example Ad-11: 2-[3-(3-Chlorophenyl)-1-{2-fluoro-4-[2-(morpholin-4-yl)ethyl]phenyl}-5-oxo-1,5-dihydro-4H-1,2,4-triazol-4-yl]-N-(propan-2-yl)acetamide (Synthesis from Reference Example P-Q2 and Reference Example P-R3-1), Example Ad-12: 2-[3-(3-Chlorophenyl)-1-{2-methoxy-4-[2-(morpholin-4-yl)ethyl]phenyl}-5-oxo-1,5-dihydro-4H-1,2,4-triazol-4-yl]-N-(propan-2-yl)acetamide (Synthesis from Reference Example P-Q2 and Reference Example P-R4-1), Example Ad-13: 2-[3-(3-Chlorophenyl)-1-{4-[2-(morpholin-4-yl)propyl]phenyl}-5-oxo-1,5-dihydro-4H-1,2,4-triazol-4-yl]-N-(propan-2-yl)acetamide (Synthesis from Reference Example P-Q2 and Reference Example P-S1), Example Ad-14: 2-[3-(3-Chlorophenyl)-1-{4-[2-(3-oxa-8-azabicyclo[3.2.1]oct-8-yl)propyl]phenyl}-5-oxo-1,5-dihydro-4H-1,2,4-triazol-4-yl]-N-(propan-2-yl)acetamide (Synthesis from Reference Example P-Q2 and Reference Example P-R5-2), Example Ad-15: 2-[3-(3-Chlorophenyl)-1-{5-[2-(morpholin-4-yl)propyl]pyridin-2-yl}-5-oxo-1,5-dihydro-4H-1,2,4-triazol-4-yl]-N-(propan-2-yl)acetamide (Synthesis from Reference Example P-Q2 and Reference Example P-R6-1), Example Ad-16: 2-[3-(3-Chlorophenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide (Synthesis from Reference Example P-Q2 and Reference Example P-R6-2), Example Ia-1: 2-(3-[3-(Methylsulfonyl)phenyl]-1-{4-[2-(morpholin-4-yl)ethyl]phenyl}-5-oxo-1,5-dihydro-4H-1,2,4-triazol-4-yl)-N-(propan-2-yl)acetamide (Synthesis from Reference Example P-Q1 and 4-[2-(4-bromophenyl)ethyl]morpholine), Example Bd-3: N-Tert-Butyl-2-[3-(3-methoxyphenyl)-1-{4-[2-(3-oxa-8-azabicyclo[3.2.1]oct-8-yl)propyl]phenyl}-5-oxo-1,5-dihydro-4H-1,2,4-triazol-4-yl]acetamide (Synthesis from Reference Example P-Q4 and Reference Example P-R5-2), Example Bd-4: N-Tert-Butyl-2-[3-(3-methoxyphenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]acetamide (Synthesis from Reference Example P-Q4 and Reference Example P-R6-2), Example Cd-2: 2-[3-(4-Fluoro-3-methoxyphenyl)-1-{4-[2-(3-oxa-8-azabicyclo[3.2.1]oct-8-yl)propyl]phenyl}-5-oxo-1,5-dihydro-4H-1,2,4-triazol-4-yl]-N-(propan-2-yl)acetamide (Synthesis from Reference Example P-Q3 and Reference Example P-R5-2), Example Cd-3: 2-[3-(4-Fluoro-3-methoxyphenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide (Synthesis from Reference Example P-Q3 and Reference Example P-R6-2), Example Cd-4: 2-[3-(4-Fluoro-3-methoxyphenyl)-1-{4-[(4-methylpiperazin-1-yl)methyl]phenyl}-5-oxo-1,5-dihydro-4H-1,2,4-triazol-4-yl]-N-(propan-2-yl)acetamide (Synthesis from Reference Example P-Q3 and 1-[(4-bromophenyl)methyl]-4-methylpiperazine), Example Ja-1: 2-[3-(6-Methoxypyridin-2-yl)-1-{4-[2-(morpholin-4-yl)ethyl]phenyl}-5-oxo-1,5-dihydro-4H-1,2,4-triazol-4-yl]-N-(propan-2-yl)acetamide (Synthesis from Reference Example P-Q5 and 4-[2-(4-bromophenyl)ethyl]morpholine), and Example Ja-2: 2-[3-(6-Methoxypyridin-2-yl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide (Synthesis from Reference Example P-Q5 and Reference Example P-R7-1).

The results of ¹H-NMR and MS of Examples Ad-8 to Ad-16, Ia-1, Bd-3, Bd-4, Cd-2 to Cd-4, Ja-1, and Ja-2 are shown in Tables 2-1 to 2-3.

TABLE 2-1

| Example | Structure | ¹H NMR | MS (ESI pos.) m/z |
|---------|-----------|--------|-------------------|
| Ad-8 | 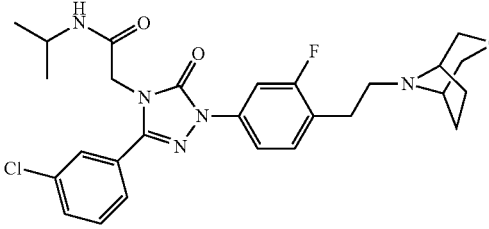 | ¹H-NMR (600 MHz, CDCl₃) δ (ppm); 1.19 (6H, d, J = 6.6 Hz), 1.85-1.94 (4H, m), 2.51 (2H, t, J = 7.6 Hz), 2.82 (2H, t, J = 7.6 Hz), 3.09 (2H, br. s.), 3.52 (2H, d, J = 9.5 Hz), 3.71 (2H, d, J = 10.3 Hz), 4.09 (1H, dq, J = 13.9, 6.8 Hz), 4.34 (2H, s), 6.28 (1H, d, J = 6.6 Hz), 7.28-7.33 (1H, m), 7.46-7.50 (1H, m), 7.51-7.54 (1H, m), 7.73-7.79 (3H, m), 7.84 (1H, t, J = 1.7 Hz) | 528([M + H]+). |

TABLE 2-1-continued

| Example | Structure | ¹H NMR | MS (ESI pos.) m/z |
|---|---|---|---|
| Ad-9 | 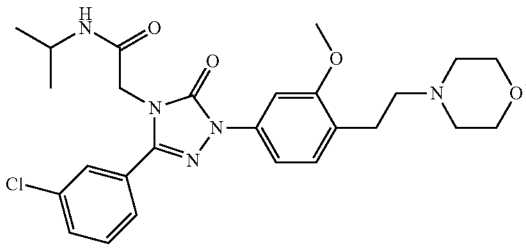 [SMILES: COc1cc(-n2nc(-c3cccc(Cl)c3)n(CC(=O)NC(C)C)c2=O)ccc1CCN1CCOCC1] | ¹H-NMR (600 MHz, CDCl₃) δ (ppm); 1.19 (6H, d, J = 6.6 Hz), 2.50-2.60 (6H, m), 2.80-2.86 (2H, m), 3.75 (4H, t, J = 4.3 Hz), 3.89 (3H, s), 4.06-4.13 (1H, m), 4.34 (2H, s), 6.34 (1H, d, J = 6.6 Hz), 7.21 (1H, d, J = 7.8 Hz), 7.46-7.49 (1H, m), 7.51-7.55 (2H, m), 7.57 (1H, d, J = 2.1 Hz), 7.75 (1H, dt, J = 7.5, 1.4 Hz), 7.85 (1H, t, J = 1.7 Hz) | 514([M + H]+). |
| Ad-10 | 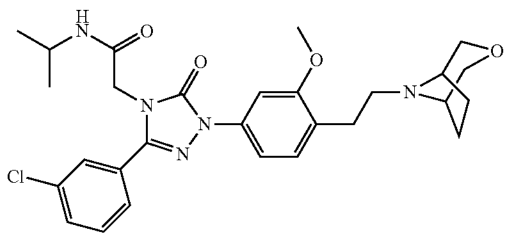 [SMILES: COc1cc(-n2nc(-c3cccc(Cl)c3)n(CC(=O)NC(C)C)c2=O)ccc1CCN1C2CCC1COC2] | ¹H-NMR (600 MHz, CDCl₃) δ (ppm); 1.19 (6H, d, J = 6.6 Hz), 1.83-1.95 (4H, m), 2.45-2.51 (2H, m), 2.77-2.84 (2H, m), 3.13 (2H, br. s.), 3.53 (2H, d, J = 9.9 Hz), 3.75 (2H, d, J = 10.3 Hz), 3.89 (3H, s), 4.09 (1H, dq, J = 13.4, 6.7 Hz), 4.34 (2H, s), 6.34 (1H, d, J = 6.6 Hz), 7.22 (1H, d, J = 8.3 Hz), 7.46-7.50 (1H, m), 7.50-7.55 (2H, m), 7.57 (1H, s), 7.75 (1H, d, J = 7.8 Hz), 7.85 (1H, s) | 540([M + H]+). |
| Ad-11 | 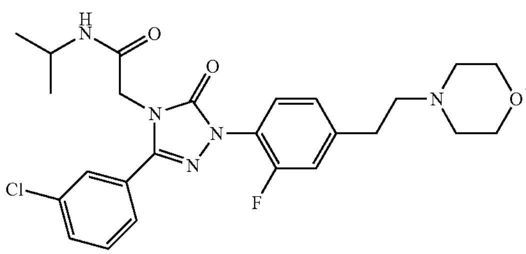 [SMILES: CC(C)NC(=O)Cn1c(-c2cccc(Cl)c2)nn(-c2ccc(CCN3CCOCC3)cc2F)c1=O] | ¹H-NMR (600 MHz, CDCl₃) δ (ppm); 1.18 (6H, d, J = 6.2 Hz), 2.52 (4H, br. s.), 2.59-2.64 (2H, m), 2.82-2.87 (2H, m), 3.74 (4H, t, J = 4.5 Hz), 4.04-4.13 (1H, m), 4.35 (2H, s), 6.47 (1H, d, J = 6.6 Hz), 7.09-7.14 (2H, m), 7.43-7.53 (3H, m), 7.76 (1H, dt, J = 7.5, 1.4 Hz), 7.85 (1H, t, J = 1.9 Hz) | 502([M + H]+). |
| Ad-12 | 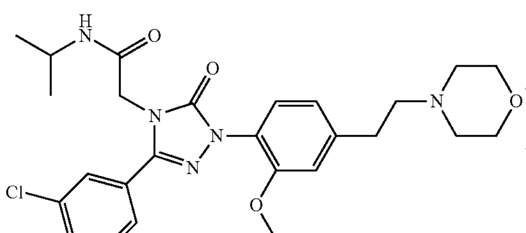 | ¹H-NMR (600 MHz, CDCl₃) δ (ppm); 1.18 (6H, d, J = 6.6 Hz), 2.53 (4H, br. s.), 2.59-2.65 (2H, m), 2.82-2.87 (2H, m), 3.72-3.78 (4H, m), 3.86 (3H, s), 4.06-4.12 (1H, m), 4.36 (2H, s), 6.70 (1H, d, J = 6.6 Hz), 6.89-6.92 (2H, m), 7.34 (1H, d, J = 8.7 Hz), 7.43-7.51 (2H, m), 7.76 (1H, dt, J = 7.4, 1.4 Hz), 7.87 (1H, t, J = 1.7 Hz) | 514([M + H]+). |
| Ad-13 | 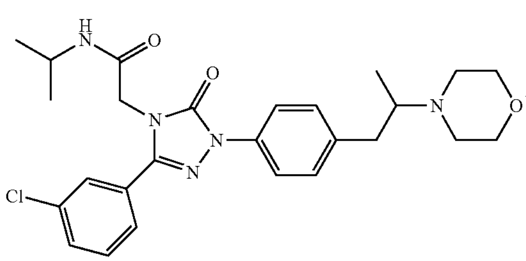 [SMILES: CC(C)NC(=O)Cn1c(-c2cccc(Cl)c2)nn(-c2ccc(CC(C)N3CCOCC3)cc2)c1=O] | ¹H-NMR (600 MHz, CDCl₃) δ (ppm); 0.97 (3H, d, J = 6.6 Hz), 1.19 (6H, d, J = 6.6 Hz), 2.46 (1H, dd, J = 13.4, 9.3 Hz), 2.58-2.66 (4H, m), 2.75-2.82 (1H, m), 3.01 (1H, dd, J = 13.2, 5.0 Hz), 3.73 (4H, t, J = 4.3 Hz), 4.05-4.13 (1H, m), 4.35 (2H, s), 6.40 (1H, d, J = 6.6 Hz), 7.24-7.28 (2H, m), 7.45-7.49 (1H, m), 7.50-7.53 (1H, m), 7.75 (1H, dt, J = 7.7, 1.3 Hz), 7.86 (1H, t, J = 1.7 Hz), 7.92 (2H, d, J = 8.7 Hz) | 498([M + H]+). |

TABLE 2-2

| | | | |
|---|---|---|---|
| Ad-14 | 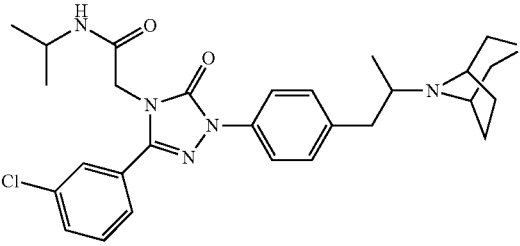 | ¹H-NMR (600 MHz, CDCl₃) δ (ppm); 0.93 (3H, d, J = 6.2 Hz), 1.20 (6H, d, J = 6.6 Hz), 1.77-1.86 (1H, m), 1.88-2.00 (3H, m), 2.46 (1H, dd, J = 13.4, 8.9 Hz), 2.52-2.59 (1H, m), 3.00 (1H, dd, J = 13.4, 3.5 Hz), 3.32-3.37 (1H, m), 3.43-3.48 (1H, m), 3.53-3.59 (2H, m), 3.78 (2H, dd, J = 10.3, 4.5 Hz), 4.06-4.14 (1H, m), 4.36 (2H, s), 6.36-6.43 (1H, m), 7.22-7.30 (2H, m), 7.46-7.51 (1H, m), 7.51-7.55 (1H, m), 7.74-7.78 (1H, m), 7.85-7.88 (1H, m), 7.93 (2H, d, J = 8.3 Hz) | 524([M + H]+). |
| Ad-15 | 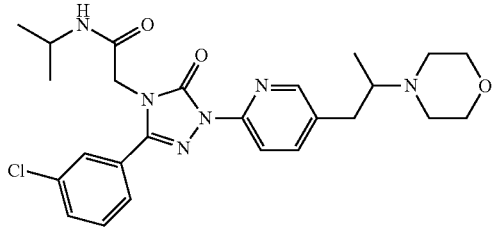 [SMILES: CC(C)NC(=O)Cn1c(-c2cccc(Cl)c2)nn(-c2ccc(CC(C)N3CCOCC3)cn2)c1=O] | ¹H-NMR (600 MHz, CDCl₃) δ (ppm); 1.00 (3H, d, J = 6.6 Hz), 1.18 (6H, d, J = 6.6 Hz), 2.51-2.58 (3H, m), 2.60-2.66 (2H, m), 2.75-2.82 (1H, m), 2.93 (1H, dd, J = 13.6, 6.2 Hz), 3.66-3.74 (4H, m), 4.07-4.13 (1H, m), 4.36 (2H, s), 6.26 (1H, d, J = 6.2 Hz), 7.44-7.48 (1H, m), 7.50-7.53 (1H, m), 7.67 (1H, dd, J = 8.3, 2.5 Hz), 7.75 (1H, dd, J = 8.9, 1.4 Hz), 7.89 (1H, t, J = 1.7 Hz), 8.05 (1H, d, J = 8.7 Hz), 8.42 (1H, d, J = 2.1 Hz) | 499([M + H]+). |
| Ad-16 | 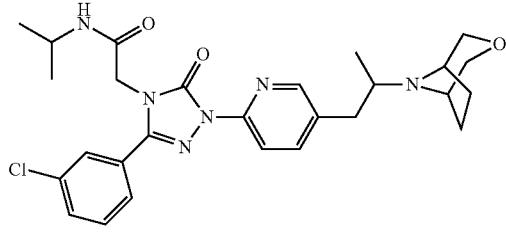 [SMILES: CC(C)NC(=O)Cn1c(-c2cccc(Cl)c2)nn(-c2ccc(CC(C)N3C4CCC3COC4)cn2)c1=O] | ¹H-NMR (800 MHz, CDCl₃) δ (ppm); 0.91 (3H, d, J = 5.8 Hz), 1.18 (6H, d, J = 6.6 Hz), 1.75-1.83 (1H, m), 1.88-1.97 (3H, m), 2.56-2.64 (2H, m), 2.84-2.90 (1H, m), 3.28 (1H, d, J = 5.4 Hz), 3.41 (1H, br. s.), 3.51-3.58 (2H, m), 3.70-3.78 (2H, m), 4.06-4.14 (1H, m), 4.36 (2H, s), 6.26 (1H, d, J = 7.4 Hz), 7.47 (1H, d, J = 7.8 Hz), 7.50-7.53 (1H, m), 7.70 (1H, dd, J = 8.5, 2.3 Hz), 7.73-7.77 (1H, m), 7.89 (1H, t, J = 1.7 Hz), 8.05 (1H, d, J = 8.3 Hz), 8.43 (1H, d, J = 2.1 Hz | 525([M + H]+). |
| Ia-1 | 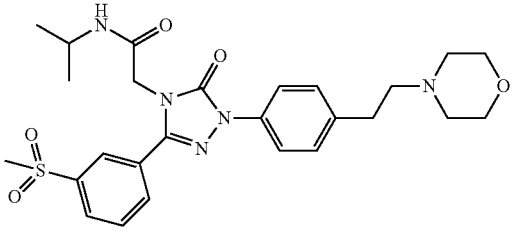 [SMILES: CC(C)NC(=O)Cn1c(-c2cccc(S(C)(=O)=O)c2)nn(-c2ccc(CCN3CCOCC3)cc2)c1=O] | ¹H-NMR (600 MHz, CDCl₃) δ (ppm); 1.19 (6H, d, J = 6.6 Hz), 2.53 (4 H, br. s.), 2.59-2.65 (2H, m), 2.81-2.87 (2H, m), 3.16 (3H, s), 3.75 (4H, t, J = 4.3 Hz), 4.04-4.13 (1H, m), 4.35 (2H, s), 6.41 (1H, d, J = 7.0 Hz), 7.31 (2H, d, J = 8.7 Hz), 7.77 (1H, t, J = 7.8 Hz), 7.93 (2H, d, J = 8.3 Hz), 8.12 (1H, d, J = 7.8 Hz), 8.22 (1H, d, J = 7.4 Hz), 8.43 (1H, s) | 528([M + H]+). |
| Bd-3 | 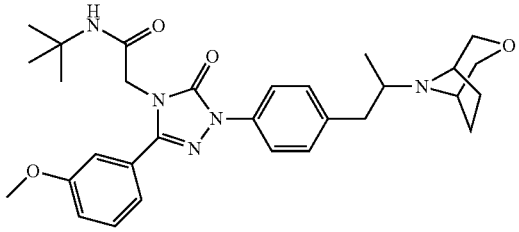 | ¹H-NMR (600 MHz, CDCl₃) δ (ppm); 0.94 (3H, d, J = 5.8 Hz), 1.37 (9H, s), 1.77-1.87 (1H, m), 1.88-2.00 (3H, m), 2.42-2.49 (1H, m), 2.52-2.60 (1H, m), 2.97-3.03 (1H, m), 3.32-3.37 (1H, m), 3.43-3.48 (1H, m), 3.53-3.59 (2H, m), 3.74-3.81 (2H, m), 3.89 (3H, s), 4.32 (2H, s), 6.46 (1H, br. s.), 7.07-7.11 (1H, m), 7.22-7.29 (2H, m), 7.34-7.36 (1H, m), 7.38 (1H, d, J = 7.4 Hz), 7.42-7.47 (1H, m), 7.95 (2H, d, J = 8.3 Hz) | 534([M + H]+). |
| Bd-4 | 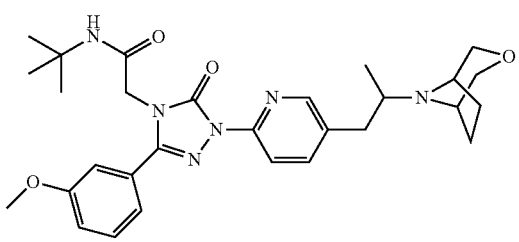 [SMILES: COc1cccc(-c2nn(-c3ccc(CC(C)N4C5CCC4COC5)cn3)c(=O)n2CC(=O)NC(C)(C)C)c1] | ¹H-NMR (600 MHz, CDCl₃) δ (ppm); 0.92 (3H, d, J = 5.8 Hz), 1.37 (9H, s), 1.75-1.84 (1H, m), 1.89-1.97 (3H, m), 2.56-2.64 (2H, m), 2.84-2.92 (1H, m), 3.27-3.32 (1H, m), 3.39-3.45 (1H, m), 3.52-3.60 (2H, m), 3.70-3.80 (2H, m), 3.88 (3H, s), 4.32 (2H, s), 6.27-6.34 (1H, m), 7.06-7.11 (1H, m), 7.34-7.37 (1H, m), 7.37-7.45 (2H, m), 7.68-7.72 (1H, m), 8.07 (1H, d, J = 8.3 Hz), 8.44 (1H, d, J = 2.1 Hz) | 535([M + H]+). |

TABLE 2-3

| | | | |
|---|---|---|---|
| Cd-2 | (structure) | ¹H-NMR (600 MHz, CDCl₃) δ (ppm): 0.94 (3H, d, J = 6.2 Hz), 1.20 (6H, d, J = 6.6 Hz), 1.78-1.87 (1H, m), 1.88-1.99 (3H, m), 2.43-2.50 (1H, m), 2.53-2.61 (1H, m), 2.97-3.03 (1H, m), 3.32-3.37 (1H, m), 3.43-3.48 (1H, m), 3.53-3.59 (2H, m), 3.77 (2H, dd, J = 10.7, 5.0 Hz), 4.01 (3H, s), 4.05-4.12 (1H, m), 4.35 (2H, s), 6.62-6.69 (1H, m), 7.23 (1H, dd, J = 10.7, 8.3 Hz), 7.25-7.29 (2H, m), 7.40 (1H, ddd, J = 8.4, 4.2, 2.3 Hz), 7.56 (1H, dd, J = 7.8, 2.1 Hz), 7.93 (2H, d, J = 8.3 Hz) | 538([M + H]+). |
| Cd-3 | (structure) | ¹H-NMR (600 MHz, CDCl₃) δ (ppm): 0.92 (3H, d, J = 5.8 Hz), 1.20 (6H, d, J = 6.6 Hz), 1.74-1.85 (1H, m), 1.88-1.98 (3H, m), 2.56-2.67 (2H, m), 2.84-2.92 (1H, m), 3.26-3.32 (1H, m), 3.39-3.44 (1H, m), 3.51-3.60 (2H, m), 3.70-3.79 (2H, m), 3.99 (3H, s), 4.06-4.13 (1H, m), 4.35 (2H, s), 6.44-6.52 (1H, m), 7.21 (1H, dd, J = 10.7, 8.3 Hz), 7.39-7.44 (1H, m), 7.56 (1H, dd, J = 7.8, 2.1 Hz), 7.69-7.74 (1H, m), 8.05 (1H, d, J = 8.3 Hz), 8.44 (1H, d, J = 2.1 Hz) | 539([M + H]+). |
| Cd-4 | (structure) | ¹H-NMR (600 MHz, DMSO-d₆) δ (ppm): 0.97-1.02 (6H, m), 2.14 (3H, s), 2.26-2.43 (8H, m), 3.47 (2H, s), 3.74-3.82 (1H, m), 3.89 (3H, s), 4.38 (2H, s), 7.24-7.29 (1H, m), 7.37-7.43 (3H, m), 7.46-7.49 (1H, m), 7.88-7.93 (2H, m), 8.16-8.22 (1H, m) | 497([M + H]+). |
| Ja-1 | (structure) | ¹H-NMR (600 MHz, CDCl₃) δ (ppm): 1.08 (6H, d, J = 6.6 Hz), 2.47-2.69 (6H, m), 2.81-2.91 (2H, m), 3.71-3.81 (4H, m), 3.98 (3H, s), 4.01-4.10 (1H, m), 5.03 (2H, s), 5.62-5.71 (1H, m), 6.81-6.88 (1H, m), 7.31 (2H, d, J = 8.7 Hz), 7.67-7.74 (1H, m), 7.75-7.81 (1H, m), 7.99 (2H, d, J = 8.7 Hz) | 481([M + H]+). |
| Ja-2 | (structure) | ¹H-NMR (600 MHz, CDCl₃) δ (ppm): 1.08 (6H, d, J = 6.6 Hz), 1.82-2.00 (4H, m), 2.47-2.61 (2H, m), 2.75-2.88 (2H, m), 3.03-3.16 (2H, m), 3.50-3.58 (2H, m), 3.68-3.81 (2H, m), 3.98 (3H, s), 4.01-4.10 (1H, m), 5.03 (2H, s), 5.64-5.71 (1H, m), 6.79-6.89 (1H, m), 7.32 (2H, d, J = 8.7 Hz), 7.68-7.75 (1H, m), 7.75-7.80 (1H, m), 7.98 (2H, d, J = 8.3 Hz) | 507([M + H]+). |

Synthesis of Example Fa-1

2-[3-(3-Fluorophenyl)-1-{4-[2-(morpholin-4-yl)ethyl]phenyl}-5-oxo-1,5-dihydro-4H-1,2,4-triazol-4-yl]-N-(propan-2-yl)acetamide

[Formula 173]

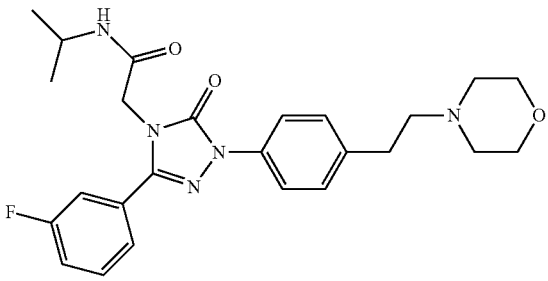

K₂CO₃ (150 mg) and 2-bromo-N-(propan-2-yl)acetamide (147 mg) were added to a suspension of the compound (200 mg) prepared in Reference Example P-N1 in DMF (4.0 mL), followed by stirring at room temperature for 14.5 hours. Water and CHCl₃ were added to the reaction solution, and then were separated between water and CHCl₃, and the aqueous layer was extracted with CHCl₃. The combined organic layer was dried over MgSO₄. The desiccant was removed by filtration. The filtrate was concentrated under reduced pressure. The residue was purified by silica gel column chromatography twice (SNAP Cartridge HP-SiL: 25 g, mobile phase: CHCl₃/MeOH/NH₄OH=99/1/0.1 to 95/5/0.5 (v/v/v) and SNAP Cartridge HP-SiL: 50 g, mobile phase: CHCl₃/MeOH/NH₄OH=99/1/0.1 to 95/5/0.5 (v/v/v)). The resulting fraction was concentrated and was stirred in n-hexane/EtOAc=6/1 (v/v, 5 mL) at room temperature for 2 hours. The precipitated product was collected by filtration to yield the title compound (138 mg, colorless solid).

MS (ESI pos.) m/z: 468 ([M+H]⁺).

¹H-NMR (600 MHz, CDCl₃)δ(ppm); 1.18 (6H, d, J=6.4 Hz), 2.53 (4H, br. s.), 2.59-2.64 (2H, m), 2.81-2.86 (2H, m), 3.75 (4H, t, J=4.8 Hz), 4.09 (1H, dq, J=14.2, 6.6 Hz), 4.36 (2H, s), 6.41 (1H, d, J=6.4 Hz), 7.22-7.27 (1H, m), 7.30 (2H, d, J=8.7 Hz), 7.52 (1H, td, J=8.0, 5.5 Hz), 7.60 (1H, dt, J=9.2, 2.1 Hz), 7.63-7.66 (1H, m), 7.91-7.95 (2H, m).

Synthesis of Example Ga-1

2-(1-{4-[2-(Morpholin-4-yl)ethyl]phenyl}-5-oxo-3-phenyl-1,5-dihydro-4H-1,2,4-triazol-4-yl)-N-(propan-2-yl)acetamide

[Formula 174]

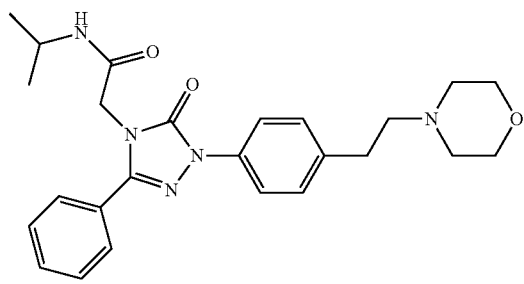

A mixture of the compound (100 mg) prepared in Example Aa-1, 10% Pd—C (0.020 g), triethylamine (0.035 mL), and MeOH (2 mL) was stirred in a hydrogen atmosphere overnight. The insoluble matter was removed through Celite (registered trademark). The filtrate was concentrated under reduced pressure to yield the title compound (89 mg, colorless solid).

MS (ESI pos.) m/z: 450 ([M+H]⁺).

¹H-NMR (600 MHz, DMSO-d6)δ(ppm); 0.99 (6H, d, J=6.9 Hz), 2.43 (4H, br. s.), 2.51-2.56 (2H, m), 2.70-2.81 (2H, m), 3.52-3.65 (4H, m), 3.70-3.85 (1H, m), 4.35 (2H, s), 7.35 (2H, d, J=8.7 Hz), 7.48-7.61 (3H, m), 7.64-7.72 (2H, m), 7.82-7.95 (2H, m), 8.08-8.22 (1H, m).

Synthesis of Example Ha-1

2-[3-(2-Bromo-5-chlorophenyl)-1-{4-[2-(morpholin-4-yl)ethyl]phenyl}-5-oxo-1,5-dihydro-4H-1,2,4-triazol-4-yl]-N-(propan-2-yl)acetamide

[Formula 175]

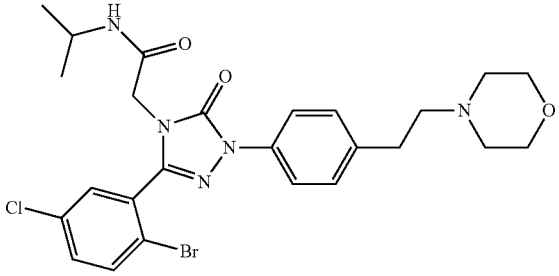

2-Bromo-N-(propan-2-yl)acetamide (470 mg) was added to a suspension of the compound (1.10 g) prepared in Reference Example P-Q1 and anhydrous K₂CO₃ (656 mg) in DMF (22 mL), followed by stirring at room temperature for 16.5 hours. Water and CHCl₃ were added to the reaction solution, and then were separated between water and CHCl₃, and the aqueous layer was extracted with CHCl₃. The combined organic layer was dried over MgSO₄, and the desiccant was removed by filtration. The filtrate was concentrated under reduced pressure. The resulting crude product was purified by silica gel column chromatography (SNAP Cartridge HP-SiL: 50 g, mobile phase: CHCl₃/MeOH/NH₄OH=99/1/0.1 to 95/5/0.5 (v/v/v)) twice. The resulting solid was stirred in a solvent mixture (15 mL, EtOAc/n-hexane=1/6 (v/v)) at room temperature, was then collected by filtration, and was dried to yield the title compound (749 mg, colorless solid).

MS (ESI pos.) m/z: 562, 564 ([M+H]⁺).

¹H-NMR (600 MHz, CDCl₃)δ(ppm); 1.11 (6H, d, J=6.6 Hz), 2.53 (4H, br. s.), 2.58-2.63 (2H, m), 2.80-2.85 (2H, m), 3.74 (4H, t, J=4.5 Hz), 3.95-4.03 (1H, m), 4.20 (2H, s), 5.93 (1H, d, J=7.4 Hz), 7.28 (2H, d, J=8.7 Hz), 7.40 (1H, dd, J=8.7, 2.5 Hz), 7.61 (1H, d, J=2.5 Hz), 7.62 (1H, d, J=8.7 Hz), 7.91 (2H, d, J=8.7 Hz).

Example Aa-15

2-[3-(3-Chlorophenyl)-1-{4-[2-(morpholin-4-yl)ethyl]phenyl}-5-oxo-1,5-dihydro-4H-1,2,4-triazol-4-yl]-N-(propan-2-yl)acetamide hydrochloride

[Formula 176]

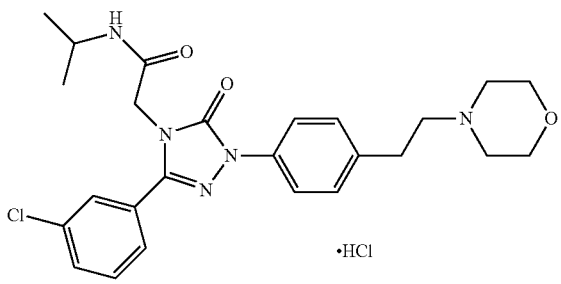

A solution of 4 M HCl in EtOAc was added to the compound (550 mg) prepared in Example Aa-1, followed by stifling at room temperature overnight. The solvent was distilled off under reduced pressure, and the residue was azeotroped with EtOAc twice. The residue was washed with Et$_2$O. The solid was collected by filtration to yield the title compound (575 mg, colorless solid).

$^1$H-NMR (500 MHz, DMSO-d6)δ(ppm); 1.00 (6H, d, J=6.5 Hz), 3.03-3.16 (4H, m), 3.34-3.41 (2H, m), 3.45-3.55 (2H, m), 3.71-3.82 (3H, m), 3.97-4.04 (2H, m), 4.39 (2H, s), 7.42 (2H, d, J=8.6 Hz), 7.57-7.62 (1H, m), 7.64-7.70 (2H, m), 7.72-7.75 (1H, m), 7.96 (2H, d, J=8.2 Hz), 8.22-8.28 (1H, m), 10.52-10.64 (1H, m).

Synthesis of Example Ad-19-1

(−)-2 43-(3-Chlorophenyl)-1-15 42-(3-oxa-8-azabicyclo [3.2.1]oct-8-yl)propyl]pyridin-2-yl} -5-oxo-1,5-dihydro-4H-1,2,4-triazol-4-yl]-N-(propan -2-yl)acetamide and Example Ad-19-2: (+)-2-[3-(3-chlorophenyl)-1-15-[2-(3-oxa-8-azabicyclo [3.2.1]oct-8-yl)propyl]pyridin-2-yl} -5-oxo-1,5-dihydro-4H-1,2,4-triazol-4-yl]-N-(propan-2-yl)acetamide

[Formula 177]

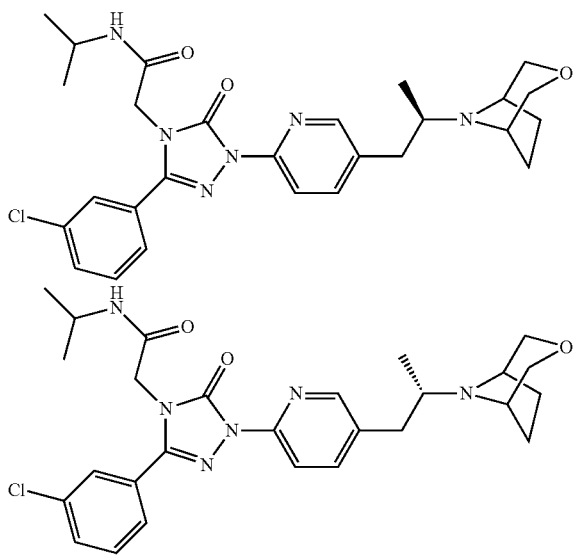

Racemic resolution of the compound (50 mg) prepared in Example Ad-16 was performed.

Fractionation Conditions
Solvent: n-hexane/EtOH=100/0 to 85/15 (v/v)
Column: CHIRALPAK AD
Flow rate: 5 mL/min The compound (5×10 mg/EtOH 1 mL) prepared in Example Ad-16 was applied to the column. Each fraction was collected by a fraction collector (time mode) to yield the title compound: Ad-19-1 (peak at a shorter retention time, 11 mg, colorless amorphous compound) and the title compound: Ad-19-2 (peak at a longer retention time, 10 mg, light yellow oily compound).

Example Ad-19-1: $[α]_D^{27}$=−2.26° (c=0.2, MeOH)
Retention Time: 13.486 min
MS (ESI pos.) m/z: 525 ([M+H]$^+$).
$^1$H-NMR (600 MHz, CDCl$_3$)δ(ppm); 0.92 (3H, d, J=6.2 Hz), 1.19 (6H, d, J=6.6 Hz), 1.75-1.84 (1H, m), 1.93 (3H, s), 2.56-2.65 (2H, m), 2.84-2.92 (1H, m), 3.27-3.32 (1H, m), 3.39-3.45 (1H, m), 3.53-3.59 (2H, m), 3.70-3.79 (2H, m), 4.07-4.15 (1H, m), 4.37 (2H, s), 6.23-6.30 (1H, m), 7.45-7.50 (1H, m), 7.50-7.55 (1H, m), 7.68-7.73 (1H, m), 7.74-7.78 (1H, m), 7.90 (1H, s), 8.06 (1H, d, J=8.3 Hz), 8.43-8.46 (1H, m).

Example Ad-19-2: $[α]_D^{28}$=+1.94° (c=0.2, MeOH)

Retention Time: 16.008 min
MS (ESI pos.) m/z: 525 ([M+H]$^+$).
$^1$H-NMR (600 MHz, CDCl$_3$)δ(ppm); 0.91 (3H, d, J=5.8 Hz), 1.19 (6H, d, J=6.6 Hz), 1.80 (1H, dd, J=11.1, 6.2 Hz), 1.88-1.98 (3H, m), 2.54-2.66 (2H, m), 2.84-2.92 (1H, m), 3.30 (1H, d, J=5.8 Hz), 3.42 (1H, br. s.), 3.52-3.60 (2H, m), 3.69-3.80 (2H, m), 4.11 (1H, dd, J=13.6, 6.6 Hz), 4.37 (2H, s), 6.29 (1H, d, J=7.4 Hz), 7.44-7.49 (1H, m), 7.50-7.55 (1H, m), 7.70 (1H, dd, J=8.3, 2.1 Hz), 7.76 (1H, d, J=7.4 Hz), 7.90 (1H, s), 8.06 (1H, d, J=8.7 Hz), 8.44 (1H, d, J=2.1 Hz).

Synthesis of Example Ad-21

2-[3-(3-Chlorophenyl)-1-[4-(2-aminoethyl)phenyl]-5-oxo-1,5-dihydro-4H-1,2,4-triazol-4-yl]-N-(propan-2-yl)acetamide

[Formula 178]

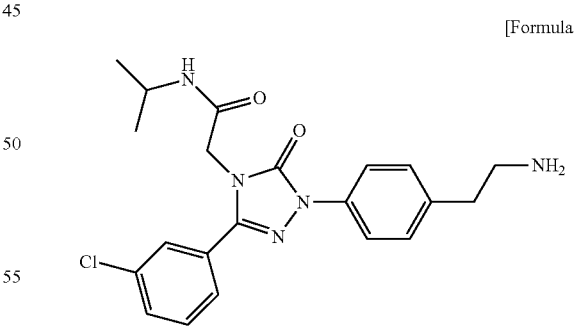

A solution of 4 M HCl in 1,4-dioxane (0.80 mL) was added to a mixture of the compound (82 mg) prepared in Reference Example P-U1 and 1,4-dioxane (2 mL), followed by stirring at room temperature for 16 hours. The solvent was distilled off under reduced pressure. The residue was purified by reverse-phase column chromatography. The resulting crude product was washed with EtOAc/n-hexane (1/4) to yield the title compound (37 mg, colorless solid).
MS (ESI pos.) m/z: 414 ([M+H]$^+$).

$^1$H-NMR (600 MHz, DMSO-d$_6$)δ(ppm); 1.00 (6H, d, J=6.6 Hz), 2.63-2.70 (2H, m), 2.76-2.81 (2H, m), 3.74-3.82 (1H, m), 4.38 (2H, s), 7.32 (2H, d, J=8.7 Hz), 7.56-7.61 (1H, m), 7.63-7.69 (2H, m), 7.72-7.74 (1H, m), 7.83-7.89 (2H, m), 8.22 (1H, d, J=7.4 Hz).

Synthesis of Example Cd-1

2-[3-(4-Fluoro-3-methoxyphenyl)-1-{5-[2-(morpholin-4-yl)ethyl]pyrimidin-2-yl}-5-oxo-1,5-dihydro-4H-1,2,4-triazol-4-yl]-N-(propan-2-yl)acetamide

[Formula 179]

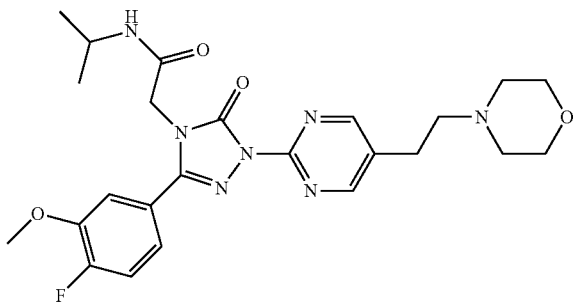

The mesyl form of the compound (35 mg) prepared in Reference Example P-T1 was prepared as in Reference Example P-I1.

The title compound (15 mg, colorless solid) was prepared from the resulting mesyl form as in Example Aa-1.

MS (ESI pos.) m/z: 500 ([M+H]$^+$).

$^1$H-NMR (600 MHz, CDCl$_3$)δ(ppm); 1.20 (6H, d, J=6.6 Hz), 2.51 (4H, br. s.), 2.63 (2H, s), 2.82 (2H, s), 3.67-3.76 (4H, m), 4.00 (3H, s), 4.05-4.14 (1H, m), 4.35 (2H, s), 6.48-6.59 (1H, m), 7.19-7.25 (1H, m), 7.42-7.48 (1H, m), 7.57-7.62 (1H, m), 8.75 (2H, s).

The following compounds were synthesized using the compound prepared in Reference Example P-Q3, as in Example Cd-1:

Example Ca-6: 2-[3-(4-Fluoro-3-methoxyphenyl)-1-{4-[2-(7-oxa-2-azaspiro[3.5]non-2-yl)ethyl]phenyl}-5-oxo-1,5-dihydro-4H-1,2,4-triazol-4-yl]-N-(propan-2-yl)acetamide, Example Ca-7: 2-[1-{4-[2-(3,6-Dihydropyridin-1(2H)-yl)ethyl]phenyl}-3-(4-fluoro-3-methoxyphenyl)-5-oxo-1,5-dihydro-4H-1,2,4-triazol-4-yl]-N-(propan-2-yl)acetamide, Example Ca-8: 2-[3-(4-Fluoro-3-methoxyphenyl)-5-oxo-1-{4-[2-(thiomorpholin-4-yl)ethyl]phenyl}-1,5-dihydro-4H-1,2,4-triazol-4-yl]-N-(propan-2-yl)acetamide, Example Ca-9: 2-[3-(4-Fluoro-3-methoxyphenyl)-1-{4-[2-(4-methylpiperidin-1-yl)ethyl]phenyl}-5-oxo-1,5-dihydro-4H-1,2,4-triazol-4-yl]-N-(propan-2-yl)acetamide, Example Ca-10: 2-[1-{4-[2-(4-Cyanopiperidin-1-yl)ethyl]phenyl}-3-(4-fluoro-3-methoxyphenyl)-5-oxo-1,5-dihydro-4H-1,2,4-triazol-4-yl]-N-(propan-2-yl)acetamide, Example Ca-11: 2-[3-(4-Fluoro-3-methoxyphenyl)-1-{4-[2-(3-methoxypiperidin-1-yl)ethyl]phenyl}-5-oxo-1,5-dihydro-4H-1,2,4-triazol-4-yl]-N-(propan-2-yl)acetamide, Example Ca-12: 2-[3-(4-Fluoro-3-methoxyphenyl)-5-oxo-1-{4-[2-(4-propylpiperidin-1-yl)ethyl]phenyl}-1,5-dihydro-4H-1,2,4-triazol-4-yl]-N-(propan-2-1)acetamide, Example Ca-13: 1-[2-(4-{3-(4-Fluoro-3-methoxyphenyl)-5-oxo-4-[2-oxo-2-(propan-2-ylamino)ethyl]-4,5-dihydro-1H-1,2,4-triazol-1-yl}phenyl)ethyl]piperidine 4-carboxamide, Example Ca-14: 2-[1-(4-{2-[4-(Dimethylamino)piperidin-1-yl]ethyl}phenyl)-3-(4-fluoro-3-methoxyphenyl)-5-oxo-1,5-dihydro-4H-1,2,4-triazol-4-yl]-N-(propan-2-yl)acetamide, Example Ca-15: 2-[3-(4-Fluoro-3-methoxyphenyl)-1-{4-[2-(octahydroisoquinolin-2(1H)-yl)ethyl]phenyl}-5-oxo-1,5-dihydro-4H-1,2,4-triazol-4-yl]-N-(propan-2-yl)acetamide, Example Ca-16: 2-[3-(4-Fluoro-3-methoxyphenyl)-1-{4-[2-(4-fluoropiperidin-1-yl)ethyl]phenyl}-5-oxo-1,5-dihydro-4H-1,2,4-triazol-4-yl]-N-(propan-2-yl)acetamide trifluoroacetate, Example Ca-17: 2-[1-(4-{2-[4-(Acetylamino)piperidin-1-yl]ethyl}phenyl)-3-(4-fluoro-3-methoxyphenyl)-5-oxo-1,5-dihydro-4H-1,2,4-triazol-4-yl]-N-(propan-2-yl)acetamide, Example Ca-18: 2-[1-{4-[2-(4,4-Difluoropiperidin-1-yl)ethyl]phenyl}-3-(4-fluoro-3-methoxyphenyl)-5-oxo-1,5-dihydro-4H-1,2,4-triazol-4-yl]-N-(propan-2-yl)acetamide trifluoroacetate, Example Ca-19: 2-[3-(4-Fluoro-3-methoxyphenyl)-5-oxo-1-(4-{2-[4-(trifluoromethyl)piperidin-1-yl]ethyl}phenyl)-1,5-dihydro-4H-1,2,4-triazol-4-yl]-N-(propan-2-yl)acetamide trifluoroacetate, Example Ca-20: 2-[1-(4-{2-[(2R,6S)-2,6-Dimethylmorpholin-4-yl]ethyl}phenyl)-3-(4-fluoro-3-methoxyphenyl)-5-oxo-1,5-dihydro-4H-1,2,4-triazol-4-yl]-N-(propan-2-yl)acetamide, Example Ca-21: 2-[1-{4-[2-(3,5-Dimethylmorpholin-4-yl)ethyl]phenyl}-3-(4-fluoro-3-methoxyphenyl)-5-oxo-1,5-dihydro-4H-1,2,4-triazol-4-yl]-N-(propan-2-yl)acetamide trifluoroacetate, Example Ca-22: 2-[3-(4-Fluoro-3-methoxyphenyl)-1-{4-[2-(3-methylmorpholin-4-yl)ethyl]phenyl}-5-oxo-1,5-dihydro-4H-1,2,4-triazol-4-yl]-N-(propan-2-yl)acetamide, Example Ca-23: 2-[1-{4-[2-(3-Ethylmorpholin-4-yl)ethyl]phenyl}-3-(4-fluoro-3-methoxyphenyl)-5-oxo-1,5-dihydro-4H-1,2,4-triazol-4-yl]-N-(propan-2-yl)acetamide, Example Ca-24: 2-[3-(4-Fluoro-3-methoxyphenyl)-5-oxo-1-{4-[2-(pyrrolidin-1-yl)ethyl]phenyl}-1,5-dihydro-4H-1,2,4-triazol-4-yl]-N-(propan-2-yl)acetamide formate, Example Ca-25: 2-[3-(4-Fluoro-3-methoxyphenyl)-1-{4-[2-(4-methylpiperazin-1-yl)ethyl]phenyl}-5-oxo-1,5-dihydro-4H-1,2,4-triazol-4-yl]-N-(propan-2-yl)acetamide trifluoroacetate, Example Ca-26: 2-[1-{4-[2-(4-Acetylpiperazin-1-yl)ethyl]phenyl}-3-(4-fluoro-3-methoxyphenyl)-5-oxo-1,5-dihydro-4H-1,2,4-triazol-4-yl]-N-(propan-2-yl)acetamide trifluoroacetate, and Example Ca-27: 2-[3-(4-Fluoro-3-methoxyphenyl)-1-{4-[2-(4-hydroxy4-methylpiperidin-1-yl)ethyl]phenyl}-5-oxo-1,5-dihydro-4H-1,2,4-triazol-4-yl]-N-(propan-2-yl)acetamide trifluoroacetate.

The retention times of LCMS (Conditions 2-1 or 2-2) and the results of MS of Examples Ca-6 to Ca-27 are shown in Tables 3-1 to 3-3.

TABLE 3-1

| Example | Structure | Salt | LC-MS conditions | Retention time (min) | MS (ESI pos.) m/z ([M + H]+) |
|---|---|---|---|---|---|
| Ca-6 | 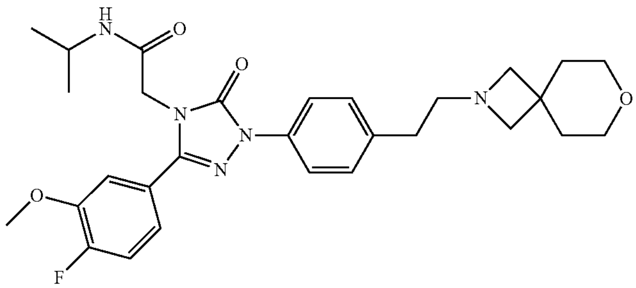 [SMILES: COc1cc(-c2nn(-c3ccc(CCN4CC5(CCOCC5)C4)cc3)c(=O)n2CC(=O)NC(C)C)ccc1F] | Free | 2-1 | 0.519 | 538 |
| Ca-7 | 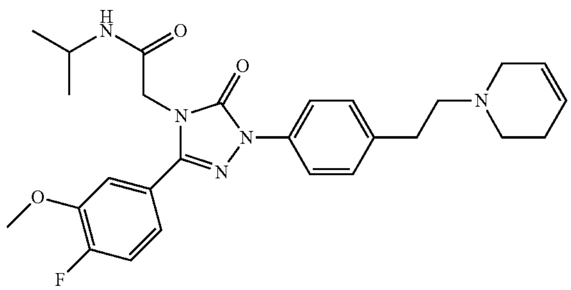 [SMILES: COc1cc(-c2nn(-c3ccc(CCN4CC=CCC4)cc3)c(=O)n2CC(=O)NC(C)C)ccc1F] | Free | 2-1 | 0.529 | 494 |
| Ca-8 | 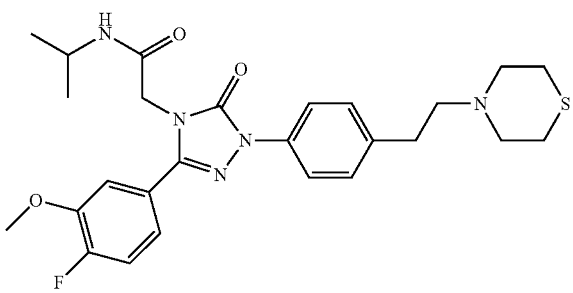 [SMILES: COc1cc(-c2nn(-c3ccc(CCN4CCSCC4)cc3)c(=O)n2CC(=O)NC(C)C)ccc1F] | Free | 2-1 | 0.529 | 514 |
| Ca-9 | 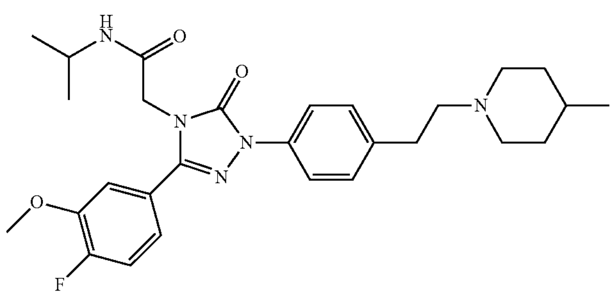 | Free | 2-1 | 0.578 | 510 |
| Ca-10 | 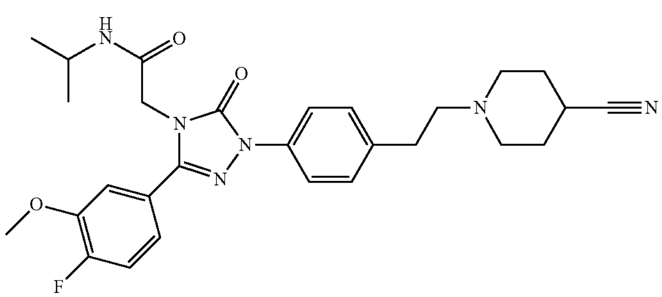 [SMILES: COc1cc(-c2nn(-c3ccc(CCN4CCC(C#N)CC4)cc3)c(=O)n2CC(=O)NC(C)C)ccc1F] | Free | 2-1 | 0.518 | 521 |

TABLE 3-1-continued

| Example | Structure | Salt | LC-MS conditions | Retention time (min) | MS (ESI pos.) m/z ([M + H]+) |
|---|---|---|---|---|---|
| Ca-11 | 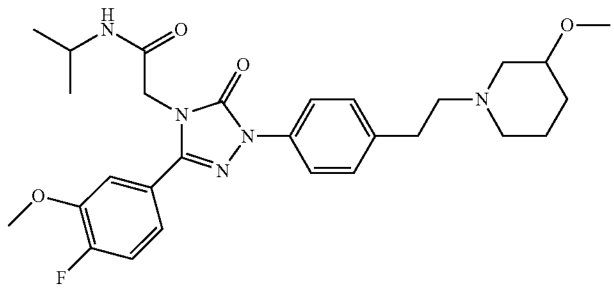 | Free | 2-1 | 0.537 | 526 |
| Ca-12 | 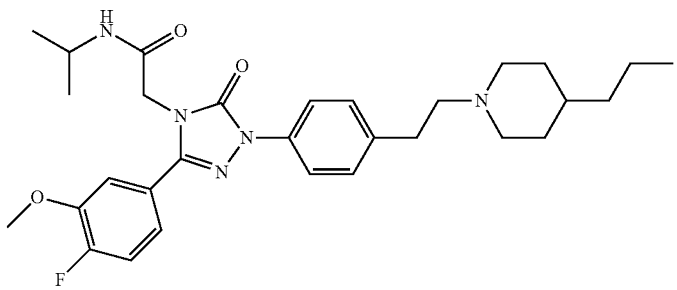 [SMILES: CCCC1CCN(CCc2ccc(-n3nc(-c4ccc(F)c(OC)c4)n(CC(=O)NC(C)C)c3=O)cc2)CC1] | Free | 2-1 | 0.07 | 538 |
| Ca-13 | 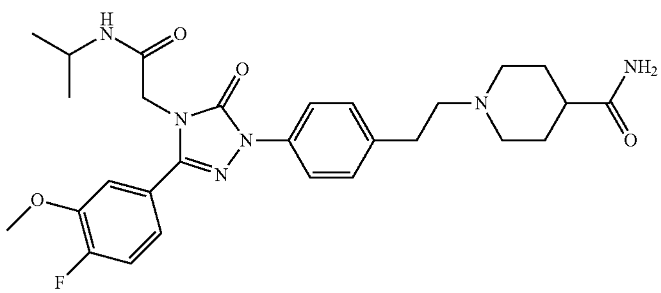 [SMILES: COc1cc(-c2nn(-c3ccc(CCN4CCC(C(N)=O)CC4)cc3)c(=O)n2CC(=O)NC(C)C)ccc1F] | Free | 2-1 | 0.475 | 539 |
| Ca-14 | 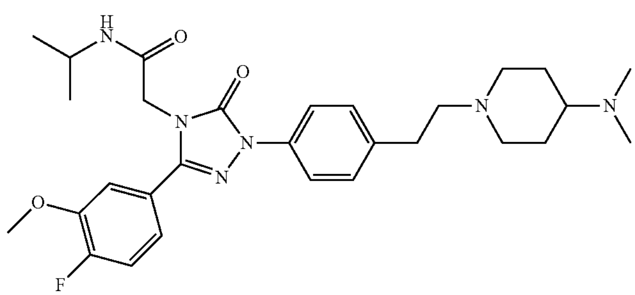 | Free | 2-2 | 0.648 | 539 |

TABLE 3-2

| | | | | | |
|---|---|---|---|---|---|
| Ca-15 | | Free | 2-1 | 0.662 | 550 |

TABLE 3-2-continued

| | | | | | |
|---|---|---|---|---|---|
| Ca-16 | | CF3CO2H | 2-1 | 0.536 | 514 |
| Ca-17 | | Free | 2-1 | 0.483 | 553 |
| Ca-18 | | CF3CO2H | 2-1 | 0.556 | 532 |
| Ca-19 | | CF3CO2H | 2-1 | 0.596 | 564 |
| Ca-20 | | Free | 2-1 | 0.551 | 526 |

TABLE 3-2-continued
| | | | | | |
|---|---|---|---|---|---|
| Ca-21 | 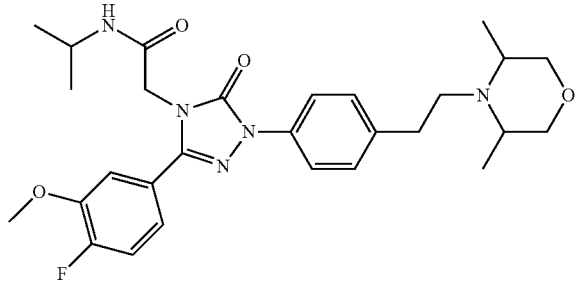 | CF3CO2H | 2-1 | 0.532 | 526 |
| Ca-22 | 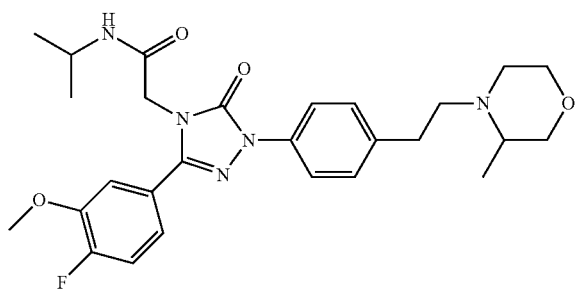 | Free | 2-1 | 0.511 | 512 |
| Ca-23 | 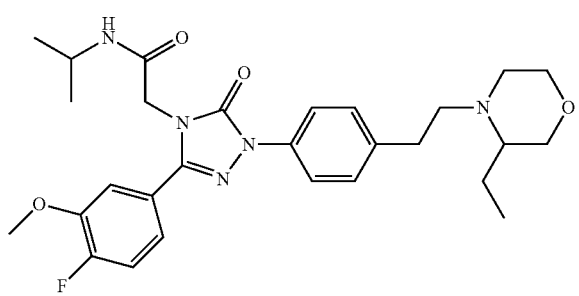 [SMILES: COc1cc(-c2nn(-c3ccc(CCN4CCOCC4C)cc3)c(=O)n2CC(=O)NC(C)C)ccc1F] | Free | 2-1 | 0.547 | 526 |
| Ca-24 | 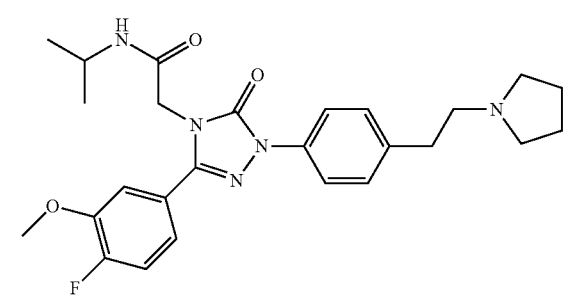 [SMILES: COc1cc(-c2nn(-c3ccc(CCN4CCCC4)cc3)c(=O)n2CC(=O)NC(C)C)ccc1F] | HCO2H | 2-1 | 0.516 | 482 |
TABLE 3-3
| | | | | | |
|---|---|---|---|---|---|
| Ca-25 | 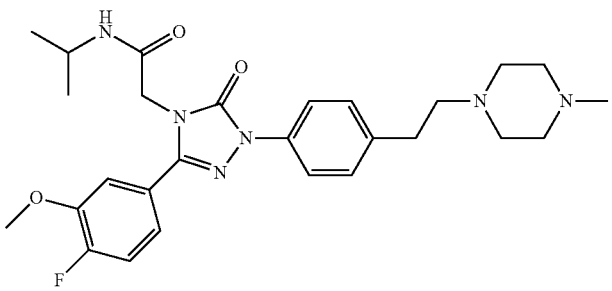 | CF3CO2H | 2-1 | 0.391 | 511 |

TABLE 3-3-continued

| Ca-26 | CF3CO2H | 2-1 | 0.481 | 539 |
| Ca-27 | CF3CO2H | 2-1 | 0.503 | 526 |

Test Example 1

Binding Test for V1b Receptor

Human V1b receptor was transiently expressed in 293FT cells (Invitrogen). The cells were collected and were homogenated in a 15 mmol/L tris-hydrochloric acid buffer (pH 7.4, containing 2 mmol/L magnesium chloride, 0.3 mmol/L ethylenediaminetetracetic acid, and 1 mmol/L glycol ether diaminetetraacetic acid). The resulting homogenate was centrifuged at 50,000×g at 4° C. for 20 minutes. The precipitate was resuspended in a 75 mmol/L tris-hydrochloric acid buffer (pH 7.4, containing 12.5 mmol/L magnesium chloride, 0.3 mmol/L ethylenediaminetetracetic acid, 1 mmol/L glycol ether diamine tetraacetic acid, and 250 mmol/L sucrose) to give a crude membrane preparation, which was stored at −80° C. until the binding test. In the binding test, the crude membrane preparation was diluted with a 50 mmol/L tris-hydrochloric acid buffer (pH 7.4, containing 10 mmol/L magnesium chloride and 0.1% bovine serum albumin), and test compound was serially diluted with DMSO. The diluted crude membrane preparation was incubated with each test compound (final concentration of 0.01 nmol/L to 1 μmol/L) and [$^3$H]AVP (final concentration: 0.4 to 1 nmol/L) at room temperature for 60 minutes. After the incubation, the mixture was suction filtered through a GF/C filter pretreated with 0.3% polyethyleneimine. The GF/C filter was dried, and a scintillator was added thereto. The radioactivity remaining on the filter was measured using TopCount (PerkinElmer Inc.). The radioactivity in the presence of 10 μmol/L of unlabeled AVP was defined as 0%, and the radioactivity in the absence of unlabeled AVP was defined as 100%. A dose-response curve was plotted from radioactivities in the presence of a test compound at various concentrations, and the 50% inhibitory concentration ($IC_{50}$ value) of the compound was calculated. The $IC_{50}$ values of the compounds of the present invention were in the range of about 1 to 1000 nM. Table 4 shows the $IC_{50}$ values of typical compounds.

TABLE 4

| V1b binding | |
| --- | --- |
| Example No. | $IC_{50}$ value (nmol/L) |
| Aa-1 | 8.6 |
| Aa-6 | 56 |
| Aa-7 | 34 |
| Aa-8 | 4.1 |
| Aa-9 | 18 |
| Aa-10 | 4.7 |
| Aa-11 | 37 |
| Aa-13 | 20 |
| Ab-2 | 41 |
| Ab-4 | 20 |
| Ab-5 | 8.6 |
| Ac-2 | 79 |
| Ad-1 | 2.5 |
| Ad-2 | 15 |
| Ad-3 | 55 |
| Ad-4 | 102 |
| Ad-5 | 97 |
| Ad-6 | 62 |
| Ba-2 | 19 |
| Ca-1 | 26 |
| Ca-2 | 10 |
| Ca-3 | 6.0 |
| Ca-5 | 4.4 |
| Cb-2 | 17 |
| Cb-4 | 8.6 |
| Cb-5 | 16 |
| Da-1 | 17 |
| Da-2 | 4.3 |
| Da-3 | 32 |
| Da-4 | 12 |
| Da-5 | 2.5 |
| Da-6 | 4.4 |
| Db-1 | 16 |
| Db-2 | 7.1 |
| Db-3 | 10 |
| Db-4 | 2.9 |
| Ea-2 | 48 |

TABLE 4-continued

V1b binding

| Example No. | IC$_{50}$ value (nmol/L) |
|---|---|
| Fa-1 | 46 |
| Ga-1 | 114 |
| Ad-7 | 3.8 |
| Ad-8 | 1.5 |
| Ad-9 | 2.3 |
| Ad-10 | 1.3 |
| Ad-13 | 2.9 |
| Ad-14 | 0.54 |
| Ad-15 | 5.1 |
| Ad-16 | 0.92 |
| Ad-17 | 3.5 |
| Ad-18 | 2.6 |
| Ba-3 | 9.4 |
| Bd-1 | 4.1 |
| Bd-2 | 3.6 |
| Ia-1 | 46 |
| Ad-19-1 | 0.59 |
| Ad-19-2 | 17 |
| Ad-20 | 96 |
| Ad-21 | 365 |
| Bd-3 | 0.21 |
| Bd-4 | 0.44 |
| Ca-6 | 10~100 |
| Ca-7 | 10~100 |
| Ca-8 | <10 |
| Ca-9 | 10~100 |
| Ca-10 | 100~1000 |
| Ca-11 | 10~100 |
| Ca-12 | 100~1000 |
| Ca-13 | 100~1000 |
| Ca-14 | 100~1000 |
| Ca-15 | 10~100 |
| Ca-16 | 10~100 |
| Ca-17 | 100~1000 |
| Ca-18 | 10~100 |
| Ca-19 | 100~1000 |
| Ca-20 | 10~100 |
| Ca-21 | 10~100 |
| Ca-22 | 10~100 |
| Ca-23 | 10~100 |
| Ca-24 | 10~100 |
| Ca-25 | 100~1000 |
| Ca-26 | 100~1000 |
| Ca-27 | 100~1000 |
| Cd-1 | 166 |
| Cd-2 | 0.51 |
| Cd-3 | 0.55 |
| Cd-4 | 863 |
| Ja-1 | 16 |
| Ja-2 | 20 |

Test Example 2

Measurement of V1b Receptor Antagonistic Activity

CHO cells (ATCC) stably expressing human V1b receptor were cultured in Ham's F-12 medium (containing 10% FBS and 0.5 mg/mL Geneticin). The cells were seeded the day before the test at 20,000 cells/well in a 96-well poly-D-lysine coated black plate. On the day of the test, the culture medium was removed, and a loading solution (1×HBSS, 10 mmol/L HEPES, 0.1% bovine serum albumin, 1.25 mmol/L Probenecid, 0.02% Pluronic F-127, 1.5 μmol/L Fluo-4-AM, pH 7.4) was added to each well, followed by incubation in a CO$_2$ incubator for 1 hour. After the incubation, the loading solution was removed. A test solution (1×HBSS, 10 mmol/L HEPES, 0.1% bovine serum albumin, 1.25 mmol/L Probenecid, pH 7.4) containing any one of test compounds was added to wells, followed by incubation in a CO$_2$ incubator for 30 minutes. The test compound was serially diluted with DMSO so as to be assayed at a final concentration of 0.1 nmol/L to 1 μmol/L. After the incubation, measurement of fluorescence intensity levels and addition of AVP were performed with Functional Drug Screening System (FDSS, Hamamatsu Photonics K.K.). AVP was added to each well at a final concentration of 2.5 nmol/L. At this concentration, AVP shows 70 to 80% of the maximum activity. The fluorescence level in the well not containing any test compound and AVP was defined as 0%, and the fluorescence level in the well not containing any test compound but containing AVP was defined as 100%. A dose-response curve was plotted from fluorescence levels after the addition of AVP in the presence of a test compound at various concentrations, and the 50% inhibitory concentration (IC$_{50}$ value) of the compound was calculated. Table 5 shows the results.

TABLE 5

| Example No. | IC$_{50}$ value (nmol/L) |
|---|---|
| Aa-1 | 9.3 |
| Aa-8 | 23 |
| Aa-10 | 20 |
| Ab-2 | 13 |
| Ab-5 | 29 |
| Ba-2 | 30 |
| Ca-2 | 11 |
| Ca-3 | 16 |
| Cb-2 | 26 |
| Da-2 | 6.3 |
| Da-5 | 6 |
| Da-6 | 12 |

INDUSTRIAL APPLICABILITY

The present invention can provide a therapeutic or preventive agent for, for example, mood disorder, anxiety disorder, schizophrenia, Alzheimer's disease, Parkinson's disease, Huntington's chorea, eating disorder, hypertension, gastrointestinal disease, drug addiction, epilepsy, cerebral infarction, cerebral ischemia, cerebral edema, head injury, inflammation, immune-related disease, or alopecia.

The invention claimed is:
1. A 1,2,4-triazolone compound represented by Formula (1A):

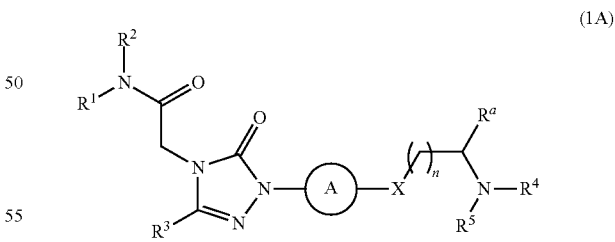

(1A)

[in Formula (1A),
R$^1$ represents a C$_{1-5}$ alkyl (the C$_{1-5}$ alkyl is optionally substituted by one to three groups selected from the group consisting of hydroxy, halogen atoms, cyano, C$_{3-7}$ cycloalkyl, and C$_{1-5}$ alkoxy), C$_{3-7}$ cycloalkyl, or 4- to 8-membered saturated heterocyclic ring;
R$^2$ represents a hydrogen atom or C$_{1-5}$ alkyl;
R$^3$ represents aryl or heteroaryl (the aryl or heteroaryl is optionally substituted by one or two groups selected from the group consisting of C$_{1-5}$ alkoxy, C$_{1-5}$ alkyl, halogen atoms, trifluoromethyl, trifluoromethoxy, cyano, hydroxy, difluoromethoxy, and $C_{1-5}$ alkylsulfonyl);

$R^4$ and $R^5$ may be the same or different and each represent a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated or unsaturated heterocyclic ring containing one or more nitrogen, oxygen, or sulfur atoms in the ring (the 4- to 8-membered saturated or unsaturated heterocyclic ring is optionally substituted by one or two groups selected from the group consisting of hydroxy, $C_{1-5}$ alkyl, $C_{1-5}$ alkoxy, halogen atoms, cyano, $C_{2-5}$ alkanoyl, and trifluoromethyl), or $R^4$ and $R^5$ optionally, together with the adjoining nitrogen atom, form a 4- to 8-membered saturated or unsaturated heterocyclic ring optionally containing one or more nitrogen, oxygen, or sulfur atoms, in addition to the adjoining nitrogen atom, in the ring (the 4- to 8-membered saturated or unsaturated heterocyclic ring is optionally substituted by one or two groups selected from the group consisting of hydroxy, $C_{1-5}$ alkyl (the $C_{1-5}$ alkyl is optionally substituted by one or two hydroxy), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl, trifluoromethyl, and amino (the amino is optionally substituted by one or two groups selected from the group consisting of $C_{1-5}$ alkyl and $C_{2-5}$ alkanoyl), and the 4- to 8-membered saturated or unsaturated heterocyclic ring optionally has a $C_{1-5}$ alkylene group crosslinking two different carbon atoms in the ring) or form 2-oxa-6-azaspiro[3.3]hept-6-yl or 7-oxa-2-azaspiro[3.5]non-2-yl;

A represents phenylene or 6-membered heteroarylene (the phenylene and 6-membered heteroarylene are optionally substituted by one or two groups selected from halogen atoms and $C_{1-5}$ alkoxy);

X represents a single bond, —O—, or —NR6—;

$R^6$ represents a hydrogen atom, $C_{1-5}$ alkyl, or $C_{2-5}$ alkanoyl;

$R^a$ represents a hydrogen atom or $C_{1-5}$ alkyl; and n is an integer of 0 to 3], or a pharmaceutically acceptable salt of the 1,2,4-triazolone compound.

2. A 1,2,4-triazolone compound represented by Formula (1A):

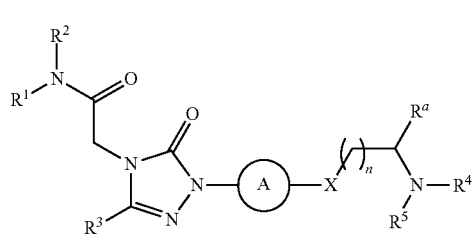

(1A)

[in Formula (1A), $R^1$ represents a $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated heterocyclic ring;

$R^2$ represents a hydrogen atom or $C_{1-5}$ alkyl;

$R^3$ represents aryl or heteroaryl (the aryl or heteroaryl is optionally substituted by one or two groups selected from the group consisting of $C_{1-5}$ alkoxy, $C_{1-5}$ alkyl, halogen atoms, trifluoromethyl, trifluoromethoxy, cyano, hydroxy, difluoromethoxy, and $C_{1-5}$ alkylsulfonyl);

$R^4$ and $R^5$ may be the same or different and each represent a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated or unsaturated heterocyclic ring containing one or more nitrogen, oxygen, or sulfur atoms in the ring (the 4- to 8-membered saturated or unsaturated heterocyclic ring is optionally substituted by one or two groups selected from the group consisting of hydroxy, $C_{1-5}$ alkyl, $C_{1-5}$ alkoxy, halogen atoms, cyano, $C_{2-5}$ alkanoyl, and trifluoromethyl), or $R^4$ and $R^5$ optionally, together with the adjoining nitrogen atom, form a 4- to 8-membered saturated or unsaturated heterocyclic ring optionally containing one or more nitrogen, oxygen, or sulfur atoms, in addition to the adjoining nitrogen atom, in the ring (the 4- to 8-membered saturated or unsaturated heterocyclic ring is optionally substituted by one or two groups selected from the group consisting of hydroxy, $C_{1-5}$ alkyl (the $C_{1-5}$ alkyl is optionally substituted by one or two hydroxy), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl, and trifluoromethyl, and the 4- to 8-membered saturated or unsaturated heterocyclic ring optionally has a $C_{1-5}$ alkylene group crosslinking two different carbon atoms in the ring) or form 2-oxa-6-azaspiro[3.3]hept-6-yl;

A represents phenylene or 6-membered heteroarylene (the phenylene and 6-membered heteroarylene are optionally substituted by one or two groups selected from halogen atoms and $C_{1-5}$ alkoxy);

X represents a single bond, —O—, or —NR$^6$—;

$R^6$ represents a hydrogen atom, $C_{1-5}$ alkyl, or $C_{2-5}$ alkanoyl;

$R^a$ represents a hydrogen atom or $C_{1-5}$ alkyl; and n is an integer of 1 to 3], or a pharmaceutically acceptable salt of the 1,2,4-triazolone compound.

3. A 1,2,4-triazolone compound represented by Formula (1a):

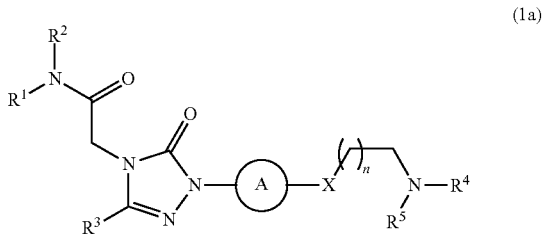

(1a)

[in Formula (1a), $R^1$ represents a $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated heterocyclic ring;

$R^2$ represents a hydrogen atom or $C_{1-5}$ alkyl;

$R^3$ represents aryl or heteroaryl (the aryl or heteroaryl is optionally substituted by one or two groups selected from the group consisting of $C_{1-5}$ alkoxy, $C_{1-5}$ alkyl, halogen atoms, trifluoromethyl, trifluoromethoxy, cyano, hydroxy, and difluoromethoxy);

$R^4$ and $R^5$ may be the same or different and each represent a hydrogen atom, $C_{1-5}$ alkyl (the $C_{1-5}$ alkyl is optionally substituted by one to three groups selected from the group consisting of hydroxy, halogen atoms, cyano, $C_{3-7}$ cycloalkyl, and $C_{1-5}$ alkoxy), $C_{3-7}$ cycloalkyl, or 4- to 8-membered saturated or unsaturated heterocyclic ring containing one or more nitrogen, oxygen, or sulfur atoms in the ring (the 4- to 8-membered saturated or unsaturated heterocyclic ring is optionally substituted by one or two groups selected from the group consisting of hydroxy, $C_{1-5}$ alkyl, $C_{1-5}$ alkoxy, halogen atoms, cyano, $C_{2-5}$ alkanoyl, and trifluoromethyl), or $R^4$ and $R^5$ optionally, together with the adjoining nitrogen atom, form a 4- to 8-membered saturated or unsaturated heterocyclic ring optionally containing one or more nitrogen, oxygen, or sulfur atoms, in addition to the adjoining nitrogen atom, in the ring (the 4- to 8-membered saturated or unsaturated heterocyclic ring is optionally substituted by one or two groups selected from the group consisting of hydroxy, $C_{1-5}$ alkyl (the $C_{1-5}$ alkyl is optionally substituted by one or two hydroxy), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl, and trifluoromethyl, and the 4- to 8-membered saturated or unsaturated heterocyclic ring optionally has a $C_{1-5}$ alkylene group crosslinking two different carbon atoms in the ring) or form 2-oxa-6-azaspiro[3.3]hept-6-yl;

A represents phenylene or 6-membered heteroarylene;

X represents a single bond, —O—, or —NR$^6$—;

$R^6$ represents a hydrogen atom, $C_{1-5}$ alkyl, or $C_{2-5}$ alkanoyl; and n is an integer of 1 to 3], or a pharmaceutically acceptable salt of the 1,2,4-triazolone compound.

4. The 1,2,4-triazolone compound or pharmaceutically acceptable salt thereof according to claim 1, wherein $R^1$ is a $C_{1-5}$ alkyl;

$R^2$ is a hydrogen atom; and $R^3$ is phenyl or pyridyl (the phenyl or pyridyl is optionally substituted by one or two groups selected from the group consisting of $C_{1-5}$ alkyl, $C_{1-5}$ alkoxy, halogen atoms, cyano, hydroxy, trifluoromethyl, difluoromethoxy, and trifluoromethoxy).

5. The 1,2,4-triazolone compound or pharmaceutically acceptable salt thereof according to claim 1, wherein A is phenylene, pyridinediyl, or pyrimidinediyl (the phenylene, pyridinediyl, and pyrimidinediyl are optionally substituted by one or two groups selected from halogen atoms and $C_{1-5}$ alkoxy).

6. The 1,2,4-triazolone compound or pharmaceutically acceptable salt thereof according to claim 1, wherein A is phenylene or pyridinediyl (the phenylene and pyridinediyl are optionally substituted by one or two groups selected from halogen atoms and $C_{1-5}$ alkoxy).

7. A 1,2,4-triazolone compound or pharmaceutically acceptable salt thereof according to claim 6, wherein A represents any one of Formulae (2) to (4):

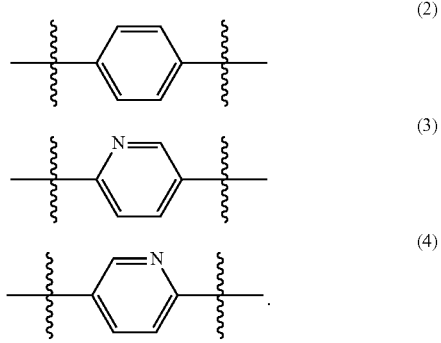

8. The 1,2,4-triazolone compound or pharmaceutically acceptable salt thereof according to claim 1, wherein X is a single bond;

n is an integer of 1; and $R^4$ and $R^5$ optionally, together with the adjoining nitrogen atom, form a 4- to 8-membered saturated or unsaturated heterocyclic ring optionally containing one or more nitrogen, oxygen, or sulfur atoms, in addition to the adjoining nitrogen atom, in the ring (the 4- to 8-membered saturated or unsaturated heterocyclic ring is optionally substituted by one or two groups selected from the group consisting of hydroxy, $C_{1-5}$ alkyl (the $C_{1-5}$ alkyl is optionally substituted by one or two hydroxy), $C_{1-5}$ alkoxy, halogen atoms, cyano, $C_{2-5}$ alkanoyl, oxo, aminocarbonyl, mono-$C_{1-5}$ alkylaminocarbonyl, di-$C_{1-5}$ alkylaminocarbonyl, and trifluoromethyl, and the 4- to 8-membered saturated or unsaturated heterocyclic ring optionally has a $C_{1-5}$ alkylene group crosslinking two different carbon atoms in the ring) or form 2-oxa-6-azaspiro[3.3]hept-6-yl.

9. The 1,2,4-triazolone compound or pharmaceutically acceptable salt thereof according to claim 1, wherein $R^4$ and $R^5$, together with the adjoining nitrogen atom, form a 5- or 6-membered saturated heterocyclic ring optionally containing one or more nitrogen, oxygen, or sulfur atoms, in addition to the adjoining nitrogen atom, in the ring (the 5- or 6-membered saturated heterocyclic ring is optionally substituted by one or two groups selected from the group consisting of hydroxy and $C_{1-5}$ alkyl, and the 5- or 6-membered saturated heterocyclic ring optionally has a $C_{1-5}$ alkylene group crosslinking two different carbon atoms in the ring) or form 2-oxa-6-azaspiro[3.3]hept-6-yl.

10. The 1,2,4-triazolone compound or pharmaceutically acceptable salt thereof according to claim 1, wherein $R^4$ and $R^5$, together with the adjoining nitrogen atom, form a 6-membered saturated heterocyclic ring optionally containing one or more oxygen atoms, in addition to the adjoining nitrogen atom, in the ring (the 6-membered saturated heterocyclic ring is optionally substituted by one or two hydroxy, and the 6-membered saturated heterocyclic ring optionally has a $C_{1-5}$ alkylene group crosslinking two different carbon atoms in the ring) or form 2-oxa-6-azaspiro[3.3]hept-6-yl.

11. One substance selected from, or a mixture of two or more substances selected from the group consisting of the following compounds and pharmaceutically acceptable salts thereof according to claim 1:

2-[3-(3-chlorophenyl)-1-{4-[2-(morpholin-4-yl)ethyl]phenyl}-5-oxo-1,5-dihydro-4H-1,2,4-triazol-4-yl]-N-(propan-2-yl)acetamide, 2-[3-(3-chlorophenyl)-1-{4-[2-(3-hydroxypyrrolidin-1-yl)ethyl]phenyl}-5-oxo-1,5-dihydro-4H-1,2,4-triazol-4-yl]-N-(propan-2-yl)acetamide, 2-[3-(3-chlorophenyl)-1-(4-{2-[3-(hydroxymethyl)pyrrolidin-1-yl]ethyl}phenyl)-5-oxo-1,5-dihydro-4H-1,2,4-triazol-4-yl]-N-(propan-2-yl)acetamide, 2-[3-(3-chlorophenyl)-1-{4-[2-(3-hydroxy-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chlorophenyl)-1-{4-[2-(8-oxa-3-azabicyclo[3.2.1]oct-3-yl)ethyl]phenyl}-5-oxo-1,5-dihydro-4H-1,2,4-triazol-4-yl]-N-(propan-2-yl)acetamide, 2-[3-(3-chlorophenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chlorophenyl)-5-oxo-1-{4-[2-(piperidin-1-yl)ethyl]phenyl}-1,5-dihydro-4H-1,2,4-triazol-4-yl]-N-(propan-2-yl)acetamide, 2-[3-(3-chlorophenyl)-1-{4-[2-(1,4-oxazepan-4-yl)ethyl]phenyl}-5-oxo-1,5-dihydro-4H-1,2,4-triazol-4-yl]-N-(propan-2-yl)acetamide, 2-[3-(3-chlorophenyl)-1-{5-[2-(morpholin-4-yl)ethyl]pyridin-2-yl}-5-oxo-1,5-dihydro-4H-1,2,4-triazol-4-yl]-N-(propan-2-yl)acetamide, 2-[3-(3-chlorophenyl)-1-{5-[2-(3-hydroxy-8-azabicyclo[3.2.1]oct-8-yl)ethyl]pyridin-2-yl}-5-oxo-1,5-dihydro-4H-1,2,4-triazol-4-yl]-N-(propan-2-yl)acetamide, 2-[3-(3-chlorophenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]-N-(propan-2-yl)acetamide, 2-[3-(3-chlorophenyl)-1-{6-[2-(morpholin-4-yl)ethyl]pyridin-3-yl}-5-oxo-1,5-dihydro-4H-1,2,4-triazol-4-yl]-N-(propan-2-yl)acetamide, N-tert-butyl-2-[3-(3-chlorophenyl)-1-{4-[2-(morpholin-4-yl)ethyl]phenyl}-5-oxo-1,5-dihydro-4H-1,2,4-triazol-4-yl]acetamide, 2-[3-(3-chlorophenyl)-1-{4-[2-(morpholin-4-yl)ethyl]phenyl}-5-oxo-1,5-dihydro-4H-1,2,4-triazol-4-yl]-N-(1,1,1-trifluoropropan-2-yl)acetamide, 2-[3-(3-chlorophenyl)-1-{4-[2-(morpholin-4-yl)ethyl]phenyl}-5-oxo-1,5-dihydro-4H-1,2,4-triazol-4-yl]-N-(1-hydroxy-2-methylpropan-2-yl)acetamide, 2-[3-(3-chlorophenyl)-1-{4-[2-(morpholin-4-yl)ethyl]phenyl}-5-oxo-1,5-dihydro-4H-1,2,4-triazol-4-yl]-N-cyclobutylacetamide, 2-[3-(3-chlorophenyl)-1-{4-[2-(morpholin-4-yl)ethyl]phenyl}-5-oxo-1,5-dihydro-4H-1,2,4-triazol-4-yl]-N-(oxetan-3-yl)acetamide, 2-[3-(3-chlorophenyl)-1-{4-[2-(morpholin-4-yl)ethyl]phenyl}-5-oxo-1,5-dihydro-4H-1,2,4-triazol-4-yl]-N-(cyclopropylmethyl)acetamide, 2-[3-(3-methoxyphenyl)-1-{4-[2-(morpholin-4-yl)ethyl]phenyl}-5-oxo-1,5-dihydro-4H-1,2,4-triazol-4-yl]-N-(propan-2-yl)acetamide, 2-[3-(4-fluoro-3-methoxyphenyl)-5-oxo-1-{4-[2-(piperidin-1-yl)ethyl]phenyl}-1,5-dihydro-4H-1,2,4-triazol-4-yl]-N-(propan-2-yl)acetamide, 2-[3-(4-fluoro-3-methoxyphenyl)-1-{4-[2-(morpholin-4-yl)ethyl]phenyl}-5-oxo-1,5-dihydro-4H-1,2,4-triazol-4-yl]-N-(propan-2-yl)acetamide, 2-[3-(4-fluoro-3-methoxyphenyl)-1-{4-[2-(3-hydroxy-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(4-fluoro-3-methoxyphenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(4-fluoro-3-methoxyphenyl)-1-{5-[2-(morpholin-4-yl)ethyl]pyridin-2-yl}-5-oxo-1,5-dihydro-4H-1,2,4-triazol-4-yl]-N-(propan-2-yl)acetamide, 2-[3-(4-fluoro-3-methoxyphenyl)-1-{5-[2-(3-hydroxy-8-azabicyclo[3.2.1]oct-8-yl)ethyl]pyridin-2-yl}-5-oxo-1,5-dihydro-4H-1,2,4-triazol-4-yl]-N-(propan-2-yl)acetamide, 2-[3-(4-fluoro-3-methoxyphenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]-N-(propan-2-yl)acetamide, 2-[3-(3-chloro-4-fluorophenyl)-5-oxo-1-{4-[2-(piperidin-1-yl)ethyl]phenyl}-1,5-dihydro-4H-1,2,4-triazol-4-yl]-N-(propan-2-yl)acetamide, 2-[3-(3-chloro-4-fluorophenyl)-1-{4-[2-(morpholin-4-yl)ethyl]phenyl}-5-oxo-1,5-dihydro-4H-1,2,4-triazol-4-yl]-N-(propan-2-yl)acetamide, 2-[3-(3-chloro-4-fluorophenyl)-1-{4-[2-(2-oxa-6-azaspiro[3.3]hept-6-yl)ethyl]phenyl}-5-oxo-1,5-dihydro-4H-1,2,4-triazol-4-yl]-N-(propan-2-yl)acetamide, 2-[3-(3-chloro-4-fluorophenyl)-1-{4-[2-(1,4-oxazepan-4-yl)ethyl]phenyl}-5-oxo-1,5-dihydro-4H-1,2,4-triazol-4-yl]-N-(propan-2-yl)acetamide, 2-[3-(3-chloro-4-fluorophenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chloro-4-fluorophenyl)-1-{4-[2-(3-hydroxy-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chloro-4-fluorophenyl)-5-oxo-1-{5-[2-(piperidin-1-yl)ethyl]pyridin-2-yl}-1,5-dihydro-4H-1,2,4-triazol-4-yl]-N-(propan-2-yl)acetamide, 2-[3-(3-chloro-4-fluorophenyl)-1-{5-[2-(morpholin-4-yl)ethyl]pyridin-2-yl}-5-oxo-1,5-dihydro-4H-1,2,4-triazol-4-yl]-N-(propan-2-yl)acetamide, 2-[3-(3-chloro-4-fluorophenyl)-1-{5-[2-(2-oxa-6-azaspiro[3.3]hept-6-yl)ethyl]pyridin-2-yl}-5-oxo-1,5-dihydro-4H-1,2,4-triazol-4-yl]-N-(propan-2-yl)acetamide, 2-[3-(3-chloro-4-fluorophenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]-N-(propan-2-yl)acetamide, 2-[3-(3-cyanophenyl)-1-{4-[2-(morpholin-4-yl)ethyl]phenyl}-5-oxo-1,5-dihydro-4H-1,2,4-triazol-4-yl]-N-(propan-2-yl)acetamide, 2-[3-(3-fluorophenyl)-1-{4-[2-(morpholin-4-yl)ethyl]phenyl}-5-oxo-1,5-dihydro-4H-1,2,4-triazol-4-yl]-N-(propan-2-yl)acetamide, 2-(1-{4-[2-(morpholin-4-yl)ethyl]phenyl}-5-oxo-3-phenyl-1,5-dihydro-4H-1,2,4-triazol-4-yl)-N-(propan-2-yl)acetamide, 2-[3-(3-chlorophenyl)-1-{3-fluoro-4-[2-(morpholin-4-yl)ethyl]phenyl}-5-oxo-1,5-dihydro-4H-1,2,4-triazol-4-yl]-N-(propan-2-yl)acetamide, 2-[3-(3-chlorophenyl)-1-{3-fluoro-4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chlorophenyl)-1-{3-methoxy-4-[2-(morpholin-4-yl)ethyl]phenyl}-5-oxo-1,5-dihydro-4H-1,2,4-triazol-4-yl]-N-(propan-2-yl)acetamide, 2-[3-(3-chlorophenyl)-1-{3-methoxy-4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide, 2-[3-(3-chlorophenyl)-1-{4-[2-(morpholin-4-yl)propyl]phenyl}-5-oxo-1,5-dihydro-4H-1,2,4-triazol-4-yl]-N-(propan-2-yl)acetamide, 2-[3-(3-chlorophenyl)-1-{4-[2-(3-oxa-8-azabicyclo[3.2.1]oct-8-yl)propyl]phenyl}-5-oxo-1,5-dihydro-4H-1,2,4-triazol-4-yl]-N-(propan-2-yl)acetamide, 2-[3-(3-chlorophenyl)-1-{5-[2-(morpholin-4-yl)propyl]pyridin-2-yl}-5-oxo-1,5-dihydro-4H-1,2,4-triazol-4-yl]-N-(propan-2-yl)acetamide, 2-[3-(3-chlorophenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide, N-tert-butyl-2-[3-(3-chlorophenyl)-1-{5-[2-(morpholin-4-yl)ethyl]pyridin-2-yl}-5-oxo-1,5-dihydro-4H-1,2,4-triazol-4-yl]acetamide, N-tert-butyl-2-[3-(3-chlorophenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]acetamide, 2-[3-(3-methoxyphenyl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide, N-tert-butyl-2-[3-(3-methoxyphenyl)-1-{5-[2-(morpholin-4-yl)ethyl]pyridin-2-yl}-5-oxo-1,5-dihydro-4H-1,2,4-triazol-4-yl]acetamide, N-tert-butyl-2-[3-(3-methoxyphenyl)-1-{5-[2-(3-oxa-8-azabicyclo[3.2.1]oct-8-yl)ethyl]pyridin-2-yl}-5-oxo-1,5-dihydro-4H-1,2,4-triazol-4-yl]acetamide, 2-[3-(2-bromo-5-chlorophenyl)-1-{4-[2-(morpholin-4-yl)ethyl]phenyl}-5-oxo-1,5-dihydro-4H-1,2,4-triazol-4-yl]-N-(propan-2-yl)acetamide, 2-(3-[3-(methylsulfonyl)phenyl]-1-{4-[2-(morpholin-4-yl)ethyl]phenyl}-5-oxo-1,5-dihydro-4H-1,2,4-triazol-4-yl)-N-(propan-2-yl)acetamide, 2-[3-(3-chlorophenyl)-1-{4-[2-(morpholin-4-yl)ethyl]phenyl}-5-oxo-1,5-dihydro-4H-1,2,4-triazol-4-yl]-N-(propan-2-yl)acetamide, (+)-2-[3-(3-chlorophenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide, (−)-2-[3-(3-chlorophenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide, 2-[3-(4-fluoro-3-methoxyphenyl)-1-{4[2-(3-oxa-8-azabicyclo[3.2.1]oct-8-yl)propyl]phenyl}-5-oxo-1,5-dihydro-4H-1,2,4-triazol-4-yl]-N-(propan-2-yl)acetamide, 2-[3-(4-fluoro-3-methoxyphenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]-N-(propan-2-yl)acetamide, N-tert-butyl-2-[3-(3-methoxyphenyl)-1-{4-[2-(3-oxa-8-azabicyclo[3.2.1]oct-8-yl)propyl]phenyl}-5-oxo-1,5-dihydro-4H-1,2,4-triazol-4-yl]acetamide, N-tert-butyl-2-[3-(3-methoxyphenyl)-1-{5-[2-(3-oxa-8-azabicyclo[3.2.1]oct-8-yl)propyl]pyridin-2-yl}-5-oxo-1,5-dihydro-4H-1,2,4-triazol-4-yl]acetamide, 2-[3-(6-methoxypyridin-2-yl)-1-{4-[2-(morpholin-4-yl)ethyl]phenyl}-5-oxo-1,5-dihydro-4H-1,2,4-triazol-4-yl]-N-(propan-2-yl)acetamide, and 2-[3-(6-methoxypyridin-2-yl)-1-{4-[2-(3-oxa-8-azabicyclo[3.2.1]oct-8-yl)ethyl]phenyl}-5-oxo-1,5-dihydro-4H-1,2,4-triazol-4-yl]-N-(propan-2-yl)acetamide.

12. A pharmaceutical composition comprising the 1,2,4-triazolone compound or pharmaceutically acceptable salt thereof according to claim 1 as an active ingredient and a pharmaceutically acceptable carrier.

13. A therapeutic agent comprising the 1,2,4-triazolone compound or pharmaceutically acceptable salt thereof according to claim 1 as an active ingredient to treat mood disorder, anxiety disorder, schizophrenia, Alzheimer's disease, Parkinson's disease, Huntington's chorea, hypertension, drug addiction, epilepsy, cerebral infarction, cerebral ischemia, cerebral edema, head injury, or inflammation.

* * * * *